US008101735B2

(12) United States Patent
Brehm et al.

(10) Patent No.: US 8,101,735 B2
(45) Date of Patent: Jan. 24, 2012

(54) PREPARATION OF PROTECTIVE ANTIGEN

(75) Inventors: John Brehm, Salisbury (GB); Ian McEntee, Salisbury (GB); Philip Vincent, Salisbury (GB); Nigel Allison, Salisbury (GB); Rossalyn Brehm, Salisbury (GB); George Jack, Salisbury (GB); Michael Herbert, Auckland (NZ); Barbara T. Solow, Monrovia, MD (US); Juan Arroyo, Frederick, MD (US); Randall K. Lapcevich, Dickerson, MD (US)

(73) Assignees: Health Protection Agency, Wiltshire, Great Britain (GB); Dynport Vaccine Company LLC, Frederick, MD (US)

( * ) Notice: Subject to any disclaimer, the term of this patent is extended or adjusted under 35 U.S.C. 154(b) by 711 days.

(21) Appl. No.: 12/042,150

(22) Filed: Mar. 4, 2008

(65) Prior Publication Data

US 2009/0042282 A1 Feb. 12, 2009

Related U.S. Application Data

(63) Continuation-in-part of application No. 11/153,865, filed on Jun. 15, 2005, now Pat. No. 7,355,027.

(60) Provisional application No. 60/579,687, filed on Jun. 16, 2004.

(30) Foreign Application Priority Data

Jun. 16, 2004 (GB) .................................. 0413475.5

(51) Int. Cl.
*C07H 21/00* (2006.01)

(52) U.S. Cl. ...................................................... 536/23.1

(58) Field of Classification Search ........................ None
See application file for complete search history.

(56) References Cited

U.S. PATENT DOCUMENTS

| | | | | |
|---|---|---|---|---|
| 5,670,333 A | 9/1997 | Alldread et al. | | |
| 7,355,027 B2 * | 4/2008 | Brehm et al. | ................ | 536/23.7 |
| 2004/0028695 A1 | 2/2004 | Park | | |

FOREIGN PATENT DOCUMENTS

| | | |
|---|---|---|
| EP | 0121352 | 10/1984 |
| WO | WO 98/08952 | 3/1998 |
| WO | WO 01/45639 | 6/2001 |
| WO | WO 02/04646 | 1/2002 |
| WO | WO 03/037370 | 5/2003 |
| WO | WO 03/040179 | 5/2003 |
| WO | WO 2004/003139 | 1/2004 |
| WO | WO 2004/024067 | 3/2004 |
| WO | WO 2005123764 A1 * | 12/2005 |

OTHER PUBLICATIONS

Federal Register, vol. 66, No. 4, Jan. 5, 2001.*

Bowie et al. (Science, 1990, 247:1306-1310).*

Burgess et al. (J. Cell Biol. 111:2129-2138, 1990).*

Lazar et al. (Mol. Cell. Biol., 8:1247-1252, 1988).*

Abrahmsen, L. et al., "Secretion of heterologous gene products to the culture medium of *Escherichia coli*" Nucleic Acids Research, vol. 14, No. 18, pp. 7487-7500, (1986).

Ahuja, N. et al., "Hydrophobic residues Phe552, Phe554, Ile562, Leu566, and Ile574 are required for oligomerization of anthrax protective antigen" Biochemical and Biophysical Research Communications, vol. 287, pp. 542-549, (2001).

Alldread, R.M. et al., "Overexpression of the thermos aquaticus B malate dehydrogenase-encoding gene in *Escherichia coli*", Gene, vol. 114, pp. 139-143, (1992).

Altschul, S.F. et al., "Basic local alignment search tool", Journal of Molecular Biology, vol. 215, pp. 403-410, (1990).

Baillie, L. et al., "Characterization of the human immune response to the UK anthrax vaccine", FEMS Immunology and Medical Microbiology, vol. 42, pp. 267-270, (2004).

Baillie, L. "The development of new vaccines against *Bacillus anthracis*" Journal of Applied Microbiology, vol. 91, pp. 609-613, (2001).

Batra, S. et al., "Trp 346 and Leu 352 residues in protective antigen are required for the expression of anthrax lethal toxin activity", Biochemical and Biophysical Research Communications, vol. 281, pp. 186-192, (2001).

Better, M. et al. "*Escherichia coli* secretion of an active chimeric antibody fragment", Science, vol. 240, pp. 1041-1043, (1988).

Bhatnagar, R. et al., "Anthrax Toxin", Critical Reviews in Microbiology, vol. 27, No. 3, pp. 167-200, (2001).

Bolivar, F. et al., "Construction and characterization of new cloning vehicles, a multipurpose cloning system", Gene, vol. 2, pp. 95-113, (1977).

Brehm, J.K. et al., "Molecular cloning and nucleotide sequence determination of the *Bacillus stearothermophilus* NCA 1503 superoxide dismutase gene and its overexpression in *Escherichia coli*", Applied Microbiology and Biotechnology, vol. 36, pp. 358-363, (1991).

Brosius, J. et al., "Gene organization and primary structure of a ribosomal RNA operon from *Escherichia coli*", Journal of Molecular Biology, vol. 148, pp. 107-127, (1981).

Chambers, S.P. et al., "The pMTL nic cloning vectors. I. Improved pUC polylinker regions to facilitate the use of sonicated DNA for nucleotide sequencing", Gene, vol. 68, issue 1, pp. 139-149, (1988).

Chambers, S.P. et al., "Physical characterisation and over-expression of the *Bacillus caldotenax* superoxide dismutase gene", FEMS Microbiology Letters, vol. 91, pp. 277-284, (1992).

(Continued)

*Primary Examiner* — Nita M Minnifield
*Assistant Examiner* — Brian J Gangle
(74) *Attorney, Agent, or Firm* — Evan Law Group LLC

(57) ABSTRACT

A polynucleotide sequence is provided comprising a nucleic acid sequence encoding recombinant Protective Antigen (rPA).

Also provided are expression vectors and host cells comprising the polynucleotide sequence of the invention, and methods for producing rPA.

25 Claims, 23 Drawing Sheets

OTHER PUBLICATIONS

Chen, Z. et al., "Efficient neutralization of anthrax toxin by chimpanzee monoclonal antibodies against protective antigen", The Journal of Infectious Diseases, vol. 193, pp. 625-633, (2006).
Denefle, P. et al., "Heterologous protein export in *Escherichia coli*: influence of bacterial signal peptides on the export of human interleukin 1β" Gene, vol. 85, pp. 499-510, (1989).
Fujimoto, K. et al., "Expression and secretion of human epidermal growth factor by *Escherichia coli* using enterotoxin signal sequences", Journal of Biotechnology, vol. 8, pp. 77-86, (1988).
Ghrayeb J. et al., "Secretion cloning vectors in *Escherichia coli*", The EMBO Journal, vol. 3, No. 10, pp. 2437-2442, (1984).
Gray, G.L. et al., "Periplasmic production of correctly processed juman growth hormone in *Escherichia coli*: natural and bacterial signal sequences are interchangeable", Gene, vol. 39, pp. 247-254, (1985).
Hoffman, C.S. et al., "Fusions of secreted proteins to alkaline phosphatise: an approach for studying protein secretion", Proceedings of the National Academy of Science, vol. 82, pp. 5107-5111, (1985).
Johnson, D.L. et al., "Refolding, purification, and characterization of human erythropoietin binding protein produced in *Escherichia coli*", Protein Expression and Purification, vol. 7, pp. 104-113, (1996).
Kadonaga, J.T. et al., "The role of the β-Lactamase signal sequence in the secretion of proteins by *Escherichia coli*", The Journal of Biological Chemistry, vol. 259, No. 4, pp. 2149-2154, (1984).
Kanehisa, M., "Use of statistical criteria for screening potential homologles in nucleic acid sequences" Nucleic Acids Research, vol. 12, No. 1, pp. 203-213, (1984).
Laffly, E. et al., "Selection of a macaque fab with framework regions like those in humans, high affinity, and ability to neutralize the protective antigen (PA) of *Bacillus anthracis* by binding to the segment of PA between residues 686 and 694", Antimicrobial Agents and Chemotherapy, vol. 49, No. 8, pp. 3414-3420, (2005).
Laughlin, E.M. et al., "Antigen-specific $CD4^+$T cells recognize epitopes of protective antigen following vaccination with an anthrax vaccine", Infection and Immunity, vol. 75, No. 4, pp. 1852-1860, (2007).
Le Calvez, H. et al., "Increased efficiency of alkaline phosphatise production levels in *Escherichia coli* using a degenerate PeIB signal sequence", Gene, vol. 170, pp. 51-55, (1996).
Lei, S-P. et al., "Characterization of the *erwinia carotovora* pelB gene and its product pectate lyase", Journal of Bacteriology, vol. 169, No. 9, pp. 4379-4383, (1987).
Little, S.F. et al., "Comparative efficacy of *Bacillus anthracis* live spore vaccine and protective antigen vaccine against anthrax in the Guinea pig", Infection and Immunity, vol. 52, No. 2, pp. 509-512, (1986).
Maclntyre, S. et al., "The role of the mature part of secretory proteins in translocation across the plasma membrane and in regulation of their synthesis in *Escherichia coli*", Biochimie, vol. 72, pp. 157-167, (1990).
Makrides, S.C. "Strategies for achieving high-level expression of genes in *Escherichia coli*", Microbiological Reviews, vol. 60, No. 3, pp. 512-538, (1996).
Michael, N.P. et al., "Physical characterisation of the *Escherichia coli* B gene encoding nitroreductase and its over-expression in *Escherichia coli* K12", FEMS Microbiology Letters, vol. 124, pp. 195-202, (1994).
Miller, C.A. et al., "Nucleotide sequence of the partition locus of *Escherichia coli* plasmid pSC101" Gene, vol. 24, pp. 309-315, (1983).
Minton, N.P. et al., "Copy number and mobilization properties of pUC plasmids", Focus, vol. 10, No. 3, p. 56, (1988).
Morioka-Fujimoto, K. et al., "Modified enterotoxin signal sequences increase secretion level of the recombinant human epidermal growth factor in *Escherichia coli*", The Journal of Biological Chemistry, vol. 266, No. 3, pp. 1728-1732, (1991).
Needleman, S.B. et al., "A general method applicable to the search for similarities in the amino acid sequence of two proteins", Journal of Molecular Biology, vol. 48, pp. 443-453, (1970).
Oka, T. et al., "Synthesis and secretion of human epidermal growth factor by *Escherichia coli*", Proceedings of the National Academy of Science, vol. 82, pp. 7212-7216, (1985).
Pearson, W.R. et al., "Improved tools for biological sequence comparison" Proceedings of the National Academy of Science, vol. 85, pp. 2444-2448, (1988).
Price, B.M. et al., "Protection against anthrax lethal toxin challenge by genetic immunization with a plasmid encoding the lethal factor protein", Infection and Immunity, vol. 69, No. 7, pp. 4509-4515, (2001).
Proudfoot, A.E.I. et al., "Extension of recombinant human RANTES by the retention of the initiating methionine produces a potent antagonist", The Journal of Biological Chemistry, vol. 271, No. 5, pp. 2599-2603, (1996).
Schein, C.H. et al., "Secretion of mammalian ribonucleases from *Escherichia coli* using the signal sequence of murine spleen ribonuclease", The Biochemical Journal, vol. 283, pp. 137-144, (1992).
Smith, T.F. et al., "Comparison of Biosequences", Advances in Applied Mathematics, vol. 2, pp. 482-489, (1981).
Sterne, M. "The use of anthrax vaccines prepared from avirulent (uncapsulated) variants of *Bacillus anthracis*", Onderstepoort Journal of Veterinary Science and Animal Industry, vol. 13, No. 2, pp. 307-312, (1939).
Villa-Komaroff, L. et al., "A bacterial clone synthesizing proinsulin", Proceedings of the National Academy of Science, vol. 75, No. 8, pp. 3727-3731, (1978).
Vodkin, M.H. et al., "Cloning of the protective antigen gene of *Bacillus anthracis*", Cell, vol. 34, pp. 693-697, (1983).
Watson, M.E.E. "Compilation of published signal sequences", Nucleic Acids Research, vol. 12, No. 13, pp. 5145-5164, (1984).
Welkos, S.L., et al., "Sequence and analysis of the DNA encoding protective antigen of *Bacillus anthracis*", Gene, vol. 69, No. 2, pp. 287-300, (1988).
Wetmur, J.G. et al., "Kinetics of renaturation of DNA", Journal of Molecular Biology, vol. 31, pp. 349-370, (1968).
Williamson, E.D. et al.,"Immunogenicity of recombinant protective antigen and efficacy against aerosol challenge with anthrax", Infection and Immunity, vol. 73, No. 9, pp. 5978-5987, (2005).
Bowie et al (Science, 1990, 257:1306-1310).
Burgess et al (J. of Cell Bio. 111:2129-2138, 1990).
Lazar et al. (Molecular and Cellular Biology, 1988, 8:1247-1252).
Bork (Genome Research, 2000,10:398-400).
Colman, Res. Immunol., 145:33-36, 1994.
Lewin, Genes IV, Oxford Univ. Press, 1990, page 68.
Sigmund, Arterioscler. Thromb. Vasc. Biol., 20:1425-1429, 2000.
Bampton et al., Brain Res., 841:123-134, 1999.
Invitrogen Product Catalog, 2001.
Novagen Catalog, 2002-2003.
By Manju Sharma et at, "Expression and Purification of Anthrax Toxin Protective Antigen from *Escherichia colt*", Protein Expression and Purification, Vol. 7, Article No. 0005, 1996, pp. 33-38.
Minton et al., The Complete Nucleotide Sequence of the Pseudomonas Gene Coding for Carboxypeptidase G2, Gene, 31 (1984) 31-38, XP002038770.
Ascenzi et al., Anthrax Toxin: A Tripartite Lethal Combination, FEBS Letters 531 (2002) 384-388.

* cited by examiner

FIG 13(A1)

```
                           ATGGAAGTTAAACAGGAGAACCGTTTGTTGAATGAATGCGAATCTAGTTCTCAGGGGTTGCTGGGCTACT
                                    10        20        30        40        50        60        70

DVC.Synthetic.rP ATGGAAGTGAAACAGGAGAACCGTCTGCTGAACGAAAGCGAATCTAGCTCTCAGGGCCTGCTGGGCTACT 70
AP.PA.wt.Sequenc ATGGAAGTTAAACAGGAGAACCGGTTATTAAATGAATCAGAATCAAGTTCCCAGGGGTTACTAGGATACT 70

                           ATTTTAGTGATTTGAATTTTCAGGCACCGATGGTTGTTACCTCTTGTACTACCGGGGATTTGTGTATTCC
                                    80        90       100       110       120       130       140

DVC.Synthetic.rP ATTTCAGCGATCTGAACTTTCAGGCACCGATGGTTGTGACCTCTAGCACGACCGGCGATCTGAGCATTCC 140
AP.PA.wt.Sequenc ATTTTAGTGATTTGAATTTTCAAGCACCCATGGTGGTTACCTCTTCTACTACAGGGGATTTATCTATTCC 140

                           TAGTTGTGAGTTGGAGAATATTCCGTGGGAGAACCAGTATTTTCAGTCTGCTATTTGGTGCGGCTTTATC
                                   150       160       170       180       190       200       210

DVC.Synthetic.rP GAGCAGCGAACTGGAGAACATTCCGAGCGAGAACCAGTACTTTCAGTCTGCGATTTGGAGCGGCTTCATC 210
AP.PA.wt.Sequenc TAGTTCTGAGTTAGAAAATATTCCATCGGAAAACCAATATTTTCAATCTGCTATTTGGTCAGGATTTATC 210
```

FIG 13(A2)

```
                  AAAGTTAAGAAGAGTGATGAGTATACCTTTGCTACTTCTGCTGATAATCATGTGACCATGTGGGTGGATG
                          220       230       240       250       260       270       280

DVC.Synthetic.rP  AAAGTGAAGAAAAGCGATGAGTATACCTTTGCGACGTCTGCGGATAACCATGTGACCATGTGGGTGGACG 280
AP.PA.wt.Sequenc  AAAGTTAAGAAGAGTGATGAATATACATTTGCTACTTCCGCTGATAATCATGTAACAATGTGGGTAGATG 280
```

```
                  ATCAGGAAGTGATTAATAAAGCTTGTAATTGTAACAAGATTCGCTTGGAGAAGGGTCGCTTGTATCAGAT
                          290       300       310       320       330       340       350

DVC.Synthetic.rP  ATCAGGAAGTGATCAACAAAGCGAGCAACAGCAACAAGATTCGCCTGGAGAAGGGTCGCCTGTATCAGAT 350
AP.PA.wt.Sequenc  ACCAAGAAGTGATTAATAAAGCTTCTAATTCTAACAAAATCAGATTAGAAAAAGGAAGATTATATCAAAT 350
```

```
                  CAAGATTCAGTATCAGCGCGAGAATCCTACTGAGAAAGGCTTGGATTTCAAGTTGTACTGGACCGATTGT
                          360       370       380       390       400       410       420

DVC.Synthetic.rP  CAAGATTCAGTATCAGCGCGAGAATCCGACCGAGAAAGGCCTGGATTTCAAACTGTACTGGACCGATAGC 420
AP.PA.wt.Sequenc  AAAAATTCAATATCAACGAGAAAATCCTACTGAAAAAGGATTGGATTTCAAGTTGTACTGGACCGATTCT 420
```

FIG 13(A3)

```
                   CAGAATAAGAAAGAAGTGATTTGTTGTGATAACTTGCAATTGCCGGAATTGAAACAGAAGTGTTGGAACT
                           430       440       450       460       470       480       490

DVC.Synthetic.rP   CAGAACAAGAAAGAAGTGATTAGCTCTGATAACCTGCAACTGCCGGAACTGAAACAGAAGAGCAGCAACA  490
AP.PA.wt.Sequenc   CAAAATAAAAAAGAAGTGATTTCTAGTGATAACTTACAATTGCCAGAATTAAAACAAAAATCTTCGAACT  490

                   GCCGCAAGAAGCGCAGTACCTGTGCTGGCCCTACGGTTCCAGATCGTGACAATGATGGCATTCCTGATTG
                           500       510       520       530       540       550       560

DVC.Synthetic.rP   GCCGCAAGAAACGCAGCACCTCTGCAGGCCCGACCGTTCCAGATCGCGACAACGATGGCATTCCGGACAG  560
AP.PA.wt.Sequenc   CAAGAAAAAAGCGAAGTACAAGTGCTGGACCTACGGTTCCAGACCGTGACAATGATGGAATCCCTGATTC  560

                   CTTGGAGGTGGAAGGTTATACGGTTGATGTGAAGAATAAACGCACTTTTCTTTGCCCGTGGATTTGTAAT
                           570       580       590       600       610       620       630

DVC.Synthetic.rP   CCTGGAAGTGGAAGGTTATACCGTTGATGTGAAGAACAAACGCACCTTTCTGAGCCCGTGGATTAGCAAC  630
AP.PA.wt.Sequenc   ATTAGAGGTAGAAGGATATACGGTTGATGTCAAAAATAAAAGAACTTTTCTTTCACCATGGATTTCTAAT  630
```

FIG 13(B1)

ATTCATGAGAAGAAAGGCTTGACCAAGTATAAATGCTGTCCTGAGAAGTGGAGCACGGCTTGTGATCCGT
640 650 660 670 680 690 700

DVC.Synthetic.rP ATTCATGAGAAGAAAGGCCTGACCAAGTACAAAAGCAGCCCGGAGAAGTGGAGCACCGCGAGCGATCCGT 700
AP.PA.wt.Sequenc ATTCATGAAAAGAAAGGATTAACCAAATATAAATCATCTCCTGAAAAATGGAGCACGGCTTCTGATCCGT 700

ATAGTGATTTTGAGAAGGTTACCGGCCGGATTGATAAGAATGTGTGCCCGGAGGCGCGTCACCCCCTTGT
710 720 730 740 750 760 770

DVC.Synthetic.rP ATAGCGACTTTGAGAAAGTGACCGGCCGCATTGATAAGAACGTGAGCCCGGAAGCGCGTCACCCACTGGT 770
AP.PA.wt.Sequenc ACAGTGATTTCGAAAAGGTTACAGGACGGATTGATAAGAATGTATCACCAGAGGCAAGACACCCCCTTGT 770

TGCAGCTTATCCGATTGTGCATGTTGATATGGAGAATATTATTCTGTGCAAGAATGAGGATCAGTGCACC
780 790 800 810 820 830 840

DVC.Synthetic.rP TGCAGCGTATCCGATTGTGCATGTTGACATGGAGAACATCATTCTGAGCAAGAACGAAGATCAGAGCACC 840
AP.PA.wt.Sequenc GGCAGCTTATCCGATTGTACATGTAGATATGGAGAATATTATTCTCTCAAAAAATGAGGATCAATCCACA 840

FIG 13(B2)

```
                     CAGAATACTGATAGTCAGACGCGCACGATCAGTAAGAATACTTGTACGAGTCGTACCCATACTAGTGAAG
                              850       860       870       880       890       900       910

DVC.Synthetic.rP     CAGAACACGGATAGCCAGACCCGCACGATCAGCAAGAACACCAGCACGAGCCGTACCCATACCAGCGAAG 910
AP.PA.wt.Sequenc     CAGAATACTGATAGTCAAACGAGAACAATAAGTAAAAATACTTCTACAAGTAGGACACATACTAGTGAAG 910
```

```
                     TGCATGGCAATGCGGAAGTGCATGCGTGGTTCTTTGATATTGGTGGGAGTGTGTGTGCGGGCTTTAGTAA
                              920       930       940       950       960       970       980

DVC.Synthetic.rP     TGCATGGCAATGCGGAAGTGCATGCGAGCTTCTTTGACATTGGTGGCAGCGTGAGCGCGGGCTTCAGCAA 980
AP.PA.wt.Sequenc     TACATGGAAATGCAGAAGTGCATGCGTCGTTCTTTGATATTGGTGGGAGTGTATCTGCAGGATTTAGTAA 980
```

```
                     TTGGAATTGCAGTACGGTGGCGATTGATCATTGCCTGTGTCTGGCGGGGGAACGTACTTGGGCTGAAACC
                              990      1000      1010      1020      1030      1040      1050

DVC.Synthetic.rP     CAGCAACAGCAGCACCGTGGCGATTGATCATAGCCTGAGCCTGGCGGGCGAACGTACCTGGGCGGAAACC 1050
AP.PA.wt.Sequenc     TTCGAATTCAAGTACGGTCGCAATTGATCATTCACTATCTCTAGCAGGGGAAAGAACTTGGGCTGAAACA 1050
```

FIG 13(B3)

ATGGGTTTGAATACGGCTGATACGGCACGTTTGAATGCGAATATTCGCTATGTGAATACTGGTACGGCTC 1060 1070 1080 1090 1100 1110 1120

DVC.Synthetic.rP ATGGGCCTGAACACGGCGGATACGGCACGTCTGAATGCGAACATTCGCTATGTGAACACCGGTACCGCGC 1120
AP.PA.wt.Sequenc ATGGGTTTAAATACCGCTGATACAGCAAGATTAAATGCCAATATTAGATATGTAAATACTGGGACGGCTC 1120

CAATCTATAACGTTTTGCCGACGACTTGGTTGGTGTTGGGCAAGAATCAGACCCTGGCGACCATTAAAGC 1130 1140 1150 1160 1170 1180 1190

DVC.Synthetic.rP CAATCTATAACGTTCTGCCGACCACGAGCCTGGTGCTGGGCAAGAATCAGACCCTGGCGACCATCAAAGC 1190
AP.PA.wt.Sequenc CAATCTACAACGTGTTACCAACGACTTCGTTAGTGTTAGGAAAAAATCAAACACTCGCGACAATTAAAGC 1190

TAAGGAGAACCAGTTGTGTCAGATTCTTGCACCTAATAATTATTATCCTTGTAAGAACTTGGCGCCGATT 1200 1210 1220 1230 1240 1250 1260

DVC.Synthetic.rP GAAAGAGAACCAGCTGTCTCAGATTCTGGCACCGAACAACTACTATCCGAGCAAGAACCTGGCACCGATT 1260
AP.PA.wt.Sequenc TAAGGAAAACCAATTAAGTCAAATACTTGCACCTAATAATTATTATCCTTCTAAAAACTTGGCGCCAATC 1260

FIG. 13(C1)

```
                   GCATTGAATGCGCAGGATGATTTCAGTTGTACTCCGATTACCATGAATTACAATCAGTTTCTTGAGTTGG
                              1270      1280      1290      1300      1310      1320      1330

DVC.Synthetic.rP   GCACTGAATGCGCAGGATGACTTCAGCAGCACCCCGATCACCATGAACTACAATCAGTTTCTGGAGCTGG 1330
AP.PA.wt.Sequenc   GCATTAAATGCACAAGACGATTTCAGTTCTACTCCAATTACAATGAATTACAATCAATTTCTTGAGTTAG 1330

                   AGAAGACGAAACAATTGCGCTTGGATACGGATCAGGTGTATGGGAATATTGCGACCTACAATTTTGAGAA
                              1340      1350      1360      1370      1380      1390      1400

DVC.Synthetic.rP   AGAAGACCAAACAACTGCGCCTGGATACCGATCAGGTGTATGGCAACATTGCGACCTACAACTTTGAGAA 1400
AP.PA.wt.Sequenc   AAAAAACGAAACAATTAAGATTAGATACGGATCAAGTATATGGGAATATAGCAACATACAATTTTGAAAA 1400

                   TGGCCGCGTTCGGGTGGATACCGGTTGGAACTGGTGTGAAGTGTTGCCGCAGATTCAGGAAACGACTGCG
                              1410      1420      1430      1440      1450      1460      1470

DVC.Synthetic.rP   CGGCCGCGTTCGCGTGGATACCGGTAGCAACTGGTCTGAAGTGCTGCCGCAGATTCAGGAAACGACCGCG 1470
AP.PA.wt.Sequenc   TGGAAGAGTGAGGGTGGATACAGGCTCGAACTGGAGTGAAGTGTTACCGCAAATTCAAGAAACAACTGCA 1470
```

FIG. 13(C2)

```
                     CGTATCATTTTTAATGGCAAAGATTTGAATCTGGTGGAACGTCGGATCGCGGCGGTTAATCCTTGTGATC
                           1480      1490      1500      1510      1520      1530      1540
DVC.Synthetic.rP     CGCATCATCTTCAACGGCAAAGATCTGAACCTGGTGGAACGTCGCATCGCGGCAGTGAACCCATCTGATC 1540
AP.PA.wt.Sequenc     CGTATCATTTTTAATGGAAAAGATTTAAATCTGGTAGAAAGGCGGATAGCGGCGGTTAATCCTAGTGATC 1540

                     CATTGGAAACGACTAAACCGGATATGACCTTGAAAGAAGCGCTTAAGATTGCATTTGGCTTTAACGAACC
                           1550      1560      1570      1580      1590      1600      1610
DVC.Synthetic.rP     CACTGGAAACGACCAAACCGGACATGACCCTGAAAGAAGCGCTGAAGATTGCATTTGGCTTCAACGAACC 1610
AP.PA.wt.Sequenc     CATTAGAAACGACTAAACCGGATATGACATTAAAAGAAGCCCTTAAAATAGCATTTGGATTTAACGAACC 1610

                     GAATGGCAACTTGCAGTATCAGGGGAAAGACATCACCGAGTTTGATTTTAATTTTGATCAACAGACCTCT
                           1620      1630      1640      1650      1660      1670      1680
DVC.Synthetic.rP     GAATGGCAACCTGCAGTATCAGGGCAAAGACATCACCGAGTTTGACTTCAACTTTGATCAACAGACCTCT 1680
AP.PA.wt.Sequenc     GAATGGAAACTTACAATATCAAGGGAAAGACATAACCGAATTTGATTTTAATTTCGATCAACAAACATCT 1680
```

FIG. 13(C3)

```
                    CAGAATATCAAGAATCAGTTGGCGGAATTGAATGCGACTAACATCTATACTGTGTTGGATAAGATCAAAT
                           1690      1700      1710      1720      1730      1740      1750

DVC.Synthetic.rP    CAGAACATCAAGAACCAGCTGGCAGAACTGAATGCGACCAACATCTACACCGTGCTGGACAAGATCAAAC 1750
AP.PA.wt.Sequenc    CAAAATATCAAGAATCAGTTAGCGGAATTAAACGCAACTAACATATATACTGTATTAGATAAAATCAAAT 1750

                    TGAATGCAAAGATGAATATTTTGATTCGTGATAAACGTTTTCATTATGATCGTAATAACATTGCGGTTGG
                           1760      1770      1780      1790      1800      1810      1820

DVC.Synthetic.rP    TGAACGCAAAGATGAACATTCTGATTCGTGACAAACGCTTCCACTATGATCGTAACAACATTGCGGTGGG 1820
AP.PA.wt.Sequenc    TAAATGCAAAAATGAATATTTTAATAAGAGATAAACGTTTTCATTATGATAGAAATAACATAGCAGTTGG 1820

                    TGCGGATGAGTGCGTTGTTAAGGAGGCTCATCGTGAAGTGATTAATTCTTGCACCGAGGGCTTGTTGTTG
                           1830      1840      1850      1860      1870      1880      1890

DVC.Synthetic.rP    TGCAGATGAAAGCGTTGTGAAAGAAGCGCATCGTGAAGTGATCAACTCTAGCACCGAAGGCCTGCTGCTG 1890
AP.PA.wt.Sequenc    GGCGGATGAGTCAGTAGTTAAGGAGGCTCATAGAGAAGTAATTAATTCGTCAACAGAGGGATTATTGTTA 1890
```

FIG. 13(D2)

GCTGTTACTAAAGAGAACACTATTATTAATCCTAGTGAGAATGGGGATACTAGTACCAACGGGATCAAGA 2110 2120 2130 2140 2150 2160 2170

DVC.Synthetic.rP GCGGTGACCAAAGAGAACACCATCATTAACCCAAGCGAGAATGGCGATACCAGCACCAACGGCATCAAGA 2170

AP.PA.wt.Sequenc GCTGTTACTAAAGAAAACACTATTATTAATCCTAGTGAGAATGGGGATACTAGTACCAACGGGATCAAGA 2170

AGATTTTGATCTTTTGTAAGAAAGGCTATGAGATTGGCTAA 2180 2190 2200 2210

DVC.Synthetic.rP AGATTCTGATCTTCAGCAAGAAAGGCTATGAGATTGGCTAA 2211

AP.PA.wt.Sequenc AAATTTTAATCTTTTCTAAAAAAGGCTATGAGATAGGATAA 2211

PREPARATION OF PROTECTIVE ANTIGEN

CROSS REFERENCE TO RELATED APPLICATIONS

This application is a continuation-in-part application of U.S. application Ser. No. 11/153,865, filed Jun. 15, 2005, entitled "*Bacillus Anthracis* Protective Antigen," (now U.S. Pat. No. 7,355,027), which claims the benefit of U.S. Provisional Application 60/579,687, filed Jun. 16, 2004, entitled "Preparation of Protective Antigen".

SEQUENCE LISTING

The instant application contains a Sequence Listing which has been submitted in ASCII format via EFS-Web and is hereby incorporated by reference in its entirety. Said ASCII copy, created on Apr. 28, 2011, is named MSQ01010.txt and is 307,748 bytes in size.

The present invention relates to polynucleotides and vectors encoding recombinant *Bacillus anthracis* protective antigen (rPA), methods of producing rPA, and uses thereof in antigenic compositions, such as vaccines.

*Bacillus anthracis* is a Gram positive, spore-forming bacterium and the causative agent of anthrax. Anthrax is a disease of domestic and land animals, and can affect humans through contact with infected animal products. In the lungs, anthrax can cause massive fluid build-up, tissue decay, toxic shock and death.

Anthrax vaccine has been manufactured by the present Applicant for over 40 years and, since 1979, has been the subject of a UK Product Licence (PL1511/0037) held by the Secretary of State for Health. However, within that time there has been little product development or advance in its manufacturing process.

The above vaccine preparation is now described in more detail. Cultures of the toxigenic, non-capsulating *B. anthracis* 34F2 "Sterne" strain [see Sterne, M. (1939). Onderstepoort J. of Veterinary Science and Animal Industry, 13, pp 307-312] are grown in multiple 500 mL volumes in a partially defined medium in Thompson bottles at 37° C. until the pH of selected culture bottles falls below pH 7.4.

At the end of the growth period (approximately 24-28 hours) the cultures are harvested by aspiration, and the pooled supernatant fluids sterilised by filtration. Potassium aluminium sulphate solution is added, and the resulting solution mixed. The pH is then adjusted to 5.8-6.2, and the resulting flocculant ('alum-precipitation') allowed to settle under gravity for up to one week at 5° C.

The precipitate is then concentrated 20-fold (by volume) by aspiration, and diluted 1:4 with a saline solution to provide a '5-fold' concentrate of anthrax vaccine precipitate (AVP). This is the antigenic composition that is used for vaccine formulation. Although the vaccine is subjected to animal tests for potency and safety prior to human use, there is no separate routine biochemical characterisation.

One further cell-free anthrax vaccine is available for human use. This vaccine is produced in the United States of America and is broadly similar to that available under PL1511/0037, except that a different *B. anthracis* strain is used and grown anaerobically. The process is fermenter-based, and the culture filtrate is absorbed on to an aluminium hydroxide suspension.

Other available vaccines comprise live, attenuated spore suspensions. However, because of the inherent risks associated with attenuated pathogens, these vaccines are usually restricted to non-human use.

Anthrax toxin consists of three distinct polypeptides known as protective antigen (PA), oedema factor (EF), and lethal factor (LF). The toxin components act in specific binary combinations of PA and EF to form oedema toxin (ET), which causes tissue oedema, and of PA and LF to form lethal toxin (LT), which is lethal to laboratory animals and causes lysis of monocyte and macrophage cells. Lethal toxin is considered to be the principal cause of anthrax-associated death as a consequence of its cytotoxic effects on peripheral macrophages and other cells.

PA acts as a target cell-binding moiety and, after a site-specific N-terminal activation by a cell-associated protease (furin), oligomerises and provides a high-affinity binding component for which EF and LF compete. Following binding of EF or LF to activated PA, the resulting ET or LT complexes become internalised by an acidic endosome compartment, and the toxin factors EF and LF are thereby delivered into the cytosol of the target cell.

EF is a calcium- and calmodulin-dependent adenylyl cyclase that catalyses the conversion of intracellular ATP to cAMP. EF is active in a variety of intracellular signalling pathways, and is thereby capable of disrupting a range of cellular processes.

LF is a $Zn^{2+}$-dependent metalloprotease that cleaves and inactivates the dual specificity, mitogen-activated protein kinase kinases MAPKK/1 and 2, MEK-1 and MEK-2, and probably other proteins.

A survey of in vitro or in vivo published data on anthrax vaccines for human use indicates the following:—

1. to date, all effective anthrax vaccines contain or produce PA (i.e. either the 83 kDa pro-form, or its activated 63 kDa derivative). In fact, the current dogma is that PA is necessary and sufficient alone to produce an effective anthrax vaccine, and efforts are underway to develop such a vaccine [see, for example, Baillie, L. (2001), 91, pp 609-613];
2. the non-capsulated, toxigenic live-spore vaccines effect a higher degree of protection against all *B. anthracis* strains so far tested than do the licensed cell-free vaccines [see Little, S. F. (1986) Inf. and Immunol. vol. 52, No. 2, pp 509-512];
3. the current cell-free vaccines are generally poorly defined and may vary significantly in effectiveness on a batch-by-batch basis. Accordingly, each batch must be individually tested for efficacy in an animal model prior to human use;
4. the current cell-free anthrax vaccine manufacturing process is evaluated only on completion of the production process and packaging of the final product. Thus, in the event that any one batch of vaccine material should not meet the validation test criteria, the contributing factors cannot be identified readily. Such factors may differ between manufactured batches and the lack of understanding exacerbates any difficulties encountered in the manufacturing process;
5. as a result of the poorly defined nature of current cell-free vaccines, these vaccines may contain quantities of PA together with LF and/or EF which, upon in vivo (or in vitro) activation of PA to the 63 kDa form, may form LT and ET and exert adverse effects on the recipient of the vaccine. Such vaccines may, of course, also contain other *B. anthracis* proteins, both secreted and lysis products, peptidoglycan, nucleic acid and carbohydrate, which may compromise protective efficacy;
6. the current cell-free vaccine compositions are highly variable in terms of LF, PA, and EF concentrations, so much so that EF may be absent from some preparations; and
7. the current cell-free compositions are highly variable in terms of total protein content. Thus, the concentration of toxin components present in a given composition may vary significantly. This, in turn, may affect efficacy and potential toxicity in humans.

Over the last few years there has been notable academic research in the anthrax field. Sharma et al. (1996) describe the expression of native PA from *E. coli*. The signal sequence of the outer membrane protein A (OmpA) was added to the 5'-end of the PA gene and allowed the purification of the protein from the *E. Coli* periplasmic space. Further research has allowed identification of the native binding sites and translocation domain of PA [see Bhatnagas, R. (2001) Critical Rev. in Microbiol., 27(3), pp 167-200; and Batra, S. (2001) Biochem. and Biophys. Res. Comm., 281, pp 186-192]. Thus, the structure and binding/translocation domains of PA have been well documented.

Recently, a second-generation "recombinant" anthrax vaccine has been proposed by The Ohio State University Research Foundation [see WO 01/45639; and Price, B. M. (2001) Inf. and Immun., vol. 69, No. 7, pp 4509-4515]. The described vaccine is based on PA and LF, wherein the LF molecule has been modified so as to be zinc metalloprotease negative. Thus, the described PA and LF components are fully capable of binding to one another to form an LT molecule, but the resulting LT molecule is not cytotoxic as there is no active zinc metalloprotease function present with the LF component.

Ahuja Nidhi et al., Biochem. and Biophys. Research Communications, Vol. 287, No. 2, 21 Sep. 2001, pp 542-549, describes PA mutants having impaired oligomerization and their potential as vaccine candidates.

Batra Smriti et al., Biochem. and Biophys. Research Communications, Vol. 281, No. 1, 16 Feb. 2001, pp 186-192 describes PA mutants having mutant residues that may have a role in membrane insertion of PA and/or translocation of LF/EF into the cytosol.

WO 02/04646 describes PA polypeptide domains capable of producing an immune response. The PA polypeptide is produced in *E. coli* and accumulates in the form of inclusion bodies.

DNA-based anthrax vaccine compositions are described in WO 2004/024067. The vaccine compositions contain anthrax nucleic acids that have been modified to optimise expression in a eukaryotic host—e.g. the patient to whom the vaccine composition is administered.

In view of the increasing threats of bio-terrorism and biological warfare, there is a need for alternative anthrax vaccines, and for vaccines that address one or more of the above-identified problems.

Thus, according to a first aspect of the present invention, there is provided a polynucleotide sequence comprising a nucleic acid sequence having at least 75% identity to SEQ ID NO: 1, wherein said nucleic acid sequence encodes recombinant *Bacillus anthracis* Protective Antigen (rPA); or a fragment of said nucleic acid sequence wherein said fragment encodes a fragment of recombinant *Bacillus anthracis* Protective Antigen (rPA).

In this regard, SEQ ID NO: 1 represents a modified nucleic acid that encodes rPA. The sequence of SEQ ID NO: 1 is approximately 70% identical to the wild-type *Bacillus anthracis* nucleic acid sequence encoding PA, provided herein as SEQ ID NO: 2.

The present inventors have found that by modifying the wild-type PA nucleic acid sequence (SEQ ID NO: 2), expression levels of rPA protein may be significantly improved. Thus, the present invention relates to non-natural nucleic acid sequences which encode for the rPA polypeptide. Particularly, the non-natural nucleic acid sequences are selected to increase expression levels of rPA expressed in heterologous systems, such as heterologous bacterial systems, e.g. *E. coli*. Preferably, the rPA polypeptide or fragment thereof, which is expressed from the modified, non-natural nucleic acid sequence (or fragment thereof) of the invention, is expressed at a level that is at least 110%, at least 120%, at least 150%, at least 200%, at least 250%, at least 300%, at least 400%, or at least 500% higher than that expressed from the wild-type nucleic acid sequence under equivalent conditions.

The polynucleotide of the invention comprises a nucleic acid sequence (or fragment thereof) that encodes rPA (or a fragment thereof). This rPA encoding nucleic acid sequence (or fragment thereof is referred to herein as the rPA nucleic acid (or fragment thereof). Thus, the polynucleotide of the present invention may comprise the rPA nucleic acid, plus other coding and/or non-coding sequences. By way of example, non-coding sequences that may be comprised in the polynucleotide of the present invention include promoter sequences and transcription/translation initiation and termination sequences.

In this regard, the rPA nucleic acid sequence of the present invention may embrace a number of modifications, which result in the same translated amino acid sequence of the encoded polypeptide. Numerous factors should be taken into account when modifying a nucleic acid sequence, for example, the degree of degeneracy available, codon usage, and predicted RNA secondary structure considerations. For example, many amino acids are designated by more than one codon, due to the "degeneracy" of the genetic code. In more detail, alanine is coded for by 4 different triplets, and serine is coded for by 6 different triplets. This degeneracy allows for DNA base composition to vary over a wide range without altering the amino acid sequence of the protein encoded by the DNA.

The wild-type polypeptide sequence of *Bacillus anthracis* UM44 PA is provided in SEQ ID NO: 5 (see also, Vodkin, M., et al., Cell, 34:693 (1983); and Welkos, S., et al., Gene, 69(2): 287 (1988)).

For sequence comparison, typically one sequence acts as a reference sequence, to which test sequences may be then compared. When using a sequence comparison algorithm, test and reference sequences are input into a computer, subsequent coordinates are designated, if necessary, and sequence algorithm program parameters are designated. The sequence comparison algorithm then calculates the percentage sequence identity for the test sequence(s) relative to the reference sequence, based on the designated program parameters.

Optimal alignment of sequences for comparison may be conducted, for example, by the local homology alignment algorithm of Smith and Waterman [Adv. Appl. Math. 2: 484 (1981)], by the algorithm of Needleman & Wunsch [J. Mol. Biol. 48: 443 (1970)] by the search for similarity method of Pearson & Lipman [Proc. Nat. Acad. Sci. USA 85: 2444 (1988)], by computer implementations of these algorithms (GAP, BESTFIT, FASTA, and TFASTA—Sequence Analysis Software Package of the Genetics Computer Group, University of Wisconsin Biotechnology Center, 1710 University Avenue, Madison, Wis. 53705), or by visual inspection [see Current Protocols in Molecular Biology, F. M. Ausubel et al., eds, Current Protocols, a joint venture between Greene Publishing Associates, In. and John Wiley & Sons, Inc. (1995 Supplement) Ausubel].

Examples of algorithms suitable for determining percent sequence similarity are the BLAST and BLAST 2.0 algorithms [see Altschul (1990) J. Mol. Biol. 215: pp. 403-410; and www.ncbi.nlm.nih.gov of the National Center for Biotechnology Information].

In one embodiment of a polypeptide homology comparison, the identity exists over a region of the sequences that is at least 10 amino acids, preferably at least 20 amino acids, more preferably at least 35 amino acids in length. In a preferred polypeptide homology comparison, the identity exists over a region of the sequences that is at least 100 amino acids, preferably at least 200 amino acids, more preferably at least 350 amino acids in length.

The terms "peptide" or "polypeptide" throughout this specification are synonymous with the term "protein", and do not refer to a specific length of the product. These terms may embrace post-translational modifications such as glycosylation, acetylation, and phosphorylation.

Reference throughout the present application to rPA polypeptides, polynucleotides and nucleic acids embraces fragments, variants and derivatives thereof. In particular, reference throughout the present application to rPA polypeptides embraces fragments, variants and derivatives thereof that have a common antigenic cross-reactivity with wild-type *Bacillus anthracis* PA (SEQ ID NO: 5). Similarly, reference throughout the present application to rPA polynucleotides and nucleic acids embraces fragments, variants and derivatives thereof that encode peptides having a common antigenic cross-reactivity with wild-type *Bacillus anthracis* PA (SEQ ID No. 5).

In one embodiment, the above-mentioned fragments, variants and derivatives may have a common antigenic cross-reactivity with one or more of the four domains of the mature 735 amino acid monomer (see SEQ ID NO: 5) described below:

DOMAIN 1: amino acids 1-258. This domain binds two $Ca^{2+}$ ions and is the cleavage site for proteases to activate the PA protein. The product of this cleavage is the amino terminal fragment a20 (20K fragment). A furin cleavage site is located at amino acids 164-167.

DOMAIN 2: amino acids 259-487. This domain is involved in the formation of hexamer and has flexible loop which aids membrane insertion.

DOMAIN 3: amino acids 488-595. This domain currently has no known function.

DOMAIN 4: amino acids 596-735. This domain is involved in receptor binding.

In preferred embodiments, polypeptide "fragments" of the invention comprise at least one of the four domains identified above. More preferably, they comprise at least two, at least three, or all four of these domains in any combination. In a particular embodiment, they comprise at least domains 2 & 3 identified above.

Each of the four domains identified above is considered to comprise important epitope(s) of wild-type *Bacillus anthracis* PA. In addition, PA epitopes have been identified as shown in the two tables below (the "B Cell" table and the "T Cell" table).

In a preferred embodiment of the invention, polynucleotides are provided that encode one or more epitopes or partial epitopes of PA. By way of example, SEQ ID NOs: 36-105 encode all or part of the first, and the third to the sixth, epitopes listed in the "B Cell" table, and all three of the epitopes listed in the "T Cell" table. SEQ ID NOs: 66-105 further encode the second epitope listed in the "B-Cell" table.

| B-Cell Epitopes from Human and Non Human Primates (NHPs) | | Epitope Position | |
|---|---|---|---|
| Immunized Species | Epitope Sequence | in rPA protein | Reference |
| *H. sapiens* | IKLNAKMNILIRDKRFHYDRN (SEQ ID NO: 107) | 581-601 | Les Baillie et al., "Characterisation of the human immune response to the UK anthrax vaccine", FEMS Immunol. Med. Microbiol. 2004 |
| *M.. fascicularis* | PLYISNPNY (SEQ ID NO: 108) | 686-694 | Laffly et al., "Selection of a macaque Fab with framework regions like those in humans, high affinity, and ability to neutralize the protective antigen of Bacillus anthracis by binding to the segment of PA between residues 686 and 694", Antimicrob. Agents Chemother. 2005 |
| *M. mulatta* | — | 488-735 | E D Williamson, et al. Infect. Immun. 2005 |
| *M. mulatta* | — | 596-735 | " |
| *M. mulatta* | — | 1-258 | " |
| *P. troglodytes* | — | 614-735 | Chen et al., Efficient neutralization of anthrax toxin by chimpanzee monoclonal antibodies against protective antigen, J. Infect. Dis.2006 |

| T-Cell Epitopes from Human and Non Human Primates (NHPs) | | Epitope | |
|---|---|---|---|
| Immunized Species | Epitope Sequence | Position in rPA protein | Reference |
| *H. sapiens* | PIYNVLPTTSLVLGKNQTLAT (SEQ ID NO: 109) | 373-393 | Laughlin et al., Antigen-specific CD4+ T cells recognize epitopes of protective antigen following vaccination, Infect. Immun. 2007 |

-continued

| T-Cell Epitopes from Human and Non Human Primates (NHPs) | | Epitope | |
|---|---|---|---|
| Immunized Species | Epitope Sequence | Position in rPA protein | Reference |
| *H. sapiens* | SLVLGKNQTLAT (SEQ ID NO: 110) | 381-392 | Laughlin et al., Antigen-specific CD4+ T cells recognize epitopes of protective antigen following vaccination, Infect. Immun. 2007 |
| *H. sapiens* | RLYQIKIQYQRENPTE (SEQ ID NO: 111) | 112-127 | Laughlin et al., Antigen-specific CD4+ T cells recognize epitopes of protective antigen following vaccination, Infect. Immun. 2007 |

The term "fragment" of a polypeptide means a peptide consisting of at least 5, preferably at least 10, more preferably at least 20, and most preferably at least 35 amino acid residues of the full-length polypeptide that is the product of the polynucleotide in question. The fragment preferably includes at least one epitope of the corresponding full-length polypeptide. The fragment may result from enzymatic break-down of the corresponding full-length polypeptide. Alternatively, a fragment of the corresponding full-length polypeptide may be produced by expressing a polynucleotide that is fragment of the corresponding full-length polynucleotide.

In preferred embodiments, the polypeptide "fragment" has an amino acid length which is at least 10%, preferably at least 20%, preferably at least 30%, preferably at least 40%, preferably at least 50%, preferably at least 70%, and more preferably at least 80%, or at least 90%, that of the length of the amino acid sequence of the corresponding full-length polypeptide. For example, the polypeptide fragment may comprise at least 100, preferably at least 150, preferably at least 200, preferably at least 300, most preferably at least 400, or at least 500, or at least 600, or at least 700, amino acid residues, of the wild-type PA polypeptide sequence (SEQ ID NO: 5).

The present invention embraces "variants". An example of a "variant" is a peptide or peptide fragment that contains one or more analogs of an amino acid (e.g. an unnatural amino acid), or a substituted linkage. In a further embodiment, a "variant" may be a mimic of the peptide or peptide fragment, which mimic reproduces at least one epitope of the peptide or peptide fragment. The mimic may be, for example, a nucleic acid mimic, preferably a DNA mimic.

The present invention also embraces "derivatives", meaning a protein comprising the peptide (or fragment, or variant thereof) in question. Thus, a derivative may include the peptide in question, and a further peptide sequence that may introduce one or more additional epitopes. The further sequence should preferably not interfere with the basic folding and thus conformational structure of the peptide in question.

Examples of a "derivative" are a fusion protein, a conjugate, and a graft. Thus, two or more peptides (or fragments, or variants) may be joined together to form a derivative. Alternatively, a peptide (or fragment, or variant) may be joined to an unrelated molecule (e.g. a second, unrelated peptide). Derivatives may be chemically synthesized, but will be typically prepared by recombinant nucleic acid methods. Additional components such as lipid, and/or polysaccharide, and/or polyketide components may be included in a derivative.

All of the molecules "fragment", "variant" and "derivative" have a common antigenic cross-reactivity and/or substantially the same in vitro or in vivo biological activity as the product of the polynucleotide in question from which they are derived. By way of example, an antibody capable of binding to a fragment, variant or derivative would be also capable of binding to the product of the polynucleotide in question.

It is a preferred feature that the fragment, variant and derivative each possess the active site of the peptide in question. Alternatively, all of the above embodiments of a peptide of the present invention share a common ability to induce a "recall response" of a T-lymphocyte which has been previously exposed to an antigenic component of a *Bacillus anthracis* infection.

An rPA peptide fragment, variant or derivative preferably has one or more of the following properties—a) able to bind to the PA receptor on a cell membrane; b) able to bind to EF and/or LF; and c) able to be cleaved by furin protease. Thus, in one embodiment, a fragment, variant or derivative of a peptide of the present invention may be identified by carrying out simple tests for the above-mentioned properties, as described in WO 03/037370 which is incorporated by reference herein.

The terms DNA "fragment", polynucleotide "fragment" and nucleic acid "fragment" used in this application refer to a polynucleotide that will usually comprise at least about 5 codons (15 nucleotides), more usually at least about 7 to 15 codons, and most preferably at least about 35 codons. This number of nucleotides is usually about the minimal length required for a successful probe that would hybridize specifically (e.g. under selective hybridization conditions) with such a sequence.

Preferably, the DNA "fragment" of the invention comprises nucleotides encoding at least one of the four PA protein domains identified above. More preferably, the DNA "fragment" comprises nucleotides encoding at least two, at least three, or all four of the domains identified above in any combination. The corresponding DNA base numbering for the four PA protein domains is as follows:

DOMAIN 1: bp 1-774 (774 bp)
DOMAIN 2: bp 775-1461 (687 bp)
DOMAIN 3: bp 1462-1785 (324 bp)
DOMAIN 4: bp 1786-2205 (420 bp)

In a particular embodiment, the DNA "fragment" comprises DNA encoding protein at least domains 2 & 3 as identified above. Examples of such fragments are given in SEQ ID Nos: 36-105, which relate to truncated versions of SEQ ID NO: 1. These truncated sequences encode domains 2 & 3 in their entirety and substantial portions of both domains 1 & 4.

In preferred embodiments, the DNA "fragment" has a nucleotide length which is at least 10%, preferably at least 20%, preferably at least 30%, preferably at least 40%, preferably at least 50%, preferably at least 70%, and more preferably at least 80% or at least 90% that of the coding sequence of the corresponding gene. For example, the fragment may comprise at least 200, 300, 400, 500 or 600, preferably at least 900, most preferably at least 1200, or at least 1500, or at least 1700, or at least 1900, or at least 2100 nucleotides of the full-length rPA nucleic acid sequence of the present invention. In particular embodiments, the DNA fragments have at least 1755, or at least 1806, or at least 1854, or at least 1857, or at least 1905, or at least 1953, or at least 2055 nucleotides of the full-length rPA sequence of the present invention.

The present invention embraces DNA "variants". A DNA variant is a DNA sequence that has substantial homology or substantial similarity to a reference sequence, such as the coding sequence (or a fragment thereof of the corresponding wild-type (natural) gene. A nucleic acid or fragment thereof is "substantially homologous" (or "substantially similar") to another if, when optimally aligned (with appropriate nucleotide insertions or deletions) with the other nucleic acid (or its complementary strand), there is nucleotide sequence identity in at least about 60% of the nucleotide bases, usually at least about 70%, more usually at least about 80%, preferably at least about 90%, and more preferably at least about 95 to 99% of the nucleotide bases. Homology determination is performed as described supra for peptides.

Alternatively, a DNA "variant" is substantially homologous (or substantially similar) with the coding sequence (or a fragment thereof of a wild-type (natural) gene when it is capable of hybridizing under selective hybridization conditions. Nucleic acid hybridization will be affected by such conditions as salt concentration (e.g. NaCl), temperature, or organic solvents, in addition to the base composition, length of the complementary strands, and the number of nucleotide base mismatches between the hybridizing nucleic acids, as will be readily appreciated by those skilled in the art. Stringent temperature conditions are preferably employed, and generally include temperatures in excess of 30° C., typically in excess of 37° C. and preferably in excess of 45° C. Stringent salt conditions will ordinarily be less than 1000 mM, typically less than 500 mM, and preferably less than 200 mM. The pH is typically between 7.0 and 8.3. However, the combination of parameters is much more important than the measure of any single parameter. See, for example, Wetmur and Davidson (1968) J. Mol. Biol. 31:349-370.

Selectivity of hybridization exists when hybridization occurs which is substantially more selective than total lack of specificity. Typically, selective hybridization will occur when there is at least about 65% homology over a stretch of at least about 14 nucleotides, preferably at least about 70%, more preferably at least about 75%, and most preferably at least about 90% (see, Kanehisa (1984) Nuc. Acids Res. 12: 203-213). The length of homology comparison, as described, may be over longer stretches, and in certain embodiments will often be over a stretch of at least about 17 nucleotides, usually at least about 20 nucleotides, more usually at least about 24 nucleotides, typically at least about 28 nucleotides, more typically at least about 32 nucleotides, and preferably at least about 36 or more nucleotides. In a preferred embodiment, the length of homology comparison is over a stretch of at least about 170 nucleotides, usually at least about 200 nucleotides, more usually at least about 240 nucleotides, typically at least about 280 nucleotides, more typically at least about 320 nucleotides, and preferably at least about 360 or more nucleotides.

The present invention embraces DNA "derivatives", meaning a DNA polynucleotide which comprises a DNA sequence (or a fragment, or variant thereof corresponding to the coding sequence of the reference gene, e.g. the wild-type *Bacillus anthracis* PA gene, and an additional DNA sequence which is not naturally associated with the DNA sequence corresponding to the coding sequence. The comments on peptide derivatives supra also apply to DNA "derivatives". A "derivative" may, for example, include two or more coding sequences of an operon. Thus, depending on the presence or absence of a non-coding region between the coding sequences, the expression product(s) of such a "derivative" may be a fusion protein, or separate peptide products encoded by the individual coding regions.

The above terms DNA "fragment", "variant", and "derivative" have in common with each other that the resulting peptide products have cross-reactive antigenic properties, which are substantially the same as those of the corresponding wild-type peptide. Preferably all of the peptide products of the above DNA molecule embodiments of the present invention bind to an antibody which also binds to the wild-type peptide. Alternatively, all of the above peptide products are capable of inducing a "recall response" of a T lymphocyte, which has been previously exposed to an antigenic component of a *Bacillus anthracis* infection.

Thus, a DNA fragment, variant or derivative may be identified by way of its encoded peptide product—for example, by carrying out the simple tests mentioned above (and described in WO 03/037370).

Polynucleotides of the present invention comprise a nucleic acid having at least 75%, preferably at least 80%, more preferably at least 85%, more preferably at least 90%, even more preferably at least 91%, 92%, 93%, 94%, 95%, 96%, 97%, 98% and most preferably 99% or 100% identity to SEQ ID NO: 1; or a fragment of said nucleic acid.

Specific polynucleotides having between 91 and 99% identity to SEQ ID NO: 1 (minus the terminal "TAA" stop codon) are provided in SEQ ID NOs: 9 to 35 as shown in the table below.

| SEQ ID NO | % Identity to SEQ ID No. 1 | No. of bases differing from SEQ ID No. 1 |
|---|---|---|
| SEQ ID No. 9 | 99.00 | 22 |
| SEQ ID No. 10 | 99.00 | 22 |
| SEQ ID No. 11 | 99.00 | 22 |
| SEQ ID No. 12 | 98.00 | 44 |
| SEQ ID No. 13 | 98.00 | 44 |
| SEQ ID No. 14 | 98.00 | 44 |
| SEQ ID No. 15 | 97.01 | 66 |
| SEQ ID No. 16 | 98.00 | 66 |
| SEQ ID No. 17 | 98.00 | 66 |
| SEQ ID No. 18 | 96.01 | 88 |
| SEQ ID No. 19 | 96.01 | 88 |
| SEQ ID No. 20 | 96.01 | 88 |
| SEQ ID No. 21 | 95.01 | 110 |
| SEQ ID No. 22 | 95.01 | 110 |
| SEQ ID No. 23 | 95.01 | 110 |
| SEQ ID No. 24 | 94.01 | 132 |
| SEQ ID No. 25 | 94.01 | 132 |
| SEQ ID No. 26 | 94.01 | 132 |
| SEQ ID No. 27 | 93.02 | 154 |
| SEQ ID No. 28 | 93.02 | 154 |
| SEQ ID No. 29 | 93.02 | 154 |
| SEQ ID No. 30 | 92.02 | 176 |
| SEQ ID No. 31 | 92.02 | 176 |
| SEQ ID No. 32 | 92.02 | 176 |
| SEQ ID No. 33 | 91.02 | 198 |
| SEQ ID No. 34 | 91.02 | 198 |
| SEQ ID No. 35 | 91.02 | 198 |

In one embodiment, polynucleotides of the invention comprise a nucleic acid having at least 75%, preferably at least 80%, more preferably at least 85%, more preferably at least 90%, even more preferably at least 91%, 92%, 93%, 94%, 95%, 96%, 97%, 98% and most preferably 99% or 100% identity to SEQ ID NO: 36. SEQ ID NO: 36 is a truncated version of SEQ ID NO: 1 and comprises base pairs 301-2055 of SEQ ID NO: 1. Specific polynucleotides having between 91 and 99% identity to SEQ ID NO: 36 are provided in SEQ ID NOs: 37 to 45 as shown in the table below.

| SEQ ID NO | % Identity to SEQ ID No. 36 | No. of bases differing from SEQ ID No. 36 |
|---|---|---|
| SEQ ID No. 37 | 98.97 | 18 |
| SEQ ID No. 38 | 98.06 | 34 |
| SEQ ID No. 39 | 97.04 | 52 |
| SEQ ID No. 40 | 95.90 | 72 |
| SEQ ID No. 41 | 94.99 | 88 |
| SEQ ID No. 42 | 93.96 | 106 |
| SEQ ID No. 43 | 93.16 | 120 |
| SEQ ID No. 44 | 92.02 | 140 |
| SEQ ID No. 45 | 91.00 | 158 |

In another embodiment, polynucleotides of the invention comprise a nucleic acid having at least 75%, preferably at least 80%, more preferably at least 85%, more preferably at least 90%, even more preferably at least 91%, 92%, 93%, 94%, 95%, 96%, 97%, 98% and most preferably 99% or 100% identity to SEQ ID NO: 46. SEQ ID NO: 46 is a truncated version of SEQ ID NO: 1 and comprises base pairs 202-2055 of SEQ ID NO: 1. Specific polynucleotides having between 91 and 99% identity to SEQ ID NO: 46 are provided in SEQ ID NOs: 47-55 as shown in the table below.

| SEQ ID NO | % Identity to SEQ ID No. 46 | No. of bases differing from SEQ ID No. 46 |
|---|---|---|
| SEQ ID No. 47 | 99.03 | 18 |
| SEQ ID No. 48 | 97.95 | 38 |
| SEQ ID No. 49 | 97.09 | 54 |
| SEQ ID No. 50 | 96.12 | 72 |
| SEQ ID No. 51 | 95.04 | 92 |
| SEQ ID No. 52 | 93.96 | 112 |
| SEQ ID No. 53 | 92.99 | 130 |
| SEQ ID No. 54 | 92.13 | 146 |
| SEQ ID No. 55 | 91.05 | 166 |

In another embodiment, polynucleotides of the invention comprise a nucleic acid having at least 75%, preferably at least 80%, more preferably at least 85%, more preferably at least 90%, even more preferably at least 91%, 92%, 93%, 94%, 95%, 96%, 97%, 98% and most preferably 99% or 100% identity to SEQ ID NO: 56. SEQ ID NO: 56 is a truncated version of SEQ ID NO: 1 and comprises base pairs 103-2055 of SEQ ID NO: 1. Specific polynucleotides having between 91 and 99% identity to SEQ ID NO: 56 are provided in SEQ ID NOs: 57-65 as shown in the table below.

| SEQ ID NO | % Identity to SEQ ID No. 56 | No. of bases differing from SEQ ID No. 56 |
|---|---|---|
| SEQ ID No. 57 | 99.08 | 18 |
| SEQ ID No. 58 | 97.95 | 40 |
| SEQ ID No. 59 | 97.03 | 58 |
| SEQ ID No. 60 | 96.01 | 78 |
| SEQ ID No. 61 | 94.98 | 98 |
| SEQ ID No. 62 | 94.06 | 116 |
| SEQ ID No. 63 | 93.04 | 136 |

-continued

| SEQ ID NO | % Identity to SEQ ID No. 56 | No. of bases differing from SEQ ID No. 56 |
|---|---|---|
| SEQ ID No. 64 | 92.01 | 156 |
| SEQ ID No. 65 | 90.99 | 176 |

In another embodiment, polynucleotides of the invention comprise a nucleic acid having at least 75%, preferably at least 80%, more preferably at least 85%, more preferably at least 90%, even more preferably at least 91%, 92%, 93%, 94%, 95%, 96%, 97%, 98% and most preferably 99% or 100% identity to SEQ ID NO: 66. SEQ ID NO: 66 is a truncated version of SEQ ID NO: 1 and comprises base pairs 301-2106 of SEQ ID NO: 1. Specific polynucleotides having between 91 and 99% identity to SEQ ID NO: 66 are provided in SEQ ID NOs: 67-75 as shown in the table below.

| SEQ ID NO | % Identity to SEQ ID No. 66 | No. of bases differing from SEQ ID No. 66 |
|---|---|---|
| SEQ ID No. 67 | 99.00 | 18 |
| SEQ ID No. 68 | 97.90 | 38 |
| SEQ ID No. 69 | 97.01 | 54 |
| SEQ ID No. 70 | 96.12 | 70 |
| SEQ ID No. 71 | 95.02 | 90 |
| SEQ ID No. 72 | 94.02 | 108 |
| SEQ ID No. 73 | 93.02 | 126 |
| SEQ ID No. 74 | 92.03 | 144 |
| SEQ ID No. 75 | 91.03 | 162 |

In another embodiment, polynucleotides of the invention comprise a nucleic acid having at least 75%, preferably at least 80%, more preferably at least 85%, more preferably at least 90%, even more preferably at least 91%, 92%, 93%, 94%, 95%, 96%, 97%, 98% and most preferably 99% or 100% identity to SEQ ID NO: 76. SEQ ID NO: 76 is a truncated version of SEQ ID NO: 1 and comprises base pairs 301-2157 of SEQ ID NO: 1. Specific polynucleotides having between 91 and 99% identity to SEQ ID NO: 76 are provided in SEQ ID NOs: 77-85 as shown in the table below.

| SEQ ID NO | % Identity to SEQ ID No. 76 | No. of bases differing from SEQ ID No. 76 |
|---|---|---|
| SEQ ID No. 77 | 99.03 | 18 |
| SEQ ID No. 78 | 98.06 | 36 |
| SEQ ID No. 79 | 96.98 | 56 |
| SEQ ID No. 80 | 96.02 | 74 |
| SEQ ID No. 81 | 95.05 | 92 |
| SEQ ID No. 82 | 93.97 | 112 |
| SEQ ID No. 83 | 93.00 | 130 |
| SEQ ID No. 84 | 92.03 | 148 |
| SEQ ID No. 85 | 90.95 | 168 |

In another embodiment, polynucleotides of the invention comprise a nucleic acid having at least 75%, preferably at least 80%, more preferably at least 85%, more preferably at least 90%, even more preferably at least 91%, 92%, 93%, 94%, 95%, 96%, 97%, 98% and most preferably 99% or 100% identity to SEQ ID NO: 86. SEQ ID NO: 86 is a truncated version of SEQ ID NO: 1 and comprises base pairs 202-2106 of SEQ ID NO: 1. Specific polynucleotides having between 91 and 99% identity to SEQ ID NO: 86 are provided in SEQ ID NOs: 87-95 as shown in the table below.

| SEQ ID NO | % Identity to SEQ ID No. 86 | No. of bases differing from SEQ ID No. 86 |
|---|---|---|
| SEQ ID No. 87 | 98.95 | 20 |
| SEQ ID No. 88 | 98.01 | 38 |
| SEQ ID No. 89 | 96.96 | 58 |
| SEQ ID No. 90 | 96.01 | 76 |
| SEQ ID No. 91 | 94.96 | 96 |
| SEQ ID No. 92 | 94.02 | 114 |
| SEQ ID No. 93 | 92.97 | 134 |
| SEQ ID No. 94 | 92.02 | 152 |
| SEQ ID No. 95 | 90.97 | 172 |

In another embodiment, polynucleotides of the invention comprise a nucleic acid having at least 75%, preferably at least 80%, more preferably at least 85%, more preferably at least 90%, even more preferably at least 91%, 92%, 93%, 94%, 95%, 96%, 97%, 98% and most preferably 99% or 100% identity to SEQ ID NO: 96. SEQ ID NO: 96 is a truncated version of SEQ ID NO: 1 and comprises base pairs 103-2157 of SEQ ID NO: 1. Specific polynucleotides having between 91 and 99% identity to SEQ ID NO: 96 are provided in SEQ ID NOs: 97-105 as shown in the table below.

| SEQ ID NO | % Identity to SEQ ID No. 96 | No. of bases differing from SEQ ID No. 96 |
|---|---|---|
| SEQ ID No. 97 | 99.03 | 20 |
| SEQ ID No. 98 | 97.96 | 42 |
| SEQ ID No. 99 | 96.98 | 62 |
| SEQ ID No. 100 | 96.01 | 82 |
| SEQ ID No. 101 | 95.04 | 102 |
| SEQ ID No. 102 | 93.97 | 124 |
| SEQ ID No. 103 | 93.00 | 144 |
| SEQ ID No. 104 | 92.02 | 164 |
| SEQ ID No. 105 | 91.15 | 182 |

In one embodiment, polynucleotide sequences of the present invention further comprise a polynucleotide encoding a secretion sequence. The polynucleotide encoding the secretion sequence is preferably cloned upstream of the rPA nucleic acid sequence, or fragment thereof, and is most preferably operatively linked to said nucleic acid sequence, or fragment thereof.

Secretion sequences may allow the encoded protein to cross and/or lodge in cell membranes, and thus attain its functional topology or be secreted from a host cell. In this regard, the secretion sequence may be for extracellular translocation of the expressed polypeptide from a host cell (e.g. a bacterial host cell) into the extracellular environment. Alternatively, the secretion sequence may be for periplasmic translocation of the expressed polypeptide from a bacterial host cell cytoplasm into the periplasmic space.

It is particularly preferred that the secretion sequence is cleavable from the expressed polypeptide during periplasmic translocation or during extracellular translocation, in which case the periplasmic/extracellular polypeptide is free of this sequence. One example of such a 'cleavable' sequence is a cpg leader sequence encoded by SEQ ID NO: 3.

The cpg leader sequence illustrated in SEQ ID NO: 3 is designed such that it has a 5'-NdeI restriction site for inserting into an expression vector at a NdeI site, and a 3'-MscI site for fusion with a rPA nucleic acid sequence, or fragment thereof, where a similar MscI site has preferably been engineered. Thus, the cpg leader is cleaved from the expressed rPA protein (or protein fragment) as it passes through a host cell membrane, leaving the 'trimmed' mature rPA protein, or fragment thereof, in the extracellular environment or periplasmic space accordingly.

Other suitable secretion sequences for use in the present invention are described in Watson (1984) Proc. Nat. Acad. Sci. USA. vol. 12: 5145; and Makrides (1996) Microbiological Reviews 60: 512-538; and include, ompA (Denefle et al. (1989) Gene 85: 4990-510; and Ghrayeb et al. (1984) EMBO J. 3: 2437-2442.); pelB (Better et al. (1988) Science 240: 1041-1043; and Lei et al. (1987) J. Bacteriol. 169: 4379-4383); including a degenerate version thereof—see Le Calvez et al. (1996) Gene 170: 51-55; phoA (Denefle et al. (1989) Gene 85: 499-510; and Oka et al. (1985) Proc. Nat. Acad. Sci. USA. 82: 7212-7216); ompT (Johnson et al. (1996) Protein Expression Purif. 7: 104-1123); lamB (Hoffman & Wright (1985) Proc. Nat. Acad. Sci. USA. 82: 5107-5111); ompF (Hoffman & Wright (1985)); beta lactamase (Kadonaga et al. (1984) J. Biol. Chem. 259: 2149-2154; and Villa-Komaroff et al. (1977) Proc. Nat. Acad. Sci. USA. 75: 3727-3731); *Staphylococcus aureus* protein A (Abrahmsen (1986) Nucl. Acids Res. 14: 7487-7500; and Macnytyre & Henning (1990) Biochimmie 72: 157-167); *Bacillus subtilis* endoglucanase (Proudfoot et al. (1996) J. Biol. Chem. 271: 2599-2603); murine RNAse (Schein et al. (1992) Biochem. J. 283: 137-144); human growth hormone (Gray et al. (1985) Gene 39: 247-254); and enterotoxins ST-II, LT-A and LT-B (Fujimoto et al. (1988) J. Biotechnol. 8: 77-86; and Morioka-Fujimoto et al. (1991) J. Biol. Chem. 266: 1728-1732).

In one embodiment, the polynucleotide sequence of the present invention comprises a nucleic acid of the present invention, or a fragment thereof, having a 3' and a 5' end, and said nucleic acid or fragment thereof has a codon encoding a methionine residue cloned to the 5' end. By way of example, the nucleic acid may be SEQ ID NO: 7 (or a fragment of SEQ ID NO: 7 that includes the 5' terminal, met-encoding codon of SEQ ID NO: 5). This methionine-encoding codon is added in order to increase stability of the final (signal-less) protein when expressed in *E. coli*. Thus, rPA protein encoded by the polynucleotide of this particular embodiment of the invention is distinguished from wild-type PA protein naturally produced in *Bacillus anthracis* by the addition of an extra methionine residue to the N-terminus.

The present invention thus also provides a polypeptide or polypeptide fragment encoded by the polynucleotide of the present invention. Polypeptides of the present invention may therefore comprise an amino acid sequence encoding rPA, or a fragment thereof, with an extra methionine residue added at the N-terminus of the rPA amino acid sequence.

In a related aspect, the present invention also provides an isolated RNA molecule that is encoded by a DNA polynucleotide sequence of the present invention, or a fragment or variant or derivative of said DNA sequence.

Also contemplated within the invention are expression vectors comprising a polynucleotide of the present invention. Expression vectors are useful for the expression of heterologous nucleic acid sequences in a host cell. As used herein, the term "heterologous" means that the polynucleotide or polypeptide sequence concerned does not naturally exist in the cell, but has been introduced into it, for example by transformation, transfection, injection etc.

Expression vectors generally are replicable polynucleotide constructs that include coding regions for a peptide, operably linked to suitable transcriptional and translational regulatory elements. Examples of regulatory elements usually included in expression vectors are promoters, enhancers, ribosomal binding sites, and transcription and translation initiation and termination sequences. These regulatory elements are operably linked to the sequence to be translated. A nucleic acid sequence is operably linked when it is placed into a functional relationship with another nucleic acid sequence. For instance, a promoter is operably linked to a coding sequence if the promoter affects its transcription or expression. Generally, "operably linked" means that the DNA sequences being linked are contiguous and, where necessary to join two protein coding regions, contiguous and in reading frame. The regulatory elements employed in the expression vectors containing a polynucleotide encoding a virulence factor are functional in the host cell used for expression.

It is preferred that the expression vector expresses the polynucleotide in the absence of a chemical inducer—i.e. a chemical inducer is not required for induction of expression from the expression vector. In one embodiment, the vector expresses the polynucleotide constitutively, with no induction of gene expression needed. In another embodiment, the vector expresses the polynucleotide in response to an environmental stimulus or stimuli—such as starvation, or limitation of nutrients or oxygen, such as when a component or components become exhausted in the growth medium.

The term "promoter" is well known in the art, encompasses relatively simple, minimal promoters to complex promoters having upstream elements and enhancers. Suitable promoters for expression in prokaryotic and eukaryotic host cells are well known in the art, and are described in, for example, Molecular Cloning. A laboratory Manual (Sambrook et al., Second edition, 1989) and Current Protocols in Molecular Biology (Ausubel et al., eds., 1994).

Appropriate promoter and other necessary vector sequences are selected so as to be functional in the host. By way of example, promoters such as the trp, lac and phage promoters (e.g. T7, T4, lambda, fd), tRNA promoters and glycolytic enzyme promoters may be used in prokaryotic hosts. It is preferred that the expression vector comprises a "strong" promoter, —i.e. a promoter that is selected so as to ensure that the encoded rPA polypeptide (or fragment thereof) is highly expressed. Examples of strong promoters include recA, malate dehydrogenase, T7, tac, etc. In this regard, a polypeptide is said to be "highly expressed" if it is expressed at levels above 20% of total host cell soluble protein, preferably above 30%, more preferably above 40% and most preferably above 50% total host cell soluble protein. A preferred "strong promoter" for use in accordance with the invention is the malate dehydrogenase (mdh) promoter (proprietary to CAMR; U.S. Pat. No. 5,670,333).

Expression vectors may contain a selectable marker—i.e. a gene encoding a protein necessary for the survival or growth of a host cell transformed with the vector. The presence of this gene ensures the growth on a selective medium of only those host cells that contain the desired vector and that express the selectable marker. Typical selection genes encode proteins that: (a) confer resistance to antibiotics or other toxic substances, e.g. ampicillin, tetracycline, neomycin, methotrexate, etc.; (b) complement auxotrophic deficiencies; or (c) supply critical nutrients not available from complex media. The selection of an appropriate vector and an appropriate selectable marker will depend on the host cell, and is well within the capabilities of an ordinary person of skill in the art.

Expression vectors typically contain all of the additional elements that are necessary for efficient expression of the nucleic acid in a host cell. Examples of suitable vectors for expression of heterologous proteins in bacterial include pET vectors (for example pET26b-Novagen), and pTrKHis (Invitrogen). Both these vectors achieve high-level expression of nucleic acid in *E. coli.* pMTL expression vectors are advantageous because they are capable of yielding high levels of recombinant protein, and can be very stable, even in the absence of selective pressure using antibiotics. Furthermore, those pMTL vectors based on the very strong *E. coli* malate dehydrogenase (mdh) promoter are particularly advantageous because induction of expression using exogenous inducer chemicals is not required (Alldread et al. (1992) Gene 14: 139-143). It is an advantage not to require an exogenous chemical inducer for regulatory reasons, since any chemical inducer may have to be rigorously and successfully removed from the final product before administration to patients.

In a particularly preferred embodiment, the expression vector is also a high copy number plasmid, such as pMTL1015 (Chambers et al. (1988) Gene 68: 139-149). pMTL015 is a derivative of pMTL4, it replicates from a mutant of the ColE1 replicon (600 copies per cell; Minton et al. (1988) Focus 10: 56) and is encoded by SEQ ID NO: 4. Plasmid pMTL1015 is essentially identical to pMTL1003 as described by Brehm et al. (1991) Appl. Microbiol. Biotechnol 36: 358-363, and has numerous advantageous features. By way of example, pMTL1015 differs from pMTL1003 in that the trp promoter has been replaced with the very powerful mdh promoter (Alldread et al. (1992) Gene 14: 139-143), and the ampicillin resistance gene has been replaced with the tetracycline resistance gene of pBR322 (Bolivar et al. (1977) Gene 2: 95). The plasmid also incorporates the pSC101 partition function (par; Miller et al. (1983) Gene 24: 309-315), the rrnB double terminator (Brosius et al. (1981) J. Mol. Biol. 148: 107-127) and the pMTL20 polylinker cloning region (Chambers et al., 1988). The par locus endows the plasmid with good segregational stability enabling antibiotic-free fermentations without plasmid loss and the tetracycline resistance marker is a biopharmaceutically acceptable drug.

An example of an expression vector suitable for use in the present invention is the vector deposited under ECACC No: 04061401.

An example of an expression vector comprising a polynucleotide according to the present invention is pMTL1015-cpg-PA-synt, deposited under ECACC No: 04052501.

The vectors containing the nucleic acids of interest can be transcribed in vitro and the resulting RNA introduced into the host cell (e.g. by injection), or the vectors can be introduced directly into host cells by methods which vary depending on the type of cellular host, including electroporation; transfection employing calcium chloride, rubidium chloride, calcium phosphate, DEAE-dextran, or other substances; microprojectile bombardment; lipofection; infection (where the vector is an infectious agent, such as a retroviral genome). The term "host cells" is meant to embrace the progeny of such cells.

The present application thus also provides a host cell comprising an expression vector as described above. It is preferred that the host cell is a bacterial cell, in particular an *E. coli* cell, such as *E. coli* strains DH5, BL21 and HMS174 (Invitrogen).

It is particularly preferred that the bacterial cell e.g. *E. coli* strain is a protease-deficient strain, since rPA protein is generally considered to be a protease-sensitive protein. One example of a protease-deficient strain of *E. coli* is *E. coli* RV308 (ATCC No: 31608).

Also provided by the present invention are methods for producing rPA comprising expressing the polynucleotide of the present invention.

In one embodiment, the polynucleotide is expressed—i.e. transcribed and translated, in a host cell. In another embodiment, the polynucleotide is DNA, which is transcribed into RNA in vitro, and then the RNA is then translated into protein in a host cell. The host cell may be a bacterial cell, such as an *E. coli* host cell. The *E. coli* host cell is preferably a protease-deficient strain, such as *E. coli* RV308 (deposited under ATCC No: 31608).

In a preferred embodiment, rPA is expressed in a host cell from the expression vector of the present invention, as described above. In this embodiment, the method may incorporate at least one, preferably two, most preferably all of the following features: —(i) the expression vector comprises the cpg leader sequence encoded by SEQ ID NO: 3; (ii) the vector is the plasmid pMTL1015, encoded by SEQ ID NO: 4; and (iii) the vector is expressed in an *E. coli* host cell such as *E. coli* RV308 (ATCC No: 31608).

In one embodiment, the method comprises the initial steps of transforming an expression vector comprising the polynucleotide of interest into a host cell, such as *E. coli* host cell and culturing the transformed host cell in a suitable growth medium.

Optionally, the culture is carried out under selective pressure, such as in the presence of an antibiotic, e.g. tetracycline, in which case it is an advantage for the expression vector to comprise a selectable marker that confers resistance to the antibiotic.

Culture parameters may be controlled, in order to control nutrients, pH and/or oxygen levels (dissolved oxygen tension—DOT) in the culture. For example, DOT may be controlled by agitation, back pressure, sparged airflow and/or oxygen supplementation. It is preferred that DOT is maintained at above 40%.

The temperature at which host cells are grown can have an effect on the level of protein that can be purified from the culture. For example, protein expression rate and protein degradation rate (such as due to protease activity) can both affect the amount of protein that can be extracted. Growing the cultured host cells comprising the claimed polynucleotide at a reduced temperature of less than, for example 40° C., has been found to give acceptable levels of rPA expression and stability. Thus, in one embodiment of the invention, host cells containing polynucleotides of the invention (e.g. expression vectors) are cultured at less than 40° C.; preferably at less than 37° C.; more preferably at less than 35° C.; more preferably at about 30° C., and most preferably at 25-30° C., such as 29° C., 28° C., 27° C., 26° C. and 25° C. Culturing host cells at these reduced temperatures may slow down the rate of rPA expression, but this may be useful if a high-level expression vector, such as the plasmid pMTL1015, is used for expression.

It is preferred that a growth medium is used that is free of animal products (i.e. products derived from animals), since this is advantageous for meeting the regulations for injectable products. Examples of suitable media include phytone peptone—based Terrific Broth, and soy peptone-based L-broth.

If a secretion sequence is used that enables extracellular secretion of the polypeptide into the growth medium then the growth medium may be harvested and undergo further purification steps to extract the polypeptide.

Alternatively, if the secretion sequence enables secretion of the polypeptide into the bacterial periplasm then the polypeptide product will be intracellular. In this case, the cells must be harvested from the culture medium (e.g. by centrifugation as a cell paste) and undergo further processing to extract the polypeptide from the cells. Suitable protocols for the harvesting of cell cultures, such as bacterial cultures, for the purification of polypeptides are well known in the art, and can be found in common laboratory manuals such as Sambrook et al. (1989) Molecular Cloning: A Laboratory Manual, Second Edition, Cold Spring Harbor Laboratory Press; and Sambrook and Russell (2001) Molecular Cloning: A Laboratory Manual, Third Edition, Cold Spring Harbor Laboratory Press.

Typically, bacterial cells can be harvested by centrifugation for extraction of either nucleic acids or polypeptides. For protein purification the conditions selected for the harvesting of cultured cells by centrifugation are generally gentler than for the extraction of nucleic acid, so as not to damage the target protein. For example, the harvesting of bacterial cells for extraction of a target polypeptide may be carried out at 4° C., by centrifugation at 4,000-5,000 g for 10-15 minutes.

It is an option for the method to further comprise testing steps, to identify the presence and/or yield of desired polypeptide, prior to further processing. In one embodiment, an ELISA-based test is carried out.

Following the fermentation (bacterial growth and harvesting) and optional testing protocols, the method may further comprise downstream processing steps in order to obtain isolated, purified, rPA protein.

The downstream processing steps employed in the present invention preferably achieve one or more of the following aims:—

- reduction in the number of chromatography steps required, compared to prior art methods;
- use of step elution rather than gradient elution for some, preferably all, chromatography steps;
- increase in the level of primary processing prior to chromatography, compared to prior art methods;
- removal of the need for the addition of conditioning agents (e.g. nucleases) where possible;
- use of techniques capable of scaling-up to at least 100 L fermentation scale; and
- use of techniques that are compatible with cGMP.

It is preferred that the purification procedure has reduced process times and volumes and/or has increased process efficiency in comparison to prior art methods. In the present invention, the number of dialysis/buffer exchange steps is preferably minimised, for example, by linking steps that generate a process stream of high conductivity with those that require a high conductivity starting material (e.g. ammonium sulphate precipitation or ion-exchange chromatography may be followed by hydrophobic interaction chromatography).

The downstream processing protocol commences with a crude mixture containing rPA polypeptide. If the rPA polypeptide is located within the host cell (e.g. within a bacterial host cell periplasm) then the cells must be treated to extract the rPA polypeptide, for example by homogenisation.

It is preferred that the method further comprises at least one separation step, carried out on the extracted rPA polypeptide. Examples of separation steps that may be included in the method are filtration steps such as diafiltration steps, and chromatography steps. In one embodiment, the method comprises at least one chromatography step and at least one filtration step.

In a particularly preferred embodiment of the present method, the extracted rPA polypeptide (together with unwanted components such as nucleic acids, other proteins, and cell debris) is subjected to diafiltration, such as tangental flow diafiltration. The purpose of this step is to alter the load of charged molecules, in preparation for subsequent separation steps, such as chromatography steps. Diafilters retain molecules of above a certain molecular weight (e.g. above 30 kDa, 40 kDa or 50 kDa) and allow dissolved substances and those below the specified molecular weight to pass through the filter. Thus, it is preferred that the method includes at least one filtration step that is a diafiltration step.

Chromatography steps may include ion-exchange chromatography (e.g. using a Q-sepharose anion exchange column) and hydrophobic charge chromatography (e.g. using a mercaptoethyl pyridine hypercel column). Other examples of suitable chromatographic techniques are known in the art and would be routinely available to a skilled person. Thus, the present method may include at least one ion-exchange chromatography step and at least one hydrophobic charge chromatography step.

In one embodiment, when the rPA polypeptide has been expressed in an *E. coli* host cell, there may be residual *E. coli* endotoxin associated with the rPA polypeptide and this can be separated from the rPA polypeptide by a (further) separation step, if necessary. In one embodiment, separation of endotoxin may be achieved by filtration, using a charged filter to which the toxin adheres.

Thus, in a specific embodiment, a method of producing rPA comprises the steps of obtaining host cells that express the polypeptide of the present invention; extracting the expressed rPA from the host cells; subjecting the extracted rPA to a diafiltration step (e.g. tangental flow diafiltration at 30 kDa); followed by at least one chromatography step selected from ion exchange chromatography and hydrophobic charge chromatography; then a further diafiltration step (which may be at a higher molecular weight cut-off e.g. 40 kDa or 50 kDa); and an optional further filtration step to remove any residual protein and/or bacterial endotoxin.

In one embodiment of the present invention, the combination of high-level gene expression (plasmid containing strong promoter), periplasmic translocation (secretion sequence), nucleic acid sequence modification (rPA nucleic acid sequence) and efficient downstream processing, results in an increase of rPA protein yields that are 10 to 20-fold above yields previously available in the prior art.

Furthermore, the downstream processing steps of the present invention allow rPA protein to be obtained that has greater than 70%, preferably greater than 80%, greater than 90%, or greater than 95%, and more preferably greater than 98% purity.

Polypeptide purity or homogeneity may be indicated by, for example, polyacrylamide gel electrophoresis of a protein sample, followed by visualizing a single polypeptide band upon staining the gel. Alternatively, higher resolution may be provided by using, for example, HPLC.

If desirable, the amino acid sequence of the polypeptides of the present invention may be determined by protein sequencing methods.

The present invention thus also provides an rPA polypeptide or fragment thereof produced by the method of the present invention. In one embodiment, the polypeptide may be identical to wild-type PA produced by *Bacillus anthracis*. In another embodiment, as described above, the polypeptide or fragment thereof may be distinguished from wild-type PA (or a fragment thereof) by the presence of an extra residue, such as a methionine residue, at the N-terminus of the rPA amino-acid sequence. For example, the polypeptide may be SEQ ID NO: 6, or a fragment thereof comprising the N-terminal methionine residue of SEQ ID NO: 6.

Also envisaged by the present invention is a kit, which may comprise one or more of a polynucleotide, an expression vector, a host cell, and a polypeptide of the present invention.

Also provided by the present invention are antigenic compositions, such as vaccine compositions, comprising a polypeptide according to the present invention.

The invention also provides methods of inducing an immune response against infection by *Bacillus anthracis* comprising administering a polypeptide of the present invention or an antigenic composition of the present invention.

Also provided by the present invention is use of a polypeptide of the present invention for manufacture of a medicament for inducing an immune response against infection by *Bacillus anthracis*.

In this regard, "inducing an immune response" may embrace protecting against infection by *Bacillus anthracis*. The protection conferred by the method and/or use of the present invention may be 100%, or may be less than 100%. Preferably, "protecting against infection by *Bacillus anthracis*" provides protection against at least 50%, preferably at least 70%, more preferably at least 80%, most preferably at least 90%, 91%, 92%, 93%, 94%, 95%, 96%, 97%, 98% or 99% of *Bacillus anthracis* infections. Preferably, "protecting against infection by *Bacillus anthracis*" provides a level of protection that is at least 50%, preferably at least 70%, more preferably at least 80%, most preferably at least 90%, 91%, 92%, 93%, 94%, 95%, 96%, 97%, 98% or 99% effective against a *Bacillus anthracis* infection.

Furthermore, the term "protecting against infection" may embrace preventing infection and treating infection. In this regard, the term "preventing" includes reducing the severity/intensity of, or initiation of, a *Bacillus anthracis* infection. The term "treating" includes post-infection therapy and amelioration of a *Bacillus anthracis* infection.

The antigenic composition may be administered by conventional routes, e.g. intravenous, subcutaneous, intraperitoneal, and mucosal routes using methods well known in the art.

Typically, such antigenic compositions are prepared as injectables, either as liquid solutions or suspensions; solid forms suitable for solution in, or suspension in, liquid prior to injection may also be prepared. The preparation may also be emulsified, or the peptide encapsulated in liposomes or microcapsules.

The active immunogenic ingredients are often mixed with excipients which are pharmaceutically acceptable and compatible with the active ingredient. Suitable excipients are, for example, water, saline, dextrose, glycerol, ethanol, or the like and combinations thereof. In addition, if desired, the vaccine may contain minor amounts of auxiliary substances such as wetting or emulsifying agents, pH buffering agents, and/or adjuvants which enhance the effectiveness of the vaccine. Examples of adjuvants which may be effective include but are not limited to: aluminum hydroxide, N-acetyl-muramyl-L-threonyl-D-isog lutamine (thr-M DP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-dipalmitoyl-sn-glycero-3-hydroxy phosphory loxy)-ethylamine (CGP 19835A, referred to as MTP-PE), and RIBI, which contains three components extracted from bacteria, monophosphoryl lipid A, trehalose dimycolate and cell wall skeleton (MPL+TDM+CWS) in a 2% squalene/Tween 80 emulsion.

The active components may be formulated into the vaccine as neutral or salt forms. Pharmaceutically acceptable salts include the acid addition salts (formed with free amino groups of the peptide) and which are formed with inorganic acids such as, for example, hydrochloric or phosphoric acids, or with organic acids such as acetic, oxalic, tartaric, maleic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The antigenic compositions are conventionally administered parenterally, by injection, for example, either subcutaneously or intramuscularly.

The antigenic compositions are for administration in a manner compatible with the dosage formulation, and in such amount as will be prophylactically and/or therapeutically effective. The quantity to be administered, which is generally in the range of 5 micrograms to 250 micrograms of antigen per dose, preferably about 50-100 μg per dose, depends on the subject to be treated, capacity of the subject's immune system to synthesize antibodies, and the degree of protection desired. Precise amounts of the active ingredient that is required to be administered may depend on the judgment of the practitioner and may be particular to each subject.

The antigenic composition may be given in a single dose schedule, or optionally in a multiple dose schedule. A multiple dose schedule is one in which a primary course of vaccination may be with 1-6 separate doses, followed by other doses given at subsequent time intervals required to maintain and or reinforce the immune response, for example, at 1-4 months for a second dose, and if needed, a subsequent dose(s) after several months. The dosage regimen will also, at least in part, be determined by the need of the individual and be dependent upon the judgment of the practitioner.

In addition, the antigenic composition containing the immunogenic antigen(s) may be administered in conjunction with other immunoregulatory agents, for example, immunoglobulins, as well as antibiotics.

Additional formulations which are suitable for other modes of administration include microcapsules, suppositories and, in some cases, oral formulations or formulations suitable for distribution as aerosols. For suppositories, traditional binders and carriers may include, for example, polyalkylene glycols or triglycerides; such suppositories may be formed from mixtures containing the active ingredient in the range of 0.5% to 10%, preferably 1%-2%.

Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and contain 10%-95% of active ingredient, preferably 25%-70%.

In one embodiment the medicament may be administered intranasally (i. n.). An intranasal composition may be administered in droplet form having approximate diameters in the range of 100-5000 μm, which in terms of volume would have droplet sizes in the approximate range of 0.001-100 μl.

Intranasal administration may be achieved by way of applying nasal droplets or via a nasal spray. In the case of nasal droplets, the droplets may typically have a diameter of approximately 1000-3000 μm and/or a volume of 1-25 μl, whereas in the case of a nasal spray, the droplets may typically have a diameter of approximately 100-1000 μm and/or a volume of 0.001-1 μl.

It is possible that, following i.n. delivery of antibodies, their passage to the lungs may be facilitated by a reverse flow of mucosal secretions.

In a different embodiment, the medicament may be delivered in an aerosol formulation. The aerosol formulation may take the form of a powder, suspension or solution.

The size of aerosol particles is one factor relevant to the delivery capability of an aerosol. Thus, smaller particles may travel further down the respiratory airway towards the alveoli than would larger particles. In one embodiment, the aerosol particles have a diameter distribution to facilitate delivery along the entire length of the bronchi, bronchioles, and alveoli. Alternatively, the particle size distribution may be selected to target a particular section of the respiratory airway, for example the alveoli.

The aerosol particles may be delivered by way of a nebulizer or nasal spray.

In the case of aerosol delivery of the medicament, the particles may have diameters in the approximate range of 0.1-50 μm, preferably 1-5 μm.

The aerosol formulation of the medicament of the present invention may optionally contain a propellant and/or surfactant.

By controlling the size of the droplets which are to be administered to a patient to within the defined range of the present invention, it is possible to avoid/minimise inadvertent antigen delivery to the alveoli and thus avoid alveoli-associated pathological problems such as inflammation and fibrotic scarring of the lungs.

Intranasal vaccination engages both T and B cell mediated effector mechanisms in nasal and bronchus associated mucosal tissues, which differ from other mucosae-associated lymphoid tissues.

Intranasal delivery of antigens allows targeting of the antigens to submucosal B cells of the respiratory system. These B cells are the major local IgA-producing cells in mammals and intranasal delivery facilitates a rapid increase in IgA production by these cells against the anthrax antigens.

In one embodiment administration of the medicament comprising an anthrax antigen stimulates IgA antibody production, and the IgA antibody binds to the anthrax antigen. In another embodiment, a mucosal and/or Th2 immune response is stimulated.

In one embodiment, the vaccine composition comprises rPA protein adsorbed to ALHYDROGEL™ adjuvant. In one embodiment, the vaccine is delivered by intramuscular injection.

The invention also provides a vector having the sequence SEQ ID NO:4.

The invention also provides a vector as deposited under ECACC No: 04061401.

The invention also provides a vector comprising a polynucleotide according to the present invention, as deposited under ECACC NO: 04052501.

Referring to the Figures of the present application:—

FIG. 1 depicts HPA clone pMTL1015-cpg-rPA-synt—i.e. the modified rPA nucleic acid sequence fused to the $cpg_2$ leader in pMTL1015 ($Tc^R$). Manipulations required to generate this plasmid are as follows: (1) sub-clone synthetic 'mature' rPA sequence from sequence verified PCR product TOPO vector (i.e. without any leader) into HPA pET22bcpg vector; (2) sub-clone cpg-SynPA from pET22bcpgSynPA into pMTL1015.

FIG. 2 demonstrates SDS-PAGE of pMTL1015 clones expressing rPA after 16 hr Shake-flask culture in phytone peptone-based Terrific Broth. The key is as follows: —

1. Blank.
2. rPA Standard (DEV030IP; 100 μg/mL)
3. pMTL1015 vector only
4. pMTL1015-ompA-PA-wt
5. pMTL1015-cpg-PA-wt
6. pMTL1015-pelB-PA-wt
7. pMTL1015-ompA-PA-synt
8. pMTL1015-cpg-PA-synt
9. pMTL1015-pelB-PA-synt
10. Molecular weight markers FIG. 3 shows a Western blot of pMTL1015 clones expressing rPA after 16 hrs Shake-flask culture in phytone peptone-based Terrific Broth. The key is as described above for FIG. 2.

1: Molecular Weight Markers
2: RV308 pMTL1015 ompA-PA-synt
3: RV308 pMTL1015 ompA-PA-wt
4: RV308 pMTL 015 pelB-PA-synt
5: RV308 pMTL1015 pelB-PA-wt
6: RV308 pMTL1015 cpg-PA-synt
7: RV308 pMTL1015 cpg-PA-wt
8: Reference DEV03031P (100 µg/mL)

Figure 10:
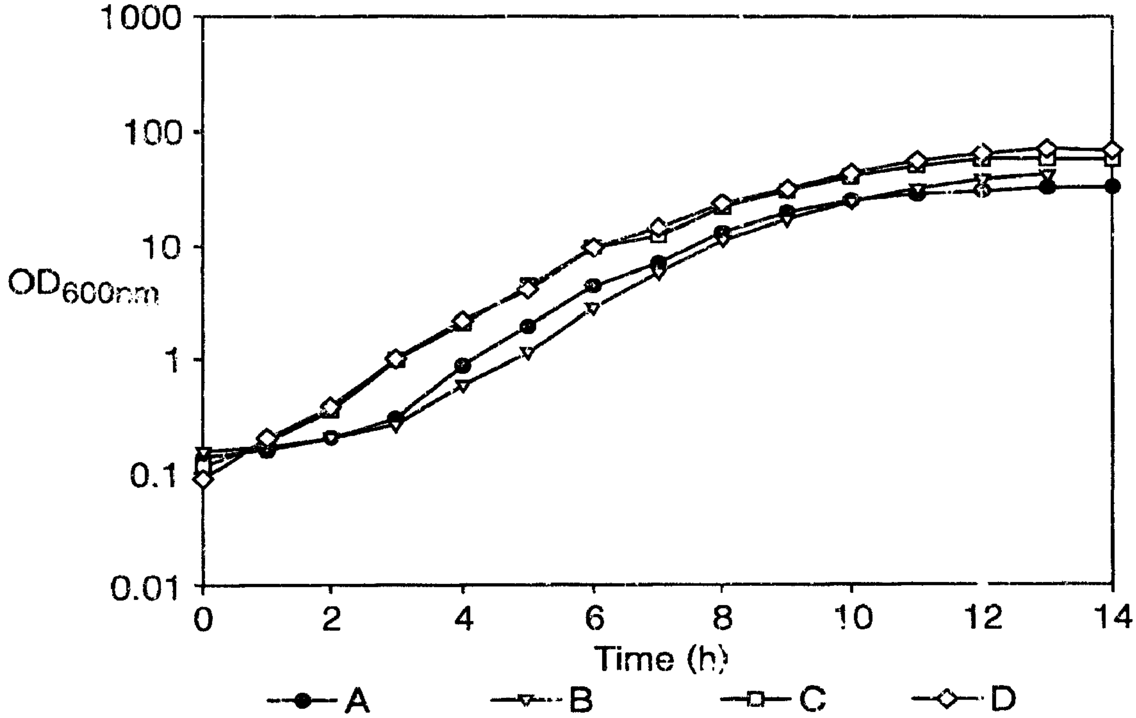

FIG. 10 shows growth of *E. coli* RV308 pMTL1015-cpg-PA-synt in production medium (Phytone peptone 12 g/L, Bacto yeast extract 60 g/L, glucose 25 g/L, magnesium sulphate heptahydrate 2 g/L, $K_2HPO_4$ 12.54 g/L, $KH_2PO_4$ 2.31 g/L and tetracycline 1.5 mg/L, pH 7.0-7.2), with varying levels of Yeast Extract, as follows: —

| | |
|---|---|
| A | 1x yeast extract |
| B | 1.5x yeast extract |
| C | 2x yeast extract |
| D | 2.5x yeast extract |

Figure 11:
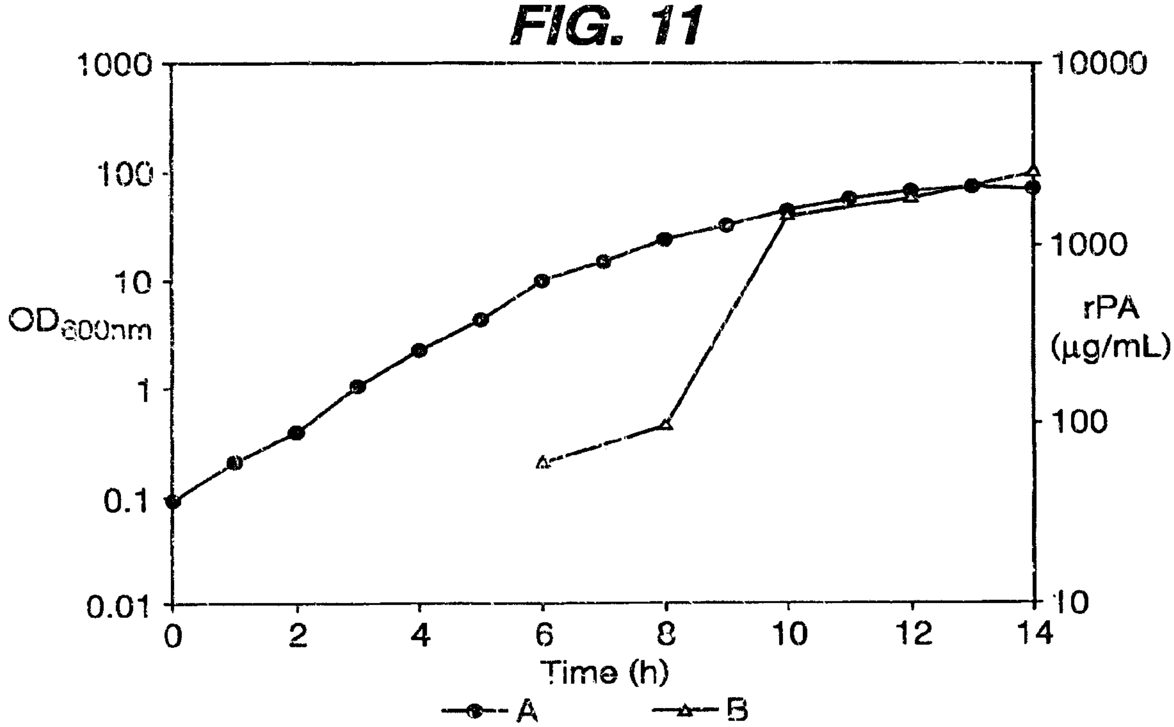

FIG. 11 shows growth curves (A) and rPA production curves (B) for *E. coli* RV308 pMTL1015-cpg-PA-synt in production medium.

Figure 12:
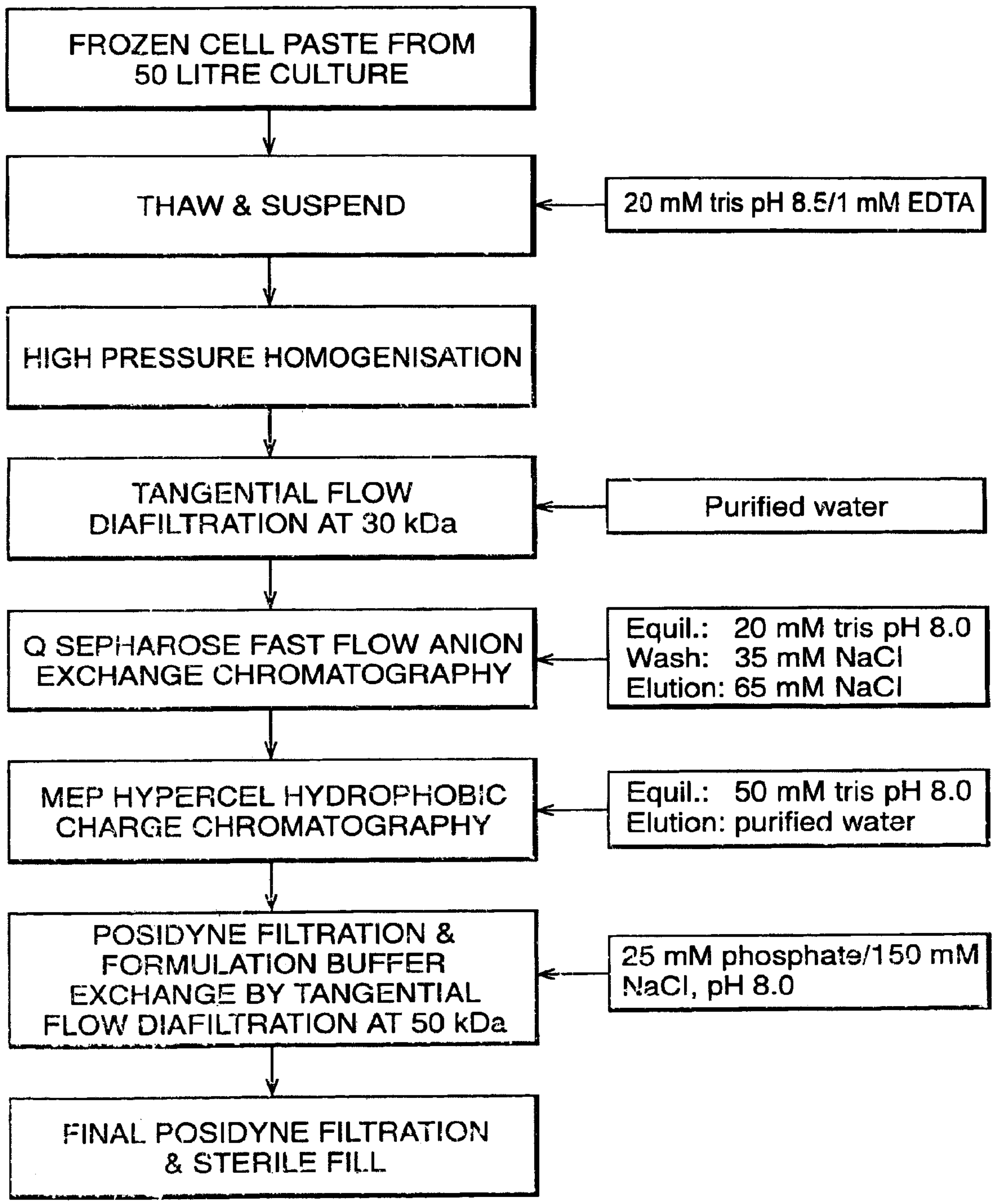

FIG. 12 is a flow chart showing the downstream processing steps for isolation of rPA.

Figure 13:
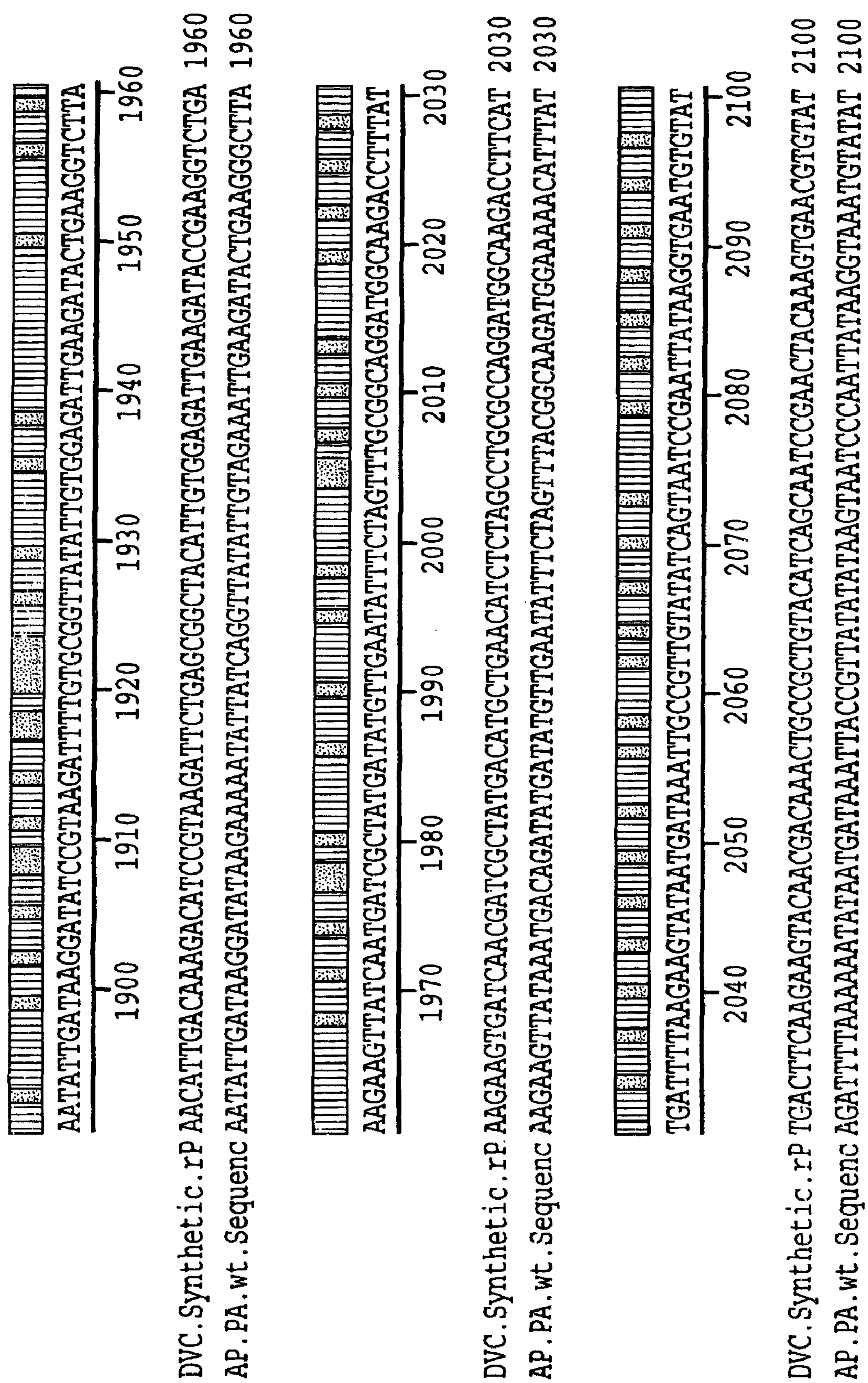

FIG. 13 (A-D) shows the sequence alignment between SEQ ID NO: 8—“DVC.Synthetic.rP” (i.e. the wild-type PA gene sequence, SEQ ID NO: 2, plus a 5' codon encoding a methionine residue), and SEQ ID NO: 7—“AP.PA.wt.Sequenc” (i.e. the modified rPA gene sequence of the present invention, SEQ ID NO: 1, plus a 5' codon encoding a methionine residue). The sequence identity is 71.2%. (The consensus sequence is disclosed as SEQ ID NO: 106.)

The invention is now described by reference to the following Examples.

EXAMPLE 1 rPA Expression Systems pMTL expression vector constructs were generated, directing expression of either the wild-type PA gene sequence or the modified rPA gene sequence, fused to either the *Erwinia carotovora* pelB or the pseudomonad carboxypeptidase $G_2$ ($cpg_2$) leader sequences. The latter sequence is described in European Patent 0 121 352, and has been shown to be efficiently processed in *E. coli*, directing soluble protein into the periplasmic space. These rPA expression constructs were compared with Dynport Vaccine Company (DVC)'s pET26b and Invitrogen pTrk vector-based constructs for evaluation.

Generation of novel rPA pMTL-based expression clones was as follows:

1. PCR amplification of the two PA-encoding nucleotide sequences (wild type and modified) fused to both the pelB, ompA and $cpg_2$ leader sequences. This generated six rPA sequence options.
2. Primary clones were constructed in a PCR product cloning vector system (e.g. Invitrogen TA Cloning).
3. Primary clones were authenticated by DNA sequence analysis of the composite PA/leader sequences.
4. The six rPA sequences were sub-cloned into pMTL1015 expression vector and the recombinant plasmids were authenticated.
5. Plasmid DNA derived from the four authenticated clones was used to transform a protease-deficient expression strain, *E. coli* RV308 (ATCC 31608).

Strategy for Comparison of rPA Expression Systems

The six clones based on the pMTL expression plasmid were evaluated in shake-flask culture in the current production medium. The existing DVC production organism was used as a control. Growth conditions and induction initiation/duration (where applicable) were standardised as much as possible to allow a true comparison of expression levels to be made under the given experimental conditions. For example, a standard cell density was used for inoculation. Production levels were compared by sampling cultures throughout growth and following chemical cell lysis using BugBuster™ (Novagen) of harvested cells, by densitometric analysis of SDS-PAGE. Western blotting was used to confirm the identity of the rPA protein band.

Media Selection Strategy

In addition to increasing the expression level of rPA by genetic manipulation, the final yield of product was raised by growing cultures to a higher cell density using a medium containing higher nutrient levels.

The strains showing the most promise in terms of rPA production levels in the current production medium were examined further, initially in shake-flask culture, using a range of potential production media. The analytical techniques used by DVC (SDS-PAGE, RP-HPLC) were used to estimate product levels throughout growth and at harvest.

EXAMPLE 2

Shake-Flask Comparisons of rPA Expression

EXAMPLE 2.1

Phytone Peptone-Based Terrific Broth

An experiment was performed to compare the expression of rPA by six pMTL1015 clones in phytone peptone-based Terrific Broth using shake-flask culture. Since previous work using the pMTL 1015 expression system at CAMR had shown that low oxygenation rates may favour product expression, cultures were set up in both baffled flasks (high oxygenation) and non-baffled flasks (low oxygenation).

The 10 mL cultures prepared as primary seed cultures for the cell banking were used to prepare seed cultures for this study. A 50 μL aliquot of the 10 mL culture was used to inoculate 50 mL of phytone peptone-based Terrific Broth in 250 mL baffled flasks. These seed cultures were incubated at 30° C. at 150 rpm for 17 h and then used to inoculate duplicate 200 mL cultures of the same medium in 1000 mL baffled flasks and single cultures of 250 mL in 500 mL non-baffled flasks. The inoculum for each culture was calculated to give a starting $OD_{600}$ of 0.1-0.2. The cultures were incubated at 30° C. and 150 rpm for 24 h. Samples (2.5 mL) were removed at 2 hourly intervals for rPA assay when the $OD_{600}$ reached 5-7. Samples were centrifuged at 4,000 rpm in a Clandon T-52 bench top centrifuge for 15 min, the supernatant decanted and the pellets stored frozen at −20° C. After 24 h growth, the duplicate baffled flask cultures were bulked and the cell mass harvested by centrifugation (Sorvall RC-3, 5000 rpm for 15 min) and the cell paste stored frozen at −20° C.

Figure 1:
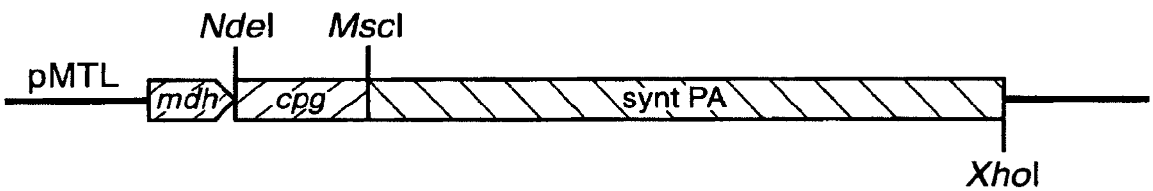
Figure 2:
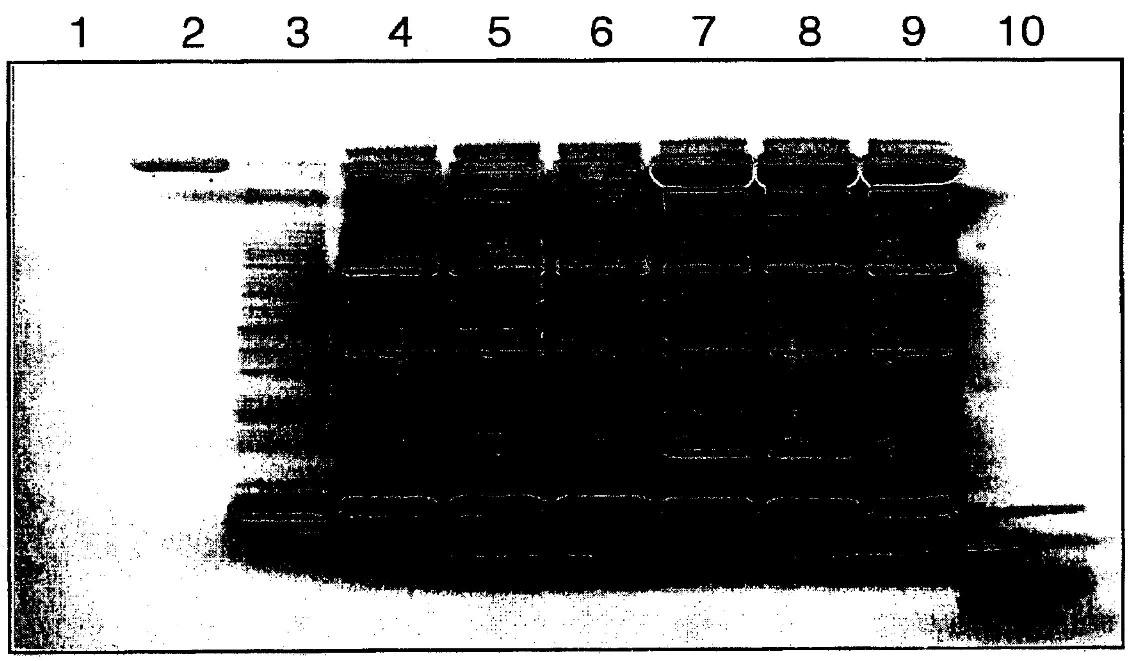
Figure 3:
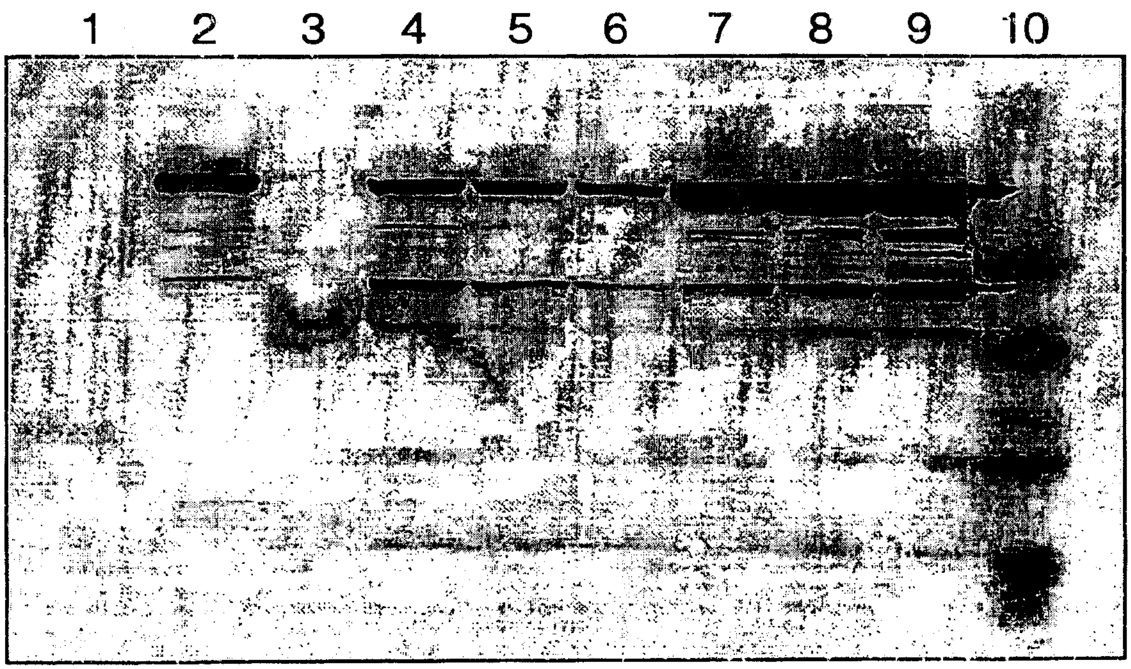

FIGS. 2 and 3 show SDS-PAGE and Western blot analysis of the 16 h samples from each of the pMTL1015 clones grown in phytone peptone-based Terrific Broth under conditions of high oxygenation (baffled flasks) following treatment with BugBuster™. It can be seen that strong protein bands are present at the expected rPA molecular mass following SDS-PAGE for the three clones expressing the synthetic gene product, with weaker bands for those clones expressing the wild type gene (FIG. 2). The amount of rPA present was estimated by comparison with the intensity of the rPA standard and confirmed by ELISA (Table 1). The Western blot analysis demonstrated the presence of some immuno-reactive material at lower molecular weights than the rPA (FIG. 3). The amount of this material relative to intact rPA was similar for all clones. It is not known at present whether this represents proteolytic degradation products or truncated expression.

TABLE 1

Comparison of rPA expression of all 12 *E. coli* clones following growth in phytone peptone-based Terrific Broth.

| | | | | rPA (μg/mL culture) | |
|---|---|---|---|---|---|
| Clone | Name | *E. coli* host | $OD_{600}$ culture | *Gel estimate | ELISA |
| 1 | pET26b-PA | BL21 (DE3) | 5.5 | <100 | 24 |
| 2 | pET26b-PA-synt | BL21 (DE3) | 3.6 | <100 | 11 |
| 3 | pTrck-pelB-PA | DH5a | 9.7 | <100 | 57 |
| 4 | pTrck-ompA-PA | DH5α | 9.7 | <100 | 74 |
| 5 | pMTL1015-pelB-PA-wt | RV308 | 17.3 | <100 | 58 |
| 6 | pMTL1015-ompA-PA-wt | RV308 | 19.7 | <100 | 135 |
| 7 | pMTL1015-cpg-PA-wt | RV308 | 20.4 | <100 | 67 |
| 8 | pMTL1015-pelB-PA-synt | RV308 | 21.1 | >>100 | 394 |
| 9 | pMTL1015-cpg-PA-synt | RV308 | 23.3 | >>100 | 496 |
| 10 | pMTL1015-ompA-PA-synt | RV308 | 25.3 | >>100 | 476 |
| 11 | pTrck-pelB-PA-synt | DH5α | 8.2 | >100 | 304 |
| 12 | pTrck-ompA-PA-synt | DH5α | 11 | >100 | 252 |

*estimate of rPA concentration from SDS-PAGE by comparison with 100 μg/mL rPA standard.

Figure 4A:
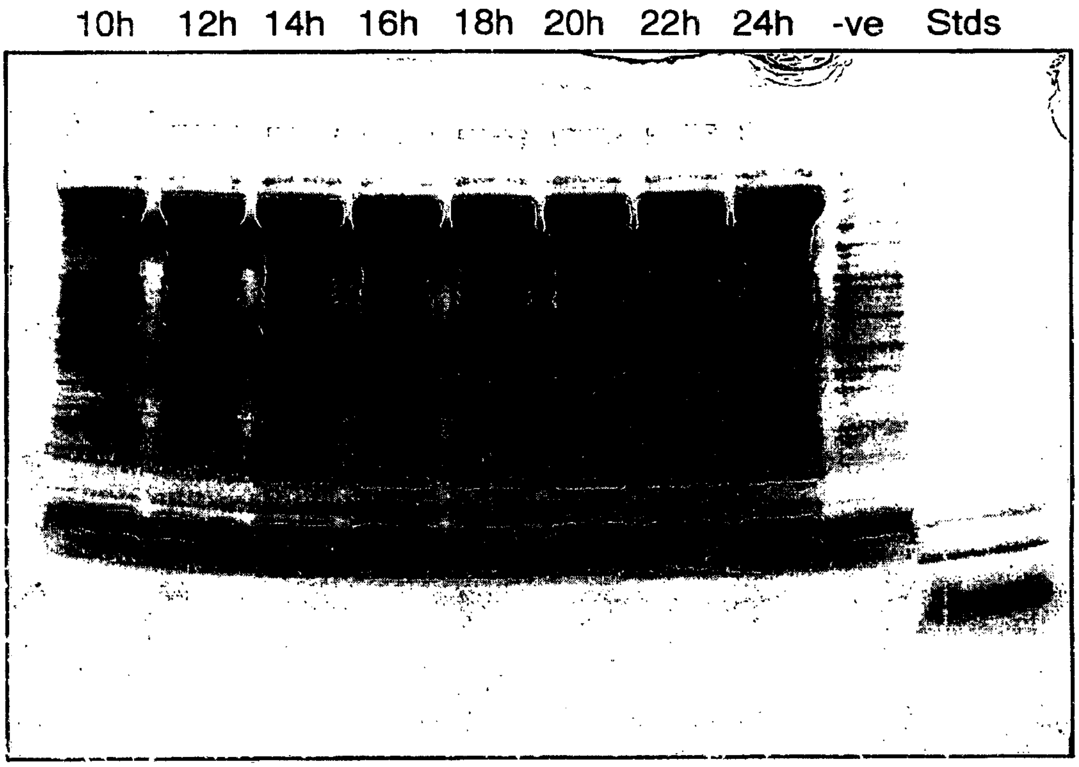
FIG. 4 shows time course analysis by (A) SDS-PAGE and (B) Western Blot of samples from Shake-flask culture of *E. coli* (pMTL1015-cpg-PA-synt) in phytone peptone-based Terrific Broth. The negative control was *E. coli* RV308 (pMTL1015).
Figure 4B:
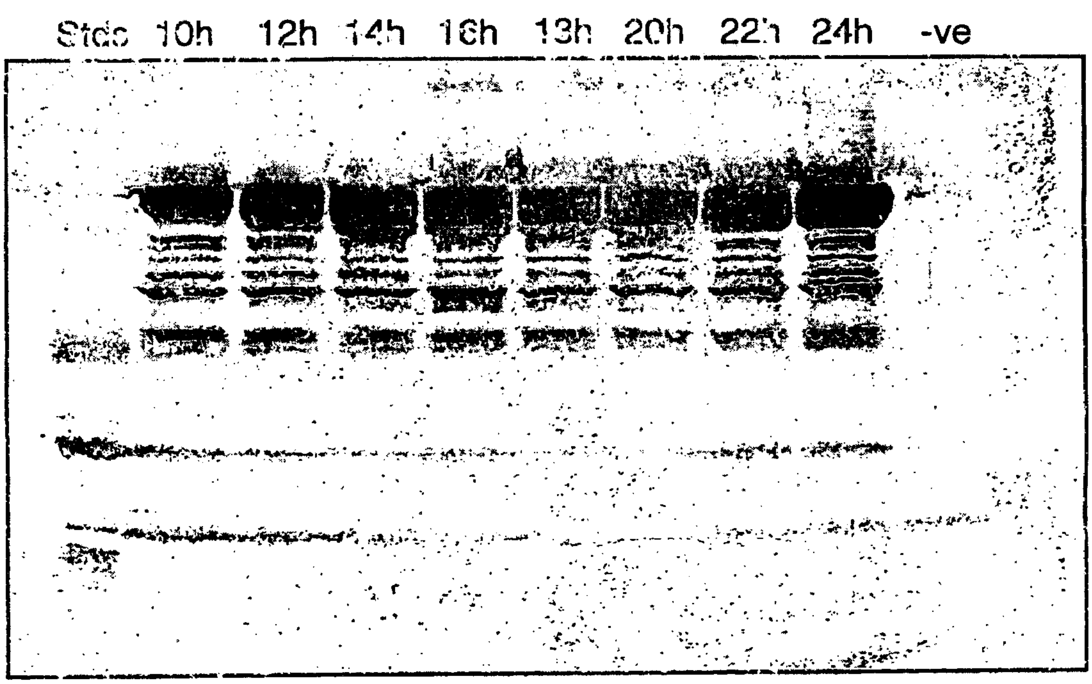

Time course samples from the pMTL1015-cpg-PA-synt clone were analysed by SDS-PAGE (Phast-gel), Western Blot (FIG. 4) and ELISA (Table 2) to determine; (a) the point at which rPA expression was maximal, and (b) whether prolonged incubation resulted in loss of product due to proteolytic activity. It can be seen that rPA expression by ELISA was optimal after 14-16 h incubation and did not change appreciably with further incubation up to 24 h (Table 2). Western blot analysis (FIG. 4) showed that the level of lower molecular weight immuno-reactive material relative to intact rPA did not change significantly with extended incubation time.

TABLE 2

Time course analysis by ELISA of samples from shake flask culture of *E. coli* (pMTL1015-cpg-PA-synt) in phytone peptone based Terrific Broth.

| Time (h) | rPA (μg/mL culture) |
|---|---|
| 10 | 107 |
| 12 | 313 |
| 14 | 507 |
| 16 | 532 |
| 18 | 488 |
| 20 | 491 |
| 22 | 487 |
| 24 | 525 |

Figure 5:
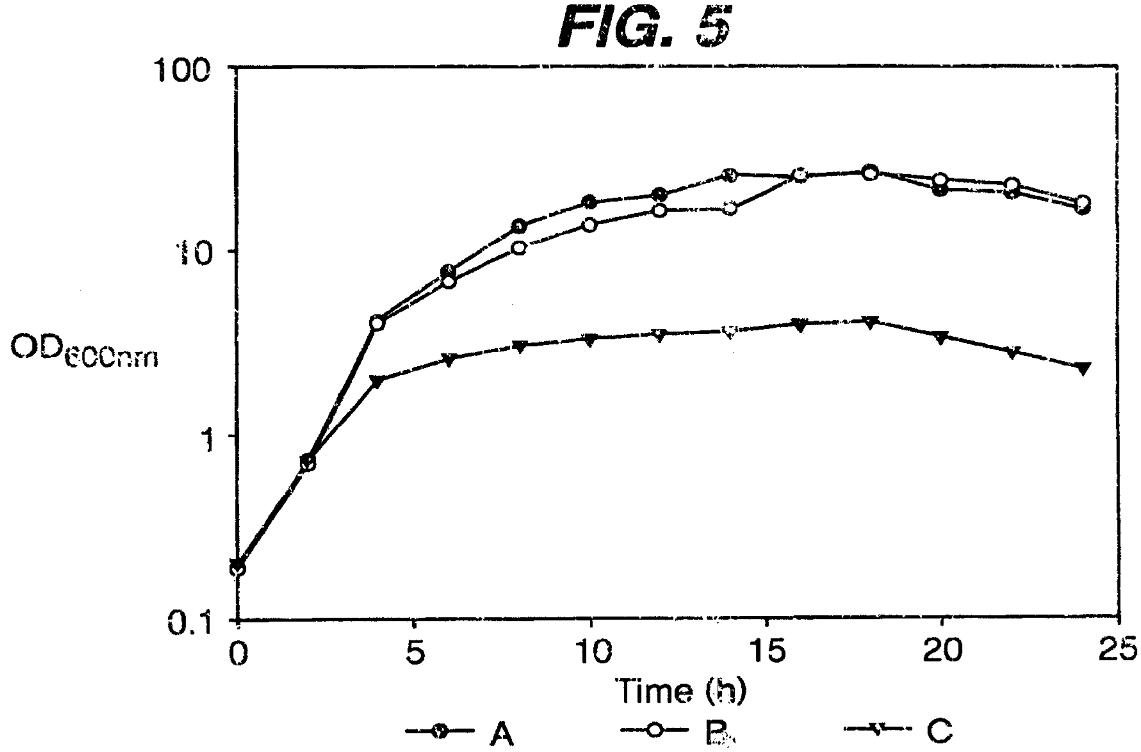
FIG. 5 shows growth curves of *E. coli* RV308 pMTL1015-ompA-PA-synt in phytone peptone-based Terrific Broth, Shake-flask culture, in baffled flasks (A and B) or non-baffled flasks (C).

FIG. 5 shows the growth curves obtained for *E. coli* RV308 (pMTL 015-ompA-PA-synt) when grown in phytone peptone-based Terrific Broth using baffled (high oxygenation) and non-baffled (low oxygenation) flasks. It can be seen that growth was substantially better in the baffled flasks. Cultures grown in non-baffled flasks reached a much lower final cell density compared with the baffled flask cultures. rPA expression was considerably lower in the cultures grown in non-baffled flasks (data not shown).

EXAMPLE 2.2

Hy-Soy-Based Semi-Defined Medium

Figure 6:
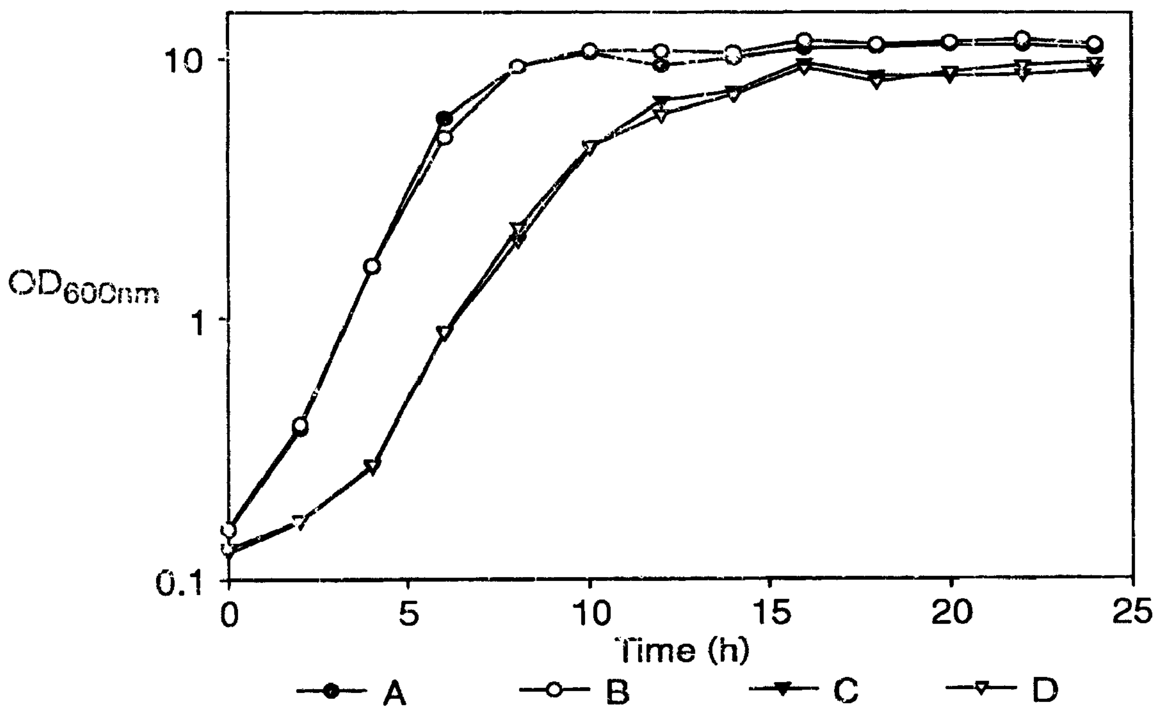
FIG. 6 shows growth curves of *E. coli* RV308 pMTL1015-ompA-PA-wt (A and B) and pMTL1015-ompA-PA-synt [C and D) in Hy-soy based semi-defined medium, Shake-flask culture.
Figure 7:
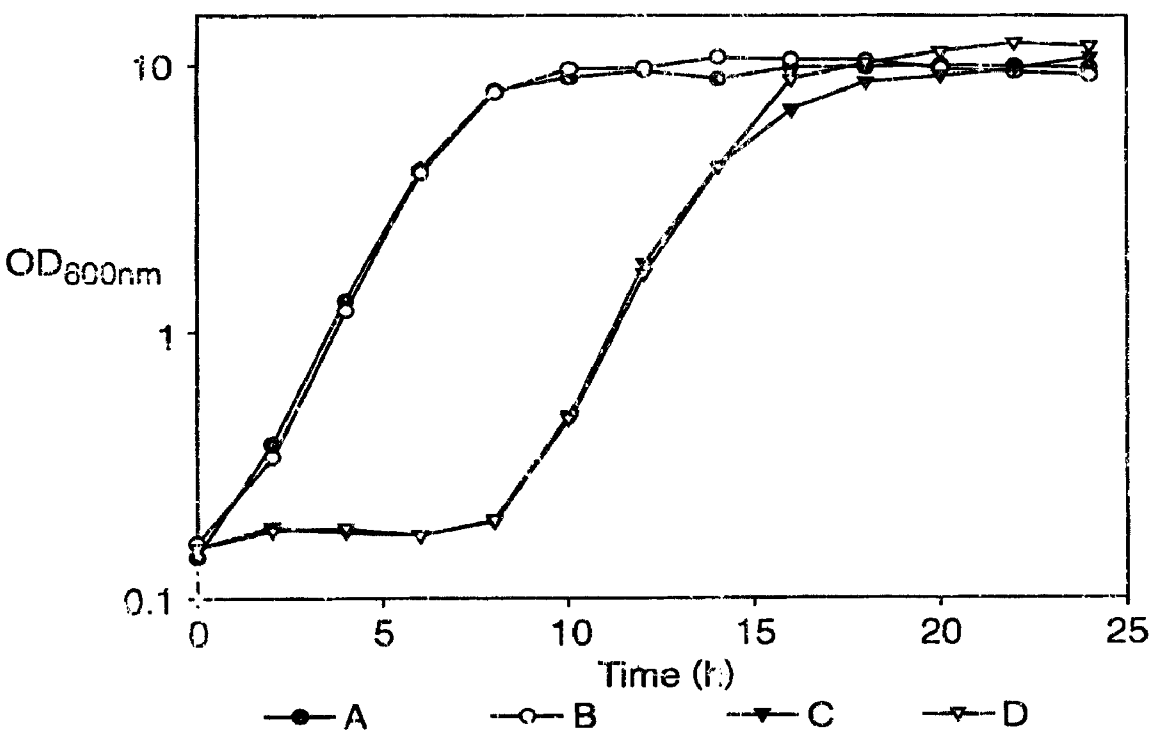
FIG. 7 shows growth curves of *E. coli* RV308 pMTL1015-pelB-PA-wt (A and B) and pMTL1015-pelB-PA-synt [C and D) in Hy-soy based semi-defined medium, Shake-flask culture.
Figure 8:
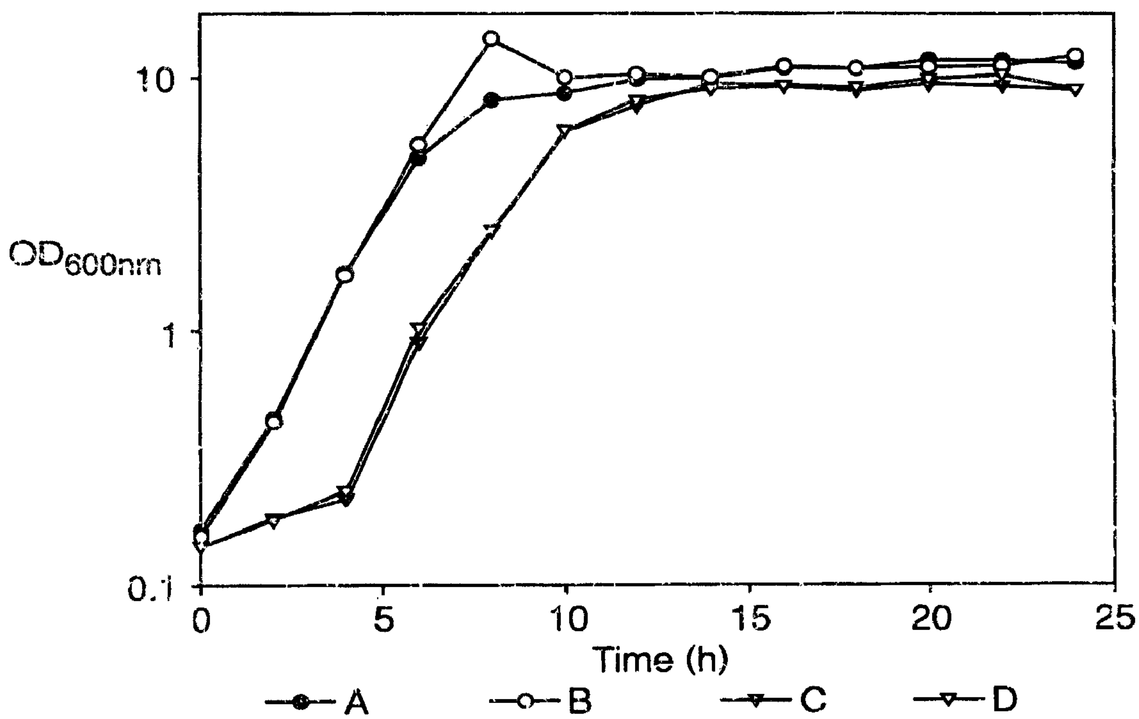
FIG. 8 shows the growth curve of *E. coli* RV308 pMTL1015-cpg-PA-wt (A and B) and pMTL1015-cpg-PA-synt [C and D) in Hy-soy based semi-defined medium, Shake-flask culture.
Figure 9:
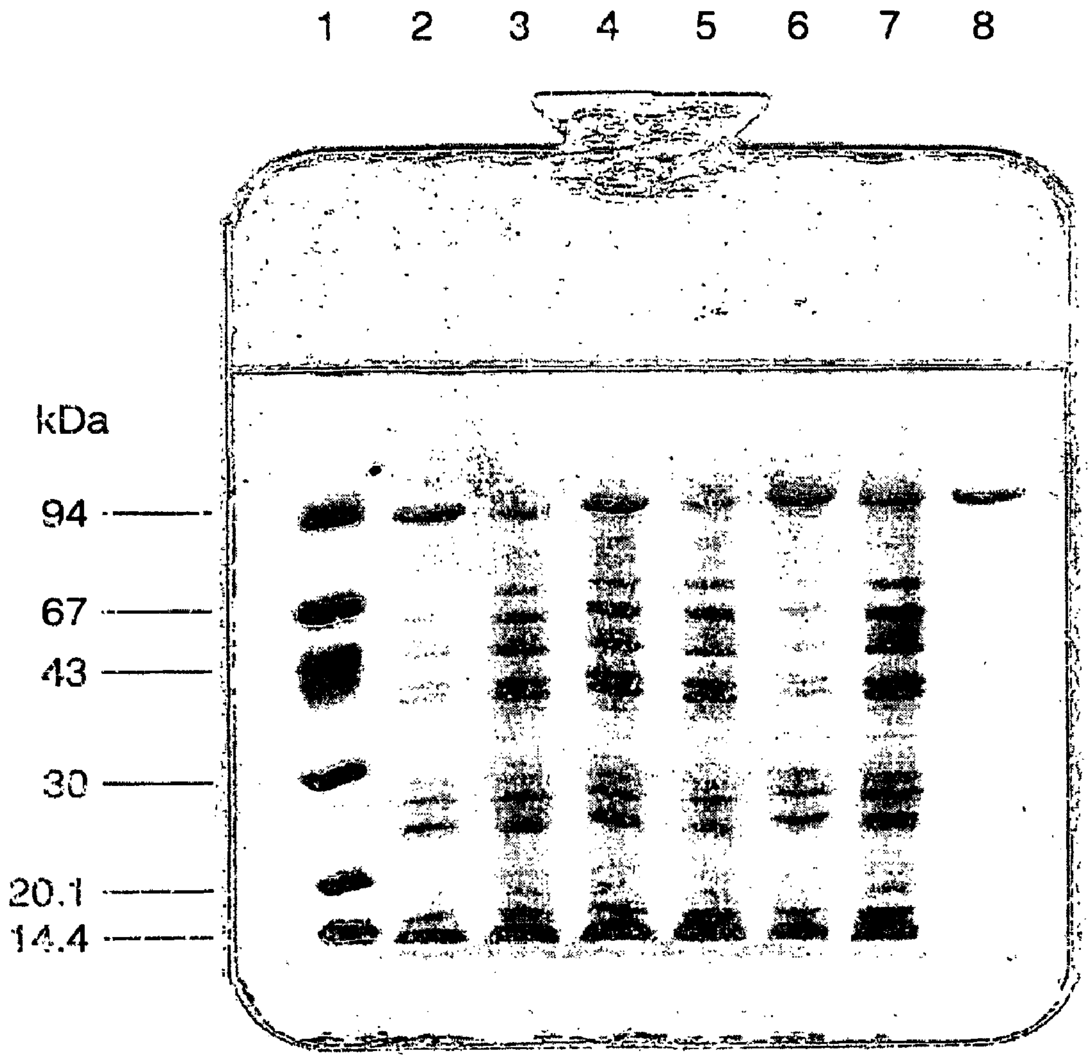
FIG. 9 shows SDS-PAGE (12.5% PHAST-GEL) of pMTL1015 clones expressing rPA in Shake-flask culture using Hy-soy based semi-defined medium. The key is as follows: —

The experiment described above (Example 2.1) was repeated using Hy-Soy based semi-defined medium in baffled flasks only. The growth curves (FIGS. 6, 7 & 8) show that lower growth rates and final cell densities were obtained in this medium compared to Terrific Broth and a lag phase of up to 8 h was obtained for the clones expressing the synthetic gene. rPA expression levels were generally lower than observed in phytone peptone-based Terrific Broth; however, a similar pattern of superior expression levels with clones expressing the synthetic gene compared with the wild-type gene was observed by SDS-PAGE (FIG. 9) and ELISA (Table 3).

TABLE 3

Comparison of rPA expression of *E. coli* pMTL1015 clones following growth in Hy-soy-based semi-defined medium.

| | | | | rPA (μg/mL culture) | |
|---|---|---|---|---|---|
| Clone Name | *E. coli* host | Sample time (h) | | *Gel estimate | ELISA |
| 5 pMTL1015-pelB-PA-wt | RV308 | 16 | | <100 | 50 |
| 6 pMTL1015-ompA-PA-wt | RV308 | 16 | | <100 | 64 |
| 7 pMTL1015-cpg-PA-wt | RV308 | 16 | | <100 | 56 |
| 8 pMTL1015-pelB-PA-synt | RV308 | 20 | | >100 | 224 |
| 9 pMTL1015-cpg-PA-synt | RV308 | 20 | | >100 | 170 |
| 10 pMTL1015-ompA-PA-synt | RV308 | 20 | | >100 | 189 |

*estimate of rPA concentration from SDS-PAGE by comparison with 100 μg/mL rPA standard

EXAMPLE 3

Fermenter Level Comparisons of rPA Expression

Evaluation of the following four down-selected clones in fermenter culture was continued:

*E. coli* RV308 pMTL1015-cpg-PA-synt

*E. coli* RV308 pMTL 015-ompA-PA-synt

*E. Coli* RV308 pMTL1015-ompA-PA-wt
*E. coli* DH5 pTrcK-pelB-PA-synt
Medium Selection 8 L fermentations were performed in each medium under conditions as previously described with DOT and pH control.

The growth curves obtained were similar to those seen previously with the same media (see FIG. 10), but the rPA yield from production medium (Run No: PRECRV0034: Table 4) was 2500 μg/mL by ELISA. This culture was fed with 80 mL of 50% glucose solution prior to glucose depletion in the culture. A growth curve for PRECRV0034 showing rPA production can be seen in FIG. 11, but data does not indicate whether the yield has reached a maximum when the culture was harvested.

In order to determine whether the improved rPA yields obtained for *E. coli* RV308 pMTL1015-cpg-PA-synt when cultured in production also occurred in the other two down-selected pMTL1015 clones, parallel fermentations were set up for all three strains under these conditions. However, the 80 mL of 50% glucose fed to the previous cultures was included from the start, raising the initial glucose concentration to 25 g/L.

*E. Coli* RV308 pMTL1015-cpg-PA-synt again gave a yield of 2500 μg/mL and *E. coli* RV308 pMTL1015-ompA-PA-synt yielded 2000 μg/mL (see PRECRV0038 and 0037, Table 4).

*E. coli* DH5a pTrcK-pelB-PA-synt was grown in PPTBgly at 8 L scale (see Table 4, PRECDH0013) with the exception that the $OD_{600}$ at induction was raised to 15. The rPA yield was not improved significantly over previous results although more biomass was produced with a higher final $OD_{600}$ of 26 at four hours post induction with IPTG.

Effect of Growth Temperature

Previous development programs incorporating the *E. coli* RV308 pMTL1015-cpg-host/vector system have indicated that expression of product is most efficient at temperatures between 25 and 30° C.

Assessment of the effect on yield and product stability of growth at lower temperatures of *E. coli* RV308 pMTL1015-cpg-PA-synt was made by culturing the strain in production medium, under conditions described above, at 30, 28 and 25° C. (see Table 4, PRECRV0039, 0040 and 0041 respectively).

The yields from production at the lower temperatures were lower than when grown at 30° C. The quality of the material produced did not improve with the reduction in temperature, with little or no reduction in minor impurity bands on SDS-PAGE/Western Blot.

Effect of Antibiotic Concentration

As a confirmation of the stability of the plasmid under reduced antibiotic selective pressure, *E. coli* RV308 pMTL1015-cpg-PA-synt was cultured in production medium, under conditions described above, with varying tetracycline concentration levels in the medium (see Table 4, PRECRV0042-0044). The tetracycline concentrations were 15 μg/mL (100%), 1.5 μg/mL (10%) and 0. The 20 seed cultures contained 15, 1.5 and 15 μg/mL respectively. Thus the fermenter with no added antibiotic relied on carryover from the secondary seed to supply any selective pressure, assuming no degradation of the tetracycline during the seed growth. The volume of seed transferred to the fermenter was 124 mL giving a nominal 0.23 μg/mL tetracycline in the fermentation medium at inoculation.

The yields in terms of final $OD_{600}$ and biomass were within the expected range, but the yield of rPA was slightly lower than expected for the 15 μg/mL control. The levels for the reduced antibiotic cultures were slightly higher. The stability of the pMTL1015-cpg-PA-synt plasmid was confirmed by tooth-picking final fermentation sample colony isolates onto selective (L-agar with 15 μg/mL tetracycline) and non-selective media. The results of 100, 98 and 96% growth on selective medium for 15, 1.5 and 0 μg/mL tetracycline fermentations respectively, indicate good stability under the conditions used. The viable count results for PPTBgluc2.5xYE fermentations are in the $2\times10^{10}$-$5\times10^{10}$ cfu/mL range.

TABLE 4

Summary Table of fermentations.

| Run no. | Clone | Medium (No.) | Seed $OD_{600}$ | Fermenter $OD_{600}$ | SDS-PAGE (mg/L) | ELISA (mg/L) |
|---|---|---|---|---|---|---|
| PRECRV0031 | pMTL1015-cpg-PA-synt | PPTBgluc | 12.6 | 34.8 | 100+ | 320 |
| PRECRV0032 | pMTL1015-cpg-PA-synt | PPTBgluc YEx1.5 | 13.0 | 44.2* | 100* | 84* |
| PRECRV0033 | pMTL1015-cpg-PA-synt | PPTBgluc YEx2 | 14.7 | 59.8 | 500++ | 1630 |
| PRECRV0034 | pMTL1015-cpg-PA-synt | PPTBgluc YEx2.5 | 14.2 | 71.6 | 500++ | 2500 |
| PRECDH0013 | pTrcK-pelB-PA-synt | PPTBgly | 2.67 | 26.2 | 100++ | 360-465 |
| PRECRV0036 | pMTL1015-ompA-PA-wt | PPTBgluc YEx2.5 | 14.8 | 43.9* | <100* | 90* |
| PRECRV0037 | pMTL1015-ompA-PA-synt | PPTBgluc YEx2.5 | 8.7 | 56.6 | 500++ | 2000 |
| PRECRV0038 | pMTL1015-cpg-PA-synt | PPTBgluc YEx2.5 | 14.7 | 62.6 | 500++ | 2500 |
| PRECRV0039 | pMTL1015-cpg-PA-synt | PPTBgluc YEx2.5 | 15.6 | 62.4 | 500++ | 2300 |
| PRECRV0040 | pMTL1015-cpg-PA-synt | PPTBgluc YEx2.5 | 15.6 | 62.2 | 500++ | 1600 |
| PRECRV0041 | pMTL1015-cpg-PA-synt | PPTBgluc YEx2.5 | 15.6 | 63.6 | 500++ | 1500 |

TABLE 4-continued

| Summary Table of fermentations. | | | | | | |
|---|---|---|---|---|---|---|
| Run no. | Clone | Medium (No.) | Seed $OD_{600}$ | Fermenter $OD_{600}$ | SDS-PAGE (mg/L) | ELISA (mg/L) |
| PRECRV0042 | pMTL1015-cpg-PA-synt | PPTBgluc YEx2.5 | 12.9 | 62.4 | 500++ | 1720 |
| PRECRV0043 | pMTL1015-cpg-PA-synt | PPTBgluc YEx2.5 | 13.2 | 66.4 | 500++ | 1800 |
| PRECRV0044 | pMTL1015-cpg-PA-synt | PPTBgluc YEx2.5 | 12.9 | 63.8 | 500++ | 2120 |

PPTB—Phytone Peptone-based Terrific Broth;
gluc—glucose;
YE—Yeast Extract

Selection of Production Strain

The results obtained to date for the clones investigated after the initial down-selection have shown that of the four, *E. coli* RV308 pMTL1015-cpg-PA-synt has, in most cases, shown the highest yield when compared with the other pMTL1015 clones under equivalent conditions.

The largest proportion of information generated has been from the *E. coli* RV308 pMTL1015-cpg-PA-synt clone, for both fermentation and DSP development and with yields in the 1.5-2.5 mg/mL range when production medium has been used. This has allowed the present applicant to select this clone as their preferred production organism for all future work.

Table 5 shows a summary of all cultures grown to date in production medium. The figures indicate that although 2500 μg/mL is achievable, a more realistic value for the yield is 2000 μg/mL.

TABLE 5

| Comparison of rPA levels relative to cell wet weight and optical density at harvest for cultures of *E. coli* RV308 pMTL1015-cpg-PA-synt containing 2.5x yeast extract. | | | | | |
|---|---|---|---|---|---|
| Run No. | Culture $OD_{600}$ | Cell Weight (g/L) | rPA Yield (mg/L) | mg rPA/ OD unit | mg rPA/g wet weight |
| PRECRV0030 | 69.8 | 85.8 | 1900 | 27.2 | 22.1 |
| PRECRV0034 | 71.6 | 102 | 2500 | 34.9 | 24.5 |
| PRECRV0038 | 62.6 | 86.5 | 2500 | 39.9 | 28.9 |
| PRECRV0039 | 62.4 | 77.5 | 2300 | 36.9 | 29.7 |
| PRECRV0040 | 62.2 | 80.4 | 1600 | 25.7 | 19.9 |
| PRECRV0041 | 63.6 | 98.5 | 1500 | 23.5 | 15.2 |
| PRECRV0042 | 62.4 | 89.1 | 1720 | 27.6 | 19.3 |
| PRECRV0043 | 66.4 | 88.8 | 1800 | 27.1 | 20.3 |
| PRECRV0044 | 63.8 | 83.9 | 2120 | 33.2 | 25.3 |
| MEAN | 65.0 | 88.1 | 1993 | 30.7 | 22.8 |

EXAMPLE 4

Upstream Process for rPA Production

Seed Banks for Clone of Interest—Clone pMTL1015-cpg-PA-synt Transformed into *E. coli* RV308 (ATCC 31608).

After sequence confirmation, a research seed bank was prepared by growth under selective pressure of tetracycline (15 mg/L) in soy peptone based L-broth (Phytone peptone 15 g/L, Bacto yeast extract 5 g/L, NaCl 5 g/L, pH 6.8-7.0). A single colony from a nutrient agar plate with tetracycline was inoculated into 100 mL medium in 500 mL baffled shake flasks and incubated at 30° C. and 150 rpm in a shaking incubator until $OD_{600}$ reached 1.5. The culture was then mixed with sterile 50% glycerol in growth medium (see above) to give a final glycerol concentration of 10%, and stored frozen at −80° C. as 1 mL aliquots in 1.8 mL cryovials.

A working research cell bank (WRCB) of 250 vials was prepared from above seed bank using the same conditions and medium for growth, however 250 μL of thawed vial contents were inoculated into 200 mL medium in 1000 mL baffled shake flasks.

Primary Seed Culture.

1 vial of WRCB was thawed and 100 μL inoculated into 10 mL soy peptone based L-Broth (see above) containing tetracycline at 15 mg/L in a 25 mL universal bottle, incubated at 30° C. with shaking at 150 rpm for 7-9 hours. This was a recovery step to ensure that the organism is viable and to give a more consistent seed production process. The final $OD_{600}$ of this step was 0.7-1.0.

Secondary Seed Culture.

This step produces the inoculum for the fermentation, and with a reasonably sized shaking incubator is capable of producing inocula sufficient for 5-250 L cultures in shake flasks. At 50 L scale, 200 μL of primary seed was inoculated into 200 mL of production medium in each of 5×1000 mL baffled shake flasks. The cultures were incubated with shaking at 150 rpm and 30° C. for 11-12 hours giving a final $OD_{600}$ of 13-16.

To prevent precipitation and caramelisation of some components during sterilisation by autoclaving, production medium is prepared by sterilising the complex component as a bulk and then adding the glucose, phosphate, magnesium and tetracycline aseptically as sterile solutions when the temperature of the components has fallen to lower than 25° C.

Production Fermentation

The seed cultures were then bulked and a volume sufficient to give a starting $OD_{600}$ of 0.2 in the fermenter was inoculated into 50 L production medium (see above) in a 72 L Applikon stirred tank fermenter. The complex medium components were sterilised, as a 40 L bulk, in situ at 121-123° C. for 30 minutes, cooled to below 25° C. and then supplemented with the remaining components to bring the total volume to 50 L.

The culture was then grown as a batch at a temperature of 30(±0.5)° C., pH 7.0 controlled by addition of sodium hydroxide and phosphoric acid. Dissolved oxygen tension was maintained at >40% by cascade step control of the following parameters: agitation (200-800 rpm), backpressure (3-7 psi), sparged airflow (25-50 Lpm) and oxygen supplementation (0-20 Lpm), in the order described.

When growth had ceased (12-14 hours), as measured by OD ($OD_{600}$ 60-65), the culture was chilled to below 15° C. and harvested by batch centrifugation (Sorvall RC-3B, H6000A rotor, 5000 rpm for 15 minutes). The harvested cell paste was stored at −20° C. until required for downstream processing. Product expression was assessed by ELISA assay from samples removed hourly from the culture.

EXAMPLE 5

Downstream Processing Steps

Cell Breakage

Approximately 4.5 kg of frozen cell paste harvest were suspended into a smooth paste with, initially, a minimum volume of 20 mM tris/1 mM EDTA pH 8.5. Further buffer was added to give an overall suspended volume of 16 L.

The suspended cells were broken by passing twice through an 'APV Gaulin' high-pressure homogeniser at a pressure of 7000 psi. The homogenate was then centrifuged for 1 hour at 5000 rpm in a 'Sorval' RC3 centrifuge. The pellet was discarded, and the supernatant (16 L approx) was retained.

Diafiltration

The centrifuged homogenate was diafiltered with 3 times its volume of purified water using a 'Millipore Pellicon' concentrator fitted with two 'Pall' OS030F07 0.5 $m^2$ 'Centrasette 2 Omega' suspended screen channel 30 kDa membranes. The concentrator was operated at a flow-rate of 17 L/min with a trans-membrane pressure of 1.6 Bar. The pH was adjusted to 8.0 and the conductivity to 2 mS/cm.

Anion Exchange and Chromatography

A 25 cm diameter chromatography column was packed with 5 L of 'Amersham' 'Q-Sepharose Fast Flow' anion exchanger to give a bed height of 10 cm. An industrial UV monitor was then connected to the effluent line. The column was operated at a flow-rate of 330 mL/min throughout. The packed column was washed with 10 L of water, then 5 L of 0.5 M sodium hydroxide, followed by purified water. 10 L of 0.5 M tris, pH 8.0, was pumped, and the column was then equilibrated with start buffer (20 mM tris, pH 8.0).

The diafiltrate was loaded, and then the loaded column was washed to baseline resolution with start buffer. The bound rPA was eluted with increasing salt steps of 10, 20, and 65 mM sodium chloride in start buffer, and the eluted peaks were collected in separate appropriately sized vessels. The eluates were assayed by SDS-PAGE and SEC-HPLC, and the fractions containing rPA at a purity of >40% were retained.

The column was regenerated by passing sequentially 10 L of 2 M sodium chloride, followed by 10 L of 1 M sodium acetate, 10 L of 0.5 M sodium hydroxide, then 10 L of 50 mM sodium hydroxide for storage.

Hydrophobic Charge Induction Chromatography

A 30 cm diameter column connected to UV monitor was packed with 20 L of 'Ciphergen' 'MEP HyperCel' at a flow rate of 7 L/min. Once packed, all further steps were performed at 800 mL/min. The column was washed with 5 L of 1 M sodium hydroxide with a contact time of no more than 40 min. The column was then washed with water, and then equilibrated with 20 L loading buffer (50 mM tris, pH 8.0). The Q pool (i.e. the pool from the previous Q chromatography step) was loaded, the column was washed with loading buffer to baseline, then the bound rPA was eluted with purified water. The collected product was assayed by SDS-PAGE and SEC-HPLC. The MEP pool (i.e. the pool from the MEP Hypercel column) was filtered through a 0.22 μm, 2000 $cm^2$ Pall 'Posidyne' filter. The column was regenerated with 10 L of 1 M sodium hydroxide, washed with purified water, and then stored in 0.2 μm filtered 50 mM sodium hydroxide.

Diafiltration and Formulation

The purified rPA was diafiltered using a 'Pall Centramate' medium screen 'Omega' 50 kDa cartridge (part No. $OSO_{350}C12$, 0.093 $m^2$). A flow-rate of 800 mL/min, and a trans-membrane pressure of 1.6 Bar were used. The diafiltration was performed versus 5 L of formulation buffer; 25 mM sodium phosphate, 150 mM sodium chloride, pH 8.0. A further filtration was performed using a 0.22 μm Pall 'Posidyne' filter of 5000 $cm^2$ area, and then the final product was dispensed into appropriate vials.

EXAMPLE 6

Construction of Variant Synthetic rPA Gene Constructs

The variant sequences set out in SEQ ID NOS: 9-105 are synthesized using solid phase chemical synthesis using nucleoside phosphoramidites. This is a well-established method in the field (see Brown T, Brown D J S. 1991. in Oligonucleotides and Analogues. A Practical Approach, ed. F Eckstein, pp. 1-24. Oxford: IRL). Typically, the synthetic gene sequences are constructed from a number of oligonucleotide sequences (40-80 bp in length) that have been generated using this chemical synthesis methodology. These oligonucleotide sequences represent both strands of the gene sequence and have their termini designed such that, post hybridization of complementary oligonucleotide pairs, the double stranded elements are bound by unique complementary overhanging sequences that enable their correct ordered assembly to generate the rPA gene "sub-fragment" sequences, typically ~500 base pairs in length. This is performed by mixing the hybridized oligonucleotide pairs with an appropriately cleaved plasmid vector (for example, a PUC or Invitrogen TOPO vector) with the addition of bacteriophage T4 ligase; both plasmid and rPA sub-fragments having compatible restriction site termini. These ligation products are used to transform competent *E. coli* host cells, generating *E. coli* clones for screening. Screening of clones is carried out using restriction enzyme analysis of isolated plasmid DNA, and selected clones authenticated by DNA sequence analysis of the cloned insert of the plasmid.

The final rPA-encoding gene product is then assembled via the isolation of the plasmid-borne "sub-fragment" DNA segments as specifically bound restriction fragments, which are then ligated together with an appropriately cleaved plasmid vector (for example, a PUC or Invitrogen TOPO vector) and the ligation mixture used to transform competent *E. coli* cells. The *E. coli* clones generated are then screened by restriction analysis and the entire cloned rPA-encoding gene sequence verified by DNA sequence analysis.

The synthetic rPA-encoding gene sequence may be generated with or without a 5'-leader sequence DNA moiety. If generated without a leader sequence, a unique Mscl restriction site is engineered at the 5'-end of the coding sequence as this will enable "in-frame" cloning to some leader sequences (e.g., ompA, pelB) which already reside in some commercially available *E. coli* expression plasmids. More typically, the choice of a larger range of leader sequences (e.gs, cpg2, ompA, pelB, phoA, ompT, lamb, omp F, beta lactamase, *Staphylococcus aureus* Protein A, *Bacillus subtilus* endoglucanase, murine RNAase, human growth hormone, enterotoxins ST-II, LT-A and LT-B) is incorporated in the original design and DNA synthesis strategy. This way, the leader sequence-rPA "cassette" is generated as a single genetic element that can then be sub-cloned into a variety of *E. coli* expression vectors for production of the rPA polypeptide product. By virtue of engineering a unique Mscl restriction site at the leader sequence-rPA-encoding gene sequence, different leader sequences may be substituted via simple sub-cloning procedures (Sambrook, J., Fritsch, E. F., Maniatis, T.

Molecular Cloning: a Laboratory Manual, $2^{nd}$ Ed. 1989. Cold Spring Harbour Laboratory Press).

EXAMPLE 7

Expression of Variant Synthetic rPA Gene CONSTRUCTS

The rPA gene encoding sequences depicted in SEQ ID NOs: 9 to 105 are cloned as leader sequence-rPA sequence "cassettes" into *E. coli* expression plasmids.

Cloning of these leader sequence-rPA sequence "cassettes" is facilitated by virtue of unique restriction sites engineered at the 5'- and 3'-ends for compatibility with the *E. coli* expression vector of choice. Typically, this would be either a NdeI or NcoI restriction site at the 5-end as this facilitates optimal positioning of the ATG initiation (metheionine) codon to the vector borne ribosome binding site (RBS) to enable efficient translation initiation of the RNA message originating from the expression vector moiety of the constructs. Restriction enzyme sites at the 3'-ends of the leader sequence-rPA sequence "cassettes" are variable and engineered to be compatible with choice of *E. coli* expression vector. The choice of available *E. coli* expression vectors is varied and examples include: pMTL series of vectors (proprietary to HPA), pET series (Novagen), pRSET, pET and pBAD series (Invitrogen), pQE series (Qiagen), pMal series (New England Biolabs), pPROTet series (Clontech), pGEX series (GE Healthcare), pEK/LIC series (EMD Biosciences), pIVEX series for cell-free expression (Roche) and bacteriophage Lambda gtll and Lambda ZAP expression vectors (Stratagene).

Expression of the rPA polypeptides elaborated from rPA-coding sequences SEQ ID Nos 9 to 105 is conducted in shake flasks or in fermenter bioreactors as described in Examples 2 and 3. The latter of these (i.e. the fermenter) attains levels of periplasmically located rPA polypeptide product at levels typically exceeding 2 grams per litre. Particularly good levels of rPA polypeptide (in the range 2.1-2.4 grams per litre) are achieved using SEQ ID NOs: 36, 46, 56, 66, 76, 86 and 96. SEQ ID NO: 36, for example, achieves a typical yield of at least 2.2 grams per litre.

Purification of the rPA polypeptide is achieved using the methods described in Example 5.

REFERENCES

Abrahmsen (1986). Nucl. Acids Res. 14: 7487-7500
Alldread et al. (1992). Gene 14: 139-143
Altschul (1990) J. Mol. Biol. 215: pgs. 403-410
Ausubel F. M. et al., Current Protocols in Molecular Biology, eds, Current Protocols, a joint venture between Greene Publishing Associates, In. And John Wiley & Sons, Inc. (1995 Supplement) Ausubel
Baillie, L. (2001), 91, pgs 609-613
Batra, S. (2001) Biochem. and Biophys. Res. Comm., 281, pgs 186-192
Better et al. (1988) Science 240:1041-1043
Bhatnagas, R. (2001) Critical Rev. in Microbiol., 27(3), 167-200
Bolivar et al. (1977) Gene 2: 95
Brehm et al. (1991) Appl. Microbiol. Biotechnol 36: 358-363
Brosius et al. (1981) J Mol Biol 148: 107-127
Chambers et al. (1988) Gene 68: 139-149
Chambers et al. (1992) FEMS Microbiol Letters 91: 277-284
Denefle et al. (1989) Gene 85: 499-510
Fujimoto et al. (1988) J. Biotechnol. 8: 77-86
Ghrayeb et al. (1984) EMBO J. 3: 2437-2442
Gray et al. (1985) Gene 39: 247-254
Hoffman & Wright (1985) Proc. Nat. Acad. Sci. USA. 82: 5107-5111
Johnson et al. (1996) Protein Expression Purif. 7: 104-1123
Kadonaga et al. (1984) J Biol. Chem. 259: 2149-2154
Kanehisa (1984) Nuc. Acids Res. 12:203-213
Le Calvez et al. (1996) Gene 170: 51-55
Lei et al. (1987) J. Bacteriol. 169: 4379-4383
Little, S. F. (1986) Inf. and Immunol. vol. 52, No. 2, 509-512
Macyntyre & Henning (1990). Biochimmie 72: 157-167
Makrides (1996) Microbiological Reviews 60: 512-538
Maniatis et al. (1991) Molecular Cloning: A laboratory Manual. Cold Spring Harbor, N.Y., Cold Spring Harbor Laboratory Press
Michael et al. (1994) FEMS Microbiol. Letters 124: 195-202
Miller et al. (1983) Gene 24: 309-315
Minton et al. (1988) Focus 10: 56
Morioka-Fujimoto et al. (1991) J. Biol. Chem. 266: 1728-1732
Needleman & Wunsch (1970) J. Mol. Biol. 48: 443
Oka et al. (1985) Proc. Nat. Acad. Sci. USA. 82: 7212-7216
Pearson & Lipman (1988) Proc. Nat. Acad. Sci. USA 85: 2444
Price, B. M. (2001) Inf. and Immun., vol. 69, No. 7, 4509-4515
Proudfoot et al. (1996) J. Biol. Chem. 271: 2599-2603
Sambrook et al. (1989) Molecular Cloning: A laboratory Manual. Second Edition. Cold Spring Harbor Laboratory Press
Sambrook and Russell (2001) Molecular Cloning: A laboratory Manual. Third Edition. Cold Spring Harbor Laboratory Press
Schein et al. (1992) Biochem. J. 283: 137-144
Sharma et al. (1996) Protein Expression and Purification. 7, 33-38
Smith and Waterman (1981) Adv. Appl. Math. 2: 484
Sterne, M. (1939) Onderstepoort J. of Veterinary Science and Animal Industry, 13, 307-312
Tucker et al. (1983) Gene 24: 309-15
Villa-Komaroff et al. (1977) Proc. Nat. Acad. Sci. USA. 75: 3727-3731
Vodkin, M. et al. (1983) Cell, 34:693
Watson, (1984) Proc. Nat. Acad. Sci. USA. vol. 12: 5145
Welkos, S., et al. (1988) Gene, 69(2): 287
Wetmur and Davidson (1968) J. Mol. Biol. 31:349-370

---

The invention claimed is:

1. An isolated polynucleotide having at least 90% sequence identity to SEQ ID NO: 36, wherein the isolated polynucleotide is an rPA polynucleotide, with the proviso that the isolated polynucleotide does not comprise the nucleic acid sequence of SEQ ID NO: 1.

2. An isolated polynucleotide according to claim 1, having at least 93% sequence identity to SEQ ID NO: 36.

3. An isolated polynucleotide according to claim 1, having at least 95% sequence identity to SEQ ID NO: 36.

4. An isolated polynucleotide according to claim 1, having at least 90% sequence identity to a SEQ ID NO. selected from the group consisting of SEQ ID NOs: 46, 56, 66, 76, 86 and 96.

5. An isolated polynucleotide according to claim 1, comprising at least 1766 nucleotides.

6. An isolated polynucleotide according to claim 1, having at least 90% identity to SEQ ID NO: 1.

7. An isolated polynucleotide according to claim 1, further comprising a polynucleotide encoding a secretion sequence.

8. An isolated polynucleotide according to claim 7, wherein said secretion sequence is selected from ompA, ompT, ompF, pelB, phoA, lamB, beta lactamase, *staphylococcus aureus* protein A, *bacillus subtilis* endoglucanase, murine RNAse, human growth hormone, enterotoxin ST-II, LT-A or LT-B, and cpg.

9. An isolated polynucleotide according to claim 7, wherein said secretion sequence is for periplasmic translocation of the expressed polypeptide from a bacterial host cell cytoplasm.

10. An isolated polynucleotide according to claim 7, wherein said secretion sequence is for extracellular translocation of the expressed polypeptide from a bacterial host cell cytoplasm.

11. An isolated polynucleotide according to claim 9, wherein said secretion sequence is cleavable from the expressed polypeptide during periplasmic translocation.

12. An isolated polynucleotide according to claim 10, wherein said secretion sequence is cleavable from the expressed polypeptide during extracellular translocation.

13. An isolated polynucleotide according to claim 7, wherein the secretion sequence is a cpg leader sequence encoded by SEQ ID NO: 3.

14. An isolated polynucleotide according to claim 1, wherein the isolated polynucleotide has a 3' and a 5' end, and wherein the isolated polynucleotide has a codon encoding a methionine residue at the 5' end.

15. An isolated polynucleotide according to claim 1, having a nucleic acid sequence selected from SEQ ID NOs: 9-105.

16. An expression vector comprising the polynucleotide of claim 1.

17. An expression vector according to claim 16, comprising a promoter that is selected so as to ensure that an rPA polypeptide is highly expressed.

18. An expression vector according to claim 17, wherein said promoter is a malate dehydrogenase (mdh) promoter.

19. An expression vector according to claim 16, further comprising a selectable marker.

20. An expression vector according to claim 16, wherein said vector is selected from a pET vector, a pTrKHis vector and a pMTL vector.

21. An expression vector according to claim 16, wherein said vector expresses the polynucleotide in the absence of a chemical inducer.

22. A host cell comprising the expression vector according to claim 16.

23. A host cell according to claim 22, wherein said host is an *E. coli* cell.

24. A host cell according to claim 23, wherein said *E. coli* cell is *E. coli* RV308.

25. An isolated polynucleotide according to claim 1, having 91 to 99% sequence identity to SEQ ID NO: 1.

* * * * *

UNITED STATES PATENT AND TRADEMARK OFFICE

CERTIFICATE OF CORRECTION

PATENT NO. : 8,101,735 B2
APPLICATION NO. : 12/042150
DATED : January 24, 2012
INVENTOR(S) : John Brehm et al.

It is certified that error appears in the above-identified patent and that said Letters Patent is hereby corrected as shown below:

On Title Page 2, Item (56) Other Publications

Col. 1, line 13, please delete "juman" and insert --human--
Col. 2, line 57, please delete "at." and insert --al.--
Col. 2, line 58, please delete "colt" and insert --*coli*--

Signed and Sealed this
Twenty-seventh Day of May, 2014

Michelle K. Lee
*Deputy Director of the United States Patent and Trademark Office*

SEQUENCE LISTING

```
<160> NUMBER OF SEQ ID NOS: 111

<210> SEQ ID NO 1
<211> LENGTH: 2208
```

<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: modified rPA gene sequence

<400> SEQUENCE: 1

```
gaagtgaaac aggagaaccg tctgctgaac gaaagcgaat ctagctctca gggcctgctg     60
ggctactatt tcagcgatct gaactttcag gcaccgatgg ttgtgacctc tagcacgacc    120
ggcgatctga gcattccgag cagcgaactg gagaacattc cgagcgagaa ccagtacttt    180
cagtctgcga tttggagcgg cttcatcaaa gtgaagaaaa gcgatgagta tacctttgcg    240
acgtctgcgg ataaccatgt gaccatgtgg gtggacgatc aggaagtgat caacaaagcg    300
agcaacagca acaagattcg cctggagaag ggtcgcctgt atcagatcaa gattcagtat    360
cagcgcgaga atccgaccga gaaaggcctg gatttcaaac tgtactggac cgatagccag    420
aacaagaaag aagtgattag ctctgataac ctgcaactgc cggaactgaa acagaagagc    480
agcaacagcc gcaagaaacg cagcacctct gcaggcccga ccgttccaga tcgcgacaac    540
gatggcattc cggacagcct ggaagtggaa ggttataccg ttgatgtgaa gaacaaacgc    600
acctttctga gcccgtggat tagcaacatt catgagaaga aaggcctgac caagtacaaa    660
agcagcccgg agaagtggag caccgcgagc gatccgtata gcgactttga gaaagtgacc    720
ggccgcattg ataagaacgt gagcccggaa gcgcgtcacc cactggttgc agcgtatccg    780
attgtgcatg ttgacatgga gaacatcatt ctgagcaaga acgaagatca gagcacccag    840
aacacggata gccagacccg cacgatcagc aagaacacca gcacgagccg tacccatacc    900
agcgaagtgc atggcaatgc ggaagtgcat gcgagcttct ttgacattgg tggcagcgtg    960
agcgcgggct tcagcaacag caacagcagc accgtggcga ttgatcatag cctgagcctg   1020
gcgggcgaac gtacctgggc ggaaaccatg ggcctgaaca cggcggatac ggcacgtctg   1080
aatgcgaaca ttcgctatgt gaacaccggt accgcgccaa tctataacgt tctgccgacc   1140
acgagcctgg tgctgggcaa gaatcagacc ctggcgacca tcaaagcgaa agagaaccag   1200
ctgtctcaga ttctggcacc gaacaactac tatccgagca agaacctggc accgattgca   1260
ctgaatgcgc aggatgactt cagcagcacc ccgatcacca tgaactacaa tcagtttctg   1320
gagctggaga agaccaaaca actgcgcctg gataccgatc aggtgtatgg caacattgcg   1380
acctacaact ttgagaacgg ccgcgttcgc gtggataccg gtagcaactg gtctgaagtg   1440
ctgccgcaga ttcaggaaac gaccgcgcgc atcatcttca acggcaaaga tctgaacctg   1500
gtggaacgtc gcatcgcggc agtgaaccca tctgatccac tggaaacgac caaaccggac   1560
atgaccctga aagaagcgct gaagattgca tttggcttca acgaaccgaa tggcaacctg   1620
cagtatcagg gcaaagacat caccgagttt gacttcaact ttgatcaaca gacctctcag   1680
aacatcaaga accagctggc agaactgaat gcgaccaaca tctacaccgt gctggacaag   1740
atcaaactga acgcaaagat gaacattctg attcgtgaca aacgcttcca ctatgatcgt   1800
aacaacattg cggtgggtgc agatgaaagc gttgtgaaag aagcgcatcg tgaagtgatc   1860
aactctagca ccgaaggcct gctgctgaac attgacaaag acatccgtaa gattctgagc   1920
ggctacattg tggagattga agataccgaa ggtctgaaag aagtgatcaa cgatcgctat   1980
gacatgctga acatctctag cctgcgccag gatggcaaga ccttcattga cttcaagaag   2040
tacaacgaca aactgccgct gtacatcagc aatccgaact acaaagtgaa cgtgtatgcg   2100
```

gtgaccaaag agaacaccat cattaaccca agcgagaatg gcgataccag caccaacggc 2160
atcaagaaga ttctgatctt cagcaagaaa ggctatgaga ttggctaa 2208

<210> SEQ ID NO 2
<211> LENGTH: 2208
<212> TYPE: DNA
<213> ORGANISM: Bacillusanthracis

<400> SEQUENCE: 2
gaagttaaac aggagaaccg gttattaaat gaatcagaat caagttccca ggggttacta 60
ggatactatt ttagtgattt gaattttcaa gcacccatgg tggttacctc ttctactaca 120
ggggatttat ctattcctag ttctgagtta gaaaatattc catcggaaaa ccaatatttt 180
caatctgcta tttggtcagg atttatcaaa gttaagaaga gtgatgaata tacatttgct 240
acttccgctg ataatcatgt aacaatgtgg gtagatgacc aagaagtgat taataaagct 300
tctaattcta acaaaatcag attagaaaaa ggaagattat atcaaataaa aattcaatat 360
caacgagaaa atcctactga aaaaggattg gatttcaagt tgtactggac cgattctcaa 420
aataaaaaag aagtgatttc tagtgataac ttacaattgc cagaattaaa acaaaaatct 480
tcgaactcaa gaaaaaagcg aagtacaagt gctggaccta cggttccaga ccgtgacaat 540
gatggaatcc ctgattcatt agaggtagaa ggatatacgg ttgatgtcaa aaataaaaga 600
acttttcttt caccatggat ttctaatatt catgaaaaga aaggattaac caaatataaa 660
tcatctcctg aaaaatggag cacggcttct gatccgtaca gtgatttcga aaaggttaca 720
ggacggattg ataagaatgt atcaccagag gcaagacacc cccttgtggc agcttatccg 780
attgtacatg tagatatgga gaatattatt ctctcaaaaa atgaggatca atccacacag 840
aatactgata gtcaaacgag aacaataagt aaaaatactt ctacaagtag gacacatact 900
agtgaagtac atggaaatgc agaagtgcat gcgtcgttct ttgatattgg tgggagtgta 960
tctgcaggat ttagtaattc gaattcaagt acggtcgcaa ttgatcattc actatctcta 1020
gcaggggaaa gaacttgggc tgaaacaatg ggtttaaata ccgctgatac agcaagatta 1080
aatgccaata ttagatatgt aaatactggg acggctccaa tctacaacgt gttaccaacg 1140
acttcgttag tgttaggaaa aaatcaaaca ctcgcgacaa ttaaagctaa ggaaaaccaa 1200
ttaagtcaaa tacttgcacc taataattat tatccttcta aaaacttggc gccaatcgca 1260
ttaaatgcac aagacgattt cagttctact ccaattacaa tgaattacaa tcaatttctt 1320
gagttagaaa aaacgaaaca attaagatta gatacggatc aagtatatgg gaatatagca 1380
acatacaatt ttgaaaatgg aagagtgagg gtggatacag gctcgaactg gagtgaagtg 1440
ttaccgcaaa ttcaagaaac aactgcacgt atcattttta atggaaaaga tttaaatctg 1500
gtagaaaggc ggatagcggc ggttaatcct agtgatccat tagaaacgac taaaccggat 1560
atgacattaa aagaagccct taaaatagca tttggattta acgaaccgaa tggaaactta 1620
caatatcaag ggaaagacat aaccgaattt gattttaatt tcgatcaaca aacatctcaa 1680
aatatcaaga atcagttagc ggaattaaac gcaactaaca tatatactgt attagataaa 1740
atcaaattaa atgcaaaaat gaatatttta ataagagata aacgttttca ttatgataga 1800
aataacatag cagttggggc ggatgagtca gtagttaagg aggctcatag agaagtaatt 1860
aattcgtcaa cagagggatt attgttaaat attgataagg atataagaaa aatattatca 1920
ggttatattg tagaaattga agatactgaa gggcttaaag aagttataaa tgacagatat 1980
gatatgttga atatttctag tttacggcaa gatggaaaaa catttataga ttttaaaaaa 2040
tataatgata aattaccgtt atatataagt aatcccaatt ataaggtaaa tgtatatgct 2100
gttactaaag aaaacactat tattaatcct agtgagaatg gggatactag taccaacggg 2160
atcaagaaaa ttttaatctt ttctaaaaaa ggctatgaga taggataa 2208

<210> SEQ ID NO 3
<211> LENGTH: 78
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: polynucleotide encoding cpg secretion sequence

<400> SEQUENCE: 3
catatgcgcc catccatcca ccgcacagcc atcgccgccg tgctggctac cgccttcgtg 60
gcgggcaccg ccctggcc 78

<210> SEQ ID NO 4
<211> LENGTH: 3527
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: plasmid pMTL1015

<400> SEQUENCE: 4
cagtaagacg ggtaagcctg ttgatgatac cgctgcctta ctgggtgcat tagccagtct 60
gaatgacctg tcacgggata tcccgaagtg gtcagactgg aaaatcagag ggcaggaact 120
gctgaacagc aaaaagtcag atagcaccac atagcagacc cgccataaaa cgccctgaga 180
agcccgtgac gggcttttct tgtattatgg gtagtttcct tgcatgaatc cataaaaggc 240
gcccaatacg caaaccgcct ctccccgcgc gttggagctt gcatgcaaat tctgcttaaa 300
agtaaattaa ttgttatcaa attgatgttg ttttggctga acggtagggt atattgtcac 360
cacctgttgg aatgttgcgc taatgcataa gcgactgtta attacgtaag ttaggttcct 420
gattacggca attaaatgca taaacgctaa acttgcgtga ctacacattc ttgagatgtg 480
gtcattgtaa acggcaattt tgtggattaa ggtcgcggca gcggagcaac atatcttagt 540
ttatcaatat aataaggagt ttcatatgac catgattacg aattcgagct cggtacccgg 600
ggatcctcta gagtcgacgt cacgcgtcca tggagatctc gaggcctgca ggcatgcaag 660
cttggcactg gccgtcgttt tacaacgtcg tgactgggaa aaccctggcg ttacccaact 720
taatcgcctt gcagcacatc ccccttttcgc gagctggcgt aatagcgaag aggcccgcac 780
cgatcgccct tcccaacagt tgcgcagcct gaatggcgaa tggcgccgat ggtagtgtgg 840
ggtctcccca tgcgagagta gggaactgcc aggcatcaaa taaaacgaaa ggctcagtcg 900
aaagactggg cctttcgttt tatctgttgt ttgtcggtga acgctctcct gagtaggaca 960
aatccgccgg gagcggattt gaacgttgcg aagcaacggc ccggagggtg gcgggcagga 1020
cgcccgccat aaactgccag gcatcaaatt aagcagaagg ccatcctgac ggatggcctt 1080
tttgcgtttc tacaaactct tttgtttatt tttctaaata cattcaaata tgtatccgct 1140
catgagacaa taaccctgat aaatgcttca ataatgatct gttaattcga gctcgcccaa 1200
ttctcatgtt tgacagctta tcatcgaata gctttaatgc ggtagtttat cacagttaaa 1260
ttgctaacgc agtcaggcac cgtgtatgaa atctaacaat gcgctcatcg tcatcctcgg 1320

-continued caccgtcacc ctggatgctg taggcatagg cttggttatg ccggtactgc cgggcctctt 1380
gcgggacatc gtccattccg acagcatcgc cagtcactat ggcgtgctgc tagcgctata 1440
tgcgttgatg caatttctat gcgcacccgt tctcggagca ctgtccgacc gctttggccg 1500
ccgcccagtc ctgctcgctt cgctacttgg agccactatc gactacgcga tcatggcgac 1560
cacacccgtc ctgtggattc tctacgccgg acgcatcgtg gccggcatca ccggcgccac 1620
aggtgcggtt gctggcgcct atatcgccga catcaccgat ggggaagatc gggctcgcca 1680
cttcgggctc atgagcgctt gtttcggcgt gggtatggtg gcaggccccg tggccggggg 1740
actgttgggc gccatctcct tgcacgcacc attccttgcg gcggcggtgc tcaacggcct 1800
caacctacta ctgggctgct tcctaatgca ggagtcgcat aagggagagc gtcgtccgat 1860
gcccttgaga gccttcaacc cagtcagctc cttccggtgg gcgcggggca tgactatcgt 1920
cgccgcactt atgactgtct tctttatcat gcaactcgta ggacaggtgc cggcagcgct 1980
ctgggtcatt ttcggcgagg accgctttcg ctggagcgcg acgatgatcg gcctgtcgct 2040
tgcggtattc ggaatcttgc acgccctcgc tcaagccttc gtcactggtc ccgccaccaa 2100
acgtttcggc gagaagcagg ccattatcgc cggcatggcg gccgacgcgc tgggctacgt 2160
cttgctggcg ttcgcgacgc gaggctggat ggccttcccc attatgattc ttctcgcttc 2220
cggcggcatc gggatgcccg cgttgcaggc catgctgtcc aggcaggtag atgacgacca 2280
tcagggacag cttcaaggat cgctcgcggc tcttaccagc ctaacttcga tcattggacc 2340
gctgatcgtc acggcgattt atgccgcctc ggcgagcaca tggaacgggt tggcatggat 2400
tgtaggcgcc gccctatacc ttgtctgcct ccccgcgttg cgtcgcggtg catggagccg 2460
ggccacctcg acctgaatgg aagccggcgg cacctcgcta acggattcac cactccaaga 2520
attggagcca atcaattctt gcggagaact gtgaatgcgc aaaccaaccc ttggcagaac 2580
atatccatcg cgtccgccat ctccagcagc cgcacgcggc gcatctcggg gggatcaact 2640
gatcaaaagg atctaggtga agatcctttt tgataatctc atgaccaaaa tcccttaacg 2700
tgagttttcg ttccactgag cgtcagaccc cgtagaaaag atcaaaggat cttcttgaga 2760 tcettttttt ctgcgcgtaa tctgctgctt gcaaacaaaa aaaccaccgc taccagcggt 2820
ggtttgtttg ccggatcaag agctaccaac tctttttccg aaggtaactg gcttcagcag 2880
agcgcagata ccaaatactg ttcttctagt gtagccgtag ttaggccacc acttcaagaa 2940
ctctgtagca ccgcctacat acctcgctct gctaatcctg ttaccagtgg ctgctgccag 3000
tggcgataag tcgtgtctta ccgggttgga ctcaagacga tagttaccgg ataaggcgca 3060
gcggtcgggc tgaacggggg gttcgtgcac acagcccagc ttggagcgaa cgacctacac 3120
cgaactgaga tacctacagc gtgagctatg agaaagcgcc acgcttcccg aagggagaaa 3180
ggcggacagg tatccggtaa gcggcagggt cggaacagga gagcgcacga gggagcttcc 3240
agggggaaac gcctggtatc tttatagtcc tgtcgggttt cgccacctct gacttgagcg 3300
tcgatttttg tgatgctcgt caggggggcg gagcctatgg aaaaacgcca gcaacgcggc 3360
ctttttacgg ttcctggcct tttgctggcc ttttgctcac atgttctttc ctgcgttatc 3420
ccctgattct gtggataacc gtattaccgc ctttgagtga gctgataccg ctcgccgcag 3480
ccgaacgacc gagcgcagcg agtcagtgag cgaggaagcg gaagagc 3527

<210> SEQ ID NO 5
<211> LENGTH: 735
<212> TYPE: PRT
<213> ORGANISM: Bacillusanthracis -continued

<400> SEQUENCE: 5

```
Glu Val Lys Gln Glu Asn Arg Leu Leu Asn Glu Ser Glu Ser Ser Ser
1               5                   10                  15

Gln Gly Leu Leu Gly Tyr Tyr Phe Ser Asp Leu Asn Phe Gln Ala Pro
            20                  25                  30

Met Val Val Thr Ser Ser Thr Thr Gly Asp Leu Ser Ile Pro Ser Ser
        35                  40                  45

Glu Leu Glu Asn Ile Pro Ser Glu Asn Gln Tyr Phe Gln Ser Ala Ile
    50                  55                  60

Trp Ser Gly Phe Ile Lys Val Lys Lys Ser Asp Glu Tyr Thr Phe Ala
65                  70                  75                  80

Thr Ser Ala Asp Asn His Val Thr Met Trp Val Asp Asp Gln Glu Val
                85                  90                  95

Ile Asn Lys Ala Ser Asn Ser Asn Lys Ile Arg Leu Glu Lys Gly Arg
            100                 105                 110

Leu Tyr Gln Ile Lys Ile Gln Tyr Gln Arg Glu Asn Pro Thr Glu Lys
        115                 120                 125

Gly Leu Asp Phe Lys Leu Tyr Trp Thr Asp Ser Gln Asn Lys Lys Glu
    130                 135                 140

Val Ile Ser Ser Asp Asn Leu Gln Leu Pro Glu Leu Lys Gln Lys Ser
145                 150                 155                 160

Ser Asn Ser Arg Lys Lys Arg Ser Thr Ser Ala Gly Pro Thr Val Pro
                165                 170                 175

Asp Arg Asp Asn Asp Gly Ile Pro Asp Ser Leu Glu Val Glu Gly Tyr
            180                 185                 190

Thr Val Asp Val Lys Asn Lys Arg Thr Phe Leu Ser Pro Trp Ile Ser
        195                 200                 205

Asn Ile His Glu Lys Lys Gly Leu Thr Lys Tyr Lys Ser Ser Pro Glu
    210                 215                 220

Lys Trp Ser Thr Ala Ser Asp Pro Tyr Ser Asp Phe Glu Lys Val Thr
225                 230                 235                 240

Gly Arg Ile Asp Lys Asn Val Ser Pro Glu Ala Arg His Pro Leu Val
                245                 250                 255

Ala Ala Tyr Pro Ile Val His Val Asp Met Glu Asn Ile Ile Leu Ser
            260                 265                 270

Lys Asn Glu Asp Gln Ser Thr Gln Asn Thr Asp Ser Gln Thr Arg Thr
        275                 280                 285

Ile Ser Lys Asn Thr Ser Thr Ser Arg Thr His Thr Ser Glu Val His
    290                 295                 300

Gly Asn Ala Glu Val His Ala Ser Phe Phe Asp Ile Gly Gly Ser Val
305                 310                 315                 320

Ser Ala Gly Phe Ser Asn Ser Asn Ser Ser Thr Val Ala Ile Asp His
                325                 330                 335

Ser Leu Ser Leu Ala Gly Glu Arg Thr Trp Ala Glu Thr Met Gly Leu
            340                 345                 350

Asn Thr Ala Asp Thr Ala Arg Leu Asn Ala Asn Ile Arg Tyr Val Asn
        355                 360                 365

Thr Gly Thr Ala Pro Ile Tyr Asn Val Leu Pro Thr Thr Ser Leu Val
    370                 375                 380

Leu Gly Lys Asn Gln Thr Leu Ala Thr Ile Lys Ala Lys Glu Asn Gln
385                 390                 395                 400

Leu Ser Gln Ile Leu Ala Pro Asn Asn Tyr Tyr Pro Ser Lys Asn Leu
                405                 410                 415
```

```
Ala Pro Ile Ala Leu Asn Ala Gln Asp Asp Phe Ser Ser Thr Pro Ile
            420                 425                 430

Thr Met Asn Tyr Asn Gln Phe Leu Glu Leu Glu Lys Thr Lys Gln Leu
        435                 440                 445

Arg Leu Asp Thr Asp Gln Val Tyr Gly Asn Ile Ala Thr Tyr Asn Phe
    450                 455                 460

Glu Asn Gly Arg Val Arg Val Asp Thr Gly Ser Asn Trp Ser Glu Val
465                 470                 475                 480

Leu Pro Gln Ile Gln Glu Thr Thr Ala Arg Ile Ile Phe Asn Gly Lys
                485                 490                 495

Asp Leu Asn Leu Val Glu Arg Arg Ile Ala Ala Val Asn Pro Ser Asp
            500                 505                 510

Pro Leu Glu Thr Thr Lys Pro Asp Met Thr Leu Lys Glu Ala Leu Lys
        515                 520                 525

Ile Ala Phe Gly Phe Asn Glu Pro Asn Gly Asn Leu Gln Tyr Gln Gly
    530                 535                 540

Lys Asp Ile Thr Glu Phe Asp Phe Asn Phe Asp Gln Gln Thr Ser Gln
545                 550                 555                 560

Asn Ile Lys Asn Gln Leu Ala Glu Leu Asn Ala Thr Asn Ile Tyr Thr
                565                 570                 575

Val Leu Asp Lys Ile Lys Leu Asn Ala Lys Met Asn Ile Leu Ile Arg
            580                 585                 590

Asp Lys Arg Phe His Tyr Asp Arg Asn Asn Ile Ala Val Gly Ala Asp
        595                 600                 605

Glu Ser Val Val Lys Glu Ala His Arg Glu Val Ile Asn Ser Ser Thr
    610                 615                 620

Glu Gly Leu Leu Leu Asn Ile Asp Lys Asp Ile Arg Lys Ile Leu Ser
625                 630                 635                 640

Gly Tyr Ile Val Glu Ile Glu Asp Thr Glu Gly Leu Lys Glu Val Ile
                645                 650                 655

Asn Asp Arg Tyr Asp Met Leu Asn Ile Ser Ser Leu Arg Gln Asp Gly
            660                 665                 670

Lys Thr Phe Ile Asp Phe Lys Lys Tyr Asn Asp Lys Leu Pro Leu Tyr
        675                 680                 685

Ile Ser Asn Pro Asn Tyr Lys Val Asn Val Tyr Ala Val Thr Lys Glu
    690                 695                 700

Asn Thr Ile Ile Asn Pro Ser Glu Asn Gly Asp Thr Ser Thr Asn Gly
705                 710                 715                 720

Ile Lys Lys Ile Leu Ile Phe Ser Lys Lys Gly Tyr Glu Ile Gly
                725                 730                 735


<210> SEQ ID NO 6
<211> LENGTH: 736
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: rPA protein sequence with N-terminal
      methionine

<400> SEQUENCE: 6

Met Glu Val Lys Gln Glu Asn Arg Leu Leu Asn Glu Ser Glu Ser Ser
1               5                   10                  15

Ser Gln Gly Leu Leu Gly Tyr Tyr Phe Ser Asp Leu Asn Phe Gln Ala
            20                  25                  30
```

-continued

```
Pro Met Val Val Thr Ser Ser Thr Thr Gly Asp Leu Ser Ile Pro Ser
        35                  40                  45

Ser Glu Leu Glu Asn Ile Pro Ser Glu Asn Gln Tyr Phe Gln Ser Ala
    50                  55                  60

Ile Trp Ser Gly Phe Ile Lys Val Lys Lys Ser Asp Glu Tyr Thr Phe
65                  70                  75                  80

Ala Thr Ser Ala Asp Asn His Val Thr Met Trp Val Asp Asp Gln Glu
                85                  90                  95

Val Ile Asn Lys Ala Ser Asn Ser Asn Lys Ile Arg Leu Glu Lys Gly
            100                 105                 110

Arg Leu Tyr Gln Ile Lys Ile Gln Tyr Gln Arg Glu Asn Pro Thr Glu
        115                 120                 125

Lys Gly Leu Asp Phe Lys Leu Tyr Trp Thr Asp Ser Gln Asn Lys Lys
    130                 135                 140

Glu Val Ile Ser Ser Asp Asn Leu Gln Leu Pro Glu Leu Lys Gln Lys
145                 150                 155                 160

Ser Ser Asn Ser Arg Lys Lys Arg Ser Thr Ser Ala Gly Pro Thr Val
                165                 170                 175

Pro Asp Arg Asp Asn Asp Gly Ile Pro Asp Ser Leu Glu Val Glu Gly
            180                 185                 190

Tyr Thr Val Asp Val Lys Asn Lys Arg Thr Phe Leu Ser Pro Trp Ile
        195                 200                 205

Ser Asn Ile His Glu Lys Lys Gly Leu Thr Lys Tyr Lys Ser Ser Pro
    210                 215                 220

Glu Lys Trp Ser Thr Ala Ser Asp Pro Tyr Ser Asp Phe Glu Lys Val
225                 230                 235                 240

Thr Gly Arg Ile Asp Lys Asn Val Ser Pro Glu Ala Arg His Pro Leu
                245                 250                 255

Val Ala Ala Tyr Pro Ile Val His Val Asp Met Glu Asn Ile Ile Leu
            260                 265                 270

Ser Lys Asn Glu Asp Gln Ser Thr Gln Asn Thr Asp Ser Gln Thr Arg
        275                 280                 285

Thr Ile Ser Lys Asn Thr Ser Thr Ser Arg Thr His Thr Ser Glu Val
    290                 295                 300

His Gly Asn Ala Glu Val His Ala Ser Phe Phe Asp Ile Gly Gly Ser
305                 310                 315                 320

Val Ser Ala Gly Phe Ser Asn Ser Asn Ser Ser Thr Val Ala Ile Asp
                325                 330                 335

His Ser Leu Ser Leu Ala Gly Glu Arg Thr Trp Ala Glu Thr Met Gly
            340                 345                 350

Leu Asn Thr Ala Asp Thr Ala Arg Leu Asn Ala Asn Ile Arg Tyr Val
        355                 360                 365

Asn Thr Gly Thr Ala Pro Ile Tyr Asn Val Leu Pro Thr Thr Ser Leu
    370                 375                 380

Val Leu Gly Lys Asn Gln Thr Leu Ala Thr Ile Lys Ala Lys Glu Asn
385                 390                 395                 400

Gln Leu Ser Gln Ile Leu Ala Pro Asn Asn Tyr Tyr Pro Ser Lys Asn
                405                 410                 415

Leu Ala Pro Ile Ala Leu Asn Ala Gln Asp Asp Phe Ser Ser Thr Pro
            420                 425                 430

Ile Thr Met Asn Tyr Asn Gln Phe Leu Glu Leu Glu Lys Thr Lys Gln
        435                 440                 445

Leu Arg Leu Asp Thr Asp Gln Val Tyr Gly Asn Ile Ala Thr Tyr Asn
    450                 455                 460
```

```
Phe Glu Asn Gly Arg Val Arg Val Asp Thr Gly Ser Asn Trp Ser Glu
465                 470                 475                 480

Val Leu Pro Gln Ile Gln Glu Thr Thr Ala Arg Ile Ile Phe Asn Gly
                485                 490                 495

Lys Asp Leu Asn Leu Val Glu Arg Arg Ile Ala Ala Val Asn Pro Ser
            500                 505                 510

Asp Pro Leu Glu Thr Thr Lys Pro Asp Met Thr Leu Lys Glu Ala Leu
        515                 520                 525

Lys Ile Ala Phe Gly Phe Asn Glu Pro Asn Gly Asn Leu Gln Tyr Gln
    530                 535                 540

Gly Lys Asp Ile Thr Glu Phe Asp Phe Asn Phe Asp Gln Gln Thr Ser
545                 550                 555                 560

Gln Asn Ile Lys Asn Gln Leu Ala Glu Leu Asn Ala Thr Asn Ile Tyr
                565                 570                 575

Thr Val Leu Asp Lys Ile Lys Leu Asn Ala Lys Met Asn Ile Leu Ile
            580                 585                 590

Arg Asp Lys Arg Phe His Tyr Asp Arg Asn Asn Ile Ala Val Gly Ala
        595                 600                 605

Asp Glu Ser Val Val Lys Glu Ala His Arg Glu Val Ile Asn Ser Ser
    610                 615                 620

Thr Glu Gly Leu Leu Leu Asn Ile Asp Lys Asp Ile Arg Lys Ile Leu
625                 630                 635                 640

Ser Gly Tyr Ile Val Glu Ile Glu Asp Thr Glu Gly Leu Lys Glu Val
                645                 650                 655

Ile Asn Asp Arg Tyr Asp Met Leu Asn Ile Ser Ser Leu Arg Gln Asp
            660                 665                 670

Gly Lys Thr Phe Ile Asp Phe Lys Lys Tyr Asn Asp Lys Leu Pro Leu
        675                 680                 685

Tyr Ile Ser Asn Pro Asn Tyr Lys Val Asn Val Tyr Ala Val Thr Lys
    690                 695                 700

Glu Asn Thr Ile Ile Asn Pro Ser Glu Asn Gly Asp Thr Ser Thr Asn
705                 710                 715                 720

Gly Ile Lys Lys Ile Leu Ile Phe Ser Lys Lys Gly Tyr Glu Ile Gly
                725                 730                 735


<210> SEQ ID NO 7
<211> LENGTH: 2211
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: modified rPA gene sequence with 5' methionine-
      encoding codon

<400> SEQUENCE: 7

atggaagtga aacaggagaa ccgtctgctg aacgaaagcg aatctagctc tcagggcctg      60

ctgggctact atttcagcga tctgaacttt caggcaccga tggttgtgac ctctagcacg     120

accggcgatc tgagcattcc gagcagcgaa ctggagaaca ttccgagcga gaaccagtac     180

tttcagtctg cgatttggag cggcttcatc aaagtgaaga aaagcgatga gtataccttt     240

gcgacgtctg cggataacca tgtgaccatg tgggtggacg atcaggaagt gatcaacaaa     300

gcgagcaaca gcaacaagat tcgcctggag aagggtcgcc tgtatcagat caagattcag     360

tatcagcgcg agaatccgac cgagaaaggc ctggatttca aactgtactg gaccgatagc     420
```

-continued

```
cagaacaaga aagaagtgat tagctctgat aacctgcaac tgccggaact gaaacagaag    480

agcagcaaca gccgcaagaa acgcagcacc tctgcaggcc cgaccgttcc agatcgcgac    540

aacgatggca ttccggacag cctggaagtg gaaggttata ccgttgatgt gaagaacaaa    600

cgcacctttc tgagcccgtg gattagcaac attcatgaga agaaaggcct gaccaagtac    660

aaaagcagcc cggagaagtg gagcaccgcg agcgatccgt atagcgactt tgagaaagtg    720

accggccgca ttgataagaa cgtgagcccg gaagcgcgtc acccactggt tgcagcgtat    780

ccgattgtgc atgttgacat ggagaacatc attctgagca agaacgaaga tcagagcacc    840

cagaacacgg atagccagac ccgcacgatc agcaagaaca ccagcacgag ccgtacccat    900

accagcgaag tgcatggcaa tgcggaagtg catgcgagct tctttgacat tggtggcagc    960

gtgagcgcgg gcttcagcaa cagcaacagc agcaccgtgg cgattgatca tagcctgagc   1020

ctggcgggcg aacgtacctg ggcggaaacc atgggcctga acacggcgga tacggcacgt   1080

ctgaatgcga acattcgcta tgtgaacacc ggtaccgcgc caatctataa cgttctgccg   1140

accacgagcc tggtgctggg caagaatcag accctggcga ccatcaaagc gaaagagaac   1200

cagctgtctc agattctggc accgaacaac tactatccga gcaagaacct ggcaccgatt   1260

gcactgaatg cgcaggatga cttcagcagc accccgatca ccatgaacta caatcagttt   1320

ctggagctgg agaagaccaa acaactgcgc ctggataccg atcaggtgta tggcaacatt   1380

gcgacctaca actttgagaa cggccgcgtt cgcgtggata ccggtagcaa ctggtctgaa   1440

gtgctgccgc agattcagga aacgaccgcg cgcatcatct tcaacggcaa agatctgaac   1500

ctggtggaac gtcgcatcgc ggcagtgaac ccatctgatc cactggaaac gaccaaaccg   1560

gacatgaccc tgaaagaagc gctgaagatt gcatttggct tcaacgaacc gaatggcaac   1620

ctgcagtatc agggcaaaga catcaccgag tttgacttca actttgatca acagacctct   1680

cagaacatca agaaccagct ggcagaactg aatgcgacca acatctacac cgtgctggac   1740

aagatcaaac tgaacgcaaa gatgaacatt ctgattcgtg acaaacgctt ccactatgat   1800

cgtaacaaca ttgcggtggg tgcagatgaa agcgttgtga aagaagcgca tcgtgaagtg   1860

atcaactcta gcaccgaagg cctgctgctg aacattgaca aagacatccg taagattctg   1920

agcggctaca ttgtggagat tgaagatacc gaaggtctga aagaagtgat caacgatcgc   1980

tatgacatgc tgaacatctc tagcctgcgc caggatggca agaccttcat tgacttcaag   2040

aagtacaacg acaaactgcc gctgtacatc agcaatccga actacaaagt gaacgtgtat   2100

gcggtgacca aagagaacac catcattaac ccaagcgaga atggcgatac cagcaccaac   2160

ggcatcaaga agattctgat cttcagcaag aaaggctatg agattggcta a            2211
```

```
<210> SEQ ID NO 8
<211> LENGTH: 2211
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Wild-type PA gene sequence plus 5' methionine-
      encoding codon

<400> SEQUENCE: 8

atggaagtta aacaggagaa ccggttatta aatgaatcag aatcaagttc ccaggggtta     60

ctaggatact attttagtga tttgaatttt caagcaccca tggtggttac ctcttctact    120

acaggggatt tatctattcc tagttctgag ttagaaaata ttccatcgga aaaccaatat    180
```

-continued

```
tttcaatctg ctatttggtc aggatttatc aaagttaaga agagtgatga atatacattt    240

gctacttccg ctgataatca tgtaacaatg tgggtagatg accaagaagt gattaataaa    300

gcttctaatt ctaacaaaat cagattagaa aaaggaagat tatatcaaat aaaaattcaa    360

tatcaacgag aaaatcctac tgaaaaagga ttggatttca agttgtactg gaccgattct    420

caaaataaaa aagaagtgat ttctagtgat aacttacaat tgccagaatt aaaacaaaaa    480

tcttcgaact caagaaaaaa gcgaagtaca agtgctggac ctacggttcc agaccgtgac    540

aatgatggaa tccctgattc attagaggta gaaggatata cggttgatgt caaaaataaa    600

agaacttttc tttcaccatg gatttctaat attcatgaaa agaaaggatt aaccaaatat    660

aaatcatctc ctgaaaaatg gagcacggct tctgatccgt acagtgattt cgaaaaggtt    720

acaggacgga ttgataagaa tgtatcacca gaggcaagac accccttgt ggcagcttat     780

ccgattgtac atgtagatat ggagaatatt attctctcaa aaaatgagga tcaatccaca    840

cagaatactg atagtcaaac gagaacaata agtaaaaata cttctacaag taggacacat    900

actagtgaag tacatggaaa tgcagaagtg catgcgtcgt tctttgatat tggtgggagt    960

gtatctgcag gatttagtaa ttcgaattca agtacggtcg caattgatca ttcactatct   1020

ctagcagggg aaagaacttg ggctgaaaca atgggtttaa ataccgctga tacagcaaga   1080

ttaaatgcca atattagata tgtaaatact gggacggctc caatctacaa cgtgttacca   1140

acgacttcgt tagtgttagg aaaaaatcaa acactcgcga caattaaagc taaggaaaac   1200

caattaagtc aaatacttgc acctaataat tattatcctt ctaaaaactt ggcgccaatc   1260

gcattaaatg cacaagacga tttcagttct actccaatta caatgaatta caatcaattt   1320

cttgagttag aaaaaacgaa acaattaaga ttagatacgg atcaagtata tgggaatata   1380

gcaacataca attttgaaaa tggaagagtg agggtggata caggctcgaa ctggagtgaa   1440

gtgttaccgc aaattcaaga aacaactgca cgtatcattt ttaatggaaa agatttaaat   1500

ctggtagaaa ggcggatagc ggcggttaat cctagtgatc cattagaaac gactaaaccg   1560

gatatgacat taaaagaagc ccttaaaata gcatttggat ttaacgaacc gaatggaaac   1620

ttacaatatc aagggaaaga cataaccgaa tttgatttta atttcgatca acaaacatct   1680

caaaatatca agaatcagtt agcggaatta aacgcaacta acatatatac tgtattagat   1740

aaaatcaaat taaatgcaaa aatgaatatt ttaataagag ataaacgttt tcattatgat   1800

agaaataaca tagcagttgg ggcggatgag tcagtagtta aggaggctca tagagaagta   1860

attaattcgt caacagaggg attattgtta aatattgata aggatataag aaaaatatta   1920

tcaggttata ttgtagaaat tgaagatact gaagggctta aagaagttat aaatgacaga   1980

tatgatatgt tgaatatttc tagtttacgg caagatggaa aaacatttat agattttaaa   2040

aaatataatg ataaattacc gttatatata agtaatccca attataaggt aaatgtatat   2100

gctgttacta aagaaaacac tattattaat cctagtgaga atggggatac tagtaccaac   2160

gggatcaaga aaattttaat cttttctaaa aaaggctatg agataggata a            2211
```

<210> SEQ ID NO 9
<211> LENGTH: 2205
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Sequence variant (99% identity) of SEQ ID No 1

<400> SEQUENCE: 9
gaagtgaaac aggagaaccg tctgctgaac gaaagcgaat ctagctctca gggcctgctg 60
ggctactatt ttagcgatct gaactttcag gcaccgatgg ttgtgacctc tagcacgacc 120
ggcgacctga gcattccgag cagcgaactg gagaacattc cgagcgagaa ccagtacttt 180
cagtctgcga tttggagcgg cttcatcaaa gtgaagaaaa gcgatgagta tacctttgcg 240
acgtctgcgg ataaccatgt gaccatgtgg gtggacgatc aggaagtgat caacaaagcg 300
agcaacagca acaagattcg cctggagaag ggtcgcctgt atcagatcaa gattcagtat 360
cagcgcgaga atccgaccga gaaaggcctg gatttcaaac tgtactggac cgatagccag 420
aacaaaaaag aagtgattag ctctgataac ctgcaactgc cggaactgaa acagaagagc 480
agcaacagcc gcaagaaacg cagcacctct gcaggcccga ccgttccaga tcgcgacaac 540
gatggcattc cggacagcct ggaagtggaa ggttataccg ttgatgtgaa gaacaaacgt 600
acctttctga gcccgtggat tagcaacatt catgagaaga aaggcctgac caagtacaaa 660
agcagcccgg agaagtggag caccgcgagc gatccgtata gcgacttcga gaaagtgacc 720
ggccgcattg ataagaacgt gagcccggaa gcgcgccacc cactggttgc agcgtatccg 780
attgtgcatg ttgacatgga gaacatcatt ctgagcaaga acgaagacca gagcacccag 840
aacacggata gccagacccg cacgatcagc aagaacacca gcacgagccg cacccatacc 900
agcgaagtgc atggcaatgc ggaagtgcat gcgagcttct ttgacattgg tggcagcgtg 960
agcgcgggct tcagcaacag caacagcagc accgtggcga ttgatcatag cctgagcctg 1020
gcgggcgaac gtacctgggc ggaaaccatg ggcctgaaca cggcggatac ggcacgtctg 1080
aatgcgaaca ttcgctatgt gaacaccggt accgcgccaa tctataacgt gctgccgacc 1140
acgagcctgg tgctgggcaa gaatcagacc ctggcgacca tcaaagcgaa agagaaccag 1200
ctgtctcaga ttctggcacc gaacaactac tatccgagca agaacctggc accgattgca 1260
ctgaatgcgc aggatgactt cagcagcacc ccgatcacca tgaactacaa tcagtttctg 1320
gagctggaga agaccaaaca actgcgcctg gataccgatc aggtttatgg caacattgcg 1380
acctacaact ttgagaacgg ccgcgttcgc gtggataccg gtagcaactg gtctgaagtg 1440
ctgccgcaga ttcaggaaac gaccgcgcgt atcattttca acggcaaaga tctgaacctg 1500
gtggaacgtc gtatcgcggc agtgaaccca tctgatccac tggaaacgac caaaccggac 1560
atgaccctga aagaagcact gaagattgca tttggcttca acgaaccgaa tggcaacctg 1620
cagtatcagg gcaaagacat caccgagttt gacttcaact ttgatcaaca gacctctcag 1680
aacatcaaga accagctggc agaactgaat gcgaccaaca tctacaccgt gctggacaag 1740
atcaaactga acgcgaagat gaacattctg attcgcgaca aacgcttcca ctatgatcgt 1800
aacaacatcg cggtgggtgc agatgaaagc gttgtgaagg aagcgcatcg tgaagtgatc 1860
aactctagca ccgaaggcct gctgctgaac attgataaag acatccgtaa gattctgagc 1920
ggctacattg tggagattga agacaccgaa ggtctgaaag aagtgatcaa cgatcgctat 1980
gatatgctga acatctctag cctgcgccag gatggcaaga ccttcattga tttcaagaag 2040
tacaacgaca aactgccgct gtacatcagc aatccgaact acaaagtgaa cgtgtatgcg 2100
gtgaccaaag agaacaccat cattaaccca agcgagaatg gcgataccag caccaacggc 2160
atcaagaaga ttctgatctt cagcaagaaa ggctatgaga ttggc 2205

<210> SEQ ID NO 10
<211> LENGTH: 2205
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Sequence variant (99% identity) of SEQ ID No 1

<400> SEQUENCE: 10

```
gaagtgaagc aggagaaccg tctgctgaac gaaagcgagt ctagctctca gggcctgctg     60
ggctactatt tcagcgatct gaactttcag gcaccgatgg ttgtgacctc tagcacgacc    120
ggcgatctga gcattccgag cagcgaactg gagaacattc cgagcgagaa ccagtacttt    180
cagtctgcga tttggagcgg cttcatcaaa gtgaagaaaa gcgatgagta tacctttgcg    240
acgtctgcgg ataaccatgt gaccatgtgg gtggacgatc aggaagtgat caacaaagca    300
agcaacagca acaagattcg cctggagaag ggtcgcctgt atcagatcaa gattcagtat    360
cagcgcgaga atccgaccga aaaaggcctg gatttcaaac tgtactggac cgatagccag    420
aacaagaaag aggtgattag ctctgataac ctgcaactgc cggaactgaa acagaagagc    480
agcaacagcc gcaagaaacg cagcacctct gcaggtccga ccgttccaga tcgcgacaac    540
gatggcattc cggacagcct ggaagtggaa ggctataccg ttgatgtgaa gaacaaacgc    600
acctttctga gcccgtggat tagcaacatt catgagaaga aaggcctgac caagtacaaa    660
agcagcccgg agaaatggag caccgcgagc gatccgtata gcgactttga gaaggtgacc    720
ggccgcattg ataagaacgt gagcccggaa gcgcgtcacc cactggttgc agcgtatccg    780
attgtgcatg ttgacatgga gaacatcatt ctgagcaaga acgaagatca gagcacccag    840
aacacggata gccagacccg cacgattagc aagaacacca gcacgagccg tacccatacc    900
agcgaagtgc atggcaatgc ggaagtgcat gcgagcttct ttgacattgg tggcagcgtg    960
agcgcgggct tcagcaacag caacagcagc accgtggcga ttgatcatag cctgagcctg   1020
gcgggcgaac gtacctgggc ggaaaccatg ggcctgaaca cggcggatac ggcacgtctg   1080
aatgcgaaca tccgctatgt gaacaccggt accgcgccaa tctataacgt tctgccgacc   1140
acgagcctgg tgctgggcaa gaatcagacc ctggcgacca tcaaagcgaa agagaaccag   1200
ctgtctcaga ttctggcacc gaacaactac tatccgagca agaacctggc gccgattgca   1260
ctgaatgcgc aggatgactt cagcagcacc ccgatcacca tgaactacaa tcagtttctg   1320
gagctggaaa agaccaaaca actgcgcctg gataccgatc aggtgtatgg caacattgcg   1380
acctacaact tcgagaacgg ccgcgttcgc gtggataccg gcagcaactg gtctgaagtg   1440
ctgccgcaga ttcaggaaac gaccgcgcgc atcatcttca acggcaaaga tctgaacctg   1500
gtggaacgtc gcatcgcggc agtgaaccca tctgatccac tggaaacgac caaaccggac   1560
atgaccctga aagaagcgct gaaaattgca tttggcttca acgagccgaa tggcaacctg   1620
cagtatcagg gcaaagacat caccgagttt gacttcaact ttgatcaaca gacctctcag   1680
aacatcaaga accagctggc agaactgaat gcgaccaaca tctacaccgt gctggacaag   1740
atcaaactga acgcaaagat gaacattctg attcgtgaca aacgctttca ctatgatcgt   1800
aacaacattg cggtgggtgc agatgaaagc gttgtgaaag aagcgcatcg tgaagtgatc   1860
aactctagca ccgaaggcct gctgctgaac attgacaaag acatccgtaa gattctgagc   1920
ggctacattg tggaaattga agataccgaa ggtctgaaag aagtgatcaa cgatcgctat   1980
gacatgctga acatctctag cctgcgccag gatggcaaga ccttcatcga cttcaagaag   2040
tacaacgaca aactgccgct gtacatcagc aatccgaact acaaagtgaa cgtgtatgcg   2100
gtgaccaaag agaacaccat cattaaccca agcgagaatg gcgataccag caccaacggc   2160
```

attaagaaga ttctgatctt cagcaagaaa ggttatgaga ttggc 2205

<210> SEQ ID NO 11
<211> LENGTH: 2205
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Sequence variant (99% identity) of SEQ ID NO. 1

<400> SEQUENCE: 11
gaagtgaaac aggagaaccg tctgctgaac gaaagcgaat ctagctctca gggcctgctg 60
ggctattatt tcagcgatct gaacttccag gcaccaatgg ttgtgacctc ttctacgacc 120
ggcgatctga gcattccgag cagcgaactg gagaacattc cgagcgagaa ccagtacttt 180
cagagcgcga tttggagcgg cttcatcaaa gtgaagaaaa gcgatgagta tacctttgcg 240
acgtctgcgg ataaccatgt gaccatgtgg gtggacgatc aggaagtgat caacaaagcg 300
agcaacagca acaagattcg cctggagaag ggtcgcctgt atcagatcaa gattcagtac 360
cagcgcgaga atccgaccga gaaaggcctg gatttcaaac tgtactggac cgatagccag 420
aacaagaaag aagtgattag ctctgataac ctgcaactgc cggaactgaa acagaagagc 480
agcaacagcc gcaagaaacg cagcacctct gcaggcccga ccgttccaga tcgcgacaac 540
gatggcattc cggacagcct ggaagtggaa ggttataccg tggatgtgaa gaacaaacgc 600
acctttctga gcccgtggat tagcaacatt catgagaaga aaggcctgac caagtacaaa 660
agcagcccgg agaagtggag caccgcgagc gatccgtata gcgactttga gaaagtgacc 720
ggccgcattg ataagaacgt gagcccggaa gcgcgtcacc cactggttgc agcgtatccg 780
attgtgcatg ttgacatgga gaacatcatt ctgagcaaga acgaagatca gagcacccag 840
aacacggata gccagacccg cacgatcagc aagaacacca gcacgagccg taccccatacc 900 agcgaagtgc atggcaatgc ggaagtgcat gcaagcttct ttgacattgg tggcagcgtg 960
agcgcgggct tcagcaacag caacagcagc accgtggcga ttgatcatag cctgagcctg 1020
gcgggcgaac gtacctgggc ggaaaccatg ggcctgaaca cggcggatac ggcacgtctg 1080
aatgcgaaca ttcgttatgt gaacaccggt accgcgccaa tctataacgt tctgccgacc 1140
acgagcctgg tgctgggcaa gaatcagacc ctggcgacca tcaaagcgaa agagaaccag 1200
ctgtctcaga ttctggcacc gaacaactac tatccgagca agaacctggc gccgattgca 1260
ctgaacgcgc aggatgactt cagcagcacc ccgatcacca tgaactacaa tcagtttctg 1320
gagctggaga agaccaaaca actgcgcctg gataccgatc aggtgtatgg caacattgcg 1380
acctacaact ttgagaacgg ccgcgttcgc gtggataccg gtagcaactg gtctgaagtg 1440
ctgccgcaga ttcaggaaac gaccgcgcgc atcatcttca acggcaaaga tctgaatctg 1500
gtggaacgcc gcatcgcggc agtgaaccca tctgatccgc tggaaacgac caaaccggat 1560
atgaccctga aagaagcgct gaagattgca tttggcttca acgaaccgaa tggcaacctg 1620
cagtatcagg gcaaagacat caccgagttt gacttcaact ttgatcaaca gacctctcag 1680
aacatcaaga accagctggc agaactgaat gcgaccaaca tctacaccgt gctggacaag 1740
atcaaactga acgcaaagat gaacattctg attcgtgaca aacgctttca ctatgatcgt 1800
aacaacattg cggtgggtgc agacgaaagc gttgtgaaag aagcgcatcg tgaagtgatc 1860
aactctagca ccgaaggcct gctgctgaac attgacaaag acatccgtaa gattctgagc 1920
ggctacattg tggagattga agataccgaa ggtctgaaag aagttatcaa cgatcgctat 1980
gacatgctga acatctctag cctgcgccag gatggcaaga ccttcattga cttcaagaag 2040
tacaacgaca aactgccgct gtacatcagc aatccgaact acaaagtgaa cgtgtatgcg 2100
gtgaccaaag agaacaccat cattaaccca agcgagaatg gcgataccag caccaacggc 2160
atcaagaaga ttctgatctt cagcaagaaa ggctatgaga ttggc 2205

<210> SEQ ID NO 12
<211> LENGTH: 2205
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Sequence variant (98% identity) of SEQ ID No 1

<400> SEQUENCE: 12
gaagtgaaac aggagaaccg tctgctgaac gaaagcgaat ctagctctca gggcctgctg 60
ggctactatt ttagcgatct gaactttcag gcaccgatgg ttgtgacctc tagcacgacc 120
ggcgacctga gcattccgag cagcgaactg gagaacattc cgagcgagaa ccagtacttt 180
cagtctgcga tttggagcgg cttcatcaaa gtgaagaaaa gcgatgagta tacctttgcg 240
acgtctgcgg ataaccatgt gaccatgtgg gtggacgatc aggaggtgat caacaaagcg 300
agcaacagca acaagattcg cctggagaag ggtcgcctgt atcagatcaa gattcagtat 360
cagcgcgaga atccgaccga gaaaggcctg gatttcaaac tgtactggac cgatagccag 420
aacaaaaaag aagtgattag ctctgataac ctgcaactgc cggaactgaa acagaagagc 480
agcaacagcc gcaagaaacg cagcaccagc gcaggcccga ccgttccaga tcgcgacaac 540
gatggcattc cggacagcct ggaagtggaa ggttataccg ttgatgtgaa gaacaaacgt 600
acctttctga gcccgtggat tagcaacatt catgagaaga agggcctgac caagtacaaa 660
agcagcccgg agaagtggag caccgcgtct gatccgtata gcgacttcga gaaagtgacc 720
ggccgcattg ataagaacgt gagcccggaa gcgcgccacc cactggttgc agcgtatccg 780
atcgtgcatg ttgacatgga gaacatcatt ctgagcaaga acgaagacca gagcacccag 840
aacacggata gccagacccg cacgatcagc aagaacacca gcacgagccg tacccatacc 900
agcgaagtgc atggcaatgc ggaagtgcat gcgagcttct tcgacattgg tggcagcgtg 960
agcgcgggct tcagcaacag caacagcagc accgtggcga ttgatcatag cctgagcctg 1020
gcgggcgaac gtacctgggc ggaaaccatg ggcctgaaca cggcggatac ggcacgtctg 1080
aatgcgaaca ttcgctatgt gaacaccggt accgcgccaa tctataacgt gctgccgacc 1140
acgagcctgg tgctgggcaa gaatcagacc ctggcgacca tcaaagcgaa agagaaccag 1200
ctgtctcaga ttctggcacc gaacaactac tatccgtcta aaaacctggc accgattgca 1260
ctgaatgcgc aggatgactt cagcagcacc ccgatcacca tgaactacaa tcagtttctg 1320
gagctggaga agaccaaaca actgcgcctg gataccgatc aggtttatgg caacattgcg 1380
acctacaact ttgagaacgg ccgcgttcgc gtggataccg gtagcaactg gtctgaagtg 1440
ctgccgcaga ttcaggaaac gaccgcgcgt atcattttta acggcaaaga tctgaacctg 1500
gtggaacgtc gtatcgcggc agtgaaccca agcgacccac tggaaacgac caagccggac 1560
atgaccctga aagaagcact gaagattgca tttggcttca acgaaccgaa tggcaacctg 1620
cagtatcagg gcaaagacat caccgagttt gacttcaact ttgatcaaca gacctctcag 1680
aacatcaaga accagctggc agaactgaat gcgaccaaca tctacaccgt gctggacaaa 1740

```
atcaaactga acgcgaagat gaacattctg attcgcgaca aacgcttcca ctatgatcgt   1800

aacaacatcg cggtgggtgc agatgaaagc gttgtgaagg aagcgcatcg tgaagtgatc   1860

aactctagca ccgaaggcct gctgctgaac attgataaag acattcgcaa gattctgagc   1920

ggctacattg tggagattga agataccgaa ggtctgaaag aagtgatcaa cgatcgctat   1980

gatatgctga acatctctag cctgcgccag gatggcaaga ccttcattga tttcaagaag   2040

tacaacgaca aactgccgct gtacatcagc aatccgaact acaaagtgaa cgtgtatgcg   2100

gtgaccaaag aaaacaccat cattaaccca agcgagaatg gcgataccag caccaacggc   2160

atcaagaaga ttctgatctt cagcaagaaa ggctatgaga ttggc                  2205
```

```
<210> SEQ ID NO 13
<211> LENGTH: 2205
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Sequence variant (98% identity) of SEQ ID No. 1

<400> SEQUENCE: 13

gaagtgaagc aggagaaccg tctgctgaac gagagcgagt ctagctctca gggcctgctg     60

ggctactatt tcagcgatct gaactttcag gcaccgatgg ttgtgacctc tagcacgacc    120

ggcgatctga gcattccgag cagcgaactg gagaacattc cgagcgagaa ccagtacttt    180

cagtctgcga tttggagcgg cttcatcaaa gtgaagaaaa gcgatgagta tacctttgcg    240

acgtctgcgg ataaccatgt gaccatgtgg gtggacgatc aggaagtgat caacaaagca    300

agcaacagca acaagattcg cctggagaag ggtcgcctgt atcagatcaa gattcagtat    360

cagcgcgaga atccgaccga aaaaggcctg gatttcaaac tgtactggac cgatagccag    420

aacaagaaag aggtgattag ctctgataac ctgcagctgc cggaactgaa acagaagagc    480

agcaacagcc gcaagaaacg cagcacctct gcgggtccga ccgttccaga tcgcgacaac    540

gatggcattc cggacagcct ggaagtggaa ggctataccg ttgatgtgaa gaacaaacgc    600

accttcctga gcccgtggat tagcaacatt catgagaaga aaggcctgac caagtacaaa    660

agcagcccgg agaaatggag caccgcgagc gatccgtata gcgattttga gaaggtgacc    720

ggccgcattg ataagaacgt gagcccggaa gcgcgtcacc cactggttgc agcgtatccg    780

attgtgcatg ttgatatgga gaacatcatt ctgagcaaga acgaagatca gagcacccag    840

aacacggata gccagacccg cacgattagc aagaacacca gcacgagccg tacccatacc    900

agcgaagtgc atggcaatgc ggaagtgcat gcgagcttct ttgacattgg tggcagcgtg    960

agcgcgggct tcagcaacag caacagcagc accgtggcga ttgatcatag cctgagcctg   1020

gcgggcgaac gtacctgggc ggaaaccatg ggcctgaaca cggcggatac ggcacgtctg   1080

aatgcgaaca tccgctatgt gaacaccggt accgcgccaa tctataacgt tctgccgacc   1140

acgagcctgg tgctgggcaa gaatcagacc ctggcgacca tcaaagcgaa agaaaaccag   1200

ctgtctcaga ttctggcacc gaacaactac tatccgagca agaacctggc gccgattgca   1260

ctgaatgcac aggatgactt cagcagcacc ccgatcacca tgaactacaa tcagtttctg   1320

gagctggaaa agaccaaaca actgcgcctg gacaccgatc aggtgtatgg caacattgcg   1380

acctacaact ttgagaacgg ccgcgttcgc gtggataccg gcagcaactg gtctgaagtg   1440

ctgccgcaga ttcaggaaac gaccgcgcgc atcatcttta acggcaaaga tctgaacctg   1500

gtggaacgtc gcatcgcggc agtgaaccca agcgatccac tggaaacgac caaaccggac   1560
```

atgaccctga aagaagcgct gaaaattgca tttggcttca acgagccgaa tggcaacctg 1620
cagtatcagg gcaaagacat caccgagttt gacttcaact tcgatcaaca gacctctcag 1680
aacatcaaga accagctggc agaactgaat gcgaccaaca tctacaccgt gctggacaag 1740
atcaaactga acgcaaagat gaacattctg attcgtgaca aacgctttca ctatgatcgt 1800
aacaacattg cggtgggtgc agacgaaagc gttgtgaaag aagcgcatcg tgaagtgatc 1860
aactctagca ccgaaggcct gctgctgaac attgacaaag atatccgtaa gattctgagc 1920
ggctacattg tggaaattga agataccgaa ggtctgaaag aagtgatcaa cgatcgctat 1980
gacatgctga acatctctag cctgcgccaa gatggcaaga ccttcatcga cttcaagaag 2040
tacaacgaca aactgccgct gtacatcagc aatccgaact acaaagtgaa cgtgtatgcg 2100
gtgaccaaag agaacaccat cattaaccca agcgagaatg gcgacacctc taccaacggc 2160
attaagaaga ttctgatctt cagcaagaaa ggttatgaga ttggc 2205

<210> SEQ ID NO 14
<211> LENGTH: 2205
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Sequence variant (98% identity) of SEQ ID No. 1

<400> SEQUENCE: 14
gaagtgaaac aggagaaccg tctgctgaac gaaagcgaat ctagctctca gggcctgctg 60
ggctattatt tcagcgatct gaacttccag gcaccaatgg ttgtgacctc ttctacgacc 120
ggcgatctga gcattccgag cagcgagctg gagaacattc cgagcgagaa ccagtacttt 180
cagagcgcga tttggagcgg cttcatcaaa gtgaagaaaa gcgatgagta tacctttgcg 240
acgtctgcgg ataaccatgt gaccatgtgg gtggacgatc aggaagtgat caacaaagca 300
agcaacagca acaagattcg cctggagaag ggtcgcctgt atcagattaa gattcagtac 360
cagcgcgaga atccgaccga gaaaggcctg gatttcaaac tgtactggac cgatagccag 420
aacaagaaag aagtgattag ctctgataac ctgcaactgc cggaactgaa acagaagagc 480
agcaacagcc gcaagaaacg cagcacctct gcaggcccga ccgttccgga tcgcgacaac 540
gatggcattc cggacagcct ggaagtggaa ggttataccg tggatgtgaa gaacaaacgc 600
accttcctga gcccgtggat tagcaacatt catgagaaga aaggcctgac caagtacaaa 660
agcagcccgg agaagtggag caccgcgagc gatccgtata gcgactttga gaaagtgacc 720
ggccgcattg ataagaacgt gagcccggaa gcgcgtcacc cactggttgc agcgtatccg 780
attgtgcatg ttgacatgga gaacatcatt ctgagcaaga acgaagatca gagcacccag 840
aacacggata gccagacccg cacgatcagc aagaacacct ctacgagccg tacccatacc 900
agcgaagtgc atggcaatgc ggaagtgcat gcaagcttct ttgacattgg tggcagcgtg 960
agcgcgggct tcagcaacag caacagcagc accgtggcga ttgatcatag cctgagcctg 1020
gcgggcgaac gtacctgggc ggaaaccatg ggcctgaaca cggcggatac ggcacgtctg 1080
aatgcgaaca ttcgttatgt gaacaccggc accgcgccaa tctataacgt tctgccgacc 1140
acgagcctgg tgctgggcaa gaatcagacc ctggcgacca tcaaagcgaa agagaaccag 1200
ctgtctcaga ttctggcacc gaacaactac tatccaagca agaacctggc gccgattgca 1260
ctgaacgcgc aggatgactt tagcagcacc ccgatcacca tgaactacaa tcagtttctg 1320

-continued

```
gaactggaga agaccaaaca actgcgcctg gataccgatc aggtgtatgg caacattgcg   1380

acctacaact ttgagaacgg ccgcgttcgc gtggataccg gtagcaactg gagcgaagtg   1440

ctgccgcaga tccaggaaac caccgcgcgc atcatcttca acggcaaaga tctgaatctg   1500

gtggaacgcc gcatcgcggc ggtgaaccca tctgatccgc tggaaacgac caaaccggat   1560

atgaccctga aagaagcgct gaagattgca tttggcttca acgaaccgaa tggcaacctg   1620

cagtatcagg gcaaagacat caccgagttt gacttcaact ttgaccaaca gacctctcag   1680

aacatcaaga accagctggc agaactgaat gcgaccaaca tctacaccgt gctggacaag   1740

atcaaactga acgcaaagat gaacattctg attcgtgaca aacgctttca ctatgatcgt   1800

aacaacattg cggtgggtgc agacgaaagc gttgtgaaag aagcgcatcg tgaagtgatc   1860

aactctagca ccgaaggtct gctgctgaac attgacaaag acatccgtaa gattctgagc   1920

ggctacattg tggagattga agataccgaa ggtctgaaag aagttatcaa cgatcgctat   1980

gatatgctga acatctctag cctgcgccag gatggcaaga cgttcattga cttcaagaag   2040

tacaacgaca aactgccgct gtacatcagc aatccgaact acaaagtgaa cgtgtatgcg   2100

gtgaccaaag agaacaccat cattaaccca agcgagaatg gcgataccag caccaacggc   2160

atcaagaaga ttctgatctt cagcaagaaa ggctatgaga ttggc                   2205
```

<210> SEQ ID NO 15
<211> LENGTH: 2205
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Sequence variant (97% identity) of SEQ ID No. 1

<400> SEQUENCE: 15

```
gaagtgaaac aggagaaccg tctgctgaac gaatctgaat ctagctctca gggcctgctg     60

ggctactatt tttctgatct gaactttcag gcaccgatgg ttgtgaccag cagcacgacc    120

ggcgacctga gcattccgag cagcgaactg gagaacattc cgagcgagaa ccagtacttt    180

cagagcgcga tttggagcgg cttcatcaaa gtgaagaaaa gcgatgagta tacctttgcg    240

acgtctgcgg ataaccatgt gaccatgtgg gtggacgatc aggaggtgat caacaaagcg    300

agcaacagca acaagattcg cctggagaag ggtcgcctgt atcagatcaa gattcagtat    360

cagcgcgaga atccgaccga gaaaggcctg gatttcaaac tgtactggac cgacagccag    420

aacaaaaaag aagtgattag ctctgataac ctgcaactgc cggaactgaa acagaagagc    480

agcaacagcc gcaagaaacg cagcacctct gcaggcccga ccgttccaga tcgcgacaac    540

gatggcattc cggatagcct ggaagtggaa ggttataccg ttgatgtgaa gaacaaacgt    600

acctttctga gcccgtggat tagcaacatt catgagaaga agggcctgac caagtacaaa    660

agcagcccgg agaagtggag caccgcgtct gatccgtata gcgacttcga gaaagtgacc    720

ggccgcattg ataagaacgt gagcccggaa gcgcgccacc cactggttgc agcgtatccg    780

atcgtgcatg ttgacatgga gaacatcatt ctgagcaaga acgaagacca gagcacccag    840

aacacggata gccagacccg cacgatcagc aagaacacca gcacgagccg tacccatacc    900

agcgaagtgc atggcaatgc ggaagtgcat gcgagcttct tcgacattgg tggcagcgtg    960

agcgcgggct tcagcaacag caacagcagc accgtggcga ttgatcatag cctgagcctg   1020

gcgggcgaac gtacctgggc agaaaccatg ggcctgaaca cggcggatac ggcacgtctg   1080

aatgcgaaca ttcgctatgt gaacaccggt accgcgccga tctataacgt gctgccgacc   1140
```

```
acgagcctgg tgctgggcaa gaatcagacc ctggcgacca tcaaagcgaa agagaaccag   1200

ctgagccaga ttctggcacc aaacaactac tatccgtcta aaaacctggc gccgattgca   1260

ctgaatgcgc aggatgactt cagcagcacc ccgatcacca tgaactacaa tcagtttctg   1320

gagctggaga agaccaaaca actgcgcctg gataccgatc aggtttacgg caacattgcg   1380

acctataact ttgagaacgg ccgcgttcgc gtggataccg gtagcaactg gtctgaagtg   1440

ctgccgcaga ttcaggaaac gaccgcgcgt atcattttta acggcaaaga tctgaacctg   1500

gtggaacgtc gtatcgcagc agtgaaccca agcgacccac tggaaacgac caagccggac   1560

atgaccctga aagaagcgct gaagattgca tttggcttca atgaaccgaa tggcaacctg   1620

cagtatcagg gcaaagacat caccgagttt gacttcaact ttgatcaaca gacctctcag   1680

aacatcaaga accagctggc agaactgaac gcgaccaaca tctacaccgt gctggacaaa   1740

atcaaactga acgcgaagat gaacattctg attcgcgaca aacgcttcca ctatgatcgt   1800

aacaacatcg cggtgggtgc agatgaaagc gttgtgaagg aagcgcatcg tgaagtgatc   1860

aactctagca ccgaaggcct gctgctgaac attgataaag acattcgcaa gattctgagc   1920

ggctacattg tggagattga agataccgaa ggtctgaaag aagtgatcaa cgatcgctat   1980

gatatgctga acatctctag cctgcgccag gatggcaaga ccttcattga tttcaagaag   2040

tacaacgaca aactgccgct gtacatcagc aatccgaact acaaagtgaa cgtgtatgcg   2100

gtgaccaaag aaaacaccat cattaaccca agcgagaatg gcgataccag caccaacggc   2160

atcaagaaga ttctgatctt cagcaagaaa ggctatgaga ttggc                   2205
```

```
<210> SEQ ID NO 16
<211> LENGTH: 2205
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Sequence variant (97% identity) of SEQ ID NO. 1

<400> SEQUENCE: 16

gaagtgaaac aggagaaccg tctgctgaac gagagcgagt ctagctctca gggcctgctg     60

ggctactatt tcagcgatct gaactttcag gcaccgatgg ttgttacctc tagcacgacc    120

ggcgatctga gcattccgag cagcgaactg gagaacattc cgagcgagaa ccagtacttt    180

cagtctgcga tttggagcgg cttcatcaaa gtgaagaaga gcgatgaata tacctttgcg    240

acgtctgcgg ataaccatgt gaccatgtgg gtggacgacc aggaggtgat caacaaagca    300

agcaacagca acaagattcg cctggagaag ggtcgcctgt atcagatcaa gatccagtat    360

cagcgcgaga atccgaccga aaaaggcctg gatttcaaac tgtactggac cgatagccag    420

aacaagaaag aggtgattag ctctgataac ctgcagctgc cggaactgaa acagaagagc    480

agcaacagcc gcaagaaacg cagcacctct gcgggtccga ccgttccaga tcgcgacaac    540

gatggcattc cggacagcct ggaagtggaa ggctataccg ttgatgtgaa gaataaacgc    600

acgttcctga gcccgtggat cagcaacatt catgaaaaga aaggcctgac caagtacaaa    660

agcagcccgg agaaatggag caccgcgagc gatccgtata gcgattttga gaaggtgacc    720

ggccgcattg ataagaacgt gagcccggaa gcgcgtcacc cactggttgc agcgtatccg    780

attgtgcatg tggatatgga gaacattatt ctgagcaaga acgaagatca gagcacccag    840

aacacggata gccagacccg taccattagc aagaacacca gcacgagccg tacccatacc    900
```

agcgaagtgc atggcaatgc ggaagtgcat gcgagcttct ttgacattgg tggcagcgtg 960
agcgcgggct tcagcaacag caacagcagc accgtggcaa ttgatcatag cctgagcctg 1020
gcgggcgaac gcacctgggc ggaaaccatg ggcctgaaca cggcggatac ggcacgtctg 1080
aatgcgaaca tccgctatgt gaacaccggt accgcgccaa tctataacgt tctgccgacc 1140
acgagcctgg tgctgggcaa gaatcagacc ctggcgacca tcaaagcgaa agaaaaccag 1200
ctgtctcaga ttctggcacc gaacaactac tatccgagca agaacctggc gccgattgcg 1260
ctgaatgcac aggatgactt tagcagcacc ccgatcacca tgaactacaa tcagtttctg 1320
gagctggaaa agaccaagca actgcgcctg gacaccgatc aggtgtatgg caacattgcg 1380
acctacaact ttgagaacgg ccgcgttcgc gtggataccg gcagcaactg gtctgaggtg 1440
ctgccgcaga ttcaggaaac gaccgcgcgc atcattttca acggcaaaga tctgaacctg 1500
gtggaacgtc gcatcgcggc agtgaaccca agcgatccac tggaaacgac caaaccggac 1560
atgaccctga aagaagcgct gaaaattgca tttggcttca acgagccgaa tggcaacctg 1620
cagtatcagg gcaaagacat caccgagttt gacttcaact tcgatcaaca gacctctcag 1680
aacatcaaga accagctggc agaactgaat gcgaccaaca tctacaccgt gctggacaag 1740
attaaactga acgcaaagat gaacattctg attcgtgata aacgctttca ctatgatcgt 1800
aacaacattg cggtgggtgc agacgaaagc gttgtgaaag aagcgcatcg tgaagtgatc 1860
aactctagca ccgaaggcct gctgctgaac attgacaaag atatccgtaa aattctgagc 1920
ggctacatcg tggaaattga agataccgaa ggtctgaaag aagtgatcaa cgatcgctat 1980
gacatgctga acatctctag cctgcgccaa gatggcaaga ccttcatcga cttcaagaag 2040
tacaacgaca aactgccgct gtacatcagc aacccgaact acaaagtgaa cgtgtatgcg 2100
gtgaccaaag agaacaccat cattaaccca agcgagaatg gcgacacctc taccaacggc 2160
attaagaaga ttctgatctt cagcaagaaa ggttatgaga ttggc 2205

<210> SEQ ID NO 17
<211> LENGTH: 2205
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Sequence variant (97% identity) of SEQ ID NO 1

<400> SEQUENCE: 17
gaagtgaagc aggagaaccg tctgctgaac gaaagcgaat ctagctctca gggcctgctg 60
ggctattatt tcagcgatct gaacttccag gcaccaatgg ttgtgacctc ttctacgacc 120
ggcgatctga gcatcccgag cagcgagctg gagaacattc cgagcgagaa ccagtacttt 180
cagagcgcga tttggagcgg cttcatcaaa gtgaagaaaa gcgatgagta tacctttgcg 240
acgtctgcag ataaccatgt gaccatgtgg gtggatgatc aggaagtgat caacaaagcg 300
agcaacagca acaagatccg cctggagaag ggtcgcctgt atcagattaa gattcagtac 360
cagcgcgaga atccgaccga gaaaggcctg gatttcaaac tgtactggac ggatagccag 420
aacaagaaag aagtgattag ctctgataac ctgcaactgc cggaactgaa acagaagagc 480
agcaacagcc gcaagaaacg cagcacctct gcaggcccga ccgttccgga ccgcgacaac 540
gatggcatcc cggacagcct ggaagtggaa ggttataccg tggatgtgaa gaacaaacgc 600
accttcctga gcccgtggat tagcaacatt catgagaaga aaggcctgac caaatacaaa 660
agcagcccgg agaagtggag caccgcgagc gatccgtata gcgactttga gaaagtgacc 720

```
ggccgcattg ataagaacgt gagcccggaa gcgcgtcatc cactggttgc agcgtatccg    780

attgtgcatg ttgacatgga gaacattatt ctgagcaaga acgaagatca gagcacccag    840

aacacggata gccagacccg cacgatcagc aagaacacct ctacgagccg tacccatacc    900

agcgaagtgc atggcaatgc ggaagtgcat gcaagcttct ttgacattgg tggcagcgtg    960

agcgcgggct tcagcaacag caacagcagc acggtggcga ttgatcatag cctgagcctg   1020

gcgggcgaac gtacctgggc ggaaaccatg ggcctgaaca ccgcggatac ggcacgtctg   1080

aatgcgaaca ttcgttatgt gaacaccggc accgcgccaa tctataacgt tctgccgacc   1140

acgagcctgg tgctgggcaa gaatcagacc ctggcgacca tcaaagcgaa agagaaccag   1200

ctgtctcaga ttctggcacc gaacaactac tatccaagca agaacctggc gccgattgca   1260

ctgaacgcgc aggatgactt tagcagcacc ccgatcacca tgaactacaa tcagtttctg   1320

gaactggaga agaccaaaca actgcgcctg gataccgatc aggtgtatgg caacattgcg   1380

acctacaact ttgagaacgg ccgcgttcgc gtggataccg gtagcaactg gagcgaagtg   1440

ctgccgcaga tccaggaaac caccgcgcgc atcattttca acggcaaaga tctgaatctg   1500

gtggaacgcc gcatcgcggc ggtgaaccca tctgacccgc tggaaacgac caaaccggat   1560

atgaccctga aagaagcgct gaagattgca tttggcttca atgaaccgaa tggcaacctg   1620

cagtatcagg gtaaagacat caccgagttt gacttcaact ttgaccaaca gacctctcag   1680

aacattaaga accagctggc agaactgaat gcgaccaaca tctacaccgt gctggacaag   1740

atcaaactga acgcaaagat gaacattctg attcgtgaca aacgctttca ctatgatcgc   1800

aacaacattg cggtgggtgc agacgaaagc gttgtgaaag aagcgcaccg tgaagtgatc   1860

aactctagca ccgaaggcct gctgctgaac attgacaaag acatccgtaa gattctgagc   1920

ggctacattg tggagatcga agataccgaa ggtctgaaag aagttattaa cgatcgctat   1980

gatatgctga acatctctag cctgcgtcag gatggcaaga ccttcattga cttcaagaag   2040

tacaacgata aactgccgct gtacatcagc aacccgaact acaaagtgaa cgtgtatgcg   2100

gtgaccaaag agaacaccat cattaaccca agcgagaatg gcgataccag caccaacggc   2160

atcaagaaga ttctgatctt cagcaagaaa ggctatgaga ttggc                   2205
```

```
<210> SEQ ID NO 18
<211> LENGTH: 2205
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Sequence variant (96% identity) of SEQ ID NO 1

<400> SEQUENCE: 18

gaagtgaaac aggagaaccg tctgctgaac gaatctgaat ctagctctca gggcctgctg     60

ggctactatt tttctgatct gaactttcag gcaccgatgg ttgtgaccag ctctacgacc    120

ggcgacctga gcattccgag cagcgaactg gagaacattc cgagcgagaa ccagtacttt    180

cagagcgcga tttggagcgg cttcatcaaa gtgaagaaaa gcgatgagta tacctttgcg    240

acgtctgcgg ataaccatgt gaccatgtgg gtggacgatc aggaggtgat caacaaagcg    300

agcaacagca acaagattcg cctggagaag ggtcgcctgt atcagatcaa gattcagtat    360

cagcgcgaga atccgaccga gaaaggcctg gatttcaaac tgtactggac cgatagccag    420

aacaaaaaag aagtgattag cagcgataac ctgcaactgc cggaactgaa gcagaagagc    480
```

-continued

```
agcaacagcc gcaagaaacg cagcacctct gcaggcccga ccgttccaga tcgcgacaac    540

gatggcattc cggatagcct ggaagtggaa ggttataccg ttgatgtgaa aaacaaacgt    600

acctttctga gcccgtggat tagcaacatt catgagaaga agggcctgac caagtacaaa    660

agcagcccgg agaagtggag caccgcgtct gatccgtata gcgacttcga gaaagtgacc    720

ggccgcattg ataaaaacgt gagcccggaa gcgcgccacc cactggttgc agcgtatccg    780

atcgtgcatg ttgacatgga gaacatcatt ctgagcaaga acgaagacca gagcacccag    840

aacacggaca gccagacccg cacgatcagc aagaacacca gcacgagccg tacccatacc    900

agcgaagtgc atggcaatgc ggaagtgcat gcgagcttct tcgacattgg tggcagcgtg    960

agcgcgggct tcagcaacag caacagcagc accgtggcga ttgatcatag cctgagcctg   1020

gcgggcgaac gtacctgggc agaaaccatg ggcctgaaca cggcggatac ggcacgtctg   1080

aatgcgaaca ttcgctatgt gaacaccggt accgcgccga tctataacgt gctgccgacc   1140

acgagcctgg tgctgggcaa gaatcagacc ctggcgacca tcaaagcgaa agagaaccag   1200

ctgagccaga ttctggcacc aaacaactac tatccgtcta aaaacctggc gccgattgca   1260

ctgaatgcgc aggatgactt cagcagcacc ccgatcacca tgaactacaa tcagtttctg   1320

gagctggaga agaccaaaca actgcgcctg gataccgatc aggtttacgg caacattgcg   1380

acctataact ttgagaacgg ccgcgttcgc gtggataccg gtagcaactg gtctgaagtg   1440

ctgccgcaga tccaggaaac gaccgcgcgt atcattttta acggcaagga cctgaacctg   1500

gtggaacgtc gtatcgcagc agtgaaccca agcgacccac tggaaacgac caagccggat   1560

atgaccctga aagaagcgct gaagattgca tttggcttca atgagccgaa tggcaacctg   1620

cagtatcagg gcaaagatat caccgagttt gacttcaact ttgaccaaca gacctctcag   1680

aacatcaaga accagctggc agaactgaac gcgaccaaca tttacaccgt gctggacaaa   1740

atcaaactga acgcgaagat gaacattctg attcgcgaca aacgcttcca ctatgatcgt   1800

aacaacatcg cggtgggtgc agatgaaagc gttgtgaagg aagcgcatcg tgaagtgatc   1860

aactctagca ccgaaggcct gctgctgaac atcgataaag acattcgcaa gattctgagc   1920

ggctacattg tggagattga agataccgaa ggtctgaaag aagtgattaa cgatcgctat   1980

gatatgctga acatttctag cctgcgccag gatggcaaga ccttcatcga tttcaagaag   2040

tacaacgaca aactgccgct gtacatcagc aatccgaact acaaagtgaa cgtgtatgcg   2100

gtgaccaaag aaaacaccat cattaaccca agcgagaatg gcgataccag caccaacggc   2160

atcaagaaga ttctgatctt cagcaagaaa ggctatgaaa ttggc                   2205
```

<210> SEQ ID NO 19
<211> LENGTH: 2205
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Sequence variant (96% identity) of SEQ ID NO 1

<400> SEQUENCE: 19

```
gaagtgaaac aggagaaccg tctgctgaac gagagcgaga gcagctctca gggcctgctg     60

ggctactatt tcagcgatct gaactttcag gcaccgatgg tggttacctc tagcacgacc    120

ggcgatctga gcattccgag cagcgaactg gagaacattc cgagcgagaa ccagtacttt    180

cagtctgcga tttggagcgg cttcatcaaa gtgaagaaga gcgatgaata tacctttgcg    240

acgagcgcgg ataaccatgt gacgatgtgg gtggacgacc aggaggtgat caacaaagca    300
```

```
agcaacagca acaagattcg cctggagaag ggtcgcctgt atcagatcaa gatccagtat    360
cagcgcgaaa atccgaccga aaaaggcctg gatttcaaac tgtactggac cgatagccag    420
aacaagaaag aggtgattag ctctgataac ctgcagctgc cggaactgaa acagaagagc    480
agcaacagcc gcaagaaacg cagcacctct gcgggtccga ccgttccaga tcgcgacaac    540
gatggcattc cggatagcct ggaagtggaa ggctataccg ttgatgtgaa gaataaacgc    600
accttcctga gcccgtggat cagcaacatt catgaaaaga aaggcctgac caagtacaaa    660
agcagcccgg agaagtggag caccgcgagc gatccgtata gcgattttga gaaggtgacc    720
ggccgcattg ataagaacgt gagcccggaa gcgcgtcacc cactggttgc agcgtatccg    780
attgtgcatg tggatatgga gaacattatt ctgagcaaga acgaagatca gagcacccag    840
aacacggata gccagacccg taccattagc aagaacacca gcacgagccg tacccatacc    900
agcgaagttc atggcaatgc ggaagtgcat gcgagcttct ttgacattgg tggcagcgtg    960
agcgcgggct tcagcaacag caacagctct accgtggcaa ttgaccatag cctgtctctg   1020
gcgggcgaac gcacctgggc ggaaaccatg ggcctgaaca cggcggatac ggcacgtctg   1080
aatgcgaaca tccgctatgt gaacaccggt accgcgccaa tctataacgt tctgccgacc   1140
acgagcctgg tgctgggcaa gaatcagacc ctggcgacca tcaaagcgaa agaaaaccag   1200
ctgtctcaga ttctggcacc gaacaactac tatccgagca agaacctggc gccgattgcg   1260
ctgaatgcac aggatgactt tagcagcacc ccgatcacca tgaactacaa tcaatttctg   1320
gagctggaaa agaccaagca gctgcgcctg gacaccgatc aggtgtatgg caacattgcg   1380
acctacaact ttgagaacgg ccgcgttcgc gtggataccg gcagcaactg gtctgaggtg   1440
ctgccacaga ttcaggaaac gaccgcgcgc atcattttca acggcaaaga tctgaacctg   1500
gtggaacgtc gcatcgcggc agtgaaccca agcgatccac tggaaacgac caaaccggac   1560
atgaccctga aagaggcgct gaaaattgca tttggcttca acgagccgaa tggcaacctg   1620
cagtatcagg gcaaagacat caccgagttt gacttcaact tcgatcaaca gacctctcag   1680
aacatcaaga accagctggc agaactgaat gcgaccaaca tctacaccgt gctggacaag   1740
attaaactga acgcaaagat gaacattctg attcgtgata aacgctttca ctatgatcgt   1800
aacaacattg cggtgggtgc agacgaaagc gttgtgaaag aagcgcatcg tgaagtgatc   1860
aactctagca ccgaaggcct gctgctgaac attgacaaag atatccgtaa aattctgagc   1920
ggctacatcg tggaaattga agataccgaa ggtctgaaag aagtgatcaa cgatcgctat   1980
gacatgctga acatctctag cctgcgccaa gatggcaaga ccttcatcga cttcaagaag   2040
tacaacgaca aactgccgct gtacatcagc aacccgaact acaaagtgaa cgtgtatgcg   2100
gtgaccaaag agaacaccat cattaacccg agcgagaatg gcgacacctc taccaacggc   2160
attaaaaaga ttctgatctt cagcaagaaa ggttatgaga ttggc                   2205
```

<210> SEQ ID NO 20
<211> LENGTH: 2205
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Sequence variant (96% identity) of SEQ ID NO 1

<400> SEQUENCE: 20

```
gaagtgaagc aggagaaccg tctgctgaac gaaagcgaat ctagctctca gggcctgctg     60
```

-continued

```
ggctattatt tcagcgatct gaacttccag gcgccaatgg ttgtgaccag ctctacgacc    120

ggcgatctga gcatcccgag cagcgagctg gagaacattc cgagcgagaa ccagtacttt    180

cagagcgcga tttggagcgg cttcatcaaa gtgaagaaaa gcgatgagta tacctttgcg    240

acgtctgcag ataaccatgt gaccatgtgg gtggatgatc aggaagtgat caacaaagcg    300

agcaacagca acaagatccg cctggagaag ggtcgcctgt atcagattaa gattcagtac    360

cagcgcgaga atccgaccga gaaaggcctg gacttcaaac tgtactggac ggatagccag    420

aacaagaaag aagtgattag ctctgataac ctgcaactgc cggaactgaa acagaagagc    480

agcaacagcc gcaagaaacg cagcacctct gcaggcccga ccgttccgga ccgcgacaac    540

gatggcatcc cggacagcct ggaagtggaa ggttataccg tggatgtgaa gaacaaacgc    600

accttcctga gcccgtggat tagcaacatt catgagaaga aaggcctgac caaatacaaa    660

agcagcccgg agaagtggag caccgcgagc gatccgtata gcgactttga gaaagtgacc    720

ggccgcattg ataagaacgt gagcccggaa gcgcgtcatc cactggttgc agcgtatccg    780

attgtgcatg ttgacatgga gaacattatt ctgagcaaaa acgaagatca gagcacccag    840

aacacggaca gccagacccg cacgatcagc aagaacacct ctacgagccg tacccatacc    900

agcgaagtgc atggcaatgc ggaagtgcat gcaagcttct ttgacattgg tggcagcgtg    960

agcgcgggct tcagcaacag caacagcagc acggtggcaa ttgatcatag cctgagcctg   1020

gcgggcgaac gtacctgggc ggaaaccatg ggcctgaaca ccgcggatac ggcacgtctg   1080

aatgcgaaca ttcgttatgt gaacaccggc accgcgccaa tctataacgt tctgccgacc   1140

acgagcctgg tgctgggcaa gaaccagacc ctggcgacca tcaaagcaaa agagaaccag   1200

ctgtctcaga ttctggcacc gaacaactac tatccaagca agaacctggc gccgattgca   1260

ctgaacgcgc aggatgattt tagcagcacc ccgatcacca tgaactacaa tcagtttctg   1320

gaactggaga agaccaaaca actgcgcctg gataccgatc aggtgtatgg caacatcgcg   1380

acctacaact ttgagaacgg ccgcgttcgc gtggataccg gttctaactg gagcgaagtg   1440

ctgccgcaga tccaggaaac caccgcgcgc atcattttca acggcaaaga tctgaatctg   1500

gtggaacgcc gcatcgcggc ggtgaaccca tctgacccgc tggaaacgac caagccggat   1560

atgaccctga aagaagcgct gaagattgcg tttggcttca atgaaccgaa tggcaacctg   1620

cagtatcagg gtaaagacat caccgagttt gacttcaact ttgaccaaca gacctctcag   1680

aacattaaga accagctggc agaactgaat gcgaccaaca tctacaccgt gctggacaag   1740

atcaaactga acgcaaagat gaacattctg attcgtgata aacgctttca ctatgatcgc   1800

aacaacattg cggtgggtgc agacgaaagc gttgtgaaag aagcgcaccg tgaagtgatc   1860

aactctagca ccgaaggcct gctgctgaac attgacaaag atattcgtaa gattctgagc   1920

ggctacattg tggagatcga agataccgaa ggtctgaaag aagttattaa cgatcgctat   1980

gatatgctga acatctctag cctgcgtcag gatggcaaga ccttcattga cttcaagaag   2040

tacaacgaca aactgccgct gtatatcagc aacccgaatt acaaagtgaa cgtgtacgcg   2100

gtgaccaaag agaacaccat cattaaccca agcgagaatg gcgataccag caccaacggc   2160

atcaagaaga ttctgatctt cagcaagaaa ggctatgaga ttggc                   2205
```

<210> SEQ ID NO 21
<211> LENGTH: 2205
<212> TYPE: DNA
<213> ORGANISM: Artificial Sequence
<220> FEATURE:
<223> OTHER INFORMATION: Description of Artificial Sequence: Synthetic
      polynucleotide <220> FEATURE:
<223> OTHER INFORMATION: Sequence variant (95% identity) of SEQ ID NO 1

<400> SEQUENCE: 21

```
gaagtgaaac aggagaaccg tctgctgaac gaatctgaat ctagctctca gggcctgctg     60
ggctactatt tttctgatct gaacttccag gcaccgatgg ttgtgaccag ctctaccacc    120
ggcgacctga gcattccgag cagcgaactg gagaacattc cgagcgagaa ccagtacttt    180
cagagcgcga tttggagcgg cttcatcaaa gtgaagaaaa gcgatgagta tacctttgcg    240
acgtctgcgg ataaccatgt gaccatgtgg gtggacgatc aggaggtgat caacaaagca    300
agcaacagca acaagattcg cctggagaag ggtcgcctgt atcagatcaa gattcagtat    360
cagcgcgaga atccgaccga gaaaggcctg gatttcaaac tgtactggac cgatagccag    420
aacaaaaaag aagtgattag cagcgataac ctgcaactgc cggaactgaa gcagaagagc    480
agcaacagcc gcaagaaacg cagcacgtct gcaggcccga ccgttccaga tcgcgacaac    540
gatggcattc cggatagcct ggaagtggaa ggttataccg ttgatgtgaa aaacaaacgt    600
acctttctga gcccgtggat tagcaacatt catgagaaga agggcctgac caagtacaaa    660
agcagcccgg agaagtggag caccgcgtct gatccgtata gcgactttga gaaagtgacc    720
ggccgcattg ataaaaacgt gagcccggag gcgcgccacc cactggttgc ggcgtatccg    780
attgtgcatg ttgacatgga aaacatcatc ctgagcaaga acgaagacca gagcacccag    840
aacacggaca gccagacccg cacgatcagc aagaacacca gcacgagccg tacgcatacc    900
agcgaagtgc atggcaatgc ggaagtgcat gcgagcttct tcgacattgg tggcagcgtg    960
agcgcgggct tcagcaacag caacagcagc accgtggcga ttgatcatag cctgagcctg   1020
gcgggcgaac gtacctgggc agaaaccatg ggcctgaaca cggcggatac ggcacgtctg   1080
aatgcgaaca ttcgctatgt gaacaccggt accgcaccga tttataacgt gctgccgacc   1140
acgagcctgg tgctgggtaa gaatcagacc ctggcgacca tcaaagcgaa agagaaccag   1200
ctgagccaga ttctggcacc aaacaactac tatccgtcta aaaacctggc gccgattgca   1260
ctgaatgcgc aggatgattt cagcagcacc ccgatcacca tgaactacaa tcagtttctg   1320
gagctggaga agaccaaaca actgcgcctg gacaccgacc aggtttacgg caacattgcg   1380
acctataact ttgagaacgg ccgcgttcgc gtggacaccg gtagcaactg gtctgaagtg   1440
ctgccgcaga tccaggaaac gaccgcgcgt atcattttta acggcaagga tctgaacctg   1500
gtggaacgtc gtatcgcagc agtgaaccca agcgacccac tggaaaccac caagccggat   1560
atgaccctga aagaagcgct gaagattgca tttggcttca atgagccgaa tggcaacctg   1620
cagtatcagg gcaaagatat caccgaattt gacttcaact ttgaccaaca gacctctcag   1680
aacatcaaga accagctggc ggaactgaac gcgaccaaca tttacaccgt gctggacaaa   1740
atcaaactga acgcgaagat gaacattctg attcgcgaca aacgcttcca ctacgatcgt   1800
aacaacatcg cggtgggcgc agatgaaagc gttgtgaagg aagcgcatcg tgaagtgatc   1860
aactctagca ccgaaggcct gctgctgaac atcgataaag acattcgcaa gattctgagc   1920
ggctacattg tggagattga ggataccgaa ggtctgaaag aagtgattaa cgatcgctat   1980
gatatgctga acatctctag cctgcgccag gatggcaaga ccttcatcga tttcaagaaa   2040
tataacgata aactgccgct gtacatcagc aatccgaact acaaagtgaa cgtgtatgcg   2100
gtgaccaaag aaaacaccat cattaaccca agcgagaatg gcgataccag caccaacggc   2160
atcaagaaga ttctgatctt cagcaagaag ggctatgaaa ttggc                   2205
```

<210> SEQ ID NO 22
<211> LENGTH: 2205
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Sequence variant (95% identity) of SEQ ID NO 1

<400> SEQUENCE: 22
gaagtgaaac aggagaaccg tctgctgaac gagagcgaga gctcttctca gggcctgctg 60
ggctactatt tcagcgatct gaactttcag gcaccgatgg ttgttacctc tagcaccacc 120
ggcgatctga gcattccgag cagcgaactg gaaaacattc cgagcgagaa ccagtacttt 180
cagtctgcga tttggagcgg cttcatcaaa gtgaagaaga gcgatgaata tacctttgcg 240
acgagcgcgg ataaccatgt gacgatgtgg gtggacgacc aggaggtgat caacaaagca 300
agcaacagca acaagattcg cctggagaag ggtcgcctgt atcagatcaa gatccagtat 360
cagcgcgaaa atccgaccga aaaaggcctg gatttcaaac tgtactggac cgatagccag 420
aacaagaaag aggttattag ctctgataac ctgcagctgc cggaactgaa acagaagagc 480
agcaacagcc gcaagaaacg cagcacctct gcgggtccga ccgttccaga tcgcgacaac 540
gatggcattc cggatagcct ggaagtggaa ggctataccg tggatgtgaa gaataagcgc 600
accttcctga gcccgtggat cagcaatatt catgaaaaga aaggcctgac gaagtacaaa 660
agcagcccgg agaaatggag caccgcgagc gatccgtata gcgattttga gaaggtgacc 720
ggccgcattg ataagaacgt gagcccggaa gcgcgtcacc cactggttgc agcgtatccg 780
attgtgcatg tggatatgga gaacattatt ctgagcaaga acgaagatca gagcacccag 840
aacacggata gccagacccg taccattagc aagaacacca gcacgagccg tacccatacc 900
agcgaagttc atggcaatgc ggaagtgcat gcgagcttct ttgacattgg tggcagcgtg 960
agcgcgggct tcagcaacag caacagctct accgtggcga ttgaccatag cctgtctctg 1020
gcgggcgagc gcacctgggc ggaaaccatg ggcctgaaca cggcggatac ggcacgtctg 1080
aatgcaaaca tccgctatgt gaacaccggt accgcgccaa tctataacgt gctgccgacc 1140
accagcctgg tgctgggcaa gaaccagacc ctggcgacca tcaaagcgaa agaaaaccag 1200
ctgagccaga ttctggcgcc gaacaactat tatccgagca agaacctggc accgattgcg 1260
ctgaatgcac aggatgactt tagcagcacg ccgatcacca tgaactacaa tcaatttctg 1320
gagctggaaa agaccaagca gctgcgcctg gacaccgatc aggtgtacgg caacattgcg 1380
acctacaact ttgagaacgg ccgcgtgcgc gtggataccg gcagcaactg gtctgaggtg 1440
ctgccacaga ttcaggaaac gaccgcgcgc atcatcttca acggcaaaga tctgaacctg 1500
gtggaacgtc gcatcgcggc agtgaaccca agcgatccac tggaaacgac caaaccggac 1560
atgaccctga aagaggcgct gaaaattgca tttggcttca acgagccgaa tggcaacctg 1620
cagtatcagg gcaaagacat caccgagttt gacttcaact tcgatcaaca gacctctcag 1680
aacatcaaga accagctggc agaactgaat gcgaccaaca tctacaccgt gctggacaag 1740
attaaactga acgcaaagat gaacattctg attcgtgata aacgctttca ctatgatcgt 1800
aacaacattg cggtgggtgc agacgaaagc gttgtgaaag aagcgcatcg tgaagtgatc 1860
aactctagca ccgaaggcct gctgctgaac attgacaaag atatccgtaa aattctgagc 1920
ggctacatcg tggaaattga agataccgaa ggtctgaaag aagtgatcaa cgatcgctat 1980
gacatgctga acatttctag cctgcgccaa gatggcaaga ccttcatcga cttcaagaag 2040

```
tacaacgaca aactgccgct gtacatcagc aacccgaact acaaagtgaa cgtttatgcg   2100

gtgaccaaag agaacaccat cattaacccg agcgagaatg gcgacacctc taccaacggc   2160

attaaaaaga ttctgatctt cagcaagaaa ggttatgaga ttggc                   2205
```

<210> SEQ ID NO 23
<211> LENGTH: 2205
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Sequence variant (95% identity) of SEQ ID NO 1

<400> SEQUENCE: 23

```
gaagtgaagc aggagaaccg tctgctgaac gaaagcgaat ctagctctca gggcctgctg     60

ggctattatt tcagcgatct gaacttccag gcgccaatgg ttgtgaccag ctctacgacc    120

ggcgatctga gcatcccgag cagcgagctg gagaacattc cgagcgagaa ccagtatttt    180

cagagcgcga tttggagcgg ctttattaaa gtgaagaaaa gcgatgagta tacctttgcg    240

acgagcgcag ataaccatgt gaccatgtgg gtggatgatc aggaagtgat caacaaagcg    300

agcaacagca acaagatccg cctggagaag ggtcgcctgt atcagattaa gatccagtac    360

cagcgcgaga atccgaccga gaaaggcctg gacttcaaac tgtactggac ggatagccag    420

aacaagaaag aagtgattag ctctgataac ctgcaactgc cggaactgaa acagaagagc    480

agcaacagcc gtaagaaacg cagcacctct gcaggcccga ccgttccgga ccgcgacaac    540

gatggcattc cggacagcct ggaagtggaa ggttataccg tggatgtgaa gaacaaacgc    600

accttcctga gcccgtggat tagcaacatt catgagaaga aaggcctgac caaatacaaa    660

agcagcccgg agaagtggag caccgcgagc gatccgtata gcgattttga gaaagtgacc    720

ggccgcattg ataagaacgt gagcccggaa gcgcgccatc cactggttgc agcgtatccg    780

attgtgcatg ttgacatgga gaacattatt ctgagcaaaa acgaagatca gagcacccag    840

aacacggaca gccagacccg cacgatcagc aagaacacct ctacgagccg tacccatacc    900

agcgaagttc atggcaatgc ggaagtgcat gcaagcttct ttgacattgg tggcagcgtg    960

agcgcgggct tcagcaacag caacagcagc acggtggcaa ttgatcatag cctgagcctg   1020

gcgggcgaac gtacctgggc ggaaaccatg ggcctgaaca ccgcggatac cgcacgtctg   1080

aatgcgaaca ttcgttatgt gaacaccggc accgcgccaa tctataacgt gctgccgacc   1140

acgagcctgg tgctgggcaa gaaccagacc ctggcgacca tcaaagcaaa agagaaccag   1200

ctgtctcaga ttctggcacc gaacaactac tatccgagca agaacctggc gccaattgca   1260

ctgaacgcgc aggatgattt ttctagcacg ccgatcacca tgaactacaa tcagtttctg   1320

gaactggaga aaaccaaaca actgcgcctg gataccgatc aggtgtatgg caacatcgcg   1380

acctacaact ttgagaacgg ccgcgttcgc gtggataccg gttctaactg gagcgaagtg   1440

ctgccgcaga tccaggaaac caccgcgcgc attatcttca acggcaaaga tctgaatctg   1500

gtggaacgcc gcatcgcggc ggtgaaccca tctgacccgc tggaaacgac caagccggat   1560

atgaccctga aagaagcgct gaagattgcg tttggcttca atgaaccgaa tggcaacctg   1620

cagtaccagg gtaaagacat caccgagttt gacttcaact tcgaccaaca gacctctcag   1680

aacattaaga accagctggc agaactgaat gcgaccaaca tctacaccgt gctggacaag   1740

atcaaactga acgcaaagat gaacattctg attcgtgata agcgctttca ctatgaccgc   1800

aacaacattg cggtgggtgc agacgaaagc gttgtgaaag aagcgcaccg tgaagtgatc   1860
```

aactctagca ccgaaggcct gctgctgaac attgacaaag atattcgtaa gattctgagc 1920
ggctacattg tggagatcga agataccgaa ggtctgaaag aagttattaa cgatcgctat 1980
gatatgctga acatctctag cctgcgtcag gatggcaaga ccttcatcga cttcaagaag 2040
tacaacgaca aactgccgct gtatatcagc aacccgaatt acaaagtgaa cgtgtacgcg 2100
gtgaccaaag agaacaccat cattaaccca agcgagaatg gcgataccag caccaacggc 2160
atcaagaaga ttctgatctt cagcaagaaa ggctatgaga ttggc 2205

<210> SEQ ID NO 24
<211> LENGTH: 2205
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Sequence variant (94% identity) of SEQ ID No 1

<400> SEQUENCE: 24
gaagtgaaac aggagaaccg tctgctgaac gaatctgaaa gcagctctca gggcctgctg 60
ggctactatt tttctgatct gaacttccag gcaccgatgg ttgtgaccag ctctaccacc 120
ggcgacctgt ctattccgag cagcgaactg gagaacattc cgagcgaaaa ccagtacttt 180
cagagcgcga tttggagcgg ctttatcaaa gtgaagaaaa gcgatgagta cacctttgcg 240
acgtctgcgg ataaccatgt gaccatgtgg gtggacgatc aggaggtgat caacaaagca 300
agcaacagca acaagattcg cctggagaag ggtcgcctgt atcagatcaa gattcagtat 360
cagcgcgaga atccgaccga gaaaggcctg gatttcaaac tgtattggac cgatagccag 420
aacaaaaaag aggtgattag cagcgataac ctgcaactgc cggaactgaa gcagaagagc 480
agcaacagcc gcaagaaacg cagcacgtct gcaggcccga ccgttccaga tcgcgacaac 540
gatggcattc cggatagcct ggaagtggaa ggttataccg ttgatgtgaa aaacaaacgt 600
acctttctga gcccgtggat tagcaacatt catgagaaga aaggcctgac caagtacaaa 660
agcagcccgg agaagtggag caccgcgtct gatccgtata gcgactttga gaaagtgacc 720
ggccgcattg ataaaaacgt gagcccggag gcgcgccacc cactggttgc ggcgtatccg 780
attgtgcatg ttgacatgga aaacatcatc ctgagcaaga acgaagacca gagcacccag 840
aacacggaca gccagacccg cacgatcagc aagaacacca gcacgagccg tacgcatacc 900
agcgaagtgc atggcaatgc ggaagtgcat gcgagcttct tcgacattgg tggcagcgtg 960
agcgcgggct tcagcaacag caacagcagc accgtggcga ttgatcatag cctgagcctg 1020
gcgggcgaac gtacctgggc agaaaccatg ggcctgaaca cggcggatac cgcacgtctg 1080
aatgcgaaca ttcgctatgt gaacaccggt accgcaccga tttataacgt gctgccgacc 1140
acgagcctgg tgctgggtaa gaatcagacc ctggcgacca tcaaagcgaa agagaaccag 1200
ctgagccaga ttctggcacc aaacaactac tacccgtcta aaaacctggc gccgattgca 1260
ctgaatgcgc aggatgattt cagcagcacc ccgatcacca tgaactataa tcagttcctg 1320
gagctggaga agaccaaaca actgcgcctg gacaccgacc aggtttacgg caacatcgcg 1380
acctataact ttgagaacgg ccgcgttcgc gtggacaccg gtagcaactg gtctgaagtg 1440
ctgccgcaga tccaggaaac gaccgcgcgt attattttta acggcaagga tctgaacctg 1500
gtggaacgtc gtattgcagc agtgaaccca agcgacccac tggaaaccac caagccggat 1560
atgaccctga aagaagcgct gaagattgca tttggcttca atgagccgaa tggcaacctg 1620

```
cagtatcagg gcaaggatat caccgaattt gacttcaact ttgaccaaca gacctctcag   1680
aacatcaaga accagctggc ggaactgaac gcgaccaaca tctacaccgt gctggacaaa   1740
atcaaactga acgcgaagat gaacattctg attcgcgaca aacgcttcca ctacgatcgt   1800
aacaacatcg cggtgggcgc agatgaaagc gttgtgaagg aagcgcatcg tgaagtgatc   1860
aactctagca cggaaggcct gctgctgaac atcgataaag acattcgcaa gattctgagc   1920
ggctacattg tggagattga ggataccgaa ggtctgaaag aagtgattaa cgatcgctat   1980
gatatgctga acatctctag cctgcgccag gatggcaaga ccttcatcga tttcaagaaa   2040
tataacgata agctgccgct gtacatcagc aatccgaact ataaagtgaa cgtgtatgcg   2100
gtgaccaaag aaaacaccat cattaaccca agcgagaatg gcgataccag caccaacggc   2160
atcaaaaaga ttctgatctt cagcaagaag ggctacgaaa ttggc                   2205
```

<210> SEQ ID NO 25
<211> LENGTH: 2205
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Sequence variant (94% identity) of SEQ ID No 1

<400> SEQUENCE: 25

```
gaagttaaac aggagaaccg tctgctgaac gagagcgaat ctagcagcca gggcctgctg     60
ggttactatt tcagcgatct gaactttcag gcaccgatgg tggtgaccag cagcaccacc    120
ggcgatctga gcattccgag ctctgaactg gaaaacattc cgagcgagaa ccagtatttt    180
cagtctgcga tttggagcgg cttcattaag gtgaaaaaaa gcgatgagta tacctttgca    240
acgtctgcgg ataaccatgt gaccatgtgg gtggatgatc aggaagtgat caacaaagcg    300
agcaacagca acaagattcg cctggaaaaa ggtcgtctgt atcagatcaa gatccagtac    360
cagcgcgaaa acccgaccga gaaaggtctg gacttcaaac tgtattggac cgatagccag    420
aacaaaaaag aggtgattag cagcgataac ctgcaactgc cggaactgaa acagaagagc    480
agcaacagcc gcaagaaacg cagcacctct gcaggcccga ccgttccaga tcgcgacaac    540
gatggcattc cggacagcct ggaagtggaa ggttataccg tggatgtgaa gaacaaacgc    600
accttcctga gcccgtggat tagcaacatt catgagaaga aaggcctgac caagtacaaa    660
agcagcccgg agaagtggag caccgcaagc gatccatata gcgattttga gaaggttacc    720
ggccgtatcg ataagaacgt gtctccggaa gcgcgtcacc cactggttgc agcgtatccg    780
attgttcatg tggacatgga gaacatcatt ctgagcaaga acgaagatca gagcacccag    840
aacacggata gccagacccg cacgatcagc aagaacacca gcacgagccg tacccacacc    900
agcgaggtgc atggcaatgc ggaagtgcat gcgagctttt ttgacattgg cggcagcgtg    960
agcgcgggct ttagcaacag caacagcagc accgtggcga ttgatcatag cctgagcctg   1020
gcgggcgagc gtacctgggc ggaaaccatg ggcctgaaca cggcggatac ggcgcgcctg   1080
aatgcgaaca ttcgctatgt gaacaccggc accgcgccga tttataacgt gctgccgacc   1140
accagcctgg tgctgggcaa gaaccagacc ctggcgacca tcaaagcgaa ggagaaccag   1200
ctgtctcaaa ttctggcacc aaacaactac tatccgagca agaacctggc accgatcgcg   1260
ctgaatgcgc aggatgattt tagcagcacc ccgatcacca tgaactacaa tcagtttctg   1320
gagctggaga agaccaaaca gctgcgcctg gataccgatc aggtgtacgg caacatcgcg   1380
acctacaact ttgagaacgg ccgcgttcgc gtggataccg gctctaactg gagcgaagtg   1440
```

```
ctgccgcaga ttcaggaaac caccgcacgc attattttca acggcaaaga tctgaacctg   1500

gtggaacgcc gcattgcggc agtgaaccca tctgacccac tggaaacgac caagccggat   1560

atgaccctga aagaagcgct gaagatcgca tttggcttca acgaaccgaa tggcaacctg   1620

cagtaccagg gcaaggacat caccgagttc gacttcaact tcgaccaaca gacctctcag   1680

aacatcaaaa accagctggc ggaactgaat gcgacgaaca tttacaccgt gctggacaag   1740

atcaaactga acgcaaagat gaacattctg attcgtgaca aacgcttcca ttatgatcgt   1800

aacaacattg cggttggtgc agacgaaagc gttgtgaagg aagcgcatcg tgaagtgatc   1860

aacagcagca ccgaaggcct gctgctgaac attgacaaag acattcgtaa aattctgagc   1920

ggctatattg tggagattga agataccgaa ggcctgaaag aagtgatcaa cgatcgctat   1980

gacatgctga acatctctag cctgcgccag gatggtaaga cgttcatcga cttcaaaaag   2040

tacaatgaca aactgccgct gtacatttct aatccgaact acaaagtgaa cgtgtatgcg   2100

gtgaccaagg aaaacacgat cattaatccg agcgagaatg gtgatacctc taccaacggc   2160

atcaagaaaa tcctgatctt cagcaagaaa ggctatgaga tcggc                   2205
```

```
<210> SEQ ID NO 26
<211> LENGTH: 2205
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Sequence variant (94% identity) of SEQ ID NO 1

<400> SEQUENCE: 26
```

```
gaagtgaagc aggagaaccg tctgctgaac gaaagcgaat ctagctctca gggtctgctg     60

ggctattatt tcagcgatct gaacttccag gcgccaatgg ttgtgaccag ctctacgacc    120

ggcgatctga gcatcccgag ctctgagctg gagaacattc cgagcgagaa ccagtatttt    180

cagagcgcga tttggagcgg ctttattaaa gtgaagaaaa gcgatgagta tacctttgcg    240

acgagcgcag ataaccatgt gaccatgtgg gtggatgatc aggaagtgat caacaaagcg    300

agcaacagca acaagatccg cctggagaag ggccgcctgt atcagattaa gatccagtac    360

cagcgcgaga atccgaccga gaaaggcctg gacttcaaac tgtactggac ggatagccag    420

aacaagaaag aagtgattag cagcgataac ctgcaactgc cggaactgaa acagaagagc    480

agcaacagcc gtaagaaacg cagcacctct gcaggcccga ccgttccgga ccgcgacaac    540

gacggcattc cggacagcct ggaagtggaa ggttataccg tggatgtgaa gaacaaacgc    600

accttcctga gcccgtggat tagcaacatt catgagaaga aaggcctgac caaatacaaa    660

tctagcccgg agaagtggag caccgcgagc gatccgtata gcgattttga gaaagtgacc    720

ggccgcattg ataagaacgt gagcccggaa gcgcgccatc cactggttgc agcgtatccg    780

attgtgcatg ttgacatgga gaacattatt ctgagcaaaa acgaagatca gagcacccag    840

aacacggaca gccagacccg cacgatcagc aagaacacct ctacgagccg tacccatacc    900

agcgaagttc atggcaatgc ggaagtgcat gcaagcttct ttgacattgg tggcagcgtg    960

agcgcgggct tcagcaacag caacagcagc acggtggcaa ttgatcatag cctgagcctg   1020

gcgggcgaac gtacctgggc ggaaaccatg ggcctgaaca ccgcggatac cgcacgtctg   1080

aatgcgaaca ttcgttatgt gaacaccggc accgcgccaa tctataacgt gctgccgacc   1140

acgagcctgg tgctgggcaa gaaccagacc ctggcgacca tcaaagcgaa agagaaccag   1200
```

-continued

```
ctgtctcaga ttctggcacc gaacaactac tatccgagca agaacctggc gccaattgca   1260

ctgaacgcgc aggatgattt ttctagcacg ccgatcacca tgaactacaa tcagtttctg   1320

gaactggaga aaaccaaaca actgcgcctg gataccgatc aggtgtatgg caacatcgca   1380

acctacaact ttgagaacgg ccgcgttcgc gtggataccg gttctaactg gagcgaagtg   1440

ctgccgcaaa tccaggaaac caccgcgcgc attatcttca acggcaaaga tctgaatctg   1500

gtggaacgcc gcatcgcggc ggtgaaccca tctgacccgc tggaaaccac caagccggat   1560

atgaccctga aagaagcgct gaagattgcg tttggcttca atgaaccgaa tggcaacctg   1620

cagtaccagg gtaaagacat caccgaattt gacttcaact tcgaccagca gacctctcag   1680

aacattaaga accagctggc agaactgaat gcgaccaaca tctacaccgt gctggataag   1740

atcaaactga acgcaaagat gaacattctg attcgtgata agcgctttca ctatgaccgc   1800

aacaacattg cggtgggtgc agacgaaagc gttgtgaaag aagcgcaccg tgaggtgatc   1860

aacagcagca ccgaaggcct gctgctgaac attgacaaag atattcgtaa gattctgagc   1920

ggctacattg tggagatcga agatacggaa ggtctgaaag aagttattaa cgatcgctat   1980

gatatgctga acatctctag cctgcgtcag gatggcaaga ccttcatcga cttcaagaag   2040

tacaacgaca aactgccgct gtatatcagc aacccgaatt acaaagtgaa cgtgtacgcg   2100

gtgaccaaag agaacaccat cattaaccca agcgagaatg gcgataccag caccaacggc   2160

atcaagaaga ttctgatctt cagcaagaaa ggctatgaga ttggc                   2205
```

```
<210> SEQ ID NO 27
<211> LENGTH: 2205
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Sequence variant (93% identity) of SEQ ID No 1

<400> SEQUENCE: 27
```

```
gaagtgaaac aggaaaatcg tctgctgaac gaatctgaaa gcagctctca gggcctgctg     60

ggctactatt tttctgatct gaacttccag gcaccgatgg ttgtgaccag ctctaccacc    120

ggcgacctgt ctattccgag cagcgaactg gagaacattc cgagcgaaaa ccagtacttt    180

cagagcgcga tttggagcgg ctttatcaaa gtgaagaaaa gcgatgagta cacctttgcg    240

acgtctgcgg ataaccatgt gaccatgtgg gtggacgacc aggaggtgat caacaaagcg    300

agcaacagca acaagattcg cctggaaaag ggtcgcctgt atcagatcaa gattcagtat    360

cagcgcgaga acccgaccga gaagggcctg gatttcaaac tgtattggac cgatagccag    420

aacaaaaaag aggtgattag cagcgataac ctgcaactgc cggagctgaa gcagaagagc    480

agcaacagcc gcaaaaaacg cagcacgtct gcaggcccga ccgttccaga tcgcgacaac    540

gatggcattc cggatagcct ggaagtggaa ggttataccg ttgatgtgaa aaacaaacgt    600

acctttctga gcccgtggat tagcaacatt catgagaaga aaggcctgac caagtacaaa    660

agcagcccgg agaagtggag caccgcatct gatccgtata gcgactttga gaaagtgacc    720

ggccgcattg ataaaaacgt gagcccggag gcgcgccatc cactggttgc agcgtatccg    780

attgtgcatg ttgatatgga aaacatcatc ctgagcaaga acgaagacca gagcacccag    840

aacaccgaca gccagacccg cacgatcagc aagaacacca gcacgagccg tacgcatacc    900

agcgaagtgc acggcaatgc agaagtgcat gcgagcttct tcgacattgg tggcagcgtg    960

agcgcgggct tcagcaactc taacagcagc accgtggcga ttgatcatag cctgagcctg   1020
```

```
gcgggcgagc gtacctgggc ggaaaccatg ggcctgaaca cggcggatac cgcgcgtctg   1080

aatgcgaaca ttcgctatgt gaacaccggt accgcaccga tttataacgt gctgccgacc   1140

acgagcctgg tgctgggtaa gaatcagacc ctggcaacca tcaaagcgaa agagaaccag   1200

ctgagccaga ttctggcacc aaacaactac tacccgagca aaaacctggc gccgattgcg   1260

ctgaatgcgc aggatgattt cagcagcacc ccgatcacca tgaactataa tcagttcctg   1320

gagctggaga agaccaaaca actgcgcctg gacacggacc aggtttacgg caacatcgcg   1380

acctataact ttgagaacgg ccgcgttcgc gtggacaccg gtagcaactg gtctgaggtg   1440

ctgccgcaga tccaggaaac gaccgcgcgt attattttta acggcaagga tctgaacctg   1500

gtggaacgtc gtattgcagc ggtgaaccca agcgacccac tggaaaccac caagccggat   1560

atgaccctga aagaagcgct gaagattgca tttggcttca atgagccgaa tggcaacctg   1620

cagtatcagg gcaaggatat caccgaattt gacttcaact ttgaccaaca gacctctcag   1680

aacatcaaga accagctggc ggaactgaac gcaaccaaca tctacaccgt gctggataaa   1740

atcaaactga acgcgaagat gaacattctg attcgcgaca aacgcttcca ctacgaccgt   1800

aacaacatcg cggtgggcgc agatgaaagc gttgtgaagg aagcgcatcg tgaagtgatc   1860

aactctagca cggaaggcct gctgctgaac atcgataaag atattcgcaa gattctgagc   1920

ggctacattg tggagattga ggataccgaa ggtctgaaag aagtgattaa cgatcgctat   1980

gatatgctga acatctctag cctgcgccag gatggcaaga ccttcatcga cttcaagaaa   2040

tataacgata agctgccgct gtacatcagc aatccgaact ataaagtgaa cgtgtatgcg   2100

gtgaccaaag aaaacaccat cattaaccca agcgaaaatg gcgataccag caccaacggc   2160

atcaaaaaga ttctgatctt cagcaagaag ggctacgaaa ttggc                   2205
```

<210> SEQ ID NO 28
<211> LENGTH: 2205
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Sequence variant (93% identity) of SEQ ID NO 1

<400> SEQUENCE: 28

```
gaagttaaac aggagaaccg tctgctgaac gagagcgaat ctagcagcca gggcctgctg     60

ggttattatt tcagcgatct gaactttcag gcaccgatgg tggtgaccag cagcaccacc    120

ggcgatctga gcattccgag cagcgaactg gaaaacattc cgagcgagaa ccagtatttt    180

cagtctgcga tttggagcgg cttcattaag gtgaaaaaaa gcgatgaata tacctttgca    240

acgtctgcgg ataaccatgt gaccatgtgg gttgatgatc aggaagtgat caacaaagcg    300

agcaacagca acaagattcg cctggaaaaa ggtcgtctgt atcagattaa gatccagtac    360

cagcgcgaaa acccgaccga gaaaggtctg gacttcaaac tgtattggac cgatagccag    420

aacaaaaaag aggtgattag cagcgataac ctgcaactgc cggaactgaa acagaagagc    480

agcaacagcc gcaagaaacg cagcacctct gcaggcccaa ccgttccgga ccgcgacaac    540

gatggcattc cggacagcct ggaagtggaa ggttataccg tggatgtgaa aaacaaacgc    600

acgttcctga gcccgtggat tagcaacatc catgagaaga aaggcctgac caagtacaag    660

agcagcccgg aaaagtggag caccgcaagc gatccatata gcgattttga gaaggttacc    720

ggccgtattg ataagaacgt gtctccggaa gcgcgtcacc cactggtggc agcgtatccg    780
```

```
attgttcatg tggacatgga aaacatcatt ctgagcaaga acgaagatca gagcacccag    840

aacacggata gccagacccg cacgatcagc aagaacacca gcacgagccg tacccacacc    900

agcgaggtgc atggcaatgc ggaagtgcat gcgagctttt ttgacattgg cggcagcgtg    960

agcgcgggct ttagcaacag caacagcagc accgtggcga ttgatcatag cctgagcctg   1020

gcgggcgagc gtacctgggc ggagaccatg gcctgaaca cggcggatac cgcgcgcctg   1080

aacgcgaaca ttcgctatgt gaacaccggc accgcgccga tttataacgt gctgccgacc   1140

accagcctgg tgctgggcaa gaaccagacc ctggcgacca tcaaagcgaa ggagaaccag   1200

ctgtctcaaa ttctggcacc aaacaactac tatccgagca agaacctggc accgatcgcg   1260

ctgaatgcgc aggatgattt tagctctacc ccgatcacca tgaactacaa tcagtttctg   1320

gagctggaga agaccaaaca gctgcgcctg gataccgatc aggtgtacgg caacatcgcg   1380

acctacaact ttgagaacgg ccgcgttcgc gtggataccg gctctaactg gagcgaagtg   1440

ctgccgcaga ttcaggaaac caccgcacgc attattttca acggcaaaga tctgaacctg   1500

gtggaacgtc gcattgcggc agtgaaccca tctgacccac tggaaacgac caagccggat   1560

atgaccctga aagaagcgct gaagatcgca tttggcttca acgaaccgaa tggcaacctg   1620

cagtaccagg gcaaggacat caccgagttc gacttcaact tcgaccaaca gacctctcag   1680

aacatcaaaa atcagctggc ggaactgaat gcgacgaaca tttacaccgt gctggacaag   1740

atcaaactga acgcaaagat gaacattctg attcgtgaca aacgcttcca ttacgatcgt   1800

aacaacattg cggttggtgc agacgagagc gttgtgaagg aagcgcatcg cgaggtgatc   1860

aacagcagca ccgaaggcct gctgctgaac attgacaaag acattcgtaa aattctgagc   1920

ggctatattg tggagatcga agataccgaa ggcctgaaag aagtgatcaa cgatcgctat   1980

gatatgctga acatctctag cctgcgccag gatggtaaga cgttcatcga cttcaaaaag   2040

tacaatgaca aactgccgct gtacatttct aatccgaact acaaagtgaa cgtgtatgcg   2100

gtgaccaagg aaaacacgat cattaatccg agcgagaatg gtgatacctc taccaacggc   2160

atcaagaaaa tcctgatctt cagcaagaaa ggctatgaga tcggc                   2205
```

```
<210> SEQ ID NO 29
<211> LENGTH: 2205
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Sequence variant (93% identity) of  SEQ ID No 1

<400> SEQUENCE: 29

gaagtgaagc aggagaaccg tctgctgaac gaaagcgaaa gcagcagcca gggtctgctg     60

ggctattatt tcagcgatct gaacttccag gcgccgatgg ttgtgaccag ctctacgacc    120

ggcgatctga gcatcccgag ctctgagctg gagaacattc cgagcgagaa ccagtatttt    180

cagagcgcga tttggagcgg ctttattaaa gtgaagaaat ctgatgagta tacctttgcg    240

acgagcgcag ataaccatgt gaccatgtgg gtggatgatc aggaagtgat caacaaagcg    300

agcaacagca acaagatccg cctggaaaag ggccgcctgt atcagattaa gatccagtac    360

cagcgcgaga atccgaccga gaaaggcctg gacttcaaac tgtactggac ggatagccag    420

aacaagaaag aagtgattag cagcgataac ctgcaactgc cggaactgaa acagaagagc    480

agcaacagcc gtaagaaacg cagcacctct gcaggcccga ccgttccgga ccgcgacaac    540

gacggcattc cggacagcct ggaagtggag ggttataccg tggatgtgaa gaacaaacgc    600
```

```
accttcctga gcccgtggat tagcaacatt catgagaaga aaggcctgac caaatacaaa    660
tctagcccgg agaagtggag caccgcgagc gatccgtata gcgattttga gaaagtgacc    720
ggccgcattg ataagaacgt gagcccagaa gcgcgccatc cactggttgc agcgtatccg    780
attgtgcatg ttgacatgga gaacattatt ctgagcaaaa acgaagatca gagcacccag    840
aacacggaca gccagacccg cacgatcagc aagaacacct ctacgagccg tacccatacc    900
agcgaagtgc atggcaatgc ggaagtgcac gcaagcttct ttgacattgg tggcagcgtg    960
agcgcgggct tcagcaacag caacagcagc acggtggcaa ttgatcatag cctgagcctg   1020
gcgggcgaac gtacctgggc agaaaccatg ggcctgaaca ccgcagatac cgcacgtctg   1080
aatgcgaaca ttcgttatgt taacaccggc accgcgccaa tctataacgt gctgccgacc   1140
acgagcctgg tgctgggcaa gaaccagacc ctggcgacca tcaaagcgaa agagaaccag   1200
ctgtctcaga ttctggcacc gaacaactac tatccgtcta agaacctggc gccaattgca   1260
ctgaacgcgc aggatgattt ttctagcacg ccgatcacca tgaactacaa tcagtttctg   1320
gaactggaga aaaccaaaca actgcgcctg gataccgatc aggtgtatgg caacatcgca   1380
acctacaact ttgagaacgg ccgcgttcgc gtggataccg gttctaactg gagcgaagtg   1440
ctgccgcaga tccaagaaac caccgcgcgc attatcttca acggcaaaga tctgaatctg   1500
gtggaacgcc gtatcgcggc ggtgaaccca tctgacccgc tggaaaccac caagccggat   1560
atgaccctga aagaagcgct gaagattgcg tttggcttca atgaaccgaa tggcaacctg   1620
cagtaccagg gtaaagacat caccgaattt gacttcaact tcgaccagca gacctctcag   1680
aacattaaga accagctggc ggaactgaat gcgaccaaca tctacaccgt gctggataaa   1740
atcaaactga acgcgaagat gaacattctg attcgtgata agcgctttca ttatgaccgc   1800
aacaacattg cggtgggtgc agacgaaagc gttgtgaaag aagcgcaccg tgaggtgatc   1860
aacagcagca ccgaaggcct gctgctgaac attgacaaag atattcgtaa gattctgagc   1920
ggctacattg tggagatcga agatacggaa ggtctgaaag aagttattaa cgatcgctat   1980
gatatgctga acatctctag cctgcgccag gatggcaaga ccttcatcga cttcaagaag   2040
tacaacgaca agctgccgct gtatatcagc aacccgaatt acaaagtgaa cgtgtacgcg   2100
gtgaccaaag agaacaccat cattaaccca agcgagaatg gcgataccag caccaacggc   2160
atcaagaaga ttctgatctt cagcaagaaa ggctatgaga ttggc                   2205
```

<210> SEQ ID NO 30
<211> LENGTH: 2205
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Sequence variant (92% identity) of SEQ ID NO 1

<400> SEQUENCE: 30

```
gaagtgaaac aggaaaatcg tctgctgaac gaaagcgaaa gcagcagcca gggcctgctg     60
ggctactatt tttctgatct gaacttccag gcaccaatgg ttgtgaccag ctctaccacc    120
ggcgacctga gcattccgag ctctgaactg gagaacattc cgagcgaaaa ccagtacttt    180
cagagcgcga tttggagcgg ctttatcaaa gtgaagaaat ctgatgagta cacctttgcg    240
acgtctgcgg ataaccatgt gaccatgtgg gttgacgacc aggaggtgat caacaaagcg    300
agcaacagca acaagattcg cctggaaaag ggtcgcctgt atcagatcaa gatccagtat    360
```

```
cagcgcgaga acccgaccga gaagggcctg gatttcaaac tgtattggac cgatagccag    420

aacaaaaaag aggtgattag cagcgataac ctgcaactgc cggagctgaa gcagaagagc    480

agcaacagcc gcaaaaaacg cagcacgtct gcaggcccga ccgtgccgga tcgcgacaac    540

gatggcattc cggatagcct ggaagtggaa ggttataccg ttgatgtgaa aaacaagcgt    600

acctttctga gcccgtggat tagcaacatt catgagaaga aaggcctgac caagtacaaa    660

agcagcccgg agaagtggag caccgcatct gatccgtata gcgacttcga gaaagtgacc    720

ggccgtattg ataaaaacgt gagcccggag gcgcgccatc cgctggttgc agcgtatccg    780

attgtgcatg ttgatatgga aaacatcatc ctgagcaaga acgaagacca gtctacccag    840

aacaccgaca gccagacccg cacgatcagc aagaacacca gcaccagccg tacgcatacc    900

agcgaagtgc acggcaatgc agaagtgcat gcgagcttct tcgacattgg tggcagcgtg    960

agcgcgggct tcagcaactc taacagcagc accgtggcga ttgatcattc tctgagcctg   1020

gcgggcgagc gtacctgggc ggaaaccatg ggcctgaaca cggcggatac ggcgcgtctg   1080

aatgcgaaca ttcgctatgt gaacaccggt accgcaccga tttataacgt gctgccgacc   1140

acgagcctgg tgctgggtaa gaatcagacc ctggcgacca tcaaagcgaa agagaaccag   1200

ctgagccaga ttctggcacc aaacaactac tacccaagca aaaacctggc gccgattgca   1260

ctgaatgcgc aggatgattt cagcagcacc ccgatcacca tgaactataa tcagttcctg   1320

gagctggaga agaccaaaca actgcgcctg gacacggacc aggtttacgg caacatcgcg   1380

acctataact ttgagaacgg ccgcgttcgc gtggacaccg gtagcaactg gtctgaagtg   1440

ctgccgcaga tccaggaaac gaccgcgcgt attattttta acggcaagga tctgaacctg   1500

gtggaacgtc gcattgcagc ggtgaaccca agcgacccac tggaaaccac caagccggat   1560

atgaccctga aagaagcgct gaagattgca tttggcttca atgagccgaa tggcaacctg   1620

cagtatcagg gcaaggatat caccgaattt gactttaact tcgaccaaca gacctctcag   1680

aacatcaaga accagctggc ggaactgaac gcaaccaaca tctacaccgt gctggataaa   1740

atcaaactga acgcgaagat gaacattctg attcgcgaca agcgctttca ctacgaccgt   1800

aacaacatcg cggtgggcgc agatgaaagc gttgtgaagg aagcgcatcg tgaggtgatc   1860

aactctagca cggaaggcct gctgctgaac attgataaag atattcgcaa aattctgagc   1920

ggctacattg tggagattga ggataccgaa ggtctgaaag aagtgattaa cgatcgctat   1980

gatatgctga acatcagcag cctgcgccag gatggcaaga ccttcatcga cttcaagaag   2040

tataacgata agctgccgct gtacatcagc aatccgaact ataaagtgaa cgtgtatgcg   2100

gtgaccaaag aaaacaccat cattaaccca agcgaaaatg gcgataccag caccaacggc   2160

atcaaaaaaa ttctgatctt cagcaagaaa ggctacgaaa ttggc                   2205
```

<210> SEQ ID NO 31
<211> LENGTH: 2205
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Sequence variant (92% identity) of SEQ ID NO 1

<400> SEQUENCE: 31

```
gaagtgaaac aggaaaaccg tctgctgaac gagagcgaat ctagcagcca gggcctgctg     60

ggctattatt tcagcgatct gaactttcag gcaccgatgg tggtgacctc tagcaccacc    120

ggcgatctga gcattccgtc tagcgaactg gaaaatatcc caagcgagaa ccagtatttt    180
```

```
cagtctgcga tttggagcgg cttcattaag gttaaaaaaa gcgatgaata tacctttgca    240

accagcgcgg ataaccatgt gaccatgtgg gttgatgatc aggaagtgat caacaaagcg    300

agcaacagca acaagattcg cctggaaaaa ggtcgcctgt atcagattaa aatccagtac    360

cagcgtgaaa acccgaccga gaaaggtctg gacttcaagc tgtattggac cgatagccag    420

aacaaaaaag aggtgattag cagcgataac ctgcaactgc cggaactgaa acagaagagc    480

agcaacagcc gcaagaaacg cagcacctct gcaggcccaa ccgttccgga ccgcgacaac    540

gatggcattc cggacagcct ggaagtggaa ggttataccg tggatgttaa aaacaaacgc    600

acgttcctga gcccgtggat tagcaacatc catgagaaga aaggcctgac caagtacaag    660

agcagcccgg aaaagtggag caccgcaagc gatccgtata gcgattttga gaaggttacc    720

ggccgtattg ataagaacgt gtctccggaa gcgcgccacc cactggtggc agcgtacccg    780

attgttcatg tggatatgga gaacatcatt ctgagcaaga acgaagatca gagcacgcag    840

aacacggata gccagacccg caccatcagc aagaacacca gcaccagccg tacccacacc    900

agcgaggtgc atggcaatgc ggaagtgcat gcgagctttt ttgacattgg cggcagcgtg    960

agcgcgggct tttctaatag caacagcagc accgtggcga tcgatcatag cctgagcctg   1020

gcgggcgagc gtacctgggc ggagaccatg ggcctgaaca cggcggatac ggcgcgtctg   1080

aacgcgaaca ttcgctatgt gaacaccggc accgcgccga tttataacgt gctgccgacc   1140

accagcctgg tgctgggcaa gaaccagacc ctggcgacca tcaaagcgaa ggaaaaccag   1200

ctgtctcaaa ttctggcgcc aaacaactac tatccgagca agaacctggc accgatcgcg   1260

ctgaatgcgc aggatgattt tagctctacc ccgattacca tgaactacaa tcagtttctg   1320

gagctggaga agaccaaaca gctgcgtctg gatacggatc aggtgtacgg caacatcgcg   1380

acgtacaact tcgagaacgg ccgcgttcgc gtggataccg gcagcaactg gagcgaagtg   1440

ctgccgcaga ttcaggaaac cacggcacgc attattttca acggcaaaga tctgaacctg   1500

gtggaacgtc gcattgcggc agtgaaccca tctgacccac tggagacgac caagccggat   1560

atgaccctga aggaggcgct gaagattgca tttggcttca acgaaccgaa cggcaacctg   1620

cagtaccagg gtaaggacat caccgaattt gacttcaact tcgaccaaca gacctctcag   1680

aacatcaaaa atcagctggc ggaactgaat gcaacgaaca tctacaccgt gctggacaag   1740

atcaaactga acgcaaaaat gaacattctg attcgtgaca aacgcttcca ttatgatcgt   1800

aacaacattg cggtgggtgc agacgaaagc gttgtgaagg aagcgcatcg cgaggtgatc   1860

aacagcagca ccgagggcct gctgctgaac attgacaaag acattcgcaa aattctgagc   1920

ggctatattg tggagatcga agataccgaa ggcctgaagg aagtgatcaa cgatcgctat   1980

gacatgctga acatttctag cctgcgccag gatggtaaga ccttcatcga cttcaagaaa   2040

tacaatgaca aactgccgct gtacattagc aatccgaact acaaagtgaa cgtgtatgcg   2100

gtgaccaagg agaacaccat cattaacccg agcgagaatg gtgataccag caccaacggc   2160

atcaaaaaaa tcctgatctt ctctaagaaa ggctatgaaa tcggc                   2205
```

<210> SEQ ID NO 32
<211> LENGTH: 2205
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Sequence variant (92% identity) of SEQ ID NO 1

<400> SEQUENCE: 32

```
gaagtgaagc aggagaaccg tctgctgaac gaaagcgaaa gcagcagcca gggtctgctg     60
ggctattatt tcagcgatct gaacttccag gcgccgatgg ttgtgaccag ctctaccacc    120
ggcgatctga gcatcccgag ctctgagctg gagaacatcc cgagcgagaa ccagtatttt    180
cagagcgcga tttggagcgg ctttattaaa gtgaaaaaat ctgatgaata tacctttgcg    240
acgagcgcag ataaccatgt gaccatgtgg gtggatgatc aggaagttat taacaaagcg    300
agcaacagca acaagatccg cctggaaaag ggccgcctgt atcagattaa gatccagtac    360
cagcgcgaga atccgaccga gaagggcctg gactttaaac tgtactggac ggatagccag    420
aacaagaaag aagtgattag cagcgacaac ctgcaactgc cggaactgaa acagaagagc    480
agcaacagcc gcaagaaacg cagcacctct gcaggcccga ccgttccgga ccgcgacaac    540
gacggcattc cggacagcct ggaagtggag ggttataccg tggatgtgaa gaacaaacgc    600
accttcctga gcccgtggat tagcaacatt catgagaaga aaggcctgac caaatacaaa    660
tctagcccgg agaagtggag caccgcgagc gatccgtata gcgattttga gaaagtgacc    720
ggccgcattg ataagaacgt gagcccagag gcgcgccatc cactggttgc ggcgtatccg    780
atcgtgcatg tggacatgga gaacattatc ctgagcaaaa acgaagacca gagcacccag    840
aacacggaca gccagacccg cacgatcagc aagaacacct ctacgtctcg tacccacacc    900
agcgaagtgc atggcaatgc ggaagtgcat gcaagcttct ttgacattgg tggcagcgtg    960
agcgcgggct tcagcaacag caacagcagc acggtggcaa ttgatcatag cctgagcctg   1020
gcgggcgaac gtacctgggc agaaaccatg ggcctgaaca ccgcagatac cgcacgtctg   1080
aatgcgaaca ttcgttatgt taacaccggc accgcgccaa tctataacgt gctgccgacc   1140
acgagcctgg tgctgggcaa gaaccagacc ctggcgacca tcaaagcgaa agagaaccag   1200
ctgagccaga ttctggcacc aaacaactac tatccgtcta agaacctggc gccgattgca   1260
ctgaacgcgc aggatgattt ttctagcacg ccgatcacca tgaactacaa tcagtttctg   1320
gagctggaga aaaccaaaca actgcgcctg gataccgatc aggtgtatgg caacattgca   1380
acctacaact ttgagaacgg ccgtgttcgc gtggataccg gttctaactg gagcgaagtg   1440
ctgccgcaga tccaagaaac gaccgcgcgc attatcttca acggcaaaga tctgaatctg   1500
gtggaacgcc gtatcgcggc ggtgaaccca tctgatccgc tggaaaccac caagccggat   1560
atgaccctga aagaagcgct gaagattgcg tttggcttca atgaaccgaa tggcaacctg   1620
cagtaccagg gtaaagacat caccgaattc gacttcaact tcgatcagca gacctctcag   1680
aacattaaga accagctggc agaactgaat gcgaccaaca tctacaccgt gctggataaa   1740
atcaaactga acgcgaagat gaacattctg attcgtgata agcgctttca ttatgaccgc   1800
aacaacattg cggtgggcgc agacgaaagc gttgtgaaag aagcgcaccg tgaggtgatc   1860
aacagcagca ccgaaggcct gctgctgaac attgacaaag atattcgtaa gattctgagc   1920
ggttacattg tggagatcga agatacggaa ggtctgaaag aagttattaa cgaccgctat   1980
gatatgctga acatctctag cctgcgccag gatggcaaga ccttcatcga tttcaagaag   2040
tacaacgaca agctgccgct gtatatcagc aacccgaatt acaaagtgaa cgtgtacgcg   2100
gtgaccaaag aaaacaccat tattaaccca agcgagaatg gcgataccag caccaacggc   2160
atcaagaaga ttctgatctt cagcaagaaa ggctatgaga ttggc                   2205
```

<210> SEQ ID NO 33
<211> LENGTH: 2205
<212> TYPE: DNA

<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Sequence variant (91% identity) of SEQ ID NO. 1

<400> SEQUENCE: 33

```
gaagtgaaac aggaaaatcg tctgctgaac gaaagcgaaa gcagcagcca gggtctgctg     60

ggctactatt tttctgatct gaattttcag gcaccaatgg ttgtgaccag ctctaccacc    120

ggcgacctga gcattccgag ctctgaactg gagaacattc cgagcgaaaa ccagtacttt    180

cagagcgcga tttggagcgg ctttatcaaa gtgaagaaat ctgacgagta cacgtttgcg    240

acctctgcgg ataaccatgt gaccatgtgg gttgacgacc aggaggtgat caacaaagcg    300

agcaacagca ataagattcg cctggaaaag ggtcgcctgt atcagatcaa gatccagtat    360

cagcgcgaga acccgaccga aaagggcctg gatttcaaac tgtattggac cgacagccag    420

aacaaaaaag aggtgattag cagcgataac ctgcaactgc cggaactgaa gcagaagagc    480

agcaacagcc gcaaaaaacg cagcacgtct gcaggcccga ccgtgccgga tcgcgataac    540

gatggcattc cggatagcct ggaagtggaa ggctataccg ttgatgtgaa aaacaagcgt    600

acctttctga gcccgtggat tagcaacatt catgagaaga aaggcctgac caagtacaaa    660

agcagcccgg agaagtggag caccgcatct gatccgtata gcgacttcga gaaggtgacc    720

ggccgtattg ataaaaacgt gagcccggag gcgcgccatc cgctggttgc agcgtatccg    780

attgtgcatg ttgatatgga aaacatcatc ctgagcaaga acgaagacca gtctacgcag    840

aacaccgaca gccagacccg cacgatcagc aagaacacca gcaccagccg cacgcatacc    900

agcgaagtgc acggcaatgc agaagtgcat gcgagcttct tcgacatcgg tggcagcgtg    960

agcgcgggct tcagcaactc taacagcagc accgttgcga ttgatcattc tctgagcctg   1020

gcgggcgagc gtacctgggc ggaaaccatg ggcctgaaca cggcggatac ggcgcgtctg   1080

aatgcgaaca ttcgctatgt gaacaccggt accgcaccga tttataacgt gctgccaacc   1140

accagcctgg tgctgggtaa aaaccagacc ctggcgacca ttaaagcgaa agagaaccag   1200

ctgagccaga ttctggcacc aaacaactac tacccaagca aaaacctggc gccgattgca   1260

ctgaatgcgc aggatgattt cagcagcacc ccgatcacca tgaactataa tcagttcctg   1320

gagctggaga agaccaaaca actgcgcctg gacacggacc aggtttacgg caacattgcg   1380

acctataact ttgagaacgg ccgcgttcgc gtggacaccg gtagcaactg gtctgaagtg   1440

ctgccgcaga tccaggaaac gaccgcgcgt attattttta acggcaagga tctgaacctg   1500

gtggaacgtc gcattgcagc ggtgaaccca agcgacccac tggaaaccac caaaccggat   1560

atgacgctga aagaagcgct gaagattgca tttggcttca atgagccgaa tggcaacctg   1620

cagtatcagg gcaaggatat caccgaattt gactttaact tcgatcaaca gacctctcag   1680

aacattaaga accagctggc ggaactgaac gcaaccaaca tctacaccgt gctggataaa   1740

atcaaactga acgcgaagat gaacatcctg attcgcgaca agcgtttcca ctacgaccgt   1800

aacaacatcg cggtgggcgc agatgaaagc gtggtgaagg aagcgcatcg tgaggtgatc   1860

aactctagca ccgaaggcct gctgctgaac attgataaag atattcgcaa aatcctgagc   1920

ggctacattg tggagattga ggataccgaa ggtctgaaag aagtgattaa cgatcgctat   1980

gatatgctga atatcagcag cctgcgccag gatggcaaga ccttcatcga cttcaagaag   2040

tataacgata agctgccgct gtacatcagc aacccgaact ataaagtgaa cgtgtatgcg   2100

gtgaccaaag agaacaccat cattaacccg agcgagaacg gcgataccag caccaacggc   2160
```

atcaaaaaga ttctgatttt cagcaagaaa ggctacgaaa tcggc 2205

<210> SEQ ID NO 34
<211> LENGTH: 2205
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Sequence variant (91% identity) of SEQ ID NO. 1

<400> SEQUENCE: 34
gaagtgaagc aggagaaccg cctgctgaac gaatctgaga gcagctctca gggcctgctg 60
ggctattact ttagcgatct gaactttcag gcaccgatgg tggtgacctc ttctaccacg 120
ggcgacctgt ctattccgag cagcgaactg gaaaacatcc cgagcgagaa ccagtacttc 180
cagtctgcaa tttggagcgg cttcattaag gtgaaaaaga gcgatgaata taccttcgcg 240
acctctgcgg ataaccatgt gaccatgtgg gtggatgacc aggaagtgat taacaaagcg 300
agcaacagca acaagattcg tctggagaag ggtcgcctgt accagattaa aattcagtac 360
cagcgcgaga acccgaccga gaagggtctg gatttcaaac tgtattggac cgatagccag 420
aacaaaaagg aggtgattag ctctgataac ctgcagctgc cggaactgaa acagaagagc 480
agcaacagcc gcaaaaaacg cagcacctct gcaggcccaa cggtgccaga ccgcgacaac 540
gatggcattc cggacagcct ggaagttgaa ggctataccg tggatgtgaa gaacaaacgc 600
acctttctga gcccgtggat tagcaacatc catgaaaaga aaggcctgac caaatataaa 660
agcagcccgg aaaagtggag caccgcgagc gatccgtaca gcgatttcga gaaagtgacc 720
ggccgcattg ataagaatgt gagcccggag gcgcgccacc cgctggtggc ggcgtatccg 780
attgtgcatg ttgatatgga gaacatcatc ctgagcaaga atgaagatca gagcacccag 840
aacacggaca gccagacccg cacgatcagc aagaacacca gcacgagccg tacccatacg 900
agcgaagttc atggcaacgc ggaagtgcat gcaagctttt tcgatattgg cggcagcgtg 960
agcgcaggct ttagcaacag caacagcagc accgtggcga ttgatcatag cctgagcctg 1020
gcgggcgaac gtacctgggc ggaaaccatg ggcctgaaca ccgcggatac cgcgcgtctg 1080
aatgcgaaca tccgttatgt gaacaccggt accgcgccga tctataatgt tctgccgacc 1140
accagcctgg tgctgggcaa gaatcaaacc ctggcgacga tcaaagcgaa ggagaaccag 1200
ctgagccaga tcctggcgcc gaacaactac tacccaagca aaaacctggc gccgattgca 1260
ctgaacgcgc aggacgattt cagcagcacc ccgattacca tgaactataa tcagttcctg 1320
gaactggaaa agaccaaaca actgcgcctg gacaccgatc aggtgtacgg caacatcgcg 1380
acctataact tcgagaacgg tcgcgtgcgt gtggacaccg gtagcaactg gagcgaagtt 1440
ctgccgcaga ttcaggagac caccgcgcgc attattttca acggcaaaga tctgaacctg 1500
gtggaacgcc gcatcgcggc ggtgaaccca tctgatccgc tggaaaccac caaaccggac 1560
atgaccctga aagaagcact gaagattgca tttggcttta acgagccgaa cggtaacctg 1620
cagtaccagg gcaaagacat caccgagttt gattttaact ttgatcagca gacctctcag 1680
aatattaaaa accagctggc agaactgaat gcaaccaaca tctacaccgt tctggataag 1740
atcaaactga acgcaaaaat gaacattctg attcgtgaca agcgcttcca ctatgatcgt 1800
aacaacattg cagtgggcgc ggacgaaagc gttgtgaagg aagcgcatcg tgaagtgatc 1860
aactctagca cggaaggcct gctgctgaac attgacaagg atatccgtaa gattctgagc 1920

-continued

```
ggctatatcg ttgaaattga ggataccgag ggtctgaagg aggtgatcaa cgaccgctat   1980

gatatgctga acattagctc tctgcgccaa gatggcaaaa ccttcatcga cttcaagaag   2040

tataatgata aactgccgct gtatatcagc aacccaaact acaaagtgaa cgtgtacgcg   2100

gtgacgaagg aaaacacgat catcaaccca agcgagaatg gcgacaccag caccaacggc   2160

attaagaaaa ttctgatttt tagcaaaaaa ggctatgaga tcggc                   2205


<210> SEQ ID NO 35
<211> LENGTH: 2205
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Sequence variant (91% identity) of SEQ ID NO. 1

<400> SEQUENCE: 35

gaagtgaagc aggagaaccg tctgctgaac gaaagcgaaa gcagcagcca aggcctgctg     60

ggctattatt tcagcgatct gaacttccag gcgccgatgg ttgtgacctc ttctaccacc    120

ggcgatctga gcatcccgag ctctgagctg gaaaacatcc cgagcgagaa ccagtatttt    180

cagagcgcga tttggagcgg ctttattaaa gttaaaaaat ctgatgaata cacctttgcg    240

acgagcgcag ataaccacgt gaccatgtgg gtggatgatc aggaagttat taacaaagcg    300

agcaacagca acaagattcg tctggaaaag ggccgcctgt atcagattaa gatccagtac    360

cagcgcgaaa atccgaccga gaagggtctg gactttaaac tgtactggac ggatagccag    420

aacaagaaag aagtgattag cagcgacaac ctgcaactgc cggaactgaa acagaagagc    480

agcaacagcc gcaagaaacg cagcacctct gcgggtccga ccgttccgga ccgcgacaac    540

gacggcattc cggacagcct ggaagtggag ggctataccg ttgatgttaa gaacaagcgc    600

accttcctga gcccgtggat tagcaacatt catgagaaga aaggcctgac caaatacaaa    660

tctagcccgg agaaatggag caccgcaagc gatccgtata gcgattttga gaaagtgacc    720

ggccgcattg ataagaacgt gagcccagag gcgcgccatc cactggtggc ggcgtatccg    780

atcgtgcatg tggacatgga gaatattatc ctgagcaaaa acgaagatca gagcacccag    840

aacacggaca gccagacccg cacgatcagc aagaacacct ctacgtctcg tacccatacc    900

agcgaagtgc atggtaacgc ggaagtgcat gcaagcttct ttgacattgg tggcagcgtg    960

agcgcgggct tcagcaacag caacagcagc acggtggcaa tcgatcatag cctgagcctg   1020

gcgggcgaac gcacctgggc agaaaccatg ggcctgaaca ccgcagatac cgcacgcctg   1080

aatgcgaaca ttcgttatgt gaacaccggc accgcgccga tctataacgt gctgccgacc   1140

acgagcctgg tgctgggcaa gaaccagacc ctggcgacca tcaaagcgaa agagaaccag   1200

ctgagccaga ttctggcacc aaacaactac tatccgtcta agaacctggc gccgattgca   1260

ctgaacgcgc aggatgactt ttctagcacg ccgatcacca tgaactacaa ccagtttctg   1320

gagctggaga aaaccaaaca gctgcgtctg gataccgatc aggtgtatgg caacattgca   1380

acctacaact tcgagaacgg ccgtgttcgt gtggataccg gtagcaactg gagcgaagtg   1440

ctgccacaga tccaggaaac gaccgcgcgc attatcttca atggcaaaga tctgaatctg   1500

gtggaacgcc gcatcgcggc ggtgaaccca tctgatccgc tggagaccac caagccggat   1560

atgaccctga aagaagcgct gaagattgcg tttggcttca atgaaccgaa tggcaacctg   1620

cagtaccagg gcaaagacat caccgaattc gacttcaact ttgatcagca gacctctcaa   1680

aacattaaga accagctggc agaactgaat gcgaccaaca tctacaccgt gctggataaa   1740
```

```
atcaaactga acgcgaagat gaacattctg attcgtgata agcgctttca ttatgaccgc   1800

aacaacatcg cggtgggcgc agacgaaagc gtggtgaaag aagcgcaccg tgaggtgatc   1860

aacagcagca ccgagggcct gctgctgaac attgataaag acattcgtaa gattctgagc   1920

ggttacattg tggagatcga agatacggaa ggcctgaaag aagttattaa cgaccgctat   1980

gatatgctga acatttctag cctgcgccag gatggcaaga ccttcatcga tttcaagaag   2040

tataacgaca agctgccgct gtatatcagc aacccgaatt acaaagtgaa cgtgtacgcg   2100

gtgaccaaag aaaacaccat tattaaccca agcgagaatg gtgataccag caccaacggc   2160

atcaagaaga ttctgatctt cagcaagaaa ggctatgaga ttggc                   2205


<210> SEQ ID NO 36
<211> LENGTH: 1755
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Truncated version of SEQ ID No: 1 (bp 301 to
      2055)

<400> SEQUENCE: 36

agcaacagca acaagattcg cctggagaag ggtcgcctgt atcagatcaa gattcagtat     60

cagcgcgaga atccgaccga gaaaggcctg gatttcaaac tgtactggac cgatagccag    120

aacaagaaag aagtgattag ctctgataac ctgcaactgc cggaactgaa acagaagagc    180

agcaacagcc gcaagaaacg cagcacctct gcaggcccga ccgttccaga tcgcgacaac    240

gatggcattc cggacagcct ggaagtggaa ggttataccg ttgatgtgaa gaacaaacgc    300

acctttctga gcccgtggat tagcaacatt catgagaaga aaggcctgac caagtacaaa    360

agcagcccgg agaagtggag caccgcgagc gatccgtata gcgactttga gaaagtgacc    420

ggccgcattg ataagaacgt gagcccggaa gcgcgtcacc cactggttgc agcgtatccg    480

attgtgcatg ttgacatgga gaacatcatt ctgagcaaga acgaagatca gagcacccag    540

aacacggata gccagacccg cacgatcagc aagaacacca gcacgagccg tacccatacc    600

agcgaagtgc atggcaatgc ggaagtgcat gcgagcttct ttgacattgg tggcagcgtg    660

agcgcgggct tcagcaacag caacagcagc accgtggcga ttgatcatag cctgagcctg    720

gcgggcgaac gtacctgggc ggaaaccatg ggcctgaaca cggcggatac ggcacgtctg    780

aatgcgaaca ttcgctatgt gaacaccggt accgcgccaa tctataacgt tctgccgacc    840

acgagcctgg tgctgggcaa gaatcagacc ctggcgacca tcaaagcgaa agagaaccag    900

ctgtctcaga ttctggcacc gaacaactac tatccgagca agaacctggc accgattgca    960

ctgaatgcgc aggatgactt cagcagcacc ccgatcacca tgaactacaa tcagtttctg   1020

gagctggaga agaccaaaca actgcgcctg gataccgatc aggtgtatgg caacattgcg   1080

acctacaact ttgagaacgg ccgcgttcgc gtggataccg gtagcaactg gtctgaagtg   1140

ctgccgcaga ttcaggaaac gaccgcgcgc atcatcttca acggcaaaga tctgaacctg   1200

gtggaacgtc gcatcgcggc agtgaaccca tctgatccac tggaaacgac caaaccggac   1260

atgaccctga aagaagcgct gaagattgca tttggcttca acgaaccgaa tggcaacctg   1320

cagtatcagg gcaaagacat caccgagttt gacttcaact ttgatcaaca gacctctcag   1380

aacatcaaga accagctggc agaactgaat gcgaccaaca tctacaccgt gctggacaag   1440

atcaaactga acgcaaagat gaacattctg attcgtgaca aacgcttcca ctatgatcgt   1500
```

```
aacaacattg cggtgggtgc agatgaaagc gttgtgaaag aagcgcatcg tgaagtgatc   1560

aactctagca ccgaaggcct gctgctgaac attgacaaag acatccgtaa gattctgagc   1620

ggctacattg tggagattga agataccgaa ggtctgaaag aagtgatcaa cgatcgctat   1680

gacatgctga acatctctag cctgcgccag gatggcaaga ccttcattga cttcaagaag   1740

tacaacgaca aactg                                                    1755
```

<210> SEQ ID NO 37
<211> LENGTH: 1755
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Sequence variant (99%) of SEQ ID No. 36

<400> SEQUENCE: 37

```
agcaacagca acaagattcg cctggagaag ggtcgcctgt atcagatcaa gattcagtat     60

cagcgcgaga atccgaccga gaaaggcctg gatttcaaac tgtactggac cgatagccag    120

aacaagaaag aagtgattag ctctgataac ctgcaactgc cggaactgaa acagaagagc    180

agcaacagcc gcaagaaacg cagcacctct gcaggcccga ccgttccaga tcgcgacaac    240

gatggcattc cggacagcct ggaagtggaa ggttataccg ttgatgtgaa gaacaaacgc    300

acctttctga gcccgtggat tagcaacatt catgagaaga aaggcctgac caagtacaaa    360

agcagcccgg agaagtggtc taccgcgagc gatccgtata gcgactttga gaaagtgacc    420

ggccgcattg ataagaacgt gagcccggaa gcgcgtcacc cactggttgc agcgtatccg    480

attgtgcatg ttgacatgga gaacatcatt ctgagcaaga acgaagatca gagcacccag    540

aacacggata gccagacccg cacgatcagc aagaacacca gcaccagccg tacccatacc    600

agcgaagtgc atggcaatgc ggaagtgcat gcgagcttct ttgacattgg tggcagcgtg    660

agcgcgggct tcagcaacag caacagcagc accgtggcga ttgatcatag cctgagcctg    720

gcgggcgaac gtacctgggc ggaaaccatg ggcctgaaca cggcggatac ggcacgtctg    780

aatgcgaaca ttcgctatgt gaacaccggt accgcgccaa tctataacgt tctgccgacc    840

acgagcctgg tgctgggcaa gaatcagacc ctggcgacca tcaaagcgaa agagaaccag    900

ctgagccaga tcctggcacc gaacaactac tatccgagca agaacctggc accgattgca    960

ctgaatgcgc aggatgactt cagcagcacc ccgatcacca tgaactacaa tcagtttctg   1020

gagctggaga agaccaaaca actgcgcctg gataccgatc aggtgtatgg caacattgcg   1080

acctacaact ttgagaacgg ccgcgttcgc gtggataccg gtagcaactg gtctgaagtg   1140

ctgccgcaga ttcaggaaac gaccgcgcgc atcatcttca acggcaaaga tctgaacctg   1200

gtggaacgtc gcatcgcggc agtgaaccca tctgacccac tggaaacgac caaaccggac   1260

atgaccctga aagaagcgct gaagattgca tttggcttca acgaaccgaa tggcaacctg   1320

cagtatcagg gcaaagacat caccgagttt gatttcaact ttgatcagca aacctctcag   1380

aacatcaaga accagctggc agaactgaat gcgaccaaca tctacaccgt gctggacaag   1440

atcaaactga acgcaaagat gaacattctg attcgtgaca aacgcttcca ctatgatcgt   1500

aacaacattg cggtgggtgc agatgagagc gttgtgaaag aagcgcatcg tgaagtgatc   1560

aactctagca cggaaggcct gctgctgaac attgacaaag acatccgcaa gattctgagc   1620

ggctacattg tggaaattga agataccgaa ggtctgaaag aagtgattaa cgatcgttat   1680
```

gacatgctga acatctctag cctgcgccag gatggcaaga ccttcattga cttcaagaag 1740
tacaacgaca aactg 1755

<210> SEQ ID NO 38
<211> LENGTH: 1755
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Sequence variant (98%) of SEQ ID No. 36

<400> SEQUENCE: 38
agcaacagca acaagattcg tctggagaag ggtcgcctgt atcagatcaa gattcagtat 60
cagcgcgaga atccgaccga gaaaggcctg gatttcaaac tgtactggac cgatagccag 120
aacaagaaag aagtgatcag ctctgataac ctgcaactgc cggaactgaa acagaagagc 180
agcaacagcc gcaagaaacg cagcacctct gcaggcccga ccgttccaga tcgtgacaac 240
gatggcattc cggacagcct ggaagtggaa ggttataccg ttgatgtgaa gaacaaacgc 300
acctttctga gcccgtggat tagcaacatt catgaaaaga aaggcctgac caagtacaaa 360
agcagcccgg agaagtggtc taccgcgagc gatccgtata gcgactttga gaaagtgacc 420
ggccgcatcg ataagaacgt gagcccggaa gcgcgtcacc cactggttgc agcgtatccg 480
attgtgcatg ttgacatgga gaacatcatt ctgagcaaga acgaagatca gagcacccag 540
aacacggata gccagacccg cacgatcagc aagaacacca gcaccagccg cacccatacc 600
agcgaagtgc atggcaatgc ggaagtgcat gcgagcttct ttgacattgg tggcagcgtg 660
agcgcgggct tcagcaacag caacagcagc accgtggcga ttgatcatag cctgagcctg 720
gcgggcgaac gtacctgggc ggaaaccatg ggcctgaaca cggcggatac ggcacgtctg 780
aatgcgaaca ttcgctatgt gaacaccggc accgcgccaa tctataacgt tctgccgacc 840
acgagcctgg tgctgggcaa gaatcagacc ctggcgacca tcaaagcgaa agagaaccag 900
ctgagccaga tcctggcacc gaacaactac tatccgagca agaacctggc accgattgca 960
ctgaatgcgc aggatgattt cagcagcacc ccgatcacca tgaactacaa tcagtttctg 1020
gagctggaga agaccaaaca actgcgcctg gataccgatc aggtgtatgg caacattgcg 1080
acctacaact ttgagaacgg tcgcgttcgc gtggataccg gtagcaactg gtctgaagtg 1140
ctgccgcaga ttcaggaaac gaccgcgcgc atcatcttca acggtaaaga tctgaacctg 1200
gtggaacgcc gcatcgcggc agtgaaccca tctgacccac tggaaacgac caaaccggac 1260
atgaccctga aagaagcgct gaagattgca tttggcttca acgaaccgaa tggcaacctg 1320
cagtatcagg gcaaagacat caccgagttc gacttcaact ttgatcagca aacctctcag 1380
aacatcaaga accagctggc agaactgaat gcgaccaaca tttacaccgt gctggacaag 1440
attaaactga acgcaaagat gaacattctg attcgtgaca aacgcttcca ctatgatcgt 1500
aacaacattg cggtgggcgc agatgagagc gttgtgaaag aagcgcatcg tgaagtgatc 1560
aactctagca cggagggcct gctgctgaac attgacaaag acatccgcaa gattctgagc 1620
ggctacattg tggaaattga agataccgaa ggtctgaaag aagtgattaa cgatcgttat 1680
gacatgctga acatctctag cctgcgccag gatggcaaga ccttcattga ctttaagaag 1740
tacaacgaca aactg 1755

<210> SEQ ID NO 39
<211> LENGTH: 1755

<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Sequence variant (97%) of SEQ ID No. 36

<400> SEQUENCE: 39

```
agcaacagca acaagattcg tctggagaag ggtcgcctgt atcagatcaa gattcagtat     60

cagcgcgaaa atccgaccga gaaaggcctg gattttaagc tgtactggac cgatagccag    120

aacaagaaag aagtgatcag ctctgataac ctgcaactgc cggaactgaa gcagaagagc    180

agcaacagcc gcaagaaacg cagcacctct gcaggcccga ccgttccaga tcgtgacaac    240

gatggcattc cggacagcct ggaggtggaa ggttataccg ttgatgtgaa gaacaaacgc    300

acctttctga gcccgtggat tagcaacatt catgaaaaga aaggcctgac caaatacaaa    360

agcagcccgg agaagtggtc taccgcgagc gatccatata gcgacttcga aaaagtgacc    420

ggccgcatcg ataagaacgt gagcccggaa gcgcgtcacc cactggttgc agcgtatccg    480

attgtgcatg ttgacatgga gaacatcatt ctgagcaaaa acgaagatca gagcacccag    540

aacacggata gccagacccg cacgatcagc aagaacacca gcaccagccg cacccatacc    600

agcgaagtgc atggcaatgc ggaagtgcat gcgagcttct ttgacattgg tggcagcgtg    660

agcgcgggct tcagcaacag caacagcagc accgtggcga ttgatcatag cctgagcctg    720

gcgggcgaac gtacctgggc ggaaaccatg ggcctgaaca cggcggatac cgcacgcctg    780

aatgcgaaca ttcgctatgt gaacaccggc accgcgccaa tctataacgt tctgccgacg    840

acgagcctgg tgctgggcaa gaatcagacc ctggcgacca tcaaagcgaa agagaaccag    900

ctgagccaga tcctggcacc gaacaactac tatccgagca agaacctggc accgattgca    960

ctgaatgcgc aggatgattt cagcagcacc ccgatcacca tgaactacaa tcagtttctg   1020

gagctggaga agaccaaaca actgcgcctg gataccgatc aggtgtatgg caacattgcg   1080

acctacaact ttgagaacgg tcgcgttcgc gtggataccg gcagcaactg gtctgaagtg   1140

ctgccgcaga ttcaggaaac gaccgcgcgt atcatcttca acggtaaaga tctgaacctg   1200

gtggaacgcc gcatcgcggc agtgaacccg tctgacccac tggaaacgac caaaccggac   1260

atgaccctga aagaagcgct gaagattgca tttggtttca acgaaccgaa tggcaacctg   1320

cagtatcagg gcaaagacat caccgagttc gacttcaact ttgatcagca aacctctcag   1380

aacatcaaga accagctggc agaactgaat gcgaccaaca tttacaccgt gctggacaag   1440

attaaactga acgcaaagat gaacattctg attcgtgaca aacgcttcca ctatgatcgt   1500

aacaacattg cggtgggcgc agatgagagc gttgtgaaag aagcgcatcg tgaggtgatc   1560

aactctagca cggagggcct gctgctgaac attgacaaag acatccgcaa gattctgagc   1620

ggctacattg tggaaattga agataccgaa ggtctgaaag aagtgattaa cgatcgttat   1680

gacatgctga acatctctag cctgcgccag gatggcaaga ccttcattga ctttaagaag   1740

tacaacgaca aactg                                                    1755
```

<210> SEQ ID NO 40
<211> LENGTH: 1755
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Sequence variant (96%) of SEQ ID No. 36

<400> SEQUENCE: 40

```
agcaacagca acaagattcg tctggagaag ggtcgcctgt atcagatcaa gattcagtat     60
cagcgcgaaa atccgaccga gaaaggcctg gattttaagc tgtactggac cgatagccag    120
aacaagaaag aagtgatcag ctctgataac ctgcagctgc cggaactgaa gcagaagagc    180
agcaacagcc gcaagaaacg cagcacctct gcaggcccga ccgttccaga tcgtgacaac    240
gatggcattc cggacagcct ggaggtggaa ggttataccg ttgatgtgaa gaacaaacgc    300
acctttctga gcccgtggat tagcaacatt catgaaaaga aaggcctgac caaatacaaa    360
agcagcccgg agaagtggtc taccgcgagc gatccatata gcgacttcga aaaagtgacc    420
ggccgcatcg ataagaatgt gagcccggaa gcgcgtcacc cactggttgc agcgtatccg    480
attgtgcatg tggacatgga gaacatcatt ctgagcaaaa acgaagatca gagcacccag    540
aacacggata gccagacccg cacgatcagc aagaacacca gcaccagccg cacccatacc    600
agcgaagtgc atggcaatgc ggaagtgcat gcgagcttct ttgacattgg tggctctgtg    660
agcgcgggct tcagcaacag caacagcagc accgtggcga ttgatcatag cctgagcctg    720
gcgggcgaac gtacctgggc ggaaaccatg ggcctgaaca cggcggatac cgcacgcctg    780
aacgcgaaca ttcgctatgt gaacaccggc accgcgccaa tctataacgt tctgccgacg    840
acgagcctgg ttctgggcaa gaatcagacc ctggcgacca tcaaagcgaa agagaaccag    900
ctgagccaga tcctggcacc gaacaactac tatccgagca agaacctggc accgattgca    960
ctgaatgcgc aggatgattt cagcagcacc ccaattacca tgaactacaa tcagtttctg   1020
gagctggaga agaccaaaca actgcgcctg gataccgatc aagtgtatgg caacattgcg   1080
acctacaact ttgagaacgg tcgcgttcgc gtggataccg gcagcaactg gtctgaagtg   1140
ctgccgcaga ttcaggaaac gaccgcgcgt atcatcttca acggtaaaga tctgaacctg   1200
gtggaacgcc gcatcgcggc agtgaacccg tctgacccgc tggaaacgac caaaccggac   1260
atgaccctga aagaagcgct gaagattgca tttggtttca acgaaccgaa tggcaacctg   1320
cagtatcagg gcaaagacat caccgagttc gacttcaact ttgatcagca aacctctcag   1380
aacatcaaga accagctggc agaactgaat gcgaccaaca tttacaccgt gctggacaag   1440
attaaactga acgcaaagat gaacattctg attcgtgaca aacgcttcca ctatgatcgt   1500
aacaacatcg cggtgggcgc agatgagagc gttgtgaaag aagcgcatcg tgaggtgatt   1560
aactctagca cggagggcct gctgctgaac attgacaaag atatccgcaa gattctgagc   1620
ggctacattg tggaaattga agataccgaa ggtctgaaag aagtgattaa cgatcgttat   1680
gacatgctga acatcagcag cctgcgccag gacggcaaga ccttcatcga ctttaagaag   1740
tacaacgaca aactg                                                    1755
```

<210> SEQ ID NO 41
<211> LENGTH: 1755
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Sequence variant (95%) of SEQ ID No. 36

<400> SEQUENCE: 41

```
agcaacagca acaagattcg tctggagaag ggtcgcctgt atcagatcaa gatccagtat     60
cagcgcgaaa atccgaccga gaaaggcctg gattttaagc tgtactggac cgatagccag    120
```

-continued

```
aacaagaaag aagtgatcag ctctgataac ctgcagctgc cggaactgaa gcagaagagc    180

agcaacagcc gcaagaaacg cagcacctct gcaggcccga ccgttccgga tcgtgacaac    240

gatggcattc cggacagcct ggaggttgaa ggttataccg tggatgtgaa gaacaaacgc    300

accttcctga gcccgtggat tagcaacatt catgaaaaaa aaggcctgac caaatacaaa    360

agcagcccgg agaagtggtc taccgcgagc gacccatata gcgacttcga aaaagtgacg    420

ggccgcatcg ataagaatgt gagcccggaa gcgcgtcacc cactggttgc agcgtatccg    480

attgtgcatg tggacatgga gaacatcatt ctgagcaaaa acgaagatca gagcacccag    540

aacacggata gccagacccg caccatcagc aagaacacca gcaccagccg cacccatacc    600

agcgaagtgc atggcaatgc agaagtgcat gcgagcttct ttgacattgg tggctctgtg    660

agcgcgggct tcagcaacag caacagcagc accgtggcga ttgatcatag cctgagcctg    720

gcgggcgaac gtacctgggc ggaaaccatg ggcctgaaca cggcggatac cgcacgcctg    780

aacgcgaaca ttcgctatgt gaacaccggc accgcgccaa tctataacgt tctgccgacg    840

acgagcctgg ttctgggcaa gaatcagacc ctggcgacca tcaaagcgaa agagaaccag    900

ctgagccaaa tcctggcacc gaacaactac tatccgagca agaacctggc accgattgca    960

ctgaatgcgc aggatgattt cagcagcacc ccaattacca tgaactacaa tcagtttctg   1020

gagctggaga agaccaaaca gctgcgcctg gataccgatc aagtgtatgg caacattgcg   1080

acctacaact ttgagaacgg tcgcgttcgc gtggataccg gcagcaactg gtctgaagtg   1140

ctgccgcaga ttcaggaaac gaccgcgcgt atcatcttta acggtaaaga tctgaacctg   1200

gtggaacgcc gcatcgcggc agtgaacccg tctgacccgc tggaaacgac caaaccggac   1260

atgaccctga aagaagcgct gaagattgca tttggtttca acgaaccaaa tggcaacctg   1320

cagtatcagg gcaaagacat caccgagttc gacttcaact ttgatcagca aacctctcag   1380

aacatcaaga accagctggc agaactgaat gcgaccaaca tttacaccgt gctggacaag   1440

attaaactga acgcaaagat gaacattctg attcgtgaca aacgcttcca ctatgatcgt   1500

aacaacattg cggtgggcgc ggatgagagc gttgtgaaag aagcgcatcg tgaggtgatt   1560

aactctagca cggagggcct gctgctgaac attgacaaag atatccgcaa gattctgagc   1620

ggctacattg tggaaattga agataccgaa ggtctgaagg aagtgattaa cgatcgttat   1680

gatatgctga acatcagcag cctgcgccag gacggcaaga ccttcatcga ctttaagaag   1740

tacaacgaca aactg                                                    1755


<210> SEQ ID NO 42
<211> LENGTH: 1755
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Sequence variant (94%) of SEQ ID No. 36

<400> SEQUENCE: 42

agcaacagca acaagattcg tctggagaag ggtcgcctgt atcagatcaa gatccagtat     60

cagcgcgaaa atccgaccga gaaaggcctg gattttaagc tgtactggac cgatagccag    120

aacaagaaag aagtgatcag ctctgataac ctgcaactgc cggaactgaa gcagaagagc    180

agcaacagcc gcaagaaacg cagcaccagc gcaggcccga ccgttccgga tcgtgacaac    240

gatggcattc cggacagcct ggaggttgaa ggttataccg tggatgtgaa gaacaaacgc    300

accttcctga gcccgtggat tagcaacatt catgaaaaaa aaggcctgac caaatacaaa    360
```

```
agcagcccgg agaagtggtc taccgcgagc gacccatata gcgacttcga aaaagtgacg    420

ggccgcatcg ataagaatgt gagcccggaa gcacgtcacc cactggttgc agcgtatccg    480

attgtgcatg tggacatgga gaacatcatt ctgagcaaaa acgaagatca gagcacgcag    540

aacacggata gccagacccg caccatcagc aagaacacca gcaccagccg cacccatacc    600

agcgaagtgc atggcaatgc agaagtgcat gcgagcttct ttgacattgg tggcagcgtg    660

agcgcgggct tcagcaacag caactctagc accgtggcga ttgatcatag cctgagcctg    720

gcgggcgaac gtacctgggc ggaaacgatg ggcctgaaca ccgcggatac cgcacgcctg    780

aacgcgaaca ttcgctacgt gaacaccggc accgcgccaa tctataacgt tctgccgacg    840

acgagcctgg ttctgggcaa gaatcagacc ctggcgacca tcaaagcgaa agagaaccag    900

ctgagccaaa tcctggcacc gaacaactac tatccgagca agaacctggc accgattgcg    960

ctgaatgcgc aggatgattt tagcagcacc ccaattacca tgaactataa ccagttcctg   1020

gagctggaga agaccaaaca gctgcgcctg gataccgatc aggtgtatgg caacattgcg   1080

acctacaact ttgagaacgg tcgcgttcgc gtggataccg gcagcaactg gtctgaagtg   1140

ctgccgcaga ttcaggaaac gaccgcgcgt atcatcttta acggtaaaga tctgaacctg   1200

gtggaacgcc gcatcgcggc agtgaacccg tctgacccgc tggaaaccac caaaccggac   1260

atgaccctga aagaagcgct gaagattgca tttggtttca acgaaccaaa tggcaacctg   1320

cagtatcagg gcaaagacat caccgagttc gatttcaact ttgatcagca gacctctcag   1380

aacatcaaga accaactggc agaactgaat gcgaccaaca tttacaccgt gctggacaag   1440

attaaactga acgcaaagat gaacattctg attcgtgaca aacgcttcca ctatgatcgt   1500

aacaacatcg cggtgggcgc ggatgagagc gttgtgaaag aagcgcatcg tgaggtgatt   1560

aactctagca cggagggcct gctgctgaac attgacaaag acattcgcaa gattctgtct   1620

ggctacattg tggaaattga agataccgaa ggtctgaagg aagtgattaa cgatcgttat   1680

gatatgctga atatcagcag cctgcgccag gacggcaaga ccttcatcga ctttaagaag   1740

tacaacgaca aactg                                                    1755
```

```
<210> SEQ ID NO 43
<211> LENGTH: 1755
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Sequence variant (93%) of  SEQ ID No. 36

<400> SEQUENCE: 43

agcaacagca acaaaattcg tctggagaag ggtcgcctgt atcagatcaa gatccagtat     60

cagcgcgaga atccgaccga gaaaggcctg gatttcaagc tgtactggac cgatagccag    120

aacaagaagg aagtgatcag ctctgataac ctgcaactgc cagaactgaa gcagaagagc    180

agcaacagcc gcaagaaacg cagcaccagc gcaggcccga ccgttccgga tcgtgacaac    240

gatggcattc cggacagcct ggaggttgaa ggttataccg tggatgtgaa gaacaaacgc    300

accttcctga gcccgtggat tagcaacatc catgaaaaga aaggcctgac caaatacaaa    360

agcagcccgg agaagtggtc taccgcgagc gacccataca gcgacttcga aaaagtgacg    420

ggccgcatcg ataagaacgt gagcccggaa gcacgtcacc cgctggttgc agcgtatccg    480

attgtgcatg tggacatgga gaacattatt ctgagcaaaa acgaagatca gagcacgcag    540
```

aacaccgata gccagacccg caccatcagc aagaacacca gcaccagccg cacccatacc 600
agcgaagtgc atggcaatgc agaagtgcat gcgagcttct ttgatattgg tggcagcgtg 660
agcgcgggct tcagcaacag caactctagc accgtggcga ttgatcatag cctgagcctg 720
gcgggcgaac gtacctgggc ggaaacgatg ggcctgaaca ccgcggatac cgcacgcctg 780
aacgcgaaca ttcgctacgt gaacaccggc accgcgccaa tctataacgt tctgccgacg 840
acgagcctgg ttctgggcaa gaatcagacc ctggcgacca tcaaagcgaa agagaaccag 900
ctgagccaaa tcctggcacc gaacaactac tatccgagca aaaacctggc accgattgcg 960
ctgaatgcgc aggatgattt tagcagcacc ccaattacca tgaactataa ccagttcctg 1020
gagctggaaa agaccaaaca gctgcgtctg gatacggatc aggtgtatgg caacattgcg 1080
acctacaact ttgagaacgg tcgcgttcgc gtggataccg gcagcaactg gtctgaagtg 1140
ctgccgcaga ttcaggaaac gaccgcgcgt atcatcttta acggtaaaga tctgaacctg 1200
gtggaacgcc gcattgcggc agtgaacccg tctgacccgc tggaaaccac caaaccggac 1260
atgaccctga aagaagcgct gaagattgca tttggtttca acgaaccaaa tggcaacctg 1320
cagtatcagg gcaaagacat caccgagttc gatttcaact ttgatcagca gacctctcag 1380
aacatcaaga atcaactggc agaactgaat gcgaccaaca tttacaccgt gctggacaag 1440
attaaactga acgcaaagat gaacattctg attcgtgaca aacgctttca ttatgatcgt 1500
aacaacatcg cggtgggcgc ggacgaaagc gttgtgaaag aggcgcaccg tgaggtgatt 1560
aactctagca cggagggcct gctgctgaac attgacaagg acatccgcaa gattctgtct 1620
ggctacattg tggaaattga agataccgaa ggtctgaaag aagtgattaa cgatcgctat 1680
gatatgctga atatcagcag cctgcgccag gacggcaaga ccttcatcga ctttaagaag 1740
tataacgaca aactg 1755

<210> SEQ ID NO 44
<211> LENGTH: 1755
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Sequence variant (92%) of SEQ ID No. 36

<400> SEQUENCE: 44
agcaacagca acaaaatccg tctggagaag ggtcgcctgt atcagatcaa gatccagtat 60
cagcgcgaga atccgaccga gaaaggcctg gatttcaagc tgtactggac cgatagccag 120
aacaagaaag aagtgatcag cagcgataac ctgcagctgc cagaactgaa gcagaagagc 180
agcaacagcc gcaagaaacg cagcacgagc gcaggcccga ccgttccgga tcgtgacaac 240
gatggcattc cggacagcct ggaggttgaa ggttataccg tggatgtgaa gaacaaacgc 300
accttcctga gcccgtggat tagcaacatc catgaaaaga aaggcctgac caaatacaaa 360
agcagcccgg agaagtggtc taccgcgagc gacccataca gcgacttcga aaaagtgacg 420
ggccgcatcg ataaaaacgt gagcccggaa gcacgtcatc cgctggttgc ggcgtatccg 480
attgtgcacg tggacatgga gaacattatt ctgagcaaga acgaagatca gagcacccag 540
aacaccgata gccagacccg caccatcagc aagaacacca gcaccagccg cacccatacc 600
agcgaagtgc atggcaacgc agaagtgcat gcgagcttct ttgatatcgg tggcagcgtg 660
agcgcgggct tcagcaacag caactcttct accgtggcga ttgatcacag cctgagcctg 720
gcgggcgaac gtacctgggc ggaaacgatg ggcctgaaca ccgcggatac cgcacgcctg 780

```
aacgcgaaca ttcgctacgt gaacaccggc accgcgccaa tttataacgt tctgccgacg    840

acgagcctgg ttctgggcaa gaaccagacc ctggcgacca tcaaagcgaa agagaaccag    900

ctgagccaaa ttctggcacc gaacaactac tatccgagca aaaacctggc accgattgcg    960

ctgaatgcgc aggatgattt tagcagcacc ccaattacca tgaactataa ccagttcctg   1020

gagctggaaa agaccaaaca gctgcgtctg gatacggatc aggtgtatgg caacattgcg   1080

acctacaact ttgagaacgg tcgcgttcgc gtggataccg gcagcaattg gagcgaagtg   1140

ctgccgcaga ttcaggaaac gaccgcgcgt atcatcttta acggtaaaga cctgaacctg   1200

gtggaacgcc gcattgcggc agtgaatccg tctgacccgc tggaaacgac caaaccggac   1260

atgaccctga aggaagcgct gaagatcgca tttggtttca acgaaccaaa tggcaacctg   1320

cagtatcaag gcaaagacat caccgagttc gatttcaact ttgatcagca gacctctcag   1380

aacatcaaga atcaactggc agaactgaat gcgaccaaca tttacaccgt gctggacaag   1440

attaaactga acgcaaagat gaatattctg attcgtgaca aacgctttca ttatgatcgt   1500

aacaacatcg cagtgggcgc ggacgaaagc gttgtgaaag aggcgcatcg tgaggtgatt   1560

aactctagca ccgagggcct gctgctgaac attgacaagg acattcgcaa gattctgtct   1620

ggctacattg tggaaattga agataccgaa ggtctgaaag aagtgattaa cgatcgctat   1680

gatatgctga acatctctag cctgcgccag gacggcaaga ccttcatcga ttttaagaag   1740

tataacgaca aactg                                                    1755
```

```
<210> SEQ ID NO 45
<211> LENGTH: 1755
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Sequence variant (91%) of SEQ ID No. 36

<400> SEQUENCE: 45

agcaacagca acaaaatccg tctggaaaag ggtcgcctgt atcagattaa gattcagtat     60

cagcgcgaga atccgaccga gaaaggcctg gatttcaagc tgtactggac cgatagccag    120

aacaagaaag aagtgatcag cagcgataac ctgcagctgc cagaactgaa gcagaagagc    180

agcaacagcc gcaagaaacg cagcaccagc gcaggcccga ccgttccgga tcgtgacaac    240

gatggcattc cggacagcct ggaggttgag ggttataccg tggacgtgaa gaacaaacgc    300

accttcctga gcccgtggat tagcaacatc catgaaaaga aaggcctgac caaatacaaa    360

agcagcccgg agaagtggtc taccgcgagc gacccataca gcgatttcga aaaagtgacg    420

ggccgtatcg ataaaaacgt gagcccggaa gcacgtcatc cgctggttgc ggcgtacccg    480

attgtgcacg tggacatgga aaacattatc ctgagcaaga acgaagatca gtctacccag    540

aacaccgata gccagacccg caccatcagc aaaaacacca gcaccagccg cacccatacg    600

agcgaagtgc atggcaacgc agaagtgcat gcgagctttt tcgatatcgg tggcagcgtg    660

agcgcaggct tcagcaacag caactctagc accgtggcga ttgatcacag cctgagcctg    720

gcgggcgaac gtacctgggc ggaaacgatg ggcctgaaca ccgcggatac cgcgcgcctg    780

aacgcgaaca ttcgctacgt taacaccggc accgcgccaa tttataacgt tctgccgacg    840

accagcctgg ttctgggcaa gaaccagacc ctggcgacca tcaaagcgaa agagaaccag    900

ctgagccaaa ttctggcacc gaacaactac tatccgagca aaaacctggc accgattgcg    960
```

ctgaatgcgc aggatgactt tagcagcacc ccaattacca tgaactataa ccagttcctg 1020
gagctggaaa agaccaaaca gctgcgtctg gatacggatc aggtgtatgg caacattgcg 1080
acctacaact ttgagaacgg tcgcgtgcgc gtggacaccg gcagcaattg gagcgaggtg 1140
ctgccgcaga ttcaggaaac gaccgcgcgc atcatcttta acggtaaaga tctgaacctg 1200
gtggaacgcc gcattgcggc agtgaatccg tctgacccgc tggaaacgac caaaccggac 1260
atgaccctga aggaagcgct gaagatcgca tttggtttca acgaaccaaa tggcaacctg 1320
cagtatcaag gcaaggacat caccgagttc gatttcaact ttgatcagca gacctctcag 1380
aacatcaaga atcaactggc agaactgaat gcgacgaaca tttataccgt gctggacaag 1440
attaaactga acgcaaagat gaatattctg attcgtgaca aacgctttca ttatgatcgt 1500
aacaacatcg cagtgggcgc ggacgaaagc gttgtgaaag aggcgcatcg tgaggtgatt 1560
aactctagca ccgagggcct gctgctgaac attgacaagg acattcgcaa gatcctgtct 1620
ggctacattg tggaaattga agataccgaa ggtctgaaag aagtgattaa cgatcgctat 1680
gatatgctga acatctctag cctgcgccag gatggcaaga ccttcatcga ttttaagaag 1740
tataacgaca aactg 1755

<210> SEQ ID NO 46
<211> LENGTH: 1854
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Truncated version of SEQ ID No: 1 (bp. 202-2055)

<400> SEQUENCE: 46
ttcatcaaag tgaagaaaag cgatgagtat acctttgcga cgtctgcgga taaccatgtg 60
accatgtggg tggacgatca ggaagtgatc aacaaagcga gcaacagcaa caagattcgc 120
ctggagaagg gtcgcctgta tcagatcaag attcagtatc agcgcgagaa tccgaccgag 180
aaaggcctgg atttcaaact gtactggacc gatagccaga acaagaaaga agtgattagc 240
tctgataacc tgcaactgcc ggaactgaaa cagaagagca gcaacagccg caagaaacgc 300
agcacctctg caggcccgac cgttccagat cgcgacaacg atggcattcc ggacagcctg 360
gaagtggaag gttataccgt tgatgtgaag aacaaacgca cctttctgag cccgtggatt 420
agcaacattc atgagaagaa aggcctgacc aagtacaaaa gcagcccgga gaagtggagc 480
accgcgagcg atccgtatag cgactttgag aaagtgaccg gccgcattga taagaacgtg 540
agcccggaag cgcgtcaccc actggttgca gcgtatccga ttgtgcatgt tgacatggag 600
aacatcattc tgagcaagaa cgaagatcag agcacccaga acacggatag ccagacccgc 660
acgatcagca agaacaccag cacgagccgt acccatacca gcgaagtgca tggcaatgcg 720
gaagtgcatg cgagcttctt tgacattggt ggcagcgtga gcgcgggctt cagcaacagc 780
aacagcagca ccgtggcgat tgatcatagc ctgagcctgg cgggcgaacg tacctgggcg 840
gaaaccatgg gcctgaacac ggcggatacg gcacgtctga atgcgaacat tcgctatgtg 900
aacaccggta ccgcgccaat ctataacgtt ctgccgacca cgagcctggt gctgggcaag 960
aatcagaccc tggcgaccat caaagcgaaa gagaaccagc tgtctcagat tctggcaccg 1020
aacaactact atccgagcaa gaacctggca ccgattgcac tgaatgcgca ggatgacttc 1080
agcagcaccc cgatcaccat gaactacaat cagtttctgg agctggagaa gaccaaacaa 1140

```
ctgcgcctgg ataccgatca ggtgtatggc aacattgcga cctacaactt tgagaacggc   1200

cgcgttcgcg tggataccgg tagcaactgg tctgaagtgc tgccgcagat tcaggaaacg   1260

accgcgcgca tcatcttcaa cggcaaagat ctgaacctgg tggaacgtcg catcgcggca   1320

gtgaacccat ctgatccact ggaaacgacc aaaccggaca tgaccctgaa agaagcgctg   1380

aagattgcat ttggcttcaa cgaaccgaat ggcaacctgc agtatcaggg caaagacatc   1440

accgagtttg acttcaactt tgatcaacag acctctcaga acatcaagaa ccagctggca   1500

gaactgaatg cgaccaacat ctacaccgtg ctggacaaga tcaaactgaa cgcaaagatg   1560

aacattctga ttcgtgacaa acgcttccac tatgatcgta acaacattgc ggtgggtgca   1620

gatgaaagcg ttgtgaaaga agcgcatcgt gaagtgatca actctagcac cgaaggcctg   1680

ctgctgaaca ttgacaaaga catccgtaag attctgagcg gctacattgt ggagattgaa   1740

gataccgaag gtctgaaaga agtgatcaac gatcgctatg acatgctgaa catctctagc   1800

ctgcgccagg atggcaagac cttcattgac ttcaagaagt acaacgacaa actg          1854
```

<210> SEQ ID NO 47
<211> LENGTH: 1854
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Sequence variant (99%) of SEQ ID No. 46

<400> SEQUENCE: 47

```
ttcatcaaag tgaagaaaag cgatgagtat acctttgcga cgtctgcgga taaccatgtg     60

accatgtggg tggacgatca ggaagtgatc aacaaagcga gcaacagcaa caaaattcgc    120

ctggagaagg gtcgcctgta tcagatcaag attcagtatc agcgcgagaa tccgaccgag    180

aaaggcctgg atttcaaact gtactggacc gatagccaga acaagaaaga agtgattagc    240

tctgataacc tgcagctgcc ggaactgaaa cagaagagca gcaacagccg caagaaacgc    300

agcaccagcg caggcccgac cgttccagat cgcgacaacg atggcattcc ggacagcctg    360

gaagtggaag gttataccgt tgatgtgaag aacaaacgca cctttctgag cccgtggatt    420

agcaacattc atgagaagaa aggcctgacc aagtacaaaa gcagcccgga gaagtggagc    480

accgcgagcg atccgtatag cgactttgaa aaagtgaccg gccgcattga taagaacgtg    540

agcccggaag cgcgtcaccc actggttgcg gcgtatccga ttgtgcatgt tgacatggag    600

aacatcattc tgagcaagaa cgaagatcag agcacccaga acacggatag ccagacccgc    660

acgatcagca agaacaccag cacgagccgt acccatacca gcgaagtgca tggcaatgcg    720

gaagtgcatg cgagcttctt tgacattggt ggcagcgtga gcgcgggctt cagcaacagc    780

aacagcagca ccgtggcgat tgatcatagc ctgagcctgg cgggcgaacg tacctgggca    840

gaaaccatgg gcctgaacac ggcggatacg gcacgtctga atgcgaacat tcgctatgtg    900

aacaccggta ccgcgccaat ctataacgtt ctgccgacca cgagcctggt gctgggcaag    960

aatcagaccc tggcgaccat caaagcgaaa gagaaccagc tgtctcagat tctggcaccg   1020

aacaactact atccgagcaa gaacctggca ccgattgcac tgaatgcgca ggatgacttc   1080

agctctaccc cgatcaccat gaactacaat caattcctgg agctggagaa gaccaagcaa   1140

ctgcgcctgg ataccgatca ggtgtatggc aacattgcga cctacaactt tgagaacggc   1200

cgcgttcgcg tggataccgg tagcaactgg tctgaagtgc tgccgcagat tcaggaaacg   1260

accgcgcgca tcatcttcaa cggcaaagat ctgaacctgg tggaacgtcg catcgcggca   1320
```

```
gtgaacccat ctgatccact ggaaacgacc aaaccggaca tgaccctgaa agaagcgctg   1380

aagattgcat ttggcttcaa cgaaccgaat ggcaacctgc agtatcaggg caaagacatc   1440

accgagtttg acttcaactt tgaccaacag acctctcaga acatcaagaa ccagctggca   1500

gaactgaatg cgaccaacat ctacaccgtg ctggacaaga tcaaactgaa cgcaaagatg   1560

aacattctga ttcgtgacaa acgcttccac tatgatcgta acaacattgc ggtgggtgca   1620

gatgaaagcg ttgtgaaaga ggcgcatcgt gaagtgatca actctagcac cgaaggcctg   1680

ctgctgaaca ttgacaaaga tatccgtaag attctgagcg gctacattgt ggagattgaa   1740

gataccgaag gtctgaaaga agtgatcaac gatcgctatg acatgctgaa catctctagc   1800

ctgcgccagg atggcaagac ctttattgac ttcaagaagt acaacgacaa actg          1854
```

<210> SEQ ID NO 48
<211> LENGTH: 1854
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Sequence variant (98%) of SEQ ID No. 46

<400> SEQUENCE: 48

```
ttcatcaaag tgaagaaaag cgatgagtat acctttgcga cgtctgcgga taatcatgtg     60

accatgtggg tggacgatca ggaagtgatc aacaaagcga gcaacagcaa caaaattcgc    120

ctggagaagg gtcgcctgta tcagatcaag attcagtatc agcgcgagaa tccgaccgag    180

aaaggcctgg acttcaaact gtactggacg gatagccaga acaagaaaga agtgattagc    240

tctgataacc tgcagctgcc ggaactgaaa cagaagagca gcaacagccg caagaaacgt    300

agcaccagcg caggcccgac cgttccagat cgcgacaacg atggcattcc ggacagcctg    360

gaagtggaag gttataccgt tgatgtgaag aacaaacgca cctttctgag cccgtggatt    420

agcaacattc atgagaagaa aggcctgacc aagtacaaaa gcagcccgga aaagtggagc    480

accgcgagcg atccgtatag cgactttgaa aaagtgaccg gccgcatcga taagaacgtg    540

agcccggaag cgcgtcaccc actggtggcg gcgtatccga ttgtgcatgt tgacatggag    600

aacatcattc tgagcaagaa cgaagatcag agcacccaga acacggatag ccagacccgc    660

acgatcagca agaacaccag cacgagccgt acccatacca gcgaagtgca tggcaatgcg    720

gaagtgcatg cgagcttctt tgacattggt ggcagcgtga gcgcgggctt cagcaacagc    780

aacagcagca ccgtggcgat tgatcatagc ctgagcctgg cgggcgaacg cacctgggca    840

gaaaccatgg gcctgaacac ggcggatacg gcacgtctga atgcgaacat tcgctatgtg    900

aacaccggta ccgcgccaat ctataacgtt ctgccgacca cgagcctggt gctgggcaag    960

aaccagaccc tggcgaccat caaagcgaaa gagaaccagc tgtctcaaat tctggcaccg   1020

aacaactact atccgagcaa gaacctggca ccgattgcac tgaatgcgca ggatgacttc   1080

agctctaccc cgatcaccat gaactacaat cagttcctgg agctggagaa gaccaagcaa   1140

ctgcgcctgg ataccgatca ggtgtatggc aacattgcga cctacaactt tgagaacggc   1200

cgcgttcgcg tggacaccgg tagcaactgg tctgaagtgc tgccgcagat tcaggaaacc   1260

accgcgcgca tcatcttcaa cggcaaagat ctgaacctgg tggaacgtcg catcgcggca   1320

gtgaacccat ctgatccact ggaaacgacc aaaccggaca tgaccctgaa agaggcgctg   1380

aagattgcat ttggcttcaa cgaaccgaat ggcaacctgc agtatcaggg caaagacatc   1440
```

accgagtttg atttcaactt tgaccaacag acctctcaga acattaagaa ccagctggca 1500
gaactgaatg cgaccaacat ctacaccgtg ctggataaga tcaaactgaa cgcaaagatg 1560
aacattctga ttcgtgacaa acgcttccac tatgatcgta acaacattgc ggtgggtgca 1620
gatgaaagcg ttgtgaaaga ggcgcatcgc gaagttatca actctagcac cgaaggcctg 1680
ctgctgaaca ttgacaaaga tatccgtaag attctgagcg gctacattgt ggagattgaa 1740
gataccgaag gtctgaaaga agtgatcaac gatcgctatg acatgctgaa catctctagc 1800
ctgcgtcagg atggcaagac ctttattgac ttcaagaaat acaacgacaa gctg 1854

<210> SEQ ID NO 49
<211> LENGTH: 1854
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Sequence variant (97%) of SEQ ID No. 46

<400> SEQUENCE: 49
ttcatcaaag ttaagaaaag cgatgagtat acctttgcga cgtctgcgga taatcatgtg 60
accatgtggg tggacgatca ggaagtgatc aacaaagcga gcaacagcaa caaaattcgc 120
ctggagaagg gccgcctgta tcagatcaag attcagtatc agcgcgagaa tccgaccgag 180
aaaggcctgg acttcaaact gtactggacg gatagccaga acaagaaaga agtgattagc 240
tctgataacc tgcagctgcc ggaactgaaa cagaagagca gcaacagccg taagaaacgt 300
agcaccagcg caggcccgac cgttccagat cgcgacaacg atggcattcc ggacagcctg 360
gaagtggaag gttataccgt tgatgtgaag aacaaacgca cctttctgag cccatggatt 420
agcaacattc atgagaagaa aggcctgacc aagtacaaaa gcagcccgga aaagtggagc 480
accgcgagcg atccgtatag cgactttgaa aaagtgaccg gccgcatcga taagaacgtg 540
agcccggaag cgcgccaccc actggtggca gcgtatccga ttgtgcatgt tgacatggag 600
aacatcattc tgagcaagaa cgaagatcag agcacccaga acacggatag ccagacccgc 660
acgatcagca agaacaccag cacgagccgt acccatacca gcgaagtgca tggcaatgcg 720
gaagtgcacg cgagcttctt tgacattggt ggcagcgtga gcgcgggctt cagcaacagc 780
aacagcagca ccgtggcgat tgatcatagc ctgagcctgg cgggcgaacg cacctgggca 840
gaaaccatgg gtctgaacac ggcggatacg gcacgtctga atgcgaacat tcgctatgtg 900
aacaccggta ccgcgccaat ctataacgtg ctgccgacca cgagcctggt gctgggcaag 960
aaccagaccc tggcgaccat caaagcgaaa gagaaccagc tgtctcagat tctggcaccg 1020
aacaactact atccgagcaa gaacctggca ccgattgcac tgaatgcgca agatgacttc 1080
agctctaccc cgatcaccat gaactacaat cagttcctgg agctggagaa gaccaagcaa 1140
ctgcgcctgg ataccgatca ggtgtatggc aacatcgcga cctacaactt tgagaacggc 1200
cgcgttcgcg tggacaccgg tagcaactgg tctgaagtgc tgccgcagat tcaggaaacc 1260
accgcgcgca ttatcttcaa cggcaaggat ctgaacctgg tggaacgccg catcgcggca 1320
gtgaacccgt ctgatccact ggaaacgacc aaaccggaca tgaccctgaa agaggcgctg 1380
aagattgcat ttggcttcaa cgaaccgaat ggcaacctgc agtatcaggg caaagacatc 1440
accgagtttg atttcaactt tgaccaacag acctctcaga acattaaaaa ccagctggcg 1500
gaactgaatg cgaccaacat ctacaccgtg ctggataaga tcaaactgaa cgcaaagatg 1560
aacattctga ttcgtgacaa acgcttccat tatgatcgta acaacattgc ggtgggtgca 1620
gatgaaagcg ttgtgaaaga ggcgcatcgc gaagttatca actctagcac cgaaggcctg 1680
ctgctgaaca ttgacaaaga tatccgtaag attctgagcg gctacattgt ggagattgaa 1740
gataccgaag gtctgaaaga agtgatcaac gatcgttatg acatgctgaa catctctagc 1800
ctgcgtcagg atggcaagac ctttattgac ttcaagaaat acaacgacaa gctg 1854

<210> SEQ ID NO 50
<211> LENGTH: 1854
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Sequence variant (96%) of SEQ ID No. 46

<400> SEQUENCE: 50
ttcattaaag ttaaaaaaag cgatgagtat acctttgcga cgtctgcgga taatcatgtg 60
accatgtggg tggacgatca ggaagtgatc aacaaagcga gcaacagcaa caaaatccgc 120
ctggagaagg gccgcctgta tcagatcaaa attcaatatc agcgcgagaa tccgaccgag 180
aaaggcctgg acttcaaact gtactggacg gatagccaga acaagaaaga agtgattagc 240
tctgataacc tgcagctgcc ggaactgaaa cagaagagca gcaacagccg taagaaacgt 300
agcaccagcg caggcccgac cgttccagat cgcgacaacg atggcattcc ggacagcctg 360
gaagtggaag gttataccgt tgatgtgaag aacaaacgca cctttctgag cccatggatt 420
agcaacattc atgagaagaa aggcctgacc aagtacaaga gcagcccgga aaagtggagc 480
accgcgagcg atccgtatag cgactttgag aaagttaccg gccgcatcga taagaacgtg 540
agcccggaag cacgccaccc actggtggca gcgtatccga ttgtgcatgt tgacatggag 600
aacatcattc tgagcaagaa cgaagatcag agcacccaga acacggatag ccagacccgc 660
acgatcagca agaacaccag cacgagccgt acccatacct ctgaagtgca tggcaatgcg 720
gaagttcatg cgagcttctt tgacattggt ggcagcgtga gcgcgggctt cagcaacagc 780
aacagcagca ccgtggcgat tgatcatagc ctgagcctgg cgggcgaacg cacctgggca 840
gaaaccatgg gtctgaacac cgcggatacg gcacgtctga atgcgaacat tcgctatgtg 900
aacaccggta ccgcgccaat ctataacgtg ctgccgacca cgagcctggt gctgggcaag 960
aaccagacgc tggcgaccat caaagcgaag gagaaccagc tgagccagat tctggcgccg 1020
aacaactact atccgagcaa gaacctggca ccgattgcac tgaatgcgca agatgacttc 1080
agctctaccc cgatcaccat gaactacaat cagttcctgg agctggaaaa gaccaagcaa 1140
ctgcgcctgg ataccgatca ggtgtatggc aacatcgcga cctacaactt tgagaacggc 1200
cgcgttcgcg tggacaccgg tagcaactgg tctgaagtgc tgccgcagat tcaggaaacc 1260
accgcgcgca ttatcttcaa cggcaaggat ctgaacctgg tggaacgccg catcgcggca 1320
gtgaacccgt ctgatccact ggaaacgacc aaaccggaca tgaccctgaa agaggcgctg 1380
aagattgcat ttggcttcaa cgaaccgaat ggcaacctgc agtatcaggg caaagacatc 1440
accgagtttg atttcaactt tgaccagcag acctctcaga acattaaaaa ccagctggcg 1500
gaactgaatg cgaccaacat ctacaccgtg ctggataaga tcaaactgaa cgcaaagatg 1560
aacattctga ttcgtgacaa acgcttccac tatgatcgta acaacattgc ggtgggtgca 1620
gatgaaagcg tggtgaaaga ggcgcatcgc gaagtgatca actctagcac cgaaggcctg 1680
ctgctgaaca ttgacaaaga tatccgtaag attctgagcg gctacattgt ggagattgaa 1740
gataccgaag gtctgaaaga agtgatcaac gatcgttatg acatgctgaa catctctagc 1800
ctgcgtcagg atggcaagac ctttattgac ttcaagaaat acaacgacaa gctg 1854

<210> SEQ ID NO 51
<211> LENGTH: 1854
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Sequence variant (95%) of SEQ ID No. 46

<400> SEQUENCE: 51
ttcattaaag ttaaaaaaag cgatgagtac acctttgcga cgagcgcgga taatcatgtg 60
accatgtggg tggacgatca ggaagtgatc aacaaagcga gcaacagcaa caaaatccgc 120
ctggagaagg gccgcctgta tcagatcaaa attcaatatc agcgcgagaa tccgaccgag 180
aaaggcctgg acttcaaact gtactggacg gatagccaga acaagaaaga agtgattagc 240
tctgataacc tgcagctgcc ggaactgaaa cagaagagca gcaacagccg taagaaacgt 300
agcaccagcg caggcccgac cgttccagat cgcgacaacg atggcattcc ggacagcctg 360
gaagtggaag gttataccgt tgatgtgaag aacaaacgca cctttctgag cccatggatt 420
tctaacattc acgagaagaa aggcctgacc aagtataaga gcagcccgga aaagtggagc 480
accgcgagcg atccgtatag cgactttgaa aaagttaccg gccgcatcga taagaacgtg 540
agcccggaag cacgtcaccc actggtggca gcgtatccga ttgtgcatgt tgacatggag 600
aacatcattc tgagcaagaa cgaagaccag agcacccaga acacggatag ccagacccgc 660
acgatcagca agaacaccag cacgagccgt acccatacct ctgaagtgca tggcaatgcg 720
gaagttcatg cgagcttctt tgacattggt ggcagcgtga gcgcgggctt cagcaacagc 780
aacagcagca ccgtggcgat tgatcatagc ctgagcctgg cgggcgaacg cacctgggca 840
gaaaccatgg gtctgaacac cgcggatacg gcacgtctga atgcgaacat tcgctacgtg 900
aacaccggta ccgcgccgat ctataacgtg ctgccgacca cgagcctggt gctgggcaag 960
aaccagacgc tggcgaccat caaagcgaag gagaaccagc tgagccagat tctggcgccg 1020
aacaactact atccgagcaa aaacctggca ccgattgcac tgaatgcgca agatgatttt 1080
agctctaccc cgatcaccat gaactacaat cagttcctgg agctggaaaa gaccaagcaa 1140
ctgcgcctgg ataccgatca ggtgtatggc aacatcgcga cctacaactt tgagaacggc 1200
cgcgttcgcg tggacaccgg tagcaactgg tctgaagtgc tgccgcagat tcaggaaacc 1260
accgcgcgca ttatcttcaa cggcaaggat ctgaacctgg tggaacgccg catcgcggca 1320
gtgaacccgt ctgatccact ggaaacgacc aagccggaca tgaccctgaa agaggcgctg 1380
aagattgcat tcggcttcaa cgaaccaaat ggcaacctgc agtatcaggg caaagacatc 1440
accgagtttg atttcaactt tgaccagcag acctctcaga acattaaaaa ccagctggcg 1500
gaactgaatg cgaccaacat ctataccgtg ctggataaga tcaaactgaa cgcaaagatg 1560
aacattctga ttcgtgacaa acgcttccat tatgatcgta acaacattgc ggtgggtgca 1620
gatgaaagcg tggtgaaaga ggcgcatcgc gaagtgatca actctagcac cgaaggcctg 1680
ctgctgaaca ttgacaaaga tatccgtaag attctgagcg gctacattgt ggagattgaa 1740
gataccgaag gtctgaaaga ggtgatcaac gatcgctatg acatgctgaa catctctagc 1800
ctgcgtcagg acggcaagac ctttattgat ttcaagaagt acaacgacaa actg 1854

<210> SEQ ID NO 52
<211> LENGTH: 1854
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Sequence variant (94%) of SEQ ID No. 46

<400> SEQUENCE: 52

```
ttcattaaag ttaaaaaaag cgatgagtac acctttgcga cgagcgcgga taatcatgtg     60
accatgtggg tggacgatca ggaagtgatc aacaaagcga gcaacagcaa caaaatccgc    120
ctggagaagg gccgcctgta tcagatcaaa attcaatatc agcgcgagaa tccgaccgag    180
aaaggcctgg acttcaaact gtactggacg gatagccaga acaaaaaaga agtgattagc    240
tctgataacc tgcagctgcc ggaactgaaa cagaagagca gcaacagccg taagaaacgt    300
agcaccagcg caggcccaac cgttccagat cgcgacaacg acggcattcc ggatagcctg    360
gaagtggaag gttataccgt tgatgtgaag aacaaacgca cctttctgag cccatggatt    420
tctaacattc acgagaagaa aggcctgacc aagtataaga gcagcccgga aaagtggagc    480
accgcgagcg atccgtatag cgactttgaa aaggttaccg gccgcatcga taagaacgtg    540
agcccggaag cacgtcaccc actggtggca gcgtatccga ttgtgcatgt tgacatggag    600
aacatcattc tgagcaagaa cgaagaccag agcacccaga acacggatag ccagacccgc    660
accatcagca agaacaccag cacgagccgt acccatacct ctgaggtgca tggcaatgcg    720
gaagttcatg cgagcttctt tgatattggt ggcagcgtga gcgcgggctt tagcaacagc    780
aacagcagca cggtggcgat tgatcatagc ctgagcctgg cgggcgaacg cacctgggca    840
gaaaccatgg gtctgaacac cgcggatacg gcgcgtctga atgcgaacat tcgctacgtg    900
aacaccggta ccgcgccgat ctacaacgtg ctgccgacca cgagcctggt gctgggcaag    960
aaccagaccc tggcgaccat caaagcgaag gagaaccagc tgagccagat tctggcgccg   1020
aacaactact atccgagcaa aaacctggca ccgattgcac tgaatgcaca agatgatttt   1080
agctctaccc cgatcaccat gaactacaat cagttcctgg agctggaaaa gaccaagcaa   1140
ctgcgcctgg acaccgatca ggtgtatggc aacatcgcga cctacaactt tgagaacggc   1200
cgcgttcgcg tggacaccgg tagcaactgg tctgaagtgc tgccgcagat tcaggaaacc   1260
accgcgcgca ttatcttcaa cggcaaggac ctgaacctgg tggaacgccg catcgcggca   1320
gtgaacccgt ctgatccgct ggaaacgacc aagccggaca tgaccctgaa agaggcgctg   1380
aagattgcat tcggcttcaa cgaaccaaat ggcaacctgc agtatcaggg caaagacatc   1440
accgaattcg atttcaactt tgaccagcag acctctcaga acattaaaaa ccagctggcg   1500
gaactgaatg cgaccaacat ctataccgtg ctggataaga tcaaactgaa cgcaaagatg   1560
aacattctga ttcgtgataa acgcttccat tatgatcgta acaacattgc ggtgggtgca   1620
gatgaaagcg tggtgaaaga ggcgcatcgc gaagtgatca actctagcac ggaaggcctg   1680
ctgctgaaca ttgacaaaga tatccgtaag attctgagcg gctacattgt ggagattgaa   1740
gataccgaag gtctgaaaga ggtgatcaac gatcgctatg acatgctgaa catctctagc   1800
ctgcgtcagg acggcaagac ctttattgat ttcaagaagt ataacgacaa actg         1854
```

<210> SEQ ID NO 53
<211> LENGTH: 1854
<212> TYPE: DNA
<213> ORGANISM: Artificial Sequence
<220> FEATURE:

-continued

<223> OTHER INFORMATION: Description of Artificial Sequence: Synthetic
polynucleotide
<220> FEATURE:
<223> OTHER INFORMATION: Sequence variant (93%) of SEQ ID No. 46

<400> SEQUENCE: 53

```
ttcattaaag ttaaaaaaag cgacgagtac acctttgcga ccagcgcgga taatcatgtg     60
accatgtggg tggatgatca ggaagtgatc aacaaagcga gcaacagcaa caaaatccgc    120
ctggagaagg gccgcctgta tcagatcaaa attcagtatc agcgcgagaa tccgaccgag    180
aaaggcctgg atttcaaact gtactggacc gatagccaga acaaaaagga agtgattagc    240
tctgacaacc tgcagctgcc ggaactgaaa cagaaaagca gcaacagccg taagaaacgt    300
agcacctctg cgggcccaac cgttccggat cgcgacaacg acggcattcc ggatagcctg    360
gaagtggaag gttataccgt tgacgtgaag aacaagcgca cctttctgag cccgtggatt    420
agcaacattc acgaaaagaa aggtctgacc aagtataaaa gcagcccgga aaagtggagc    480
accgcgagcg atccatatag cgactttgaa aaggttacgg gccgcatcga taagaacgtg    540
agcccggaag cgcgtcaccc actggtggca gcgtatccaa ttgtgcatgt tgacatggag    600
aacatcattc tgagcaagaa cgaagaccag agcacccaga acacggatag ccagacgcgt    660
accattagca aaaacacgag cacgagccgt acccatacca gcgaggtgca tggcaatgcg    720
gaagtgcatg cgagcttctt tgacattggt ggcagcgtga gcgcgggctt tagcaacagc    780
aacagcagca cggtggcgat tgatcatagc ctgagcctgg cgggcgagcg cacctgggca    840
gaaaccatgg gtctgaacac cgcggatacg gcgcgtctga atgcaaacat ccgctacgtg    900
aacaccggca ccgcgccgat ctacaacgtg ctgccgacca ccagcctggt gctgggcaag    960
aaccaaaccc tggcgacgat caaagcgaag gagaaccagc tgtctcagat tctggcgccg   1020
aacaactact atccgagcaa aaacctggca ccgattgcgc tgaatgcaca ggatgacttt   1080
agctctaccc cgatcaccat gaactacaat cagttcctgg agctggaaaa gaccaagcaa   1140
ctgcgcctgg acaccgatca ggtgtatggc aacattgcga cctacaactt tgagaacggc   1200
cgcgttcgcg tggacaccgg tagcaactgg tctgaagtgc tgccgcagat tcaggaaacc   1260
accgcgcgca tcattttcaa cggcaaggat ctgaacctgg tggaacgccg catcgcggca   1320
gtgaacccgt ctgatccgct ggaaaccacc aagccggaca tgaccctgaa agaggcactg   1380
aagattgcat tcggcttcaa cgaaccaaat ggcaacctgc agtatcaagg caaggatatc   1440
accgaattcg atttcaactt tgaccagcag acctctcaga acattaaaaa ccagctggca   1500
gaactgaacg cgaccaacat ctataccgtg ctggataaga ttaagctgaa tgcaaagatg   1560
aacattctga ttcgtgataa acgcttccat tatgatcgta acaacattgc ggtgggtgca   1620
gatgaaagcg ttgtgaaaga ggcgcatcgc gaagtgatca actctagcac ggaaggcctg   1680
ctgctgaaca tcgacaaaga tattcgcaag atcctgagcg gctacatcgt ggagatcgaa   1740
gataccgaag gtctgaaaga ggtgattaac gatcgctatg acatgctgaa catctctagc   1800
ctgcgtcagg atggcaagac ctttattgat ttcaagaaat ataacgacaa actg         1854
```

<210> SEQ ID NO 54
<211> LENGTH: 1854
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Sequence variant (92%) of SEQ ID No. 46

-continued

<400> SEQUENCE: 54

```
ttcattaaag tgaaaaaaag cgacgagtac acgtttgcga ccagcgcgga taatcatgtg     60
accatgtggg tggatgatca ggaagttatc aacaaagcaa gcaatagcaa caagatccgc    120
ctggagaaag gccgcctgta tcagatcaaa attcagtatc agcgcgagaa tccgaccgag    180
aaaggcctgg atttcaaact gtactggacc gacagccaga acaaaaagga agtgatcagc    240
tctgacaacc tgcagctgcc ggaactgaag cagaagagca gcaacagccg taagaaacgt    300
agcacctctg cgggcccaac cgttccggat cgcgacaacg acggcattcc ggattctctg    360
gaagtggaag gttataccgt tgacgtgaaa aacaagcgca cctttctgag cccgtggatt    420
agcaacattc acgaaaagaa gggtctgacc aagtataaaa gcagcccgga aaagtggagc    480
accgcgagcg atccatatag cgactttgaa aaggttaccg gccgcatcga taagaacgtg    540
agcccggaag cgcgccaccc actggtggca gcgtatccaa ttgtgcatgt tgacatggag    600
aacattattc tgagcaagaa cgaagaccag agcacccaga acacggatag ccagacgcgt    660
accattagca aaaacacgag cacgagccgt acccatacca gcgaggtgca tggcaatgcg    720
gaagtgcatg cgagcttctt tgacattggt ggcagcgtga gcgcgggctt tagcaacagc    780
aacagcagca cggtggcgat tgatcatagc ctgagcctgg cgggcgagcg cacctgggca    840
gaaaccatgg gtctgaacac cgcggatacc gcgcgtctga atgcaaacat ccgctacgtg    900
aacaccggca ccgcgccgat ctacaacgtg ctgccgacca ccagcctggt gctgggcaag    960
aaccaaaccc tggcgacgat caaagcgaag gagaaccagc tgtctcagat tctggcgccg   1020
aacaactatt atccgagcaa aaacctggca ccgattgcgc tgaacgcgca ggatgacttt   1080
agcagcaccc cgatcaccat gaactacaac cagttcctgg agctggaaaa gaccaagcaa   1140
ctgcgcctgg acaccgatca ggtgtacggc aacattgcga cctacaactt tgagaacggc   1200
cgcgttcgcg tggacaccgg tagcaactgg tctgaagtgc tgccgcagat tcaggaaacc   1260
accgcgcgca tcattttcaa cggcaaggat ctgaacctgg tggaacgccg catcgcggca   1320
gtgaacccgt ctgatccgct ggaaaccacg aagccggaca tgaccctgaa agaggcactg   1380
aagattgcat tcggcttcaa cgaaccaaat ggcaacctgc agtatcaggg caaagatatc   1440
accgaattcg atttcaactt tgaccagcaa acctctcaga acattaaaaa ccagctggca   1500
gaactgaacg cgaccaacat ctataccgtg ctggataaga ttaagctgaa tgcaaagatg   1560
aatattctga ttcgtgataa acgtttccat tatgatcgta acaacattgc ggtgggtgca   1620
gatgaaagcg ttgtgaaaga ggcgcatcgc gaagtgatca actctagcac ggaaggcctg   1680
ctgctgaaca tcgacaaaga tattcgcaag atcctgagcg gctacatcgt ggagatcgaa   1740
gataccgaag gtctgaaaga ggtgattaac gatcgctatg acatgctgaa catctctagc   1800
ctgcgtcagg atggcaaaac ctttattgat ttcaagaaat ataacgataa actg         1854
```

<210> SEQ ID NO 55
<211> LENGTH: 1854
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Sequence variant (91%) of SEQ ID No. 46

<400> SEQUENCE: 55

```
ttcattaaag tgaaaaaaag cgacgaatac acgtttgcga ccagcgcgga taatcatgtt     60
accatgtggg tggacgatca ggaagtgatc aacaaagcaa gcaatagcaa caagatccgc    120
```

```
ctggagaaag gccgcctgta tcagatcaaa attcagtatc agcgcgagaa tccgaccgag    180
aaaggcctgg atttcaaact gtactggacc gacagccaga acaaaaagga agtgatcagc    240
agcgacaacc tgcagctgcc ggaactgaag cagaagagca gcaactctcg taagaaacgt    300
agcacctctg cgggcccaac cgttccggat cgcgataacg acggcattcc ggattctctg    360
gaagtggagg gttataccgt tgacgtgaaa aacaagcgca cctttctgag cccgtggatt    420
agcaacattc acgaaaagaa gggtctgacc aagtataaaa gcagcccgga aaagtggagc    480
accgcgagcg acccatatag cgactttgaa aaggtgaccg gccgcatcga caagaacgtg    540
agcccggaag cgcgccaccc actggtggca gcgtatccaa ttgtgcatgt tgacatggag    600
aacattattc tgagcaagaa cgaagaccag agcacccaga acaccgatag ccagacgcgt    660
accattagca aaaacacgag cacgagccgt acccatacct ctgaggtgca tggcaatgcg    720
gaagtgcatg cgagcttctt tgacattggc ggcagcgtga gcgcgggctt cagcaacagc    780
aacagcagca cggtggcgat tgatcatagc ctgagcctgg cgggcgagcg cacctgggca    840
gaaaccatgg gtctgaacac cgcggatacg gcgcgtctga atgcaaacat ccgctacgtg    900
aacaccggca ccgcgccgat ctacaacgtg ctgccgacca ccagcctggt gctgggcaag    960
aaccaaaccc tggcgacgat caaagcgaag gagaaccagc tgagccagat tctggcgccg   1020
aacaactatt atccgagcaa aaacctggca ccgattgcgc tgaacgcgca ggatgacttt   1080
agcagcaccc cgattaccat gaactacaac cagttcctgg agctggaaaa gaccaagcag   1140
ctgcgcctgg ataccgatca ggtgtacggc aacattgcga cctacaactt cgagaacggc   1200
cgcgttcgcg tggacaccgg tagcaactgg tctgaagtgc tgccgcagat tcaggaaacc   1260
accgcgcgca tcatttttaa cggcaaggat ctgaacctgg tggaacgccg catcgcggca   1320
gttaacccgt ctgatccgct ggaaaccacg aagccggaca tgaccctgaa agaggcactg   1380
aagattgcat ttggcttcaa cgaaccaaat ggtaacctgc agtatcaggg caaagatatc   1440
accgaattcg attttaactt cgatcagcaa acctctcaga acattaaaaa ccagctggca   1500
gaactgaacg cgaccaacat ctataccgtg ctggataaga ttaagctgaa tgcaaagatg   1560
aatattctga ttcgtgataa acgtttccat tatgatcgta acaacattgc ggtgggtgca   1620
gatgaaagcg ttgtgaaaga ggcgcatcgc gaagtgatca actctagcac ggaaggcctg   1680
ctgctgaaca tcgacaaaga tatccgcaag atcctgagcg gctacatcgt ggagatcgaa   1740
gataccgaag gtctgaaaga ggtgattaac gatcgctatg acatgctgaa catctctagc   1800
ctgcgtcaag atggcaaaac ctttattgat ttcaagaaat ataacgataa actg          1854
```

<210> SEQ ID NO 56
<211> LENGTH: 1953
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Truncated version of SEQ ID No. 1 (bp. 103-2055)

<400> SEQUENCE: 56

```
gtgacctcta gcacgaccgg cgatctgagc attccgagca gcgaactgga gaacattccg     60
agcgagaacc agtactttca gtctgcgatt tggagcggct tcatcaaagt gaagaaaagc    120
gatgagtata cctttgcgac gtctgcggat aaccatgtga ccatgtgggt ggacgatcag    180
gaagtgatca acaaagcgag caacagcaac aagattcgcc tggagaaggg tcgcctgtat    240
```

```
cagatcaaga ttcagtatca gcgcgagaat ccgaccgaga aaggcctgga tttcaaactg    300
tactggaccg atagccagaa caagaaagaa gtgattagct ctgataacct gcaactgccg    360
gaactgaaac agaagagcag caacagccgc aagaaacgca gcacctctgc aggcccgacc    420
gttccagatc gcgacaacga tggcattccg gacagcctgg aagtggaagg ttataccgtt    480
gatgtgaaga acaaacgcac ctttctgagc ccgtggatta gcaacattca tgagaagaaa    540
ggcctgacca agtacaaaag cagcccggag aagtggagca ccgcgagcga tccgtatagc    600
gactttgaga aagtgaccgg ccgcattgat aagaacgtga gcccggaagc gcgtcaccca    660
ctggttgcag cgtatccgat tgtgcatgtt gacatggaga acatcattct gagcaagaac    720
gaagatcaga gcacccagaa cacggatagc cagacccgca cgatcagcaa gaacaccagc    780
acgagccgta cccataccag cgaagtgcat ggcaatgcgg aagtgcatgc gagcttcttt    840
gacattggtg gcagcgtgag cgcgggcttc agcaacagca acagcagcac cgtggcgatt    900
gatcatagcc tgagcctggc gggcgaacgt acctgggcgg aaaccatggg cctgaacacg    960
gcggatacgg cacgtctgaa tgcgaacatt cgctatgtga acaccggtac cgcgccaatc   1020
tataacgttc tgccgaccac gagcctggtg ctgggcaaga atcagaccct ggcgaccatc   1080
aaagcgaaag agaaccagct gtctcagatt ctggcaccga acaactacta tccgagcaag   1140
aacctggcac cgattgcact gaatgcgcag gatgacttca gcagcacccc gatcaccatg   1200
aactacaatc agtttctgga gctggagaag accaaacaac tgcgcctgga taccgatcag   1260
gtgtatggca acattgcgac ctacaacttt gagaacggcc gcgttcgcgt ggataccggt   1320
agcaactggt ctgaagtgct gccgcagatt caggaaacga ccgcgcgcat catcttcaac   1380
ggcaaagatc tgaacctggt ggaacgtcgc atcgcggcag tgaacccatc tgatccactg   1440
gaaacgacca aaccggacat gaccctgaaa gaagcgctga agattgcatt tggcttcaac   1500
gaaccgaatg gcaacctgca gtatcagggc aaagacatca ccgagtttga cttcaacttt   1560
gatcaacaga cctctcagaa catcaagaac cagctggcag aactgaatgc gaccaacatc   1620
tacaccgtgc tggacaagat caaactgaac gcaaagatga acattctgat tcgtgacaaa   1680
cgcttccact atgatcgtaa caacattgcg gtgggtgcag atgaaagcgt tgtgaaagaa   1740
gcgcatcgtg aagtgatcaa ctctagcacc gaaggcctgc tgctgaacat tgacaaagac   1800
atccgtaaga ttctgagcgg ctacattgtg gagattgaag ataccgaagg tctgaaagaa   1860
gtgatcaacg atcgctatga catgctgaac atctctagcc tgcgccagga tggcaagacc   1920
ttcattgact tcaagaagta caacgacaaa ctg                                1953
```

<210> SEQ ID NO 57
<211> LENGTH: 1953
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Sequence variant (99%) of SEQ ID No. 56

<400> SEQUENCE: 57

```
gtgacctcta gcacgaccgg cgatctgagc attccgagca gcgaactgga gaacattccg     60
agcgagaacc agtactttca gagcgcgatt tggagcggct tcatcaaagt gaagaaaagc    120
gatgagtata cctttgcgac gtctgcggat aaccatgtga ccatgtgggt ggacgatcag    180
gaagtgatca acaaagcgag caacagcaac aagattcgcc tggagaaggg tcgcctgtat    240
```

-continued

```
cagatcaaga ttcagtatca gcgcgagaat ccgaccgaga aaggcctgga cttcaaactg    300

tactggaccg atagccagaa caagaaggaa gtgattagct ctgataacct gcaactgccg    360

gaactgaaac agaagagcag caacagccgc aagaaacgca gcacctctgc aggccccgacc   420

gttccagatc gcgacaacga tggcatcccg gacagcctgg aagtggaagg ttataccgtt    480

gatgtgaaga acaaacgcac cttcctgagc ccatggatta gcaacattca tgagaagaaa    540

ggcctgacca agtacaaaag cagcccggag aagtggagca ccgcgagcga tccgtatagc    600

gactttgaga aagtgaccgg ccgcattgat aagaacgtga gcccggaagc gcgtcaccca    660

ctggttgcag cgtatccgat tgtgcatgtt gacatggaga acatcattct gagcaagaac    720

gaagatcaga gcacccagaa cacggatagc cagacccgca cgatcagcaa gaacaccagc    780

acgagccgta cccataccag cgaagtgcat ggcaatgcgg aagtgcatgc gagcttcttt    840

gacattggtg gcagcgtgag cgcgggcttc agcaacagca acagcagcac cgtggcgatt    900

gatcatagcc tgagcctggc gggcgaacgt acctgggcgg aaaccatggg cctgaacacg    960

gcggatacgg cacgtctgaa tgcgaacatt cgctatgtga acaccggtac cgcgccaatt   1020

tataacgttc tgccgaccac cagcctggtg ctgggcaaga atcagaccct ggcgacgatc   1080

aaagcgaaag agaaccagct gtctcagatt ctggcaccga acaactacta tccgtctaaa   1140

aacctggcac cgattgcact gaatgcgcag gatgacttca gcagcacccc gatcaccatg   1200

aactacaatc agtttctgga gctggagaag accaaacaac tgcgcctgga taccgatcag   1260

gtgtatggca acattgcgac ctacaacttt gagaacggcc gcgttcgcgt ggataccggt   1320

agcaactggt ctgaagtgct gccgcagatt caggaaacga ccgcgcgcat catcttcaac   1380

ggcaaagatc tgaacctggt ggaacgtcgc atcgcggcag tgaacccatc tgatccgctg   1440

gaaacgacca aaccggacat gaccctgaaa gaagcgctga agattgcatt tggctttaac   1500

gaaccgaatg gcaacctgca gtatcagggc aaagacatca ccgagtttga cttcaacttt   1560

gatcaacaga cctctcagaa catcaagaac cagctggcag aactgaatgc gaccaacatc   1620

tacaccgtgc tggataagat caaactgaac gcaaagatga acattctgat tcgtgacaaa   1680

cgcttccact atgatcgtaa caacattgcg gtgggtgcag atgaaagcgt tgtgaaagaa   1740

gcgcatcgtg aagtgatcaa ctctagcacc gaaggcctgc tgctgaacat tgacaaagac   1800

atccgtaaga ttctgagcgg ctacattgtg gagattgaag ataccgaagg tctgaaagaa   1860

gtgatcaacg atcgctatga catgctgaac atctctagcc tgcgccagga tggcaagacc   1920

ttcattgact tcaagaagta caacgacaaa ctg                                1953
```

<210> SEQ ID NO 58
<211> LENGTH: 1953
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Sequence variant (98%) of SEQ ID No. 56

<400> SEQUENCE: 58

```
gtgacctcta gcacgaccgg cgatctgagc attccgagca gcgaactgga gaacattccg     60

agcgagaacc agtactttca gagcgcgatt tggagcggct tcatcaaagt gaagaaaagc    120

gatgagtata cctttgcgac gtctgcggat aaccatgtga ccatgtgggt ggacgatcag    180

gaagtgatca acaaagcgag caacagcaac aagattcgcc tggagaaggg tcgcctgtat    240

caaattaaga ttcagtatca gcgcgagaat ccgaccgaga aaggcctgga cttcaaactg    300
```

-continued

```
tactggaccg atagccagaa caagaaggaa gtgattagct ctgataacct gcagctgccg    360

gaactgaaac agaagagcag caacagccgc aagaaacgca gcacctctgc aggcccgacc    420

gttccagatc gcgacaacga tggcatcccg gacagcctgg aagtggaagg ttataccgtt    480

gatgtgaaga acaaacgcac cttcctgagc ccatggatca gcaacattca tgagaagaaa    540

ggcctgacca agtacaaaag cagcccggag aagtggagca ccgcgagcga tccgtatagc    600

gactttgaga aagtgaccgg ccgcattgat aagaacgtga gcccggaagc gcgtcaccca    660

ctggttgcag cgtatccgat tgtgcatgtt gacatggaga acatcattct gagcaagaac    720

gaagatcaga gcacccagaa cacggatagc cagacccgca cgattagcaa gaacaccagc    780

acgagccgta cccataccag cgaggtgcat ggcaatgcgg aagtgcatgc gagcttcttt    840

gacattggtg gcagcgtgag cgcgggcttc tctaacagca acagcagcac cgtggcgatt    900

gatcatagcc tgagcctggc gggcgaacgt acctgggcgg aaaccatggg cctgaacacg    960

gcggatacgg cacgtctgaa tgcgaacatt cgctatgtga acaccggtac cgcgccaatt   1020

tataatgttc tgccgaccac cagcctggtg ctgggcaaga atcagaccct ggcgaccatc   1080

aaagcgaaag agaaccagct gtctcagatt ctggcaccga acaactacta tccgtctaaa   1140

aacctggcac cgattgcact gaatgcgcag gatgacttca gcagcacccc gatcaccatg   1200

aactacaacc agttcctgga actggagaag accaaacaac tgcgcctgga taccgatcag   1260

gtgtatggca acattgcgac ctacaacttt gaaaacggcc gtgttcgcgt ggataccggt   1320

agcaactggt ctgaagtgct gccgcagatt caggaaacga ccgcgcgcat catcttcaac   1380

ggcaaagatc tgaacctggt ggaacgtcgc atcgcggcag tgaacccatc tgatccgctg   1440

gaaacgacca aaccggacat gaccctgaaa gaagcgctga agattgcatt tggctttaac   1500

gagccgaatg gcaacctgca gtatcagggc aaagacatca ccgagtttga ctttaacttt   1560

gatcaacaga cctctcagaa catcaagaac cagctggcag aactgaatgc gaccaacatc   1620

tacacggtgc tggataagat caaactgaac gcaaagatga acattctgat ccgtgacaaa   1680

cgcttccact atgatcgcaa caacattgcg gtgggtgcag atgaaagcgt tgtgaaagaa   1740

gcgcatcgtg aagtgatcaa cagcagcacc gaaggcctgc tgctgaacat tgacaaagac   1800

atccgtaaga ttctgagcgg ctacattgtg gagattgaag ataccgaagg tctgaaagaa   1860

gtgatcaacg atcgctatga catgctgaac atctctagcc tgcgccagga tggcaagacc   1920

ttcattgact tcaagaagta caacgacaaa ctg                                1953
```

<210> SEQ ID NO 59
<211> LENGTH: 1953
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Sequence variant (97%) of SEQ ID NO. 56

<400> SEQUENCE: 59

```
gtgacctcta gcacgaccgg cgatctgagc attccgagca gcgaactgga gaacattccg     60

agcgagaacc agtactttca gagcgcgatt tggagcggct tcatcaaagt gaagaaaagc    120

gatgagtata ccttcgcgac gtctgcggat aaccatgtga ccatgtgggt ggacgatcag    180

gaagtgatca acaaagcgag caacagcaac aaaattcgcc tggagaaggg tcgcctgtat    240

caaattaaga ttcagtatca gcgcgagaat ccgaccgaaa aaggcctgga ctttaagctg    300
```

-continued

```
tactggaccg atagccagaa caagaaggaa gtgattagct ctgataacct gcagctgccg    360

gaactgaaac agaagagcag caacagccgc aagaaacgca gcacctctgc aggcccgacc    420

gttccagatc gcgacaacga tggcatcccg gacagcctgg aagtggaagg ttataccgtg    480

gatgtgaaga acaaacgcac cttcctgagc ccatggatca gcaacattca tgagaagaaa    540

ggcctgacca agtacaaaag cagcccggag aagtggagca ccgcgagcga tccgtatagc    600

gactttgaga aagtgaccgg ccgcattgat aagaacgtga gcccggaagc gcgtcaccca    660

ctggttgcag cgtatccgat tgtgcatgtg gacatggaga acatcattct gagcaagaac    720

gaagatcaga gcacccagaa cacggattct cagacccgca cgattagcaa gaacaccagc    780

acgagccgta cccataccag cgaggtgcat ggcaatgcgg aagtgcatgc gagcttcttt    840

gacattggtg gcagcgtgag cgcgggcttc tctaacagca acagcagcac cgtggcgatt    900

gatcatagcc tgagcctggc gggcgaacgt acctgggcgg aaaccatggg cctgaacacg    960

gcggatacgg cacgtctgaa tgcgaacatt cgctatgtga acaccggtac cgcgccaatt   1020

tataatgttc tgccgaccac cagcctggtg ctgggcaaga atcagaccct ggcgaccatc   1080

aaagcgaaag agaaccagct gtctcagatt ctggcaccga acaactacta tccgtctaaa   1140

aacctggcac cgattgcact gaatgcgcag gatgacttca gcagcacccc gatcaccatg   1200

aactacaacc agttcctgga actggagaag accaaacaac tgcgcctgga taccgatcag   1260

gtttatggca acattgcgac ctacaacttt gaaaacggcc gtgttcgcgt ggataccggt   1320

agcaactggt ctgaagtgct gccgcagatt caggaaacga ccgcgcgcat catcttcaac   1380

ggcaaagatc tgaacctggt ggaacgtcgc atcgcggcag ttaacccatc tgatccgctg   1440

gaaacgacca aaccggacat gaccctgaaa gaagcgctga agattgcatt tggctttaac   1500

gagccgaatg gcaacctgca gtatcagggc aaagacatca ccgagtttga ctttaacttt   1560

gatcaacaga cctctcagaa catcaagaac cagctggcag aactgaatgc gaccaacatc   1620

tacacggtgc tggataagat caaactgaac gcaaagatga acattctgat ccgtgacaaa   1680

cgcttccact atgatcgcaa caacattgcg gtgggtgcag atgaaagcgt ggttaaagaa   1740

gcgcatcgtg aagtgatcaa cagcagcacc gaaggcctgc tgctgaacat tgacaaagac   1800

atccgtaaga ttctgagcgg ctacattgtg gagattgaag ataccgaggg tctgaaagaa   1860

gtgatcaacg atcgctatga catgctgaac atcagcagcc tgcgccagga tggcaagacc   1920

ttcattgact tcaagaagta caacgacaaa ctg                                 1953
```

<210> SEQ ID NO 60
<211> LENGTH: 1953
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Sequence variant (96%) of SEQ ID No. 56

<400> SEQUENCE: 60

```
gtgacctcta gcacgaccgg cgatctgagc attccgagca gcgaactgga gaacattccg     60

agcgagaacc agtactttca gagcgcgatt tggagcggct tcatcaaagt gaagaaaagc    120

gatgagtata ccttcgcgac ctctgcggac aaccatgtga ccatgtgggt ggacgatcag    180

gaagtgatca acaaagcgag caacagcaac aaaattcgcc tggagaaggg tcgcctgtat    240

caaattaaga ttcagtatca gcgcgagaat ccgaccgaaa aaggcctgga ctttaaactg    300

tactggaccg atagccagaa caagaaggaa gtgattagct ctgataacct gcagctgccg    360
```

```
gaactgaaac agaagagcag caacagccgc aagaaacgca gcaccagcgc aggcccgacc    420
gtgccagacc gcgacaacga tggcatcccg gatagcctgg aagtggaagg ttataccgtg    480
gatgtgaaga acaaacgcac cttcctgagc ccatggatta gcaacattca tgagaagaaa    540
ggcctgacca agtacaaaag cagcccggag aagtggagca ccgcgagcga tccgtatagc    600
gactttgaga aagtgaccgg ccgcattgac aagaacgtga gcccggaagc gcgtcaccca    660
ctggttgcag cgtatccgat tgtgcatgtg gacatggaga acatcattct gagcaagaac    720
gaagatcaga gcacccagaa cacggattct cagacccgca cgattagcaa gaacaccagc    780
acgagccgca cccataccag cgaggtgcat ggcaatgcgg aagtgcatgc gagcttcttt    840
gacattggtg gcagcgtgag cgcgggcttc tctaacagca acagcagcac cgtggcgatt    900
gatcacagcc tgagcctggc gggcgaacgt acctgggcgg aaaccatggg cctgaacacg    960
gcggatacgg cacgcctgaa tgcgaacatt cgctatgtga acaccggtac cgcgccaatt   1020
tataatgttc tgccgaccac cagcctggtg ctgggcaaga atcagaccct ggcgaccatc   1080
aaagcgaaag agaaccagct gtctcagatt ctggcaccga acaactacta tccgtctaaa   1140
aacctggcac cgattgcact gaatgcgcag gatgatttca gctctacccc gatcaccatg   1200
aactacaacc agttcctgga actggagaag acgaaacaac tgcgcctgga taccgatcag   1260
gtttatggca acattgcgac ctacaacttt gaaaacggcc gtgttcgcgt ggataccggt   1320
agcaactggt ctgaagtgct gccgcagatt caggaaacga ccgcgcgcat catcttcaac   1380
ggcaaagatc tgaacctggt ggaacgtcgc atcgcggcag ttaacccatc tgatccgctg   1440
gaaacgacca agccggacat gaccctgaaa gaagcgctga agattgcatt tggctttaac   1500
gagccgaatg gcaacctgca gtatcagggc aaagacatca ccgagtttga ctttaacttt   1560
gatcaacaga cctctcagaa catcaagaac cagctggcag aactgaatgc gaccaacatc   1620
tacacggttc tggataagat caaactgaac gcaaagatga acattctgat ccgtgacaaa   1680
cgtttccatt atgatcgtaa caacatcgcg gtgggtgcag atgaaagcgt ggttaaagaa   1740
gcgcatcgtg aagtgatcaa cagcagcacc gaaggcctgc tgctgaacat tgacaaagac   1800
atccgtaaga ttctgagcgg ctacattgtg gagattgaag ataccgaggg tctgaaagaa   1860
gtgatcaacg atcgctatga tatgctgaac atcagcagcc tgcgccagga tggcaagacc   1920
ttcattgact tcaagaagta caacgacaaa ctg                                1953
```

<210> SEQ ID NO 61
<211> LENGTH: 1953
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Sequence variant (95%) of SEQ ID No. 56

<400> SEQUENCE: 61

```
gtgacctcta gcacgaccgg cgatctgagc attccgagca gcgaactgga gaacattccg     60
agcgagaacc agtacttcca gagcgcgatt tggagcggct tcatcaaagt taagaaaagc    120
gatgagtata ccttcgcgac ctctgcggac aaccatgtga ccatgtgggt ggacgatcag    180
gaagtgatca acaaagcgag caacagcaac aaaattcgcc tggagaaggg tcgcctgtat    240
caaattaaga ttcagtatca gcgcgagaat ccaaccgaaa aaggcctgga ctttaaactg    300
tactggaccg atagccagaa taagaaggaa gtgatcagct ctgataacct gcagctgccg    360
```

-continued

```
gaactgaaac agaagagcag caacagccgc aagaaacgca gcaccagcgc gggcccgacc    420

gtgccagacc gcgacaacga tggcatcccg gatagcctgg aagtggaagg ttataccgtg    480

gatgtgaaga acaaacgcac cttcctgagc ccatggatta gcaacattca tgagaagaaa    540

ggcctgacca agtacaaaag cagcccggag aagtggagca ccgcgagcga tccgtatagc    600

gactttgaga aagtgacggg ccgcattgac aagaacgtga gcccggaagc gcgtcaccca    660

ctggttgcag cgtatccgat tgtgcatgtg gacatggaga acatcattct gagcaagaac    720

gaagatcaga gcacccagaa cacggattct cagacccgca cgattagcaa aaacaccagc    780

acgagccgca cccataccag cgaggtgcat ggcaatgcgg aagtgcatgc gagcttcttt    840

gacattggtg gcagcgtgag cgcgggcttc tctaacagca acagcagcac cgtggcgatt    900

gatcacagcc tgagcctggc gggcgaacgt acctgggcgg aaaccatggg cctgaacacc    960

gcggatacgg cacgcctgaa tgcgaacatt cgctatgtga acaccggtac cgcgccgatt   1020

tataatgttc tgccgaccac cagcctggtg ctgggcaaga atcagaccct ggcgaccatt   1080

aaagcgaaag agaaccagct gtctcagatt ctggcaccga acaactacta tccgtctaaa   1140

aacctggcac cgattgcact gaatgcgcag gatgatttca gctctacccc gatcaccatg   1200

aactacaacc agttcctgga actggagaag acgaaacaac tgcgcctgga caccgatcag   1260

gtttatggca acattgcgac ctacaacttt gaaaacggcc gtgtgcgcgt ggataccggt   1320

agcaactggt ctgaagtgct gccgcagatt caggaaacga ccgcgcgcat catcttcaac   1380

ggcaaagatc tgaacctggt ggaacgtcgc atcgcggcag ttaacccatc tgatccgctg   1440

gaaacgacca agccggacat gaccctgaag gaagcgctga agattgcatt tggctttaac   1500

gagccgaatg gcaacctgca gtatcagggc aaagacatca ccgagtttga ttttaacttt   1560

gatcaacaga cctctcagaa catcaagaac cagctggcag aactgaacgc gaccaacatc   1620

tacacggttc tggataagat caaactgaac gcaaagatga acattctgat ccgtgacaaa   1680

cgttttcatt atgatcgtaa caacatcgca gtgggtgcag atgaaagcgt ggttaaagaa   1740

gcgcatcgtg aagtgatcaa cagcagcacc gagggcctgc tgctgaacat tgacaaagac   1800

atccgtaaga ttctgagcgg ctacattgtg gaaattgaag ataccgaggg tctgaaagaa   1860

gtgatcaacg atcgctatga tatgctgaac atcagcagcc tgcgccagga tggcaagacc   1920

ttcattgact tcaagaagta caacgacaaa ctg                                1953
```

<210> SEQ ID NO 62
<211> LENGTH: 1953
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Sequence variant (94%) of SEQ ID No. 56

<400> SEQUENCE: 62

```
gtgacctcta gcacgaccgg cgatctgagc attccgagca gcgaactgga gaacattccg     60

agcgagaacc agtacttcca gagcgcgatt tggagcggct tcatcaaagt taagaaaagc    120

gatgagtata ccttcgcgac ctctgcggac aaccatgtga ccatgtgggt ggacgaccag    180

gaagtgatca acaaagcgag caacagcaac aaaattcgcc tggagaaggg tcgcctgtat    240

caaattaaga ttcagtatca gcgcgagaat ccaaccgaaa aaggcctgga ctttaaactg    300

tactggaccg atagccagaa taagaaggaa gtgatcagct ctgacaacct gcagctgccg    360

gaactgaaac agaagtctag caacagccgc aagaaacgca gcaccagcgc gggcccgacc    420
```

```
gtgccagacc gcgacaacga tggcatcccg gatagcctgg aagtggaagg ttatacggtg    480

gatgtgaaga acaaacgcac cttcctgagc ccatggatta gcaacattca tgagaagaaa    540

ggcctgacca agtacaaaag cagcccggag aagtggagca ccgcgagcga tccgtatagc    600

gactttgaga aagtgacggg ccgcattgac aagaacgtga gcccggaagc acgtcaccca    660

ctggttgcag cgtatccgat tgtgcatgtg gacatggaga acatcattct gagcaagaac    720

gaagatcaga gcacccagaa cacggattct cagacccgca cgatcagcaa aaacaccagc    780

acgagccgca cccataccag cgaggtgcat ggcaatgcgg aagtgcatgc gagcttcttt    840

gacatcggcg gcagcgtgag cgcgggtttc tctaacagca acagcagcac cgtggcgatt    900

gatcacagcc tgagcctggc gggtgaacgt acctgggcgg aaaccatggg cctgaacacc    960

gcggatacgg cacgcctgaa tgcgaacatt cgctatgtga acaccggtac cgcgccgatt   1020

tataatgttc tgccgaccac cagcctggtg ctgggcaaga atcagaccct ggcgaccatt   1080

aaagcgaaag agaaccagct gtctcagatt ctggcaccga acaactacta tccgagcaaa   1140

aacctggcac cgattgcact gaatgcgcag gatgatttca gctctacccc gattaccatg   1200

aactacaacc agttcctgga actggagaag accaagcaac tgcgcctgga caccgatcag   1260

gtttatggca acattgcgac ctacaacttt gaaaacggcc gtgtgcgcgt ggatacgggc   1320

agcaactggt ctgaagtgct gccgcagatc caggaaacga ccgcgcgcat catcttcaac   1380

ggcaaagatc tgaacctggt ggaacgtcgc atcgcggcag ttaacccatc tgatccgctg   1440

gaaacgacca agccggatat gaccctgaag gaagcactga agattgcgtt tggctttaac   1500

gagccgaatg gcaacctgca gtatcagggc aaagacatca ccgagtttga ttttaacttt   1560

gatcaacaga cctctcagaa cattaagaac cagctggcag aactgaacgc gaccaacatc   1620

tacaccgttc tggataaaat caaactgaac gcgaagatga acattctgat tcgtgataaa   1680

cgttttcatt atgatcgtaa caacatcgca gtgggtgcag atgaaagcgt ggttaaagaa   1740

gcgcatcgtg aagtgatcaa cagcagcacc gagggcctgc tgctgaacat tgacaaggac   1800

atccgtaaaa ttctgagcgg ctacattgtg gaaattgaag ataccgaggg tctgaaagaa   1860

gtgatcaacg atcgctatga tatgctgaac atcagcagcc tgcgccagga tggcaagacc   1920

ttcattgact tcaagaagta caacgacaaa ctg                                1953
```

<210> SEQ ID NO 63
<211> LENGTH: 1953
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Sequence variant (93%) of SEQ ID No. 56

<400> SEQUENCE: 63

```
gtgacctctt ctacgaccgg cgatctgagc attccgagca gcgaactgga gaacattccg     60

agcgaaaacc agtactttca gagcgcgatt tggagcggct tcatcaaagt taagaaaagc    120

gatgagtata ccttcgcgac cagcgcggac aaccatgtga ccatgtgggt ggacgaccag    180

gaagtgatca acaaagcgag caacagcaac aaaattcgcc tggagaaggg tcgcctgtac    240

cagattaaga ttcagtatca gcgcgagaac ccaaccgaaa aaggcctgga ctttaaactg    300

tactggaccg atagccagaa taagaaggaa gtgatcagct ctgacaacct gcagctgccg    360

gaactgaaac agaagtctag caacagccgt aagaaacgta gcaccagcgc gggcccgacc    420
```

-continued gtgccagacc gcgacaacga tggcatcccg gatagcctgg aggtggaagg ttatacggtg 480
gatgtgaaga ataaacgcac cttcctgagc ccatggatta gcaacattca tgagaagaaa 540
ggcctgacca aatacaaaag cagcccggag aagtggagca ccgcgagcga tccgtattct 600
gactttgaga aagtgacggg ccgcattgac aagaacgtga gcccggaagc acgtcaccca 660
ctggtggcag cgtatccgat tgtgcatgtg gacatggaga acatcattct gagcaagaac 720
gaagatcaga gcacccagaa cacggattct cagacccgca cgatcagcaa aaacaccagc 780
acgagccgca cccataccag cgaagtgcat ggcaatgcgg aagttcatgc gagcttcttt 840
gacattggcg gcagcgttag cgcgggtttc tctaacagca acagcagcac cgtggcgatt 900
gatcacagcc tgagcctggc gggtgaacgt acctgggcgg aaaccatggg cctgaacacc 960
gcggatacgg cacgcctgaa tgcgaacatt cgctatgtga acaccggtac cgcgccgatt 1020
tacaatgtgc tgccgaccac cagcctggtg ctgggcaaga atcagaccct ggcgaccatt 1080
aaagcgaaag agaaccaact gtctcagatt ctggcaccga acaactacta tccgagcaaa 1140
aacctggcac cgattgcact gaatgcgcag gatgatttca gcagcacccc gattaccatg 1200
aactacaacc agttcctgga actggagaag accaagcaac tgcgcctgga caccgatcag 1260
gtttatggca acattgcgac ctacaacttt gaaaacggcc gcgtgcgcgt ggatacgggc 1320
agcaactggt ctgaagtgct gccgcagatc caggaaacga ccgcgcgcat catcttcaac 1380
ggcaaagatc tgaacctggt ggaacgtcgc atcgcggcag ttaacccatc tgatccgctg 1440
gaaacgacca agccggatat gaccctgaag gaagcactga agatcgcgtt tggctttaac 1500
gagccgaatg gcaacctgca gtatcagggc aaagacatca ccgagtttga ttttaacttt 1560
gatcaacaga cctctcagaa cattaagaac cagctggcag aactgaacgc gaccaacatc 1620
tacaccgttc tggataaaat caaactgaac gcgaagatga acattctgat tcgtgataag 1680
cgtttccatt atgatcgtaa caacatcgca gtgggtgcag atgaaagcgt ggttaaagaa 1740
gcgcatcgcg aagtgatcaa cagcagcacc gagggcctgc tgctgaacat tgacaaggac 1800
atccgtaaaa ttctgagcgg ctatattgtg gaaattgaag ataccgaggg tctgaaagag 1860
gtgatcaacg atcgctatga tatgctgaac atcagcagcc tgcgccagga tggcaagacc 1920
ttcattgact tcaagaagta taacgacaaa ctg 1953

<210> SEQ ID NO 64
<211> LENGTH: 1953
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Sequence variant (92%) of SEQ ID No. 56

<400> SEQUENCE: 64
gtgacctctt ctacgaccgg cgatctgagc attccgagca gcgaactgga gaacattccg 60
agcgaaaacc agtacttcca gagcgcgatt tggtctggct tcatcaaagt taagaaaagc 120
gatgagtaca ccttcgcgac cagcgcggac aaccatgtga ccatgtgggt ggacgaccag 180
gaagtgatca acaaagcgag caacagcaac aaaattcgcc tggagaaggg tcgtctgtat 240
cagattaaga ttcagtatca gcgcgaaaac ccgaccgaaa aaggcctgga ctttaaactg 300
tactggaccg atagccagaa taagaaggaa gtgatcagct ctgacaacct gcagctgccg 360
gaactgaaac agaagtctag caacagccgt aagaaacgta gcaccagcgc gggcccgacc 420
gtgccagacc gcgacaacga tggcatcccg gatagcctgg aggtggaagg ttatacggtg 480
gatgtgaaga ataagcgcac cttcctgagc ccatggatta gcaacattca tgagaagaaa 540
ggcctgacca aatacaaaag cagcccggag aagtggagca ccgcgagcga tccatattct 600
gattttgaga aagtgaccgg ccgcattgac aagaacgtga gcccggaagc acgtcaccca 660
ctggtggcag cgtatccgat tgtgcatgtg gacatggaga acatcattct gagcaagaac 720
gaagatcaga gcacccagaa caccgattct cagacccgta cgatcagcaa aaataccagc 780
acgagccgca cccataccag cgaagtgcat ggcaatgcgg aagttcatgc gagcttcttt 840
gacattggcg gcagcgttag cgcgggtttt agcaacagca acagcagcac cgtggcgatt 900
gatcacagcc tgagcctggc gggtgaacgt acgtgggcgg aaaccatggg cctgaacacc 960
gcggatacgg cacgcctgaa cgcgaacatt cgctatgtga ataccggtac cgcgccgatt 1020
tacaacgtgc tgccgaccac cagcctggtg ctgggcaaga atcagaccct ggcgaccatt 1080
aaagcgaaag agaaccaact gtctcagatt ctggcaccga acaactacta tccgagcaaa 1140
aacctggcac cgattgcact gaatgcgcag gatgatttca gcagcacccc gattaccatg 1200
aactacaacc agttcctgga actggagaaa accaagcaac tgcgcctgga caccgaccag 1260
gtttatggca acattgcgac ctacaacttt gaaaacggcc gcgtgcgcgt ggatacgggc 1320
agcaactggt ctgaagtgct gccgcagatc caggaaacga ccgcgcgtat catcttcaac 1380
ggcaaggatc tgaacctggt ggaacgccgc atcgcggcag ttaacccatc tgatccgctg 1440
gaaacgacca agccggatat gaccctgaag gaagcactga agatcgcgtt tggctttaac 1500
gagccgaatg gcaacctgca gtatcagggc aaagacatca ccgagtttga ttttaacttt 1560
gatcaacaga cctctcagaa cattaagaac cagctggcgg agctgaacgc aaccaacatc 1620
tacaccgttc tggataaaat caaactgaac gcgaagatga acattctgat tcgcgataag 1680
cgtttccatt atgatcgtaa caacatcgca gtgggtgcag atgaaagcgt ggttaaagaa 1740
gcgcatcgcg aagtgatcaa cagcagcacc gaaggcctgc tgctgaacat tgacaaagac 1800
atccgcaaaa ttctgagcgg ctatattgtg gaaattgagg atacggaggg tctgaaagag 1860
gtgatcaacg atcgctatga tatgctgaac atcagcagcc tgcgccagga tggcaagacc 1920
ttcattgact tcaagaagta taacgacaaa ctg 1953

<210> SEQ ID NO 65
<211> LENGTH: 1953
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Sequence variant (91%) of SEQ ID No. 56

<400> SEQUENCE: 65
gtgacctctt ctacgaccgg tgatctgagc attccgagca gcgaactgga gaacattccg 60
agcgaaaacc agtacttcca gagcgcgatt tggtctggtt tcatcaaagt taagaaaagc 120
gatgagtaca cgttcgcgac cagcgcggac aaccatgtga ccatgtgggt ggacgaccag 180
gaagtgatca acaaagcgag caacagcaac aaaattcgcc tggagaaggg tcgtctgtat 240
cagattaaga tccagtatca gcgcgaaaac ccgaccgaaa aaggcctgga ctttaaactg 300
tactggaccg atagccagaa taagaaggaa gtgatcagct ctgacaacct gcagctgccg 360
gaactgaaac agaagtctag caacagccgt aagaaacgta gcaccagcgc gggcccgacc 420
gtgccagacc gtgacaacga tggcatcccg gatagcctgg aggtggaagg ctataccgtg 480

```
gacgtgaaga ataagcgtac cttcctgagc ccatggatta gcaacattca tgagaagaaa    540

ggcctgacca aatacaaaag cagcccggag aagtggagca ccgcgagcga tccatattct    600

gattttgaga aagtgaccgg ccgcattgac aagaacgtga gcccggaagc acgccacccg    660

ctggtggcag cgtatccgat tgtgcatgtg gacatggaga acatcattct gagcaagaac    720

gaagatcaga gcacccagaa caccgattct cagacccgta cgattagcaa aaataccagc    780

acgagccgca cgcataccag cgaagtgcat ggcaatgcgg aagttcatgc gagcttcttt    840

gacattggcg gcagcgttag cgcgggtttt agcaacagca acagcagcac ggtggcgatt    900

gatcacagcc tgagcctggc gggtgaacgt acgtgggcgg aaaccatggg cctgaacacc    960

gcggatacgg cacgcctgaa cgcgaacatt cgctatgtga ataccggtac cgcgccgatc   1020

tacaacgtgc tgccgaccac cagcctggtg ctgggcaaga atcagaccct ggcgaccatt   1080

aaagcgaaag agaaccaact gtctcagatt ctggcaccga acaactacta tccaagcaaa   1140

aacctggcac cgattgcact gaatgcgcag gatgatttca gcagcacccc gattaccatg   1200

aactacaacc agttcctgga actggagaaa accaagcaac tgcgcctgga caccgaccag   1260

gtttatggca acattgcgac ctacaacttt gaaaacggcc gcgtgcgcgt ggatacgggc   1320

agcaactggt ctgaagtgct gccgcagatc caggagacca ccgcgcgtat cattttcaac   1380

ggcaaggatc tgaacctggt ggaacgccgc atcgcggcag ttaacccatc tgatccgctg   1440

gaaacgacca agccggatat gaccctgaag gaagcactga agatcgcgtt tggctttaac   1500

gagccgaatg gcaacctgca gtatcagggc aaagatatca ccgaatttga ttttaacttt   1560

gatcaacaga cctctcagaa cattaagaac cagctggcgg agctgaacgc aaccaacatc   1620

tacaccgttc tggataaaat caaactgaac gcgaagatga acattctgat ccgcgataag   1680

cgcttccatt atgatcgtaa caacatcgca gtgggtgcag atgaaagcgt ggttaaggaa   1740

gcgcatcgcg aagtgattaa cagcagcacc gaaggcctgc tgctgaacat tgataaagac   1800

atccgcaaaa ttctgagcgg ctatattgtg gaaattgagg ataccgaggg cctgaaagag   1860

gtgatcaacg atcgctatga catgctgaac atcagcagcc tgcgccagga tggcaagacc   1920

ttcattgact tcaaaaagta taacgacaaa ctg                                1953
```

<210> SEQ ID NO 66
<211> LENGTH: 1806
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Truncated version of SEQ ID No. 1 (bp 301-2106)

<400> SEQUENCE: 66

```
agcaacagca acaagattcg cctggagaag ggtcgcctgt atcagatcaa gattcagtat     60

cagcgcgaga atccgaccga gaaaggcctg gatttcaaac tgtactggac cgatagccag    120

aacaagaaag aagtgattag ctctgataac ctgcaactgc cggaactgaa acagaagagc    180

agcaacagcc gcaagaaacg cagcacctct gcaggcccga ccgttccaga tcgcgacaac    240

gatggcattc cggacagcct ggaagtggaa ggttataccg ttgatgtgaa gaacaaacgc    300

acctttctga gcccgtggat tagcaacatt catgagaaga aaggcctgac caagtacaaa    360

agcagcccgg agaagtggag caccgcgagc gatccgtata gcgactttga gaaagtgacc    420

ggccgcattg ataagaacgt gagcccggaa gcgcgtcacc cactggttgc agcgtatccg    480

attgtgcatg ttgacatgga gaacatcatt ctgagcaaga acgaagatca gagcacccag    540
```

```
aacacggata gccagacccg cacgatcagc aagaacacca gcacgagccg tacccatacc    600

agcgaagtgc atggcaatgc ggaagtgcat gcgagcttct ttgacattgg tggcagcgtg    660

agcgcgggct tcagcaacag caacagcagc accgtggcga ttgatcatag cctgagcctg    720

gcgggcgaac gtacctgggc ggaaaccatg ggcctgaaca cggcggatac ggcacgtctg    780

aatgcgaaca ttcgctatgt gaacaccggt accgcgccaa tctataacgt tctgccgacc    840

acgagcctgg tgctgggcaa gaatcagacc ctggcgacca tcaaagcgaa agagaaccag    900

ctgtctcaga ttctggcacc gaacaactac tatccgagca agaacctggc accgattgca    960

ctgaatgcgc aggatgactt cagcagcacc ccgatcacca tgaactacaa tcagtttctg   1020

gagctggaga agaccaaaca actgcgcctg gataccgatc aggtgtatgg caacattgcg   1080

acctacaact ttgagaacgg ccgcgttcgc gtggataccg gtagcaactg gtctgaagtg   1140

ctgccgcaga ttcaggaaac gaccgcgcgc atcatcttca acggcaaaga tctgaacctg   1200

gtggaacgtc gcatcgcggc agtgaaccca tctgatccac tggaaacgac caaaccggac   1260

atgaccctga aagaagcgct gaagattgca tttggcttca acgaaccgaa tggcaacctg   1320

cagtatcagg gcaaagacat caccgagttt gacttcaact ttgatcaaca gacctctcag   1380

aacatcaaga accagctggc agaactgaat gcgaccaaca tctacaccgt gctggacaag   1440

atcaaactga acgcaaagat gaacattctg attcgtgaca aacgcttcca ctatgatcgt   1500

aacaacattg cggtgggtgc agatgaaagc gttgtgaaag aagcgcatcg tgaagtgatc   1560

aactctagca ccgaaggcct gctgctgaac attgacaaag acatccgtaa gattctgagc   1620

ggctacattg tggagattga agataccgaa ggtctgaaag aagtgatcaa cgatcgctat   1680

gacatgctga acatctctag cctgcgccag gatggcaaga ccttcattga cttcaagaag   1740

tacaacgaca aactgccgct gtacatcagc aatccgaact acaaagtgaa cgtgtatgcg   1800

gtgacc                                                               1806
```

<210> SEQ ID NO 67
<211> LENGTH: 1806
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Sequence variant (99%) of SEQ ID No. 66

<400> SEQUENCE: 67

```
agcaacagca acaagattcg cctggagaag ggtcgcctgt atcagatcaa gattcagtat     60

cagcgtgaga atccgaccga gaaaggcctg gatttcaaac tgtactggac cgatagccag    120

aacaagaaag aagtgattag ctctgataat ctgcaactgc cggaactgaa acagaagagc    180

agcaacagcc gcaagaaacg cagcacctct gcgggcccga ccgttccaga tcgcgacaac    240

gatggcattc cggacagcct ggaagtggaa ggttataccg ttgatgtgaa gaacaaacgc    300

acctttctga gcccgtggat tagcaacatt catgagaaga aaggcctgac caagtataaa    360

agcagcccgg agaagtggag caccgcgagc gatccgtata gcgacttcga gaaagtgacc    420

ggccgcattg ataagaacgt gagcccggaa gcacgccacc cactggttgc agcgtatccg    480

attgtgcatg ttgacatgga gaacatcatt ctgagcaaga acgaagatca gagcacccag    540

aacacggata gccagacccg cacgatcagc aaaaacacca gcacgagccg tacccatacc    600

agcgaagtgc atggcaatgc ggaagtgcat gcgagcttct ttgacattgg tggcagcgtg    660
```

```
agcgcgggct tcagcaacag caacagcagc accgtggcga ttgatcatag cctgagcctg    720

gcgggcgaac gtacctgggc ggaaaccatg ggcctgaaca cggcggatac ggcacgtctg    780

aatgcgaaca ttcgctatgt gaacaccggt accgcgccaa tctacaacgt tctgccgacc    840

acgagcctgg tgctgggcaa gaatcagacc ctggcgacca tcaaagcgaa agagaaccag    900

ctgtctcaga ttctggcacc gaacaactac tatccgagca agaacctggc accgattgca    960

ctgaatgcgc aggatgactt cagcagcacc ccgatcacca tgaactacaa ccagtttctg   1020

gagctggaga agaccaaaca actgcgcctg gataccgatc aggtgtatgg caacattgcg   1080

acctacaact ttgagaacgg ccgcgttcgc gtggataccg gtagcaactg gtctgaagtg   1140

ctgccgcaga ttcaggaaac gaccgcgcgc atcattttca acggcaaaga tctgaacctg   1200

gtggaacgtc gcatcgcggc agtgaaccca tctgatccac tggaaacgac caaaccggac   1260

atgaccctga aagaagcgct gaagattgca tttggcttca acgaaccgaa tggcaacctg   1320

cagtatcagg gtaaggacat caccgagttt gactttaact ttgatcaaca gacctctcag   1380

aacattaaga accagctggc agaactgaat gcgaccaaca tctacaccgt gctggacaag   1440

atcaaactga acgcaaagat gaacattctg attcgtgaca aacgcttcca ctatgatcgt   1500

aacaacattg cggtgggcgc agatgaaagc gttgtgaaag aagcgcatcg tgaagtgatc   1560

aactctagca ccgaaggcct gctgctgaac attgacaaag acatccgtaa gatcctgagc   1620

ggctacattg tggagatcga agataccgaa ggtctgaaag aagtgatcaa cgatcgctat   1680

gacatgctga acatctctag cctgcgccag gatggcaaga ccttcattga cttcaagaag   1740

tacaacgaca aactgccgct gtacatcagc aatccgaact acaaagtgaa cgtgtatgcg   1800

gtgacc                                                              1806
```

<210> SEQ ID NO 68
<211> LENGTH: 1806
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Sequence variant (98%) of SEQ ID No. 66

<400> SEQUENCE: 68

```
agcaacagca acaagattcg cctggagaag ggtcgcctgt atcagatcaa gattcagtat     60

cagcgtgaga atccgaccga gaaaggcctg gatttcaaac tgtactggac cgatagccag    120

aacaagaagg aagtgattag ctctgataat ctgcaactgc cggaactgaa acagaagagc    180

agcaacagcc gcaagaaacg cagcacctct gcgggcccga ccgttccaga tcgcgacaac    240

gatggcattc cggacagcct ggaggtggaa ggttataccg ttgatgtgaa gaacaaacgc    300

acctttctga gcccgtggat tagcaacatt catgagaaga aaggcctgac caagtataaa    360

agcagcccgg agaagtggag caccgcgagc gatccgtata gcgacttcga gaaagtgacc    420

ggccgcattg ataagaacgt gagcccggaa gcacgccacc cactggttgc agcgtatccg    480

attgtgcatg tggacatgga gaacatcatt ctgagcaaga acgaagatca gagcacccag    540

aacacggata gccagacccg cacgatcagc aaaaacacca gcacgagccg tacccatacc    600

agcgaagttc atggcaacgc ggaagtgcat gcgagcttct ttgacattgg tggcagcgtg    660

agcgcgggct tcagcaacag caactctagc accgtggcga ttgatcatag cctgagcctg    720

gcgggcgaac gtacctgggc ggaaaccatg ggcctgaaca cggcggatac ggcacgtctg    780

aatgcgaaca ttcgctatgt gaacaccggt accgcgccaa tctacaacgt tctgccgacc    840
```

```
acgagcctgg tgctgggcaa gaatcagacc ctggcgacca tcaaagcgaa agagaaccag     900
ctgtctcaga ttctggcacc gaataactac tatccgagca agaacctggc accgattgca     960
ctgaacgcgc aggatgactt cagcagcacc ccgatcacca tgaactacaa ccagtttctg    1020
gagctggaaa agaccaaaca actgcgcctg gataccgatc aggtgtatgg caacattgcg    1080
acctacaact ttgagaacgg ccgcgttcgc gtggataccg gtagcaactg gtctgaagtg    1140
ctgccgcaga ttcaggaaac gaccgcgcgc atcattttca acggcaaaga tctgaacctg    1200
gtggaacgtc gcatcgcggc agtgaaccca agcgatccac tggaaaccac caaaccggac    1260
atgaccctga aagaagcgct gaagattgca tttggcttca acgaaccgaa tggcaacctg    1320
cagtatcagg gtaaggacat caccgagttt gactttaact ttgatcaaca gacgtctcag    1380
aacattaaga accagctggc agaactgaat gcgaccaaca tctacaccgt gctggacaag    1440
atcaaactga acgcaaagat gaacattctg attcgtgaca aacgcttcca ctatgatcgt    1500
aacaacattg cggtgggcgc agatgaaagc gttgtgaaag aagcgcatcg tgaagtgatc    1560
aactctagca ccgaaggtct gctgctgaac attgacaaag acatccgtaa gatcctgagc    1620
ggctacattg tggagatcga agataccgaa ggcctgaaag aagtgatcaa tgatcgctat    1680
gacatgctga acatctctag cctgcgccag gatggcaaga ccttcattga cttcaaaaag    1740
tacaacgaca aactgccgct gtacatcagc aatccgaact acaaagtgaa cgtgtatgcg    1800
gtgacc                                                               1806
```

```
<210> SEQ ID NO 69
<211> LENGTH: 1806
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Sequence variant (97%) of SEQ ID No. 66

<400> SEQUENCE: 69
```

```
agcaacagca acaagattcg cctggagaag ggtcgcctgt atcagatcaa gattcagtat      60
cagcgtgaga atccgaccga gaaaggcctg gatttcaaac tgtactggac cgatagccag     120
aacaagaagg aagtgattag ctctgataat ctgcaactgc cggaactgaa acagaagagc     180
agcaacagcc gcaagaaacg cagcacctct gcgggcccga ccgttccaga tcgcgacaac     240
gatggcattc cggatagcct ggaggtggaa ggttataccg ttgatgtgaa gaacaaacgc     300
acctttctga gcccgtggat tagcaacatt catgagaaga aaggcctgac caagtataaa     360
agcagcccgg agaagtggag cacggcgagc gatccgtata gcgacttcga gaaagtgacc     420
ggccgcattg ataagaacgt gagcccggaa gcacgccacc cactggttgc agcgtatccg     480
attgtgcatg tggacatgga gaacatcatt ctgagcaaga acgaagatca gagcacccag     540
aacaccgata gccagacccg cacgatcagc aaaaacacca gcacgagccg tacccatacc     600
agcgaagttc atggcaacgc ggaagtgcat gcgagcttct ttgacattgg tggcagcgtg     660
agcgcgggct tcagcaacag caactctagc accgtggcga ttgatcatag cctgagcctg     720
gcgggcgaac gtacctgggc ggaaaccatg ggcctgaaca cggcggatac ggcacgtctg     780
aatgcgaaca ttcgctatgt gaacaccggt accgcaccaa tctacaacgt tctgccgacc     840
acgagcctgg tgctgggcaa gaatcagacc ctggcgacca tcaaagcgaa agagaaccag     900
ctgtctcaga ttctggcacc gaataactac tatccgagca agaacctggc accgattgca     960
```

```
ctgaacgcgc aggatgactt cagcagcacc ccgatcacca tgaactacaa ccagtttctg   1020
gagctggaaa agaccaaaca actgcgcctg gataccgatc aggtgtatgg caacattgcg   1080
acctacaact ttgagaacgg ccgcgttcgc gtggataccg gtagcaactg gtctgaagtg   1140
ctgccgcaga ttcaggaaac gaccgcgcgt atcattttca acggcaaaga tctgaacctg   1200
gtggaacgtc gcatcgcggc agtgaatccg agcgatccac tggaaaccac caaaccggac   1260
atgaccctga aagaagcgct gaagattgca tttggcttca acgaaccgaa cggcaacctg   1320
cagtatcagg gtaaggacat caccgagttc gactttaact ttgatcaaca gacgtctcag   1380
aacattaaga accagctggc agaactgaat gcgaccaaca tctacaccgt gctggacaag   1440
atcaaactga acgcaaagat gaacattctg attcgtgaca aacgcttcca ctatgatcgt   1500
aacaacattg cggtgggcgc ggatgaaagc gttgtgaaag aagcgcatcg tgaagtgatt   1560
aactctagca ccgaaggtct gctgctgaac attgacaaag acatccgcaa gatcctgagc   1620
ggctacattg tggagatcga agacaccgaa ggcctgaaag aagtgatcaa tgatcgctat   1680
gacatgctga acatctctag cctgcgccag gatggcaaga ccttcatcga ctttaaaaag   1740
tacaacgaca aactgccact gtacatcagc aatccgaact acaaagtgaa cgtgtatgcg   1800
gtgacc                                                              1806
```

<210> SEQ ID NO 70
<211> LENGTH: 1806
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Sequence variant (96%) of SEQ ID No. 66

<400> SEQUENCE: 70

```
agcaacagca acaagattcg cctggagaaa ggtcgcctgt atcagatcaa gattcagtat     60
cagcgtgaga atccgaccga gaaaggcctg gatttcaaac tgtactggac cgatagccag    120
aacaagaagg aagtgattag ctctgacaat ctgcaactgc cggaactgaa acagaagagc    180
agcaacagcc gcaagaagcg cagcacctct gcgggcccaa ccgttccaga tcgcgacaac    240
gatggcattc cggatagcct ggaagtggaa ggttataccg ttgatgtgaa gaacaaacgc    300
acctttctga gcccgtggat tagcaacatt catgagaaga aaggcctgac caagtataaa    360
agcagcccgg agaagtggag caccgcgagc gatccgtata gcgatttcga gaaagtgacc    420
ggccgcattg ataagaacgt gagcccggaa gcacgccacc cactggttgc agcgtatccg    480
attgtgcatg tggacatgga gaacatcatt ctgagcaaga acgaagacca gagcacccag    540
aacaccgata gccagacgcg cacgatcagc aaaaacacca gcacgagccg tacccatacc    600
agcgaagttc atggcaacgc ggaagtgcat gcgagcttct ttgacattgg tggcagcgtg    660
agcgcgggct ttagcaacag caactctagc accgtggcga ttgatcatag cctgagcctg    720
gcgggcgaac gtacctgggc ggaaaccatg ggcctgaaca cggcggacac ggcacgtctg    780
aatgcgaaca ttcgctatgt gaacaccggt accgcaccaa tctacaacgt tctgccgacc    840
acgagcctgg tgctgggcaa gaatcagacc ctggcgacca tcaaagcgaa agagaaccag    900
ctgtctcaga ttctggcacc gaataactac tatccgagca agaacctggc accgattgca    960
ctgaacgcgc aagatgactt cagcagcacc ccgatcacca tgaactacaa ccagtttctg   1020
gagctggaaa agacgaaaca actgcgcctg gataccgatc aggtgtatgg caacattgcg   1080
acctacaact tcgagaacgg ccgcgttcgc gtggacaccg gtagcaactg gtctgaagtg   1140
```

ctgccgcaga ttcaggaaac caccgcgcgt atcattttca acggcaaaga tctgaacctg 1200
gtggagcgtc gcatcgcggc agtgaatcca agcgatccgc tggaaaccac caaaccggac 1260
atgaccctga aagaagcgct gaagattgca tttggcttca acgaaccgaa cggcaacctg 1320
cagtatcagg gtaaggacat caccgagttc gattttaact ttgatcagca gacgtctcag 1380
aacattaaga accagctggc agaactgaat gcgaccaaca tctacaccgt gctggacaag 1440
atcaaactga acgcaaagat gaacattctg attcgtgaca aacgcttcca ctatgatcgt 1500
aacaacattg cggtgggcgc ggatgaaagc gttgtgaaag aagcgcatcg tgaagtgatt 1560
aactctagca ccgaaggtct gctgctgaac attgataaag acatccgcaa gatcctgagc 1620
ggctacattg tggagatcga agacaccgaa ggcctgaaag aagtgatcaa tgatcgctat 1680
gacatgctga acatctctag cctgcgccag gatggcaaga ccttcatcga ttttaaaaag 1740
tacaacgaca aactgccgct gtacatcagc aatccgaact acaaagtgaa cgtgtatgcg 1800
gtgacc 1806

<210> SEQ ID NO 71
<211> LENGTH: 1806
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Sequence variant (95%) of SEQ ID No. 66

<400> SEQUENCE: 71
agcaacagca acaagattcg cctggagaaa ggtcgcctgt atcagatcaa gattcagtat 60
cagcgtgaga atccgaccga gaaaggcctg gatttcaaac tgtactggac cgatagccag 120
aacaagaagg aagtgattag ctctgacaat ctgcaactgc cggaactgaa acagaagagc 180
agcaacagcc gcaagaagcg cagcacctct gcgggcccga ccgttccaga tcgcgacaac 240
gatggcattc cggatagcct ggaagtggaa ggttataccg ttgatgtgaa gaacaagcgc 300
acctttctga gcccgtggat tagcaacatt catgagaaga aaggcctgac caagtataaa 360
agcagcccgg agaagtggag caccgcgagc gatccgtata gcgatttcga gaaagtgacc 420
ggccgcattg ataagaacgt gagcccggaa gcacgccatc cactggttgc agcgtatccg 480
attgtgcatg tggacatgga gaacatcatt ctgagcaaga acgaagacca gagcacccag 540
aacaccgatt ctcagacgcg cacgatcagc aaaaacacca gcacgagccg tacccacacc 600
agcgaagttc atggcaacgc ggaagtgcat gcgtctttct ttgacattgg tggcagcgtg 660
agcgcgggct ttagcaacag caactctagc accgtggcga ttgatcatag cctgagcctg 720
gcgggcgaac gtacctgggc ggaaaccatg ggcctgaaca cggcggacac ggcacgtctg 780
aacgcgaaca ttcgctatgt gaacaccggt accgcaccaa tctacaacgt tctgccgacc 840
acgagcctgg tgctgggcaa gaatcagacc ctggcgacca tcaaagcgaa agagaaccag 900
ctgtctcaga ttctggcacc gaataactac tatccgagca agaacctggc accgattgca 960
ctgaacgcgc aagatgactt cagcagcacc ccgatcacca tgaactacaa ccagtttctg 1020
gagctggaaa agaccaaaca actgcgcctg gataccgatc aggtgtatgg caacattgcg 1080
acctacaact tcgagaacgg ccgcgttcgc gtggacaccg gtagcaactg gtctgaagtg 1140
ctgccgcaga tccaggaaac caccgcgcgt atcattttca acggcaaaga tctgaacctg 1200
gtggagcgtc gcatcgcggc agtgaatcca agcgatccgc tggaaaccac caaaccggac 1260
atgaccctga aagaagcgct gaagattgca tttggcttca acgaaccgaa cggcaacctg 1320
cagtatcagg gtaaggacat caccgagttc gattttaact ttgatcagca gacgagccag 1380
aacattaaga accagctggc agaactgaat gcgaccaaca tctacaccgt gctggacaag 1440
atcaaactga acgcaaaaat gaacattctg attcgtgaca aacgcttcca ctatgatcgt 1500
aacaacattg cggtgggcgc ggatgaaagc gttgtgaaag aagcgcatcg tgaagtgatt 1560
aactctagca ccgaaggtct gctgctgaac attgataaag acatccgcaa gatcctgagc 1620
ggctacattg tggagatcga agacacggaa ggcctgaaag aagtgattaa tgatcgctat 1680
gacatgctga atatcagcag cctgcgccag gatggcaaga ccttcatcga ttttaaaaag 1740
tacaacgaca aactgccact gtacatcagc aatccgaact acaaagtgaa cgtgtatgcg 1800
gtgacc 1806

<210> SEQ ID NO 72
<211> LENGTH: 1806
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Sequence variant (94%) of SEQ ID No. 66

<400> SEQUENCE: 72
agcaacagca acaagattcg cctggagaaa ggtcgcctgt atcagatcaa gattcagtat 60
cagcgtgaga atccgaccga gaaaggcctg gatttcaaac tgtactggac cgatagccag 120
aacaagaagg aagtgattag ctctgacaat ctgcaactgc cggaactgaa acagaagagc 180
agcaacagcc gtaagaagcg cagcacctct gcgggtccga ccgttccaga tcgcgacaac 240
gatggcattc cggatagcct ggaagtggaa ggctataccg ttgatgtgaa gaacaagcgc 300
acctttctga gcccgtggat tagcaacatt catgagaaga aaggcctgac caaatataaa 360
agcagcccgg agaagtggag caccgcgagc gatccgtata gcgatttcga gaaagtgacc 420
ggccgtattg ataagaacgt gagcccggaa gcacgccacc cactggttgc agcgtatccg 480
attgtgcatg tggacatgga gaacatcatt ctgagcaaga acgaagacca gagcacccag 540
aacaccgatt ctcagacgcg cacgatcagc aaaaacacca gcacgagccg tacccatacc 600
agcgaagttc atggcaacgc ggaagtgcat gcgtctttct ttgacattgg cggcagcgtg 660
agcgcgggtt tcagcaacag caactctagc accgtggcga ttgatcatag cctgagcctg 720
gcgggcgaac gcacctgggc ggaaaccatg ggcctgaaca cggcggacac ggcacgtctg 780
aacgcgaaca tccgctacgt gaacaccggt accgcaccaa tctataacgt tctgccgacc 840
acgagcctgg ttctgggcaa gaatcagacc ctggcgacca tcaaagcgaa ggagaaccag 900
ctgtctcaga ttctggcgcc gaacaactac tatccgagca agaacctggc accgattgca 960
ctgaacgcgc aagatgactt cagcagcacc ccgatcacca tgaactataa tcagtttctg 1020
gagctggaaa agaccaaaca actgcgcctg gataccgacc aggtgtatgg caacattgca 1080
acctacaact tcgagaacgg ccgcgttcgc gtggacaccg gtagcaactg gtctgaagtg 1140
ctgccgcaga ttcaggaaac caccgcgcgc atcattttta acggcaaaga tctgaatctg 1200
gtggagcgtc gcatcgcggc agtgaatcca agcgatccgc tggaaaccac caaaccggac 1260
atgaccctga aagaagcgct gaagattgca ttcggcttca acgaaccgaa cggcaacctg 1320
cagtaccagg gtaaggacat caccgagttc gattttaact ttgatcagca gacgagccag 1380
aacattaaaa accagctggc agaactgaat gcgaccaaca tctacaccgt gctggacaag 1440

```
atcaaactga acgcaaaaat gaacattctg attcgtgaca aacgctttca ctatgatcgt   1500

aataacattg cggtgggcgc ggatgaaagc gtggtgaaag aagcgcatcg tgaagtgatt   1560

aactctagca ccgaaggtct gctgctgaac attgataaag acatccgcaa gatcctgagc   1620

ggctacattg tggagatcga agacacggaa ggcctgaagg aagtgattaa tgatcgctat   1680

gacatgctga acatcagcag cctgcgccag gatggcaaga ccttcatcga ttttaaaaag   1740

tacaacgata aactgccact gtacatcagc aacccgaact acaaagtgaa cgtgtatgcg   1800

gtgacc                                                              1806
```

<210> SEQ ID NO 73
<211> LENGTH: 1806
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Sequence variant (93%) of SEQ ID No. 66

<400> SEQUENCE: 73

```
agcaacagca acaagattcg cctggagaag ggtcgcctgt atcagatcaa gattcagtat     60

cagcgtgaga atccgaccga gaaaggcctg gatttcaaac tgtactggac cgatagccag    120

aacaagaagg aagtgattag ctctgacaat ctgcaactgc cggaactgaa acagaagagc    180

agcaacagcc gtaagaagcg cagcacctct gcgggcccga cggttccaga tcgcgacaac    240

gatggcattc cggatagcct ggaagtggaa ggttataccg ttgatgtgaa aaacaagcgc    300

acctttctgt ctccgtggat tagcaacatt catgagaaga aaggcctgac caaatataaa    360

agcagcccgg agaagtggag caccgcgagc gatccgtata gcgatttcga gaaagtgacc    420

ggccgtattg ataagaacgt gagcccggaa gcacgccacc cactggttgc agcgtatccg    480

attgtgcatg tggacatgga gaacatcatt ctgagcaaga acgaagacca gagcacccag    540

aacaccgata gccagacgcg cacgatcagc aaaaacacct ctacgagccg tacccatacc    600

agcgaagttc atggcaacgc ggaagtgcat gcaagcttct ttgacattgg cggcagcgtg    660

agcgcgggtt tcagcaacag caactctagc accgtggcga ttgatcattc tctgagcctg    720

gcgggcgaac gcacctgggc ggaaaccatg ggtctgaaca ccgcggacac ggcacgtctg    780

aacgcgaaca tccgctacgt gaacaccggc accgcaccaa tctataacgt tctgccgacc    840

acgagcctgg ttctgggcaa gaatcagacc ctggcgacca tcaaagcgaa ggagaaccag    900

ctgtctcaga ttctggcgcc gaacaactac tatccgagca agaacctggc accgattgca    960

ctgaacgcgc aagatgactt cagcagcacc ccgatcacca tgaactataa tcagtttctg   1020

gagctggaaa aaaccaaaca actgcgcctg gataccgacc aggtgtatgg caacattgca   1080

acctacaact tcgagaacgg ccgcgttcgc gtggacaccg gtagcaactg gtctgaagtg   1140

ctgccgcaga ttcaggaaac caccgcgcgc atcattttta acggcaaaga tctgaatctg   1200

gtggagcgtc gcatcgcggc ggtgaatcca agcgatccgc tggagaccac caagccggac   1260

atgaccctga aagaagcgct gaagattgca ttcggcttca acgaaccgaa cggcaacctg   1320

cagtaccagg gtaaggacat caccgagttc gattttaact ttgaccagca gacgagccag   1380

aacattaaaa accagctggc agaactgaat gcgaccaaca tctacaccgt gctggataag   1440

atcaaactga acgcaaaaat gaacattctg attcgtgaca aacgctttca ctatgatcgt   1500

aataacattg cggtgggcgc ggatgaaagc gtggtgaaag aagcgcatcg tgaagtgatt   1560
```

aacagcagca ccgaaggtct gctgctgaac attgataaag acatccgcaa gatcctgagc 1620
ggctacattg tggaaatcga agacacggaa ggcctgaagg aagtgattaa tgatcgctat 1680
gatatgctga acatcagcag cctgcgccag gacggcaaga ccttcatcga ttttaaaaag 1740
tacaacgata aactgccact gtacatcagc aacccgaact acaaagtgaa cgtgtatgcg 1800
gtgacc 1806

<210> SEQ ID NO 74
<211> LENGTH: 1806
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Sequence variant (92%) of SEQ ID No. 66

<400> SEQUENCE: 74
agcaacagca acaagattcg cctggagaag ggtcgcctgt atcagattaa gattcagtat 60
cagcgtgaga atccgaccga gaaaggcctg gatttcaaac tgtactggac cgatagccag 120
aacaagaagg aagtgattag ctctgacaat ctgcaactgc cggaactgaa acagaagagc 180
agcaacagcc gtaagaaacg cagcacctct gcgggcccga cggttccaga tcgcgacaac 240
gatggcatcc cggatagcct ggaagtggaa ggttacaccg tggatgtgaa aaacaagcgc 300
acctttctgt ctccgtggat tagcaacatt catgagaaga aaggcctgac caaatataaa 360
agcagcccgg agaagtggag caccgcgagc gatccgtata gcgatttcga gaaagtgacc 420
ggtcgtattg ataagaacgt gagcccggaa gcacgccatc cactggttgc agcgtatccg 480
attgtgcacg tggacatgga gaacatcatt ctgagcaaga acgaggacca gagcacccag 540
aacaccgata gccagacgcg cacgatcagc aaaaacacct ctacgagccg tacccatacc 600
agcgaagttc atggcaacgc ggaagtgcat gcaagcttct ttgacatcgg cggcagcgtg 660
agcgcgggtt tcagcaacag caactctagc accgtggcga ttgatcattc tctgagcctg 720
gcgggcgaac gcacctgggc ggaaaccatg ggtctgaaca ccgcggacac ggcacgtctg 780
aacgcgaata ttcgctacgt gaacaccggc accgcgccaa tctataacgt tctgccgacg 840
acgagcctgg ttctgggcaa gaatcagacc ctggcgacca ttaaagcgaa ggagaaccag 900
ctgtctcaga ttctggcacc gaacaactac tatccgagca aaaacctggc accgattgca 960
ctgaacgcgc aagatgactt cagcagcacc ccgatcacca tgaactataa tcagtttctg 1020
gagctggaaa aaaccaaaca actgcgcctg gataccgacc aggtgtatgg caacatcgca 1080
acctacaact tcgaaaacgg ccgcgttcgc gtggacaccg gcagcaactg gtctgaagtg 1140
ctgccgcaga tccaggagac caccgcgcgc atcattttta acggcaaaga tctgaacctg 1200
gtggagcgtc gcattgcggc ggtgaatcca agcgatccgc tggagaccac caagccggac 1260
atgaccctga aagaagcgct gaagattgca ttcggcttca acgaaccgaa cggcaacctg 1320
cagtatcagg gtaaggacat caccgaattc gattttaact ttgaccagca gaccagccag 1380
aacattaaaa accagctggc agaactgaat gcgaccaaca tctacaccgt gctggataag 1440
atcaaactga acgcaaaaat gaacattctg attcgtgaca agcgctttca ctatgatcgt 1500
aataacattg cggtgggcgc ggatgaaagc gtggttaaag aagcgcatcg tgaagtgatt 1560
aacagcagca ccgaaggtct gctgctgaac attgataagg acatccgcaa gatcctgagc 1620
ggctacatcg tggaaatcga agacacggaa ggcctgaagg aagtgattaa tgatcgctat 1680
gatatgctga acatcagcag cctgcgccag gacggcaaga ccttcatcga ttttaaaaag 1740
tacaacgata aactgccact gtacattagc aacccgaact acaaagtgaa cgtgtatgcg 1800
gtgacc 1806

<210> SEQ ID NO 75
<211> LENGTH: 1806
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Sequence variant (91%) of SEQ ID No. 66

<400> SEQUENCE: 75
agcaacagca ataagattcg cctggagaag ggtcgcctgt atcagattaa gattcagtat 60
cagcgcgaga atccgaccga gaaaggcctg gatttcaaac tgtactggac cgatagccag 120
aacaagaaag aggtgattag ctctgacaac ctgcaactgc cggaactgaa acagaagagc 180
agcaacagcc gtaagaaacg cagcacctct gcgggcccga cggttccaga tcgcgacaac 240
gatggcattc cggatagcct ggaagtggaa ggttataccg tggatgtgaa gaacaagcgc 300
acctttctgt ctccgtggat tagcaacatt catgagaaga aaggcctgac gaagtataaa 360
agcagcccgg agaagtggag cacggcgagc gatccgtata gcgatttcga aaaggtgacc 420
ggtcgtattg acaagaacgt gagcccggaa gcacgccatc cactggttgc agcgtatccg 480
attgtgcacg tggacatgga gaatatcatc ctgtctaaga acgaggacca gagcacccag 540
aacaccgata gccagacccg cacgattagc aaaaacacca gcacgagccg tacccatacg 600
agcgaagttc atggcaacgc ggaagtgcat gcgagcttct ttgacatcgg cggcagcgtg 660
agcgcgggtt tcagcaacag caactctagc accgtggcaa ttgatcattc tctgagcctg 720
gcgggcgaac gcacgtgggc ggaaaccatg ggtctgaaca ccgcggacac cgcacgtctg 780
aacgcgaata ttcgctacgt gaacaccggc accgcgccga tctataacgt gctgccgacc 840
accagcctgg ttctgggcaa gaaccagacc ctggcgacca tcaaagcaaa ggagaaccag 900
ctgtctcaga ttctggcgcc gaacaactac tatccgagca aaaacctggc accaattgca 960
ctgaacgcgc aagatgactt cagcagcacc ccgatcacca tgaactataa tcagtttctg 1020
gagctggaaa aaaccaagca actgcgcctg gataccgacc aggtttatgg caacatcgcg 1080
acctacaact ttgaaaacgg ccgcgtgcgc gtggacaccg gcagcaactg gtctgaagtg 1140
ctgccgcaga tccaggagac caccgcgcgc atcattttca acggcaaaga tctgaacctg 1200
gtggagcgtc gtattgcagc ggtgaatcca agcgatccgc tggagaccac caagccggac 1260
atgaccctga aagaagcgct gaagattgca ttcggcttca acgaaccgaa cggcaacctg 1320
cagtatcagg gtaaggacat taccgaattc gattttaact ttgaccagca gaccagccag 1380
aacattaaaa accagctggc agaactgaac gcgaccaaca tctacaccgt gctggataag 1440
attaaactga acgcaaaaat gaacatcctg attcgtgaca agcgctttca ctatgatcgt 1500
aataacattg cggtgggcgc ggacgaaagc gtggttaaag aagcgcatcg tgaagtgatc 1560
aacagcagca ccgaaggtct gctgctgaac attgataaag atattcgcaa aatcctgagc 1620
ggctacatcg tggaaatcga agatacggaa ggcctgaaag aagtgatcaa tgatcgctac 1680
gatatgctga atatcagcag cctgcgccag gacggcaaga ccttcatcga ttttaaaaag 1740
tacaacgata aactgccact gtacattagc aacccgaact acaaagtgaa cgtttatgcg 1800
gtgacc 1806

<210> SEQ ID NO 76
<211> LENGTH: 1857
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Truncated version of SEQ ID No. 1 (bp. 301-2157)

<400> SEQUENCE: 76

```
agcaacagca acaagattcg cctggagaag ggtcgcctgt atcagatcaa gattcagtat     60
cagcgcgaga atccgaccga gaaaggcctg gatttcaaac tgtactggac cgatagccag    120
aacaagaaag aagtgattag ctctgataac ctgcaactgc cggaactgaa acagaagagc    180
agcaacagcc gcaagaaacg cagcacctct gcaggcccga ccgttccaga tcgcgacaac    240
gatggcattc cggacagcct ggaagtggaa ggttataccg ttgatgtgaa gaacaaacgc    300
acctttctga gcccgtggat tagcaacatt catgagaaga aaggcctgac caagtacaaa    360
agcagcccgg agaagtggag caccgcgagc gatccgtata gcgactttga gaaagtgacc    420
ggccgcattg ataagaacgt gagcccggaa gcgcgtcacc cactggttgc agcgtatccg    480
attgtgcatg ttgacatgga gaacatcatt ctgagcaaga acgaagatca gagcacccag    540
aacacggata gccagacccg cacgatcagc aagaacacca gcacgagccg tacccatacc    600
agcgaagtgc atggcaatgc ggaagtgcat gcgagcttct ttgacattgg tggcagcgtg    660
agcgcgggct tcagcaacag caacagcagc accgtggcga ttgatcatag cctgagcctg    720
gcgggcgaac gtacctgggc ggaaaccatg ggcctgaaca cggcggatac ggcacgtctg    780
aatgcgaaca ttcgctatgt gaacaccggt accgcgccaa tctataacgt tctgccgacc    840
acgagcctgg tgctgggcaa gaatcagacc ctggcgacca tcaaagcgaa agagaaccag    900
ctgtctcaga ttctggcacc gaacaactac tatccgagca agaacctggc accgattgca    960
ctgaatgcgc aggatgactt cagcagcacc ccgatcacca tgaactacaa tcagtttctg   1020
gagctggaga agaccaaaca actgcgcctg gataccgatc aggtgtatgg caacattgcg   1080
acctacaact ttgagaacgg ccgcgttcgc gtggataccg gtagcaactg gtctgaagtg   1140
ctgccgcaga ttcaggaaac gaccgcgcgc atcatcttca acggcaaaga tctgaacctg   1200
gtggaacgtc gcatcgcggc agtgaaccca tctgatccac tggaaacgac caaaccggac   1260
atgaccctga aagaagcgct gaagattgca tttggcttca acgaaccgaa tggcaacctg   1320
cagtatcagg gcaaagacat caccgagttt gacttcaact ttgatcaaca gacctctcag   1380
aacatcaaga accagctggc agaactgaat gcgaccaaca tctacaccgt gctggacaag   1440
atcaaactga acgcaaagat gaacattctg attcgtgaca aacgcttcca ctatgatcgt   1500
aacaacattg cggtgggtgc agatgaaagc gttgtgaaag aagcgcatcg tgaagtgatc   1560
aactctagca ccgaaggcct gctgctgaac attgacaaag acatccgtaa gattctgagc   1620
ggctacattg tggagattga agataccgaa ggtctgaaag aagtgatcaa cgatcgctat   1680
gacatgctga acatctctag cctgcgccag gatggcaaga ccttcattga cttcaagaag   1740
tacaacgaca aactgccgct gtacatcagc aatccgaact acaaagtgaa cgtgtatgcg   1800
gtgaccaaag agaacaccat cattaaccca agcgagaatg gcgataccag caccaac      1857
```

<210> SEQ ID NO 77
<211> LENGTH: 1857
<212> TYPE: DNA

<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Sequence variant (99%) of SEQ ID No. 76

<400> SEQUENCE: 77

```
agcaacagca acaagattcg cctggagaag ggtcgcctgt atcagatcaa gattcagtat     60
cagcgcgaga atccgaccga gaaaggcctg gatttcaaac tgtactggac cgatagccag    120
aacaagaaag aagtgattag ctctgataac ctgcaactgc cggaactgaa acagaagagc    180
agcaacagcc gcaagaaacg cagcacctct gcaggcccga ccgttccaga tcgcgacaac    240
gatggcattc cggacagcct ggaagttgaa ggttataccg ttgatgtgaa gaacaaacgc    300
acctttctga gcccgtggat cagcaacatt catgagaaga aaggcctgac caagtacaaa    360
agcagcccgg agaagtggag caccgcgagc gatccgtata gcgactttga gaaagtgacc    420
ggccgcattg ataagaacgt gagcccggaa gcgcgtcacc cactggttgc agcgtatccg    480
attgtgcatg ttgacatgga gaacatcatt ctgagcaaga acgaagatca gagcacccag    540
aacacggata gccagacccg cacgatcagc aagaacacca gcacgtctcg tacccatacc    600
agcgaagtgc atggcaatgc ggaagtgcat gcgagcttct ttgacattgg tggcagcgtg    660
agcgcgggct tcagcaacag caacagcagc accgtggcga ttgatcatag cctgagcctg    720
gcgggcgaac gtacctgggc ggaaaccatg ggcctgaaca cggcggatac ggcacgtctg    780
aatgcgaaca ttcgctatgt gaacaccggt accgcgccaa tctataacgt tctgccgacc    840
acgagcctgg tgctgggcaa gaatcagacc ctggcgacca tcaaagcgaa agagaaccag    900
ctgtctcaga ttctggcacc gaacaactac tatccgagca agaacctggc accgattgca    960
ctgaatgcgc aggatgactt cagcagcacc ccgatcacca tgaactacaa tcagtttctg   1020
gagctggaga agaccaaaca actgcgcctg gataccgatc aggtgtatgg caacattgcg   1080
acctacaact ttgagaacgg ccgcgttcgc gtggataccg gtagcaactg gagcgaagtg   1140
ctgccgcaga ttcaggaaac gaccgcgcgc attatcttca acggcaaaga tctgaacctg   1200
gtggaacgtc gcatcgcggc agtgaaccca tctgatccac tggaaacgac caaaccggac   1260
atgaccctga aagaagcgct gaagattgca tttggcttca acgaaccgaa tggcaacctg   1320
cagtatcagg gcaaagacat caccgagttt gacttcaact ttgatcaaca gacctctcag   1380
aacatcaaga accagctggc agaactgaat gcgaccaaca tctacaccgt gctggacaag   1440
atcaaactga acgcaaagat gaacatcctg attcgtgaca aacgcttcca ctatgatcgt   1500
aacaacattg cggtgggtgc agatgaaagc gtggtgaaag aagcgcatcg tgaagtgatc   1560
aacagcagca ccgaaggcct gctgctgaac attgacaaag acattcgtaa gattctgagc   1620
ggctacattg tggagattga agataccgaa ggtctgaaag aagtgatcaa cgatcgctat   1680
gacatgctga acatctctag cctgcgccag gatggcaaga ccttcattga cttcaagaag   1740
tacaacgaca aactgccgct gtacatctct aatccgaact acaaagtgaa cgtgtatgcg   1800
gtgaccaaag agaacaccat cattaaccca agcgagaatg gcgataccag caccaac      1857
```

<210> SEQ ID NO 78
<211> LENGTH: 1857
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:

<223> OTHER INFORMATION: Sequence variant (98%) of SEQ ID No. 76

<400> SEQUENCE: 78
agcaacagca acaagattcg cctggagaag ggtcgcctgt atcagatcaa gattcagtat 60
cagcgcgaga atccgaccga gaaaggcctg gatttcaaac tgtactggac cgatagccag 120
aacaagaaag aagtgattag ctctgataac ctgcaactgc cggaactgaa acagaagagc 180
agcaacagcc gcaagaaacg cagcacctct gcaggcccga ccgttccaga tcgcgacaac 240
gatggcattc cggacagcct ggaagttgaa ggttataccg ttgatgtgaa gaacaaacgc 300
acctttctga gcccgtggat cagcaacatt catgagaaga aaggcctgac caagtacaaa 360
agcagcccgg agaagtggag caccgcgagc gatccgtata gcgactttga aaaagtgacc 420
ggccgcattg ataagaacgt gagcccggaa gcgcgtcacc cactggttgc ggcgtatccg 480
attgtgcatg ttgacatgga gaacatcatt ctgagcaaga acgaggatca gagcacccag 540
aacacggata gccagacccg caccatcagc aagaacacca gcacgtctcg tacccatacc 600
agcgaagtgc atggcaatgc ggaagtgcat gcgagcttct ttgacattgg tggcagcgtg 660
agcgcaggct tcagcaacag caacagcagc accgtggcga ttgatcatag cctgagcctg 720
gcgggcgaac gtacctgggc ggaaaccatg ggcctgaaca cggcagatac ggcacgtctg 780
aatgcgaaca ttcgctatgt gaacaccggt accgcgccaa tttataacgt tctgccgacc 840
acgagcctgg tgctgggcaa gaatcagacc ctggcgacca tcaaagcgaa agagaaccag 900
ctgtctcaga ttctggcacc gaacaactac tatccgagca agaacctggc accgattgca 960
ctgaatgcgc aggatgactt cagcagcacg ccgatcacca tgaactacaa tcagtttctg 1020
gagctggaaa agaccaaaca actgcgcctg gataccgatc aggtgtatgg caacattgcg 1080
acctacaact ttgagaacgg ccgcgttcgt gtggataccg gtagcaactg gagcgaagtg 1140
ctgccgcaga tccaggaaac gaccgcgcgc attatcttca acggcaaaga tctgaacctg 1200
gtggaacgtc gcatcgcggc agtgaaccca tctgatccac tggaaacgac caaaccggac 1260
atgaccctga aagaggcgct gaagattgca tttggcttca acgaaccgaa tggcaacctg 1320
cagtatcagg gcaaagacat taccgagttt gacttcaact ttgatcaaca gacctctcag 1380
aacatcaaga accagctggc agaactgaat gcgaccaaca tctacaccgt gctggacaag 1440
atcaaactga acgcgaagat gaacatcctg attcgcgaca aacgcttcca ctatgatcgt 1500
aacaacattg cggtgggtgc agatgaaagc gtggtgaaag aagcgcatcg tgaagtgatc 1560
aacagcagca ccgaaggcct gctgctgaac attgacaaag acattcgtaa gatcctgagc 1620
ggctacattg tggagattga agacaccgaa ggtctgaaag aagtgatcaa cgatcgctat 1680
gatatgctga acatctctag cctgcgccag gatggcaaga ccttcattga cttcaagaag 1740
tacaacgaca aactgccgct gtacatctct aatccgaact acaaagtgaa cgtgtatgcg 1800
gtgaccaaag agaacaccat cattaaccca agcgagaatg gcgataccag caccaac 1857

<210> SEQ ID NO 79
<211> LENGTH: 1857
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Sequence variant (97%) of SEQ ID No. 76

<400> SEQUENCE: 79
agcaacagca acaagattcg cctggagaag ggtcgcctgt atcagatcaa gattcagtat 60

```
cagcgcgaga atccgaccga gaaaggcctg gatttcaagc tgtactggac cgatagccag    120

aacaagaaag aagtgattag ctctgataac ctgcaactgc cggaactgaa acagaagagc    180

agcaacagcc gcaagaaacg cagcacctct gcaggcccga ccgttccaga tcgcgacaac    240

gatggcattc cggacagcct ggaggttgaa ggttataccg ttgatgtgaa gaacaaacgc    300

accttcctga gcccgtggat ctctaacatt catgagaaga aaggcctgac caagtacaaa    360

agcagcccgg agaagtggag caccgcgagc gatccgtata gcgactttga aaaagtgacc    420

ggccgcattg ataagaacgt gagcccggaa gcacgtcacc cactggttgc ggcgtacccg    480

attgtgcatg ttgacatgga gaacatcatt ctgagcaaga acgaagatca gagcacccag    540

aacacggata gccagacccg taccatcagc aagaacacca gcacgtctcg tacccatacc    600

agcgaagtgc atggcaatgc ggaagtgcat gcgagctttt ttgacattgg tggcagcgtg    660

agcgcaggct tcagcaacag caacagcagc accgtggcga ttgatcatag cctgagcctg    720

gcgggcgaac gtacctgggc ggaaaccatg ggcctgaaca cggcagatac ggcacgtctg    780

aatgcgaaca ttcgctatgt gaacaccggt accgcgccaa tttataacgt tctgccgacc    840

acgagcctgg tgctgggcaa gaatcagacc ctggcgacca tcaaagcgaa agagaaccag    900

ctgagccaga ttctggcacc gaacaactac tatccgagca agaacctggc gccgattgca    960

ctgaatgcgc aggatgactt cagcagcacg ccgattacca tgaactacaa tcagtttctg   1020

gagctggaaa agaccaaaca actgcgcctg gataccgatc aggtgtatgg caacattgcg   1080

acctacaact ttgagaacgg ccgcgttcgc gtggataccg gtagcaactg gagcgaagtg   1140

ctgccgcaga tccaggaaac gaccgcgcgc attatcttta acggcaaaga tctgaacctg   1200

gtggaacgtc gcatcgcggc agtgaaccca tctgatccac tggaaacgac caaaccggac   1260

atgaccctga aagaggcgct gaagattgca ttcggcttca acgaaccgaa tggcaacctg   1320

cagtatcagg gcaaagacat taccgagttt gacttcaact ttgatcaaca gacctctcag   1380

aacatcaaga accagctggc agaactgaat gcgaccaaca tctacaccgt gctggacaag   1440

atcaaactga acgcgaaaat gaacatcctg attcgcgaca aacgcttcca ctatgatcgt   1500

aacaacattg cggtgggtgc agatgaaagc gtggtgaaag aagcgcatcg cgaagtgatc   1560

aacagcagca ccgaaggcct gctgctgaac attgacaaag acatccgtaa gatcctgagc   1620

ggctacatcg tggagattga agacaccgaa ggtctgaaag aagtgattaa cgatcgctat   1680

gatatgctga acatctctag cctgcgtcag gatggcaaga ccttcattga cttcaagaag   1740

tacaacgaca aactgccgct gtacatctct aatccgaact ataaagtgaa cgtgtatgcg   1800

gtgaccaaag agaacaccat cattaaccca agcgagaatg gcgataccag caccaac      1857
```

<210> SEQ ID NO 80
<211> LENGTH: 1857
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Sequence variant (96%) of SEQ ID No. 76

<400> SEQUENCE: 80

```
agcaacagca acaagattcg cctggagaag ggtcgcctgt atcagatcaa gatccagtat     60

cagcgcgaga atccgaccga gaaaggcctg gatttcaagc tgtactggac cgatagccag    120

aacaagaaag aagtgattag ctctgacaac ctgcaactgc cggaactgaa gcagaaaagc    180
```

-continued

```
agcaacagcc gcaagaaacg cagcacctct gcaggcccga ccgttccgga tcgcgacaac    240

gatggcattc cggacagcct ggaggttgaa ggctataccg ttgatgtgaa gaacaaacgc    300

accttcctga gcccgtggat ctctaacatt catgagaaga aaggcctgac caagtacaaa    360

agcagcccgg agaagtggag caccgcgagc gatccgtata gcgactttga aaaagtgacc    420

ggccgcattg ataagaacgt gagcccggaa gcacgtcacc cactggttgc ggcgtacccg    480

attgtgcatg ttgacatgga gaacatcatt ctgagcaaga acgaagatca gagcacccag    540

aacacggata gccagacccg taccatcagc aagaacacca gcacgtctcg tacccatacc    600

agcgaagtgc atggtaatgc ggaagtgcat gcgagctttt ttgacattgg tggcagcgtg    660

agcgcaggct ttagcaacag caacagcagc acggtggcga ttgatcatag cctgagcctg    720

gcgggcgaac gtacctgggc ggaaaccatg ggcctgaaca cggcagatac cgcacgtctg    780

aatgcgaaca ttcgctatgt gaacaccggt accgcgccaa tttataacgt tctgccgacc    840

acgagcctgg tgctgggcaa gaatcagacc ctggcgacca tcaaagcgaa agagaaccag    900

ctgagccaga ttctggcacc gaacaactac tatccaagca aaaacctggc gccgattgca    960

ctgaatgcgc aggatgactt cagcagcacg ccgattacca tgaactacaa tcagtttctg   1020

gagctggaaa agaccaagca actgcgcctg gataccgatc aggtgtatgg caacattgcg   1080

acctacaact ttgagaacgg ccgcgttcgc gtggataccg gtagcaactg gagcgaagtg   1140

ctgccgcaga tccaggaaac gaccgcgcgc attatcttta acggcaaaga tctgaacctg   1200

gtggaacgtc gcatcgcggc agtgaaccca tctgatccac tggaaaccac caaaccggac   1260

atgaccctga aagaggcgct gaagattgca ttcggcttca acgaaccgaa tggcaacctg   1320

cagtatcagg gcaaagacat taccgagttt gatttcaact tcgatcaaca gacctctcag   1380

aacatcaaga accagctggc agaactgaat gcgaccaaca tctacaccgt gctggacaag   1440

atcaaactga acgcgaaaat gaacatcctg attcgcgaca aacgcttcca ctatgatcgt   1500

aacaacattg cggtgggtgc agatgaaagc gtggtgaaag aagcgcatcg cgaagtgatc   1560

aacagcagca ccgaaggcct gctgctgaac attgacaaag acatccgtaa gatcctgagc   1620

ggctacatcg tggagattga agacaccgaa ggtctgaaag aagtgattaa cgatcgctat   1680

gatatgctga acatctctag cctgcgtcag gatggcaaga ccttcattga cttcaagaag   1740

tacaacgaca aactgccgct gtacatttct aatccgaact ataaagtgaa cgtgtatgcg   1800

gtgaccaaag agaacacgat cattaaccca agcgagaatg gcgataccag caccaac      1857
```

```
<210> SEQ ID NO 81
<211> LENGTH: 1857
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Sequence variant (95%) of SEQ ID No. 76

<400> SEQUENCE: 81

agcaacagca acaagatccg cctggagaag ggtcgcctgt atcagatcaa gatccagtat     60

cagcgcgaaa atccgaccga gaaaggcctg gatttcaagc tgtactggac cgatagccag    120

aacaagaaag aagtgattag ctctgacaac ctgcaactgc cggaactgaa gcagaaaagc    180

agcaacagcc gcaagaaacg cagcacctct gcaggcccga ccgtgccgga tcgcgacaac    240

gatggcattc cggacagcct ggaggttgaa ggctataccg ttgatgtgaa gaacaaacgc    300

accttcctga gcccgtggat ctctaacatt cacgagaaga aaggcctgac caagtacaaa    360
```

agcagcccgg agaagtggag caccgcgagc gatccgtatt ctgactttga aaaagtgacc 420
ggccgcattg ataagaacgt gagcccggaa gcacgtcacc cactggttgc ggcgtacccg 480
attgtgcatg tggacatgga gaacatcatt ctgagcaaga acgaagatca gagcacccag 540
aatacggata gccagacccg taccatcagc aagaacacca gcacgagccg tacccatacc 600
agcgaagtgc atggtaatgc ggaagtgcat gcgagctttt ttgacattgg tggcagcgtg 660
agcgcaggct ttagcaacag caacagcagc acggtggcga ttgatcatag cctgagcctg 720
gcgggcgaac gtacctgggc ggaaaccatg ggcctgaaca cggcagatac cgcacgtctg 780
aatgcgaaca ttcgctatgt taacaccggt accgcaccaa tttataacgt tctgccgacc 840
acgagcctgg tgctgggcaa gaatcagacc ctggcgacca tcaaagcgaa agagaaccag 900
ctgagccaga ttctggcacc gaacaactac tatccaagca aaaacctggc gccgattgca 960
ctgaatgcgc aggatgactt cagcagcacg ccgattacca tgaactacaa ccagtttctg 1020
gagctggaaa agaccaagca actgcgcctg gataccgatc aggtttatgg caacattgcg 1080
acctacaact ttgagaacgg ccgcgtgcgc gtggataccg gtagcaactg gagcgaagtg 1140
ctgccgcaga tccaggaaac gaccgcgcgc attatcttta acggcaaaga tctgaacctg 1200
gtggaacgtc gcatcgcggc agtgaaccca tctgatccac tggaaaccac caaaccggac 1260
atgaccctga aagaggcgct gaagattgca ttcggcttca atgaaccgaa tggcaacctg 1320
cagtatcagg gcaaagacat taccgagttt gacttcaact tcgatcaaca gacctctcag 1380
aacatcaaga accagctggc ggaactgaac gcgaccaaca tctacaccgt gctggacaag 1440
atcaaactga acgcgaaaat gaacatcctg attcgcgaca aacgcttcca ttatgatcgt 1500
aacaacattg cggtgggtgc agatgaaagc gtggttaaag aagcgcatcg cgaagtgatc 1560
aacagcagca ccgaaggcct gctgctgaac attgacaaag acattcgtaa gatcctgagc 1620
ggctacatcg tggaaattga agataccgag ggtctgaaag aggtgattaa cgatcgctat 1680
gatatgctga acatctctag cctgcgtcag gatggcaaga ccttcattga cttcaagaag 1740
tacaacgaca aactgccgct gtacatttct aatccgaact ataaagtgaa cgtgtatgcg 1800
gtgaccaaag agaacacgat cattaaccca agcgagaatg gcgataccag caccaac 1857

<210> SEQ ID NO 82
<211> LENGTH: 1857
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Sequence variant (94%) of SEQ ID No. 76

<400> SEQUENCE: 82
agcaacagca acaagattcg tctggagaag ggtcgcctgt atcagatcaa gatccagtat 60
cagcgcgaaa atccgaccga gaagggcctg gatttcaagc tgtactggac cgatagccag 120
aacaagaaag aagtgattag ctctgacaac ctgcagctgc cggaactgaa gcagaaaagc 180
agcaacagcc gcaagaaacg cagcacctct gcaggcccga ccgtgccgga tcgcgacaac 240
gatggcattc cggacagcct ggaggttgaa ggctataccg ttgatgtgaa gaacaaacgc 300
accttcctga gcccgtggat ctctaacatt cacgagaaga aaggcctgac caagtacaaa 360
agcagcccgg agaagtggag caccgcgagc gatccgtatt ctgactttga aaaagtgacc 420
ggccgcattg ataagaacgt gagcccggaa gcacgccacc cactggtggc ggcgtacccg 480

-continued

```
attgtgcatg tggacatgga gaacatcatt ctgagcaaga acgaagatca gagcacccag    540

aatacggata gccagacccg taccatcagc aaaaacacca gcaccagccg tacgcatacc    600

agcgaagttc atggtaatgc ggaagtgcat gcgagctttt ttgatattgg tggcagcgtg    660

agcgcaggct ttagcaacag caacagcagc acggtggcga ttgatcatag cctgagcctg    720

gcgggcgaac gtacctgggc ggaaaccatg ggcctgaaca cggcagatac cgcgcgtctg    780

aatgcgaaca ttcgctacgt taacaccggt accgcaccaa tttataacgt tctgccgacc    840

accagcctgg tgctgggcaa gaatcagacc ctggcaacca tcaaagcgaa agagaaccag    900

ctgagccaga ttctggcacc gaacaactac tatccaagca aaaacctggc gccgattgca    960

ctgaatgcgc aggatgactt cagcagcacg ccgattacca tgaactacaa ccagtttctg   1020

gagctggaaa agaccaagca actgcgcctg gatacggatc aggtgtatgg caacatcgcg   1080

acctataact ttgagaacgg ccgcgtgcgc gtggataccg gtagcaactg gagcgaagtg   1140

ctgccgcaga tccaggaaac gaccgcgcgc attatcttta acggcaaaga tctgaacctg   1200

gtggaacgtc gcatcgcagc ggtgaaccca tctgatccac tggaaaccac caaaccggat   1260

atgaccctga aagaggcgct gaagattgcg ttcggcttca atgaaccgaa tggcaacctg   1320

cagtatcaag gcaaagacat taccgagttt gacttcaact tcgaccaaca gacctctcag   1380

aacatcaaga accagctggc ggaactgaac gcgaccaaca tctacaccgt gctggacaag   1440

atcaaactga acgcgaaaat gaacatcctg attcgcgaca aacgcttcca ttatgatcgt   1500

aacaacattg cggtgggtgc agatgaaagc gtggttaaag aagcgcatcg cgaagtgatc   1560

aacagcagca ccgaaggcct gctgctgaac attgacaaag acattcgtaa gattctgagc   1620

ggctacattg tggaaattga agataccgag ggtctgaaag aggtgatcaa cgatcgctat   1680

gacatgctga acatctctag cctgcgtcag gatggcaaga ccttcatcga cttcaagaag   1740

tacaacgaca aactgccgct gtacatttct aatccgaact ataaagttaa cgtgtatgca   1800

gtgaccaaag agaacacgat cattaaccca agcgagaatg gcgataccag caccaac      1857
```

<210> SEQ ID NO 83
<211> LENGTH: 1857
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Sequence variant (93%) of SEQ ID No. 76

<400> SEQUENCE: 83

```
agcaacagca acaagattcg tctggagaag ggccgcctgt atcagatcaa gatccagtac     60

cagcgcgaaa atccgaccga gaagggcctg gatttcaagc tgtactggac cgatagccag    120

aataagaaag aagtgattag ctctgataac ctgcagctgc cggaactgaa gcagaaaagc    180

agcaacagcc gcaagaaacg cagcacctct gcaggcccga ccgtgccgga tcgcgacaac    240

gatggcattc cagacagcct ggaggtggaa ggctacaccg ttgatgtgaa gaacaaacgc    300

accttcctga gcccgtggat ctctaacatt cacgagaaga aaggcctgac caagtataaa    360

agcagcccgg agaagtggag caccgcgagc gacccgtata gcgactttga aaaagtgacc    420

ggccgcattg ataagaacgt gagcccggaa gcacgccacc cactggtggc ggcgtacccg    480

attgtgcatg tggacatgga aaacatcatt ctgagcaaga acgaagacca gagcacccag    540

aacacggata gccagacccg taccatcagc aaaaacacca gcacctctcg tacgcatacc    600

agcgaagttc atggtaatgc ggaagtgcat gcgagctttt tcgatattgg tggcagcgtg    660
```

```
agcgcaggct ttagcaacag caacagcagc acggtggcga ttgatcatag cctgagcctg    720

gcgggcgaac gtacctgggc ggaaaccatg ggcctgaaca cggcagatac cgcgcgtctg    780

aatgcgaaca ttcgctacgt taacaccggt accgcaccaa tttataacgt tctgccgacc    840

accagcctgg tgctgggcaa gaatcagacc ctggcaacca tcaaagcgaa agagaaccag    900

ctgagccaga ttctggcgcc gaacaactac tatccaagca aaaacctggc gccgattgca    960

ctgaatgcgc aggatgactt cagcagcacg ccgattacca tgaactacaa ccagtttctg   1020

gagctggaaa agaccaagca actgcgcctg gatacggatc aggtgtatgg caacatcgca   1080

acctataact ttgagaacgg ccgcgtgcgc gttgataccg gtagcaactg gagcgaagtg   1140

ctgccgcaga tccaggaaac gaccgcgcgc attattttta acggcaaaga tctgaacctg   1200

gtggagcgtc gcatcgcagc ggttaaccca tctgatccac tggaaaccac caaaccggat   1260

atgaccctga aagaggcgct gaagattgcg ttcggcttca atgaaccgaa tggcaacctg   1320

cagtatcaag gcaaagacat caccgagttc gacttcaact ttgaccagca gacctctcaa   1380

aacatcaaga accagctggc ggaactgaac gcgaccaaca tctacaccgt gctggacaag   1440

atcaaactga acgcgaaaat gaacatcctg attcgcgaca aacgcttcca ttatgatcgt   1500

aacaacattg cggtgggtgc agatgaaagc gtggtgaaag aagcgcatcg cgaagtgatc   1560

aacagcagca ccgaaggcct gctgctgaac attgacaaag acattcgtaa gattctgagc   1620

ggctacattg tggaaattga agataccgag ggtctgaaag aggtgatcaa cgatcgctat   1680

gatatgctga acatctctag cctgcgtcag gatggtaaga ccttcatcga ctttaagaag   1740

tacaacgaca aactgccgct gtatatttct aatccgaact ataaagttaa cgtgtatgca   1800

gtgaccaaag agaacacgat cattaacccg agcgagaatg gcgataccag caccaac      1857
```

<210> SEQ ID NO 84
<211> LENGTH: 1857
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Sequence variant (92%) of SEQ ID No. 76

<400> SEQUENCE: 84

```
agcaacagca acaagattcg tctggagaag ggccgcctgt atcagatcaa gatccagtac     60

cagcgcgaaa atccgaccga gaagggcctg gatttcaagc tgtactggac cgatagccag    120

aataagaaag aagtgattag ctctgataac ctgcagctgc cggaactgaa gcagaaaagc    180

agcaacagcc gcaaaaaacg cagcacctct gcaggcccga ccgtgccgga tcgcgacaac    240

gatggcattc cggacagcct ggaggtggaa ggctacaccg ttgatgtgaa gaacaaacgc    300

accttcctga gcccgtggat ctctaacatt cacgagaaga aaggcctgac caagtataaa    360

agcagcccgg agaagtggag caccgcgagc gacccgtata gcgattttga aaaagtgacc    420

ggccgcattg ataagaacgt gagcccggaa gcacgccatc cactggtggc ggcgtaccca    480

attgtgcacg tggacatgga aaacatcatt ctgagcaaga acgaagacca gagcacgcag    540

aacaccgata gccagacccg caccatcagc aagaacacca gcacctctcg tacgcatacc    600

agcgaagttc atggtaatgc ggaagtgcat gcgagctttt tcgatattgg tggcagcgtg    660

agcgcaggct ttagcaacag caacagcagc accgtggcga ttgatcatag cctgagcctg    720

gcgggcgaac gtacctgggc ggaaaccatg ggcctgaaca cggcagatac cgcgcgtctg    780
```

```
aacgcgaaca ttcgctacgt taacaccggt accgcaccaa tttataacgt tctgccgacc     840

accagcctgg tgctgggcaa gaatcagacc ctggcaacca tcaaagcgaa agagaatcag     900

ctgagccaga ttctggcgcc gaacaactac tatccaagca aaaacctggc gccgattgca     960

ctgaacgcgc aggacgactt cagcagcacg ccgattacca tgaactacaa ccagtttctg    1020

gagctggaaa agaccaagca actgcgcctg gacacggatc aagtgtatgg caacatcgca    1080

acctataatt ttgagaacgg ccgcgtgcgc gttgataccg gtagcaactg gagcgaagtg    1140

ctgccgcaga tccaggaaac gacggcgcgt attattttta acggcaaaga tctgaacctg    1200

gtggagcgtc gcatcgcagc ggttaaccca tctgatccac tggaaaccac caaaccggat    1260

atgaccctga aagaggcgct gaagattgcg ttcggcttca atgaaccgaa tggcaacctg    1320

cagtatcagg gcaaagacat caccgagttc gacttcaact ttgaccagca gacctctcaa    1380

aacattaaga accagctggc ggaactgaac gcgaccaaca tctataccgt gctggacaag    1440

atcaaactga acgcgaaaat gaacatcctg attcgcgaca aacgcttcca ttatgatcgt    1500

aacaacattg cggtgggcgc agatgaaagc gtggtgaaag aagcgcatcg cgaagtgatc    1560

aacagcagca ccgaaggcct gctgctgaac atcgacaaag acattcgtaa gattctgagc    1620

ggctacattg tggaaattga agataccgag ggtctgaaag aggtgatcaa cgatcgctat    1680

gatatgctga acatctctag cctgcgtcag gatggtaaga ccttcatcga ttttaagaag    1740

tacaacgaca aactgccgct gtatatttct aatccgaact ataaagttaa cgtgtacgca    1800

gtgaccaaag agaacacgat cattaacccg agcgagaatg gtgataccag caccaac       1857
```

<210> SEQ ID NO 85
<211> LENGTH: 1857
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Sequence variant (91%) of SEQ ID No. 76

<400> SEQUENCE: 85

```
agcaacagca acaagattcg tctggagaaa ggccgcctgt atcagatcaa gatccagtac      60

cagcgcgaaa atccgaccga gaagggcctg gatttcaagc tgtactggac cgatagccag     120

aataagaaag aagtgattag ctctgataac ctgcagctgc cggaactgaa gcagaaaagc     180

agcaacagcc gcaaaaaacg tagcacctct gcaggcccga ccgtgccgga tcgcgacaac     240

gatggcattc cagacagcct ggaggtggaa ggctacaccg ttgatgtgaa gaacaaacgc     300

accttcctga gcccgtggat ctctaacatt cacgagaaga agggcctgac caagtataaa     360

agctctccgg agaagtggag caccgcgagc gacccgtata gcgattttga aaaagtgacc     420

ggccgtattg ataaaaatgt gagcccggaa gcacgccatc cactggtggc ggcgtacccg     480

attgtgcacg tggacatgga aaacatcatt ctgagcaaga acgaagacca gagcacgcaa     540

aacaccgata gccagacccg caccatcagc aagaacacca gcaccagccg tacgcatacc     600

agcgaagtgc atggtaatgc ggaagtgcat gcgagctttt ttgatattgg tggcagcgtg     660

agcgcgggct ttagcaacag caacagcagc accgtggcga ttgatcatag cctgagcctg     720

gcgggcgaac gtacctgggc ggaaaccatg ggcctgaaca ccgcagatac cgcgcgtctg     780

aacgcgaaca ttcgctacgt taacaccggc accgcaccaa tttataacgt tctgccgacc     840

accagcctgg tgctgggtaa gaatcagacc ctggcaacca tcaaagcgaa agagaaccag     900

ctgagccaga ttctggcgcc gaacaactat tatccaagca aaaacctggc gccgattgca     960
```

ctgaacgcgc aggacgactt cagcagcacg ccgattacca tgaactacaa ccagtttctg 1020
gagctggaaa agaccaaaca gctgcgcctg gacacggacc aagtgtatgg caacatcgca 1080
acctacaatt ttgagaacgg ccgtgtgcgc gtggataccg gtagcaactg gagcgaagtg 1140
ctgccgcaga tccaggaaac cacggcgcgc attatcttca acggcaagga tctgaacctg 1200
gtggagcgcc gcatcgcagc ggttaaccca tctgatccac tggaaaccac gaaaccggat 1260
atgaccctga aagaggcact gaagattgcg ttcggcttca atgaaccgaa tggcaacctg 1320
cagtatcagg gcaaggacat caccgagttc gatttcaact ttgaccagca gacctctcaa 1380
aacattaaaa accagctggc ggaactgaac gcgaccaaca tctatacggt tctggacaag 1440
attaaactga acgcgaagat gaacattctg attcgcgata aacgcttcca ttatgatcgc 1500
aacaacattg cggtgggcgc agatgaaagc gtggtgaaag aagcgcatcg cgaagttatc 1560
aacagcagca ccgaaggcct gctgctgaac atcgacaaag acattcgtaa gattctgtct 1620
ggctacattg ttgaaattga agataccgag ggtctgaaag aggtgatcaa cgatcgctac 1680
gatatgctga acatctctag cctgcgtcag gacggtaaga ccttcatcga ttttaaaaaa 1740
tacaacgaca agctgccgct gtatatcagc aatccgaact ataaagtgaa cgtgtatgca 1800
gtgaccaagg agaacacgat cattaacccg agcgagaatg gtgataccag caccaac 1857

<210> SEQ ID NO 86
<211> LENGTH: 1905
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Truncated version of SEQ ID No. 1 (bp. 202-2106)

<400> SEQUENCE: 86
ttcatcaaag tgaagaaaag cgatgagtat acctttgcga cgtctgcgga taaccatgtg 60
accatgtggg tggacgatca ggaagtgatc aacaaagcga gcaacagcaa caagattcgc 120
ctggagaagg gtcgcctgta tcagatcaag attcagtatc agcgcgagaa tccgaccgag 180
aaaggcctgg atttcaaact gtactggacc gatagccaga acaagaaaga agtgattagc 240
tctgataacc tgcaactgcc ggaactgaaa cagaagagca gcaacagccg caagaaacgc 300
agcacctctg caggcccgac cgttccagat cgcgacaacg atggcattcc ggacagcctg 360
gaagtggaag gttataccgt tgatgtgaag aacaaacgca cctttctgag cccgtggatt 420
agcaacattc atgagaagaa aggcctgacc aagtacaaaa gcagcccgga gaagtggagc 480
accgcgagcg atccgtatag cgactttgag aaagtgaccg gccgcattga taagaacgtg 540
agcccggaag cgcgtcaccc actggttgca gcgtatccga ttgtgcatgt tgacatggag 600
aacatcattc tgagcaagaa cgaagatcag agcacccaga acacggatag ccagacccgc 660
acgatcagca agaacaccag cacgagccgt acccatacca gcgaagtgca tggcaatgcg 720
gaagtgcatg cgagcttctt tgacattggt ggcagcgtga gcgcgggctt cagcaacagc 780
aacagcagca ccgtggcgat tgatcatagc ctgagcctgg cgggcgaacg tacctgggcg 840
gaaaccatgg gcctgaacac ggcggatacg gcacgtctga atgcgaacat tcgctatgtg 900
aacaccggta ccgcgccaat ctataacgtt ctgccgacca cgagcctggt gctgggcaag 960
aatcagaccc tggcgaccat caaagcgaaa gagaaccagc tgtctcagat tctggcaccg 1020
aacaactact atccgagcaa gaacctggca ccgattgcac tgaatgcgca ggatgacttc 1080
agcagcaccc cgatcaccat gaactacaat cagtttctgg agctggagaa gaccaaacaa 1140
ctgcgcctgg ataccgatca ggtgtatggc aacattgcga cctacaactt tgagaacggc 1200
cgcgttcgcg tggataccgg tagcaactgg tctgaagtgc tgccgcagat tcaggaaacg 1260
accgcgcgca tcatcttcaa cggcaaagat ctgaacctgg tggaacgtcg catcgcggca 1320
gtgaacccat ctgatccact ggaaacgacc aaaccggaca tgaccctgaa agaagcgctg 1380
aagattgcat ttggcttcaa cgaaccgaat ggcaacctgc agtatcaggg caaagacatc 1440
accgagtttg acttcaactt tgatcaacag acctctcaga acatcaagaa ccagctggca 1500
gaactgaatg cgaccaacat ctacaccgtg ctggacaaga tcaaactgaa cgcaaagatg 1560
aacattctga ttcgtgacaa acgcttccac tatgatcgta acaacattgc ggtgggtgca 1620
gatgaaagcg ttgtgaaaga agcgcatcgt gaagtgatca actctagcac cgaaggcctg 1680
ctgctgaaca ttgacaaaga catccgtaag attctgagcg gctacattgt ggagattgaa 1740
gataccgaag gtctgaaaga agtgatcaac gatcgctatg acatgctgaa catctctagc 1800
ctgcgccagg atggcaagac cttcattgac ttcaagaagt acaacgacaa actgccgctg 1860
tacatcagca atccgaacta caaagtgaac gtgtatgcgg tgacc 1905

<210> SEQ ID NO 87
<211> LENGTH: 1905
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Sequence variant (99%) of SEQ ID No. 86

<400> SEQUENCE: 87
ttcatcaaag tgaagaaaag cgatgagtat acctttgcga cgtctgcgga taaccatgtg 60
accatgtggg tggacgatca ggaagtgatc aacaaagcga gcaacagcaa caagattcgc 120
ctggagaagg gccgcctgta tcagatcaag attcagtatc agcgcgagaa tccgaccgag 180
aaaggcctgg atttcaaact gtactggacc gatagccaga acaagaaaga agtgattagc 240
tctgataacc tgcaactgcc ggaactgaaa cagaagagca gcaacagccg caagaaacgc 300
agcacctctg caggcccgac cgttccagat cgcgacaacg atggcattcc ggacagcctg 360
gaagtggaag gttataccgt tgatgtgaag aacaaacgca cctttctgag cccgtggatt 420
agcaacattc atgagaagaa aggcctgacc aagtacaaaa gcagcccgga aaagtggagc 480
accgcgagcg atccgtatag cgactttgag aaagtgaccg gccgcattga taagaacgtg 540
agcccggaag cgcgtcaccc actggttgca gcgtatccga ttgtgcatgt tgacatggag 600
aacatcattc tgagcaagaa cgaagatcag agcacccaga acacggatag ccagacccgc 660
acgatcagca agaacaccag cacgagccgt acccatacca gcgaggtgca tggcaatgcg 720
gaagtgcatg cgagcttctt tgacattggt ggcagcgtga gcgcgggctt cagcaatagc 780
aacagcagca ccgtggcgat tgatcatagc ctgagcctgg cgggcgaacg tacctgggcg 840
gaaaccatgg gcctgaacac ggcggatacc gcacgtctga acgcgaacat tcgctatgtg 900
aacaccggta ccgcgccgat ctataacgtt ctgccgacca cgagcctggt gctgggtaaa 960
aatcagaccc tggcgacgat caaagcgaaa gagaaccagc tgtctcagat tctggcaccg 1020
aacaactact atccgagcaa gaacctggca ccgattgcac tgaatgcaca ggatgacttt 1080
agcagcaccc cgatcaccat gaactacaat cagtttctgg aactggagaa gaccaaacaa 1140

```
ctgcgcctgg ataccgatca ggtgtatggc aacattgcga cctacaactt tgagaacggc   1200

cgcgttcgcg tggataccgg tagcaactgg tctgaagtgc tgccgcagat tcaggaaacg   1260

accgcgcgca tcatcttcaa cggcaaagat ctgaacctgg tggaacgtcg catcgcggca   1320

gtgaacccat ctgatccact ggaaacgacc aaaccggaca tgaccctgaa agaagcgctg   1380

aagattgcat ttggcttcaa cgagccaaat ggcaacctgc agtatcaggg caaagacatc   1440

accgagttcg acttcaactt tgatcaacag acctctcaga acatcaagaa ccagctggca   1500

gaactgaatg cgaccaacat ctacaccgtg ctggacaaga tcaaactgaa cgcgaagatg   1560

aacattctga ttcgtgacaa acgcttccac tatgatcgta acaacattgc ggtgggtgca   1620

gatgaaagcg ttgtgaagga agcgcatcgt gaagtgatca actctagcac cgaaggcctg   1680

ctgctgaaca tcgacaaaga catccgtaag attctgagcg gctacattgt ggagattgaa   1740

gataccgaag gtctgaaaga agtgatcaac gatcgctatg acatgctgaa catttctagc   1800

ctgcgccagg atggcaagac cttcattgac ttcaagaagt acaacgacaa actgccgctg   1860

tacatcagca atccgaacta caaagtgaac gtgtatgcgg tgacc                   1905
```

```
<210> SEQ ID NO 88
<211> LENGTH: 1905
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Sequence variant (98%) of SEQ ID No. 86

<400> SEQUENCE: 88
```

```
ttcatcaaag tgaagaaaag cgatgagtat acctttgcga cgagcgcgga taaccatgtg     60

accatgtggg tggacgatca ggaagtgatc aacaaagcga gcaacagcaa caagattcgc    120

ctggagaagg gccgcctgta tcagatcaag attcagtatc agcgcgagaa tccgaccgag    180

aaaggcctgg atttcaaact gtactggacc gatagccaga acaagaaaga agtgattagc    240

tctgataacc tgcaactgcc ggaactgaaa cagaagagca gcaacagccg caagaaacgc    300

agcacctctg caggcccgac cgttccagat cgtgacaacg atggcatccc ggacagcctg    360

gaagtggaag gttataccgt tgatgtgaag aacaaacgca cctttctgag cccgtggatt    420

agcaacattc atgagaagaa aggcctgacc aagtataaaa gcagcccgga aaagtggagc    480

accgcgagcg atccgtatag cgactttgag aaagtgaccg gccgcattga taagaacgtg    540

agcccggaag cgcgccaccc actggttgca gcgtatccga ttgtgcatgt tgacatggag    600

aacatcattc tgagcaagaa cgaggatcag agcacccaga acacggatag ccagacgcgc    660

acgatcagca agaacaccag cacgagccgt acccatacca gcgaggtgca tggcaatgcg    720

gaagtgcatg cgagcttctt tgacattggt ggcagcgtga gcgcgggctt cagcaattct    780

aacagcagca ccgtggcgat tgatcatagc ctgagcctgg cgggcgaacg tacctgggcg    840

gaaaccatgg gcctgaacac ggcggatacc gcacgtctga acgcgaacat tcgctatgtg    900

aacaccggta ccgcgccgat ctataacgtt ctgccgacca cgagcctggt gctgggtaaa    960

aatcagaccc tggcgaccat caaagcgaaa gaaaaccagc tgtctcagat tctggcaccg   1020

aacaactact atccgagcaa gaacctggca ccgattgcac tgaatgcaca ggatgacttt   1080

agcagcaccc cgatcaccat gaactacaat cagtttctgg agctggagaa gaccaaacaa   1140

ctgcgcctgg ataccgatca ggtgtatggc aacattgcga cctacaactt tgagaacggc   1200

cgcgttcgcg tggataccgg tagcaactgg tctgaagtgc tgccgcagat tcaggaaacg   1260
```

accgcgcgca tcatcttcaa cggcaaagat ctgaacctgg tggaacgtcg catcgcggca 1320
gtgaacccat ctgatccact ggaaacgacc aaaccggaca tgaccctgaa agaagcgctg 1380
aagattgcat ttggcttcaa cgagccaaat ggcaacctgc agtaccaggg caaagacatc 1440
accgagttcg acttcaactt tgatcaacag acctctcaga acatcaaaaa ccagctggca 1500
gaactgaatg cgaccaacat ctacaccgtg ctggacaaga tcaaactgaa cgcgaagatg 1560
aacattctga ttcgtgacaa acgcttccac tatgatcgta acaacattgc ggtgggtgca 1620
gatgaaagcg tggtgaagga agcgcatcgt gaagtgatca actctagcac cgaaggcctg 1680
ctgctgaaca tcgacaaaga cattcgtaag attctgagcg gctacattgt ggaaattgaa 1740
gataccgaag gtctgaagga agtgatcaac gatcgctatg acatgctgaa catttctagc 1800
ctgcgccagg atggcaagac cttcattgac ttcaagaagt acaacgacaa actgccgctg 1860
tacatcagca atccgaacta caaagtgaac gtttatgcgg tgacc 1905

<210> SEQ ID NO 89
<211> LENGTH: 1905
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Sequence variant (97%) of SEQ ID No. 86

<400> SEQUENCE: 89
ttcatcaaag tgaagaaaag cgatgagtat acctttgcga cgagcgcgga taaccatgtg 60
accatgtggg tggacgatca ggaagtgatc aacaaagcga gcaacagcaa caagattcgc 120
ctggagaagg gccgcctgta tcagatcaag attcagtatc agcgcgagaa tccgaccgag 180
aaaggcctgg atttcaaact gtactggacc gatagccaga acaagaaaga agtgattagc 240
tctgataacc tgcaactgcc ggaactgaag cagaagagca gcaacagccg caagaaacgc 300
agcacctctg caggcccgac cgtgccagat cgtgacaacg atggcatccc agacagcctg 360
gaagtggaag gttataccgt tgatgttaag aacaaacgca cctttctgag cccgtggatt 420
agcaacattc atgagaagaa aggcctgacc aagtataaaa gcagcccgga aaagtggagc 480
accgcaagcg atccgtatag cgactttgag aaagtgaccg gccgcattga caagaacgtg 540
agcccggaag cgcgccaccc actggttgca gcgtatccga ttgtgcatgt tgacatggag 600
aacatcattc tgagcaagaa cgaggatcag agcacccaga acacggatag ccagacgcgc 660
acgatcagca agaacaccag cacgagccgt acccatacca gcgaggtgca tggcaatgcg 720
gaagtgcatg cgagcttctt tgacattggc ggcagcgtga gcgcaggctt cagcaattct 780
aacagcagca ccgtggcgat tgatcatagc ctgagcctgg cgggcgaacg tacctgggcg 840
gaaaccatgg gcctgaacac ggcggatacc gcacgtctga acgcgaacat tcgctatgtg 900
aacaccggta ccgcgccgat ctataacgtg ctgccgacca cgagcctggt tctgggtaaa 960
aatcagaccc tggcgaccat caaagcgaaa gaaaaccagc tgtctcagat tctggcaccg 1020
aacaactact atccgagcaa gaacctggca ccgattgcac tgaatgcaca ggatgacttt 1080
agcagcaccc cgatcaccat gaactacaat cagtttctgg agctggaaaa gaccaaacaa 1140
ctgcgcctgg ataccgatca ggtgtatggt aacattgcga cctacaactt tgagaacggc 1200
cgcgttcgcg tggataccgg tagcaactgg tctgaagtgc tgccgcagat tcaggaaacg 1260
accgcgcgca tcattttcaa cggcaaagat ctgaacctgg tggaacgtcg catcgcggcg 1320
gtgaacccgt ctgatccact ggaaacgacc aaaccggata tgaccctgaa agaagcgctg 1380
aagattgcgt ttggcttcaa cgagccaaat ggcaacctgc agtaccaggg caaagacatc 1440
accgagttcg acttcaactt tgatcaacag acctctcaga acatcaaaaa ccagctggca 1500
gaactgaatg cgaccaacat ctacaccgtg ctggacaaga tcaaactgaa cgcgaagatg 1560
aacattctga ttcgtgacaa acgcttccac tatgatcgta acaacattgc ggtgggtgca 1620
gatgaaagcg tggtgaagga agcgcatcgt gaggtgatca actctagcac cgaaggcctg 1680
ctgctgaaca tcgacaaaga cattcgtaaa atcctgagcg gctacattgt ggaaattgaa 1740
gataccgaag gtctgaagga agtgatcaac gatcgctatg acatgctgaa catttctagc 1800
ctgcgccagg atggcaagac cttcattgac ttcaagaagt acaacgacaa actgccgctg 1860
tacatcagca atccgaacta caaagtgaac gtttatgcgg tgacc 1905

<210> SEQ ID NO 90
<211> LENGTH: 1905
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Sequence variant (96%) of SEQ ID No. 86

<400> SEQUENCE: 90
ttcatcaaag tgaagaaaag cgatgagtat acctttgcga cgagcgcgga taaccatgtg 60
accatgtggg tggacgatca ggaagtgatc aacaaagcga gcaacagcaa caagattcgc 120
ctggagaagg gccgcctgta tcagatcaag attcagtatc agcgcgagaa tccgaccgag 180
aaaggcctgg atttcaaact gtactggacc gatagccaga acaagaaaga ggtgattagc 240
tctgataacc tgcaactgcc ggaactgaag cagaagagca gcaacagccg caagaaacgc 300
agcacctctg caggcccgac cgtgccagat cgtgacaacg atggcatccc agacagcctg 360
gaagtggaag gttataccgt tgatgttaag aacaaacgca cctttctgag cccatggatt 420
agcaacattc atgagaagaa aggcctgacc aagtataaaa gcagcccgga aaagtggagc 480
accgcaagcg atccgtatag cgactttgag aaagtgaccg gccgcattga caaaaacgtg 540
agcccggaag cgcgccatcc actggttgca gcgtacccga ttgtgcatgt tgacatggag 600
aacatcattc tgagcaagaa cgaggatcag agcacccaga acacggatag ccagacgcgc 660
acgatcagca agaacaccag cacgagccgt acccacacca gcgaggtgca tggcaatgcg 720
gaagtgcatg cgagcttctt tgacattggc ggcagcgtga gcgcaggctt tagcaattct 780
aacagcagca ccgtggcgat tgatcatagc ctgagcctgg cgggcgaacg tacctgggcg 840
gaaaccatgg gcctgaacac ggcggatacc gcacgtctga acgcgaacat tcgctatgtg 900
aacaccggta ccgcgccgat ctacaacgtg ctgccgacca cgagcctggt tctgggtaaa 960
aatcagaccc tggcgaccat caaagcgaaa gaaaaccagc tgtctcagat tctggcaccg 1020
aacaactact atccgagcaa gaacctggca ccgattgcac tgaatgcaca ggatgacttt 1080
agcagcaccc cgatcaccat gaactataat cagtttctgg agctggaaaa gaccaaacaa 1140
ctgcgcctgg ataccgatca ggtgtatggt aacattgcga cctacaactt cgagaacggc 1200
cgtgttcgcg tggataccgg cagcaactgg tctgaagtgc tgccgcagat tcaggaaacg 1260
accgcgcgca tcattttcaa cggcaaagat ctgaacctgg tggaacgtcg catcgcggcg 1320
gtgaacccgt ctgatccgct ggaaacgacc aaaccggata tgaccctgaa agaagcgctg 1380
aagattgcgt ttggtttcaa cgagccaaat ggcaacctgc agtaccaggg caaagacatc 1440
accgaattcg acttcaactt tgatcaacag acctctcaga acatcaaaaa ccagctggca 1500
gaactgaatg cgaccaacat ctacaccgtg ctggacaaga tcaaactgaa cgcgaagatg 1560
aacattctga ttcgtgacaa gcgcttccac tatgatcgta acaacattgc ggtgggtgca 1620
gatgaaagcg tggtgaagga agcgcatcgc gaggtgatca actctagcac cgaaggcctg 1680
ctgctgaaca tcgacaaaga cattcgtaaa atcctgagcg gctatattgt ggaaattgaa 1740
gataccgaag gtctgaagga agtgatcaac gatcgctatg acatgctgaa catttctagc 1800
ctgcgccagg atggcaagac cttcattgac ttcaagaagt acaacgacaa actgccgctg 1860
tacatcagca atccgaacta caaagtgaac gtttatgcgg tgacc 1905

<210> SEQ ID NO 91
<211> LENGTH: 1905
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Sequence variant (95%) of SEQ ID No. 86

<400> SEQUENCE: 91
ttcatcaaag tgaagaaaag cgatgagtat acctttgcga cgagcgcgga taaccatgtg 60
accatgtggg tggacgatca ggaagtgatc aacaaagcga gcaacagcaa caaaattcgc 120
ctggagaagg gccgcctgta tcaaatcaag attcagtatc agcgcgagaa tccgaccgag 180
aaaggcctgg atttcaaact gtactggacc gatagccaga acaagaaaga ggtgattagc 240
tctgacaacc tgcagctgcc ggaactgaag cagaagagca gcaacagccg caagaaacgc 300
agcacctctg caggcccgac cgtgccagat cgtgacaacg atggcatccc agacagcctg 360
gaagtggaag gttataccgt tgatgttaag aacaaacgca cctttctgag cccatggatt 420
agcaacattc atgagaaaaa aggcctgacc aagtataaaa gcagcccgga aaagtggagc 480
accgcaagcg atccgtatag cgattttgag aaagtgaccg gccgcattga caaaaacgtg 540
agcccggaag cgcgccatcc actggttgca gcgtacccga ttgtgcatgt tgatatggag 600
aacatcattc tgagcaagaa cgaggatcag agcacccaga acacggatag ccagacgcgc 660
acgatcagca agaacaccag cacgagccgt acccacacca gcgaggtgca tggcaatgca 720
gaagtgcatg cgagcttctt cgacattggc ggcagcgtga gcgcaggctt tagcaattct 780
aacagcagca ccgtggcgat tgatcatagc ctgagcctgg cgggcgaacg tacctgggcg 840
gaaaccatgg gcctgaacac ggcggatacc gcgcgtctga acgcgaacat tcgctatgtg 900
aacacgggta ccgcgccgat ctacaacgtg ctgccgacca ccagcctggt tctgggtaaa 960
aatcagaccc tggcgaccat caaagcgaaa gaaaaccagc tgtctcagat tctggcaccg 1020
aacaactact atccgagcaa gaacctggca ccgattgcgc tgaatgcaca ggatgacttt 1080
agcagcaccc cgatcaccat gaactataat cagtttctgg agctggaaaa gaccaagcaa 1140
ctgcgcctgg ataccgatca ggtgtatggt aacattgcga cctacaactt cgagaacggc 1200
cgtgttcgcg tggataccgg cagcaactgg tctgaagtgc tgccgcagat tcaagaaacg 1260
accgcgcgca tcatcttcaa cggcaaagat ctgaacctgg tggaacgtcg catcgcggcg 1320
gtgaacccgt ctgatccgct ggaaacgacc aaaccggaca tgaccctgaa agaagcactg 1380
aagattgcgt ttggtttcaa cgagccaaat ggcaacctgc agtaccaggg caaagacatc 1440
accgaattcg acttcaactt tgatcagcag acctctcaga acatcaaaaa ccagctggca 1500

-continued

```
gaactgaacg cgaccaacat ctacaccgtg ctggacaaga tcaagctgaa cgcgaagatg   1560

aacattctga ttcgtgacaa gcgctttcac tatgatcgta acaacattgc ggtgggtgca   1620

gatgaaagcg tggtgaagga agcgcatcgc gaggtgatca actctagcac cgaaggcctg   1680

ctgctgaaca tcgacaaaga cattcgtaaa atcctgagcg gctatattgt ggaaattgaa   1740

gataccgaag gtctgaagga agtgatcaac gatcgctatg acatgctgaa catttctagc   1800

ctgcgccagg atggcaagac cttcattgac ttcaagaagt acaacgacaa actgccgctg   1860

tacattagca atccgaacta caaagtgaat gtttatgcgg tgacc                  1905
```

<210> SEQ ID NO 92
<211> LENGTH: 1905
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Sequence variant (94%) of SEQ ID No. 86

<400> SEQUENCE: 92

```
ttcattaaag tgaagaaaag cgatgagtat acctttgcaa cgagcgcgga taaccatgtg     60

accatgtggg tggacgatca ggaagtgatc aacaaagcga gcaacagcaa caaaattcgc    120

ctggaaaagg gccgcctgta tcaaatcaag attcagtatc agcgcgagaa tccgaccgag    180

aaaggcctgg atttcaaact gtactggacc gatagccaaa acaagaaaga ggtgatttct    240

tctgacaacc tgcagctgcc ggaactgaag cagaagagca gcaacagccg caagaaacgc    300

agcacctctg caggcccgac cgtgccagat cgtgacaacg atggcatccc ggacagcctg    360

gaagtggaag gttataccgt tgatgttaag aacaaacgca cctttctgag cccatggatt    420

agcaacattc atgagaaaaa aggcctgacc aagtataaaa gcagcccgga aaagtggagc    480

accgcgagcg atccgtatag cgattttgag aaagtgaccg gccgcattga caaaaacgtg    540

agcccggaag cgcgccatcc actggttgca gcgtacccga ttgtgcatgt tgatatggag    600

aacatcatcc tgagcaagaa cgaggatcag agcacccaga atacggatag ccagacgcgc    660

acgatcagca agaacaccag cacgagccgt acccacacca gcgaggtgca tggcaatgca    720

gaagtgcatg cgagcttctt cgacattggc ggcagcgtga gcgcaggctt tagcaacagc    780

aacagcagca ccgtggcaat tgatcacagc ctgtctctgg cgggcgaacg tacctgggcg    840

gaaaccatgg gcctgaacac ggcggatacc gcgcgtctga acgcgaacat tcgttatgtg    900

aacacgggta ccgcgccgat ctacaacgtg ctgccgacca ccagcctggt gctgggtaaa    960

aatcagaccc tggcgaccat caaagcgaaa gaaaaccagc tgtctcagat tctggcgccg   1020

aataactact atccgagcaa gaacctggca ccaattgcgc tgaatgcaca ggatgacttt   1080

agcagcaccc cgatcaccat gaactataat cagtttctgg agctggaaaa gaccaagcaa   1140

ctgcgcctgg ataccgatca ggtgtatggt aacattgcga cctacaactt cgagaacggc   1200

cgtgttcgcg tggataccgg cagcaactgg tctgaagtgc tgccgcagat tcaggaaacg   1260

accgcgcgca tcatcttcaa cggcaaagat ctgaacctgg tggaacgtcg catcgcggcg   1320

gtgaacccga gcgatccgct ggaaacgacc aaaccggaca tgaccctgaa agaagcactg   1380

aagattgcgt ttggtttcaa cgagccaaat ggcaacctgc agtaccaggg caaagacatc   1440

accgaattcg acttcaactt tgatcagcag acctctcaga acatcaaaaa ccagctggca   1500

gaactgaacg cgaccaacat ctacaccgtg ctggacaaga tcaagctgaa cgcgaagatg   1560

aacattctga ttcgcgacaa gcgctttcat tatgatcgta acaacattgc ggtgggtgca   1620
```

gatgaaagcg tggtgaagga agcgcatcgc gaggtgatca actctagcac cgaaggcctg 1680
ctgctgaaca tcgacaaaga cattcgtaaa atcctgagcg gctatattgt tgaaattgag 1740
gataccgaag gtctgaagga agtgatcaac gatcgctatg acatgctgaa catttctagc 1800
ctgcgccagg atggcaagac cttcattgac ttcaagaagt acaacgacaa actgccgctg 1860
tacattagca acccgaacta caaagtgaat gtttatgcgg tgacc 1905

<210> SEQ ID NO 93
<211> LENGTH: 1905
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Sequence variant (93%) of SEQ ID No. 86

<400> SEQUENCE: 93
ttcattaaag tgaagaaaag cgatgagtat acctttgcaa cgagcgcgga taaccatgtg 60
accatgtggg tggacgatca ggaagtgatc aacaaagcga gcaacagcaa caaaattcgc 120
ctggaaaagg gccgcctgta tcaaatcaag attcagtatc agcgcgagaa tccgaccgag 180
aaaggcctgg atttcaaact gtactggacc gatagccaaa acaagaaaga ggtgatttct 240
tctgataacc tgcagctgcc ggagctgaag cagaagagca gcaacagccg caagaaacgc 300
agcaccagcg caggcccgac cgtgccggat cgtgacaacg atggcatccc ggacagcctg 360
gaagtggaag gttataccgt tgatgtgaag aacaaacgca cctttctgag cccatggatt 420
agcaacattc acgaaaaaaa aggcctgacc aagtataaaa gcagcccgga aaagtggagc 480
accgcgagcg atccgtatag cgattttgag aaagtgaccg gccgcattga caaaaacgtg 540
agcccggaag cgcgccatcc actggttgca gcgtacccga ttgtgcatgt ggatatggag 600
aacatcatcc tgagcaaaaa cgaggatcag agcacccaga atacggatag ccagacgcgc 660
acgatcagca aaaacaccag cacgagccgt acccacacca gcgaggtgca tggcaatgca 720
gaagtgcatg cgagcttctt cgacattggc ggcagcgtga gcgcaggctt tagcaacagc 780
aacagcagca ccgtggcaat tgatcatagc ctgtctctgg cgggcgaacg tacctgggcg 840
gaaaccatgg gcctgaacac ggcggatacc gcgcgtctga acgcgaacat tcgttatgtg 900
aacacgggta ccgcgccgat ctacaacgtt ctgccgacca ccagcctggt gctgggtaaa 960
aatcaaaccc tggcgaccat caaagcgaaa gaaaaccagc tgtctcagat cctggcgcca 1020
aacaactact atccgtctaa gaacctggca ccaattgcgc tgaatgcaca ggatgacttt 1080
agcagcaccc cgatcaccat gaactataat cagtttctgg agctggaaaa gaccaagcag 1140
ctgcgcctgg ataccgatca ggtgtatggt aacattgcga cctacaactt cgagaacggc 1200
cgtgttcgcg tggataccgg cagcaactgg tctgaagtgc tgccgcagat tcaggaaacg 1260
accgcgcgca tcatcttcaa cggcaaagat ctgaacctgg tggaacgtcg catcgcggcg 1320
gtgaacccga gcgacccgct ggaaaccacc aaaccggaca tgaccctgaa agaagcactg 1380
aagattgcgt ttggtttcaa cgagccaaat ggcaacctgc agtaccaggg caaagacatc 1440
accgaattcg acttcaattt tgatcagcag acctctcaga acatcaaaaa ccagctggca 1500
gaactgaacg cgaccaacat ttacaccgtg ctggacaaga tcaagctgaa cgcgaagatg 1560
aacattctga ttcgcgacaa gcgctttcat tatgatcgta acaacattgc ggtgggtgca 1620
gatgaaagcg tggtgaagga agcgcatcgc gaggttatca actctagcac ggaaggcctg 1680

```
ctgctgaaca tcgacaaaga cattcgtaaa atcctgagcg gctatattgt tgaaattgag   1740

gataccgaag gtctgaagga agtgatcaac gatcgctatg acatgctgaa catttctagc   1800

ctgcgccagg atggcaagac cttcattgac ttcaagaagt acaacgacaa gctgccgctg   1860

tacattagca acccgaacta caaggtgaat gtttatgcgg tgacc                   1905
```

<210> SEQ ID NO 94
<211> LENGTH: 1905
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Sequence variant (92%) of SEQ ID No. 86

<400> SEQUENCE: 94

```
ttcattaaag tgaagaaaag cgatgagtat acctttgcaa cgagcgcgga taaccatgtg     60

accatgtggg tggacgatca ggaggtgatc aacaaagcga gcaacagcaa caaaattcgc    120

ctggaaaaag gccgcctgta tcagatcaag attcagtatc aacgcgagaa cccgaccgaa    180

aaaggcctgg atttcaaact gtactggacc gatagccaga acaagaaaga ggtgatttct    240

tctgataacc tgcaactgcc ggagctgaag cagaagagca gcaacagccg caagaaacgc    300

agcaccagcg caggcccgac cgtgccggac cgcgacaacg atggcattcc ggatagcctg    360

gaagtggaag gttataccgt tgatgttaag aacaaacgta cgtttctgag cccatggatc    420

agcaacattc acgaaaaaaa aggcctgacc aagtataaaa gcagcccgga aaagtggagc    480

accgcgagcg atccgtatag cgattttgaa aaagtgaccg gccgcattga taaaaacgtg    540

agcccggaag cacgccatcc gctggttgcg gcgtacccga ttgtgcatgt ggatatggag    600

aatatcatcc tgagcaagaa cgaggatcag agcacgcaga ataccgatag ccagacgcgt    660

acgatcagca aaaacaccag cacgagccgt acccacacca gcgaggtgca tggcaacgcg    720

gaagtgcatg cgagcttctt cgacattggc ggcagcgtga gcgcgggctt tagcaacagc    780

aacagcagca ccgttgcaat tgatcatagc ctgtctctgg caggcgaacg tacctgggcg    840

gagaccatgg gcctgaacac ggcggatacc gcgcgcctga acgcgaacat tcgttatgtg    900

aacaccggta ccgcgccgat ctacaacgtg ctgccgacca ccagcctggt gctgggtaaa    960

aatcagaccc tggcgaccat caaagcgaaa gaaaaccagc tgtctcagat cctggcacca   1020

aacaactact atccgagcaa gaacctggca ccaattgcgc tgaatgcaca ggatgacttt   1080

agcagcaccc cgatcacgat gaactataac cagtttctgg agctggaaaa gaccaagcag   1140

ctgcgcctgg ataccgatca ggtgtatggt aacattgcaa cctacaactt cgagaacggc   1200

cgtgttcgcg tggataccgg cagcaactgg tctgaagtgc tgccgcagat tcaggaaacc   1260

accgcgcgca tcatcttcaa cggcaaagat ctgaacctgg tggaacgtcg catcgcggcg   1320

gtgaacccga gcgacccgct ggaaaccacc aaaccggaca tgaccctgaa agaagcgctg   1380

aagattgcgt ttggtttcaa tgagccgaat ggcaacctgc agtaccaggg caaagacatc   1440

accgaattcg acttcaattt tgatcaacag acctctcaga acatcaaaaa ccagctggca   1500

gagctgaacg cgaccaacat ttacaccgtg ctggacaaga tcaagctgaa cgcgaagatg   1560

aatattctga ttcgcgacaa gcgctttcat tatgatcgta acaacattgc ggtgggtgca   1620

gatgaaagcg tggtgaagga agcgcatcgc gaggtgatca actctagcac ggaaggcctg   1680

ctgctgaaca tcgacaaaga cattcgtaaa atcctgagcg gctacattgt tgaaattgaa   1740

gacaccgaag gtctgaagga agtgatcaac gatcgctatg acatgctgaa catttctagc   1800
```

ctgcgccagg atggcaagac cttcattgac ttcaagaagt acaacgacaa gctgccactg 1860
tatatttcta acccaaacta caaggtgaat gtttatgcgg tgacc 1905

<210> SEQ ID NO 95
<211> LENGTH: 1905
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Sequence variant (91%) of SEQ ID No. 86

<400> SEQUENCE: 95
ttcattaaag tgaagaaaag cgacgagtac acctttgcaa cgagcgcgga taaccatgtg 60
accatgtggg ttgacgatca ggaggttatt aataaagcga gcaacagcaa caaaattcgt 120
ctggaaaaag gccgcctgta tcagatcaag attcagtatc aacgtgagaa cccgaccgaa 180
aaaggcctgg attttaaact gtactggacc gatagccaga acaagaaaga ggtgatttct 240
tctgataacc tgcagctgcc ggagctgaag cagaagagca gcaacagccg caagaaacgc 300
agcaccagcg cgggcccgac cgtgccggat cgcgacaacg atggcattcc ggacagcctg 360
gaagtggaag gttataccgt tgatgttaag aacaaacgca cctttctgag cccatggatc 420
agcaacattc acgaaaaaaa aggcctgacc aagtataaaa gcagcccgga aaagtggagc 480
accgcgtctg atccgtatag cgattttgaa aaagtgaccg gccgcattga taaaaacgtg 540
agcccggaag cacgccatcc gctggttgcg gcgtatccga ttgtgcatgt ggatatggaa 600
aatatcatcc tgagcaagaa cgaggatcag agcacccaga ataccgatag ccagacgcgt 660
acgatcagca aaaacaccag cacgagccgt acccatacca gcgaggtgca cggcaacgcg 720
gaagtgcatg cgagcttctt cgacattggc ggcagcgtga gcgcgggctt tagcaacagc 780
aacagcagca cggtggcaat tgatcatagc ctgtctctgg caggcgaacg tacctgggcg 840
gagaccatgg gcctgaacac ggcggatacc gcgcgcctga acgcaaacat tcgttatgtg 900
aacaccggta ccgcgccgat ctataacgtg ctgccgacca ccagcctggt gctgggtaaa 960
aatcagacgc tggcgaccat caaagcgaaa gaaaaccagc tgtctcagat cctggcacca 1020
aacaactact atccgagcaa gaacctggca ccaatcgcgc tgaatgcgca ggatgatttc 1080
agcagcaccc cgatcacgat gaactataac cagtttctgg agctggaaaa gaccaagcag 1140
ctgcgcctgg ataccgatca ggtgtacggt aacattgcga cctataactt cgagaacggc 1200
cgcgttcgcg tggataccgg cagcaactgg tctgaagtgc tgccgcagat tcaggaaacc 1260
accgcgcgca tcatcttcaa cggcaaagat ctgaacctgg tggaacgtcg catcgcagcg 1320
gtgaacccga gcgacccgct ggaaaccacc aaaccggaca tgaccctgaa agaagcactg 1380
aagattgcgt ttggtttcaa cgagccgaat ggcaacctgc agtaccaagg caaagacatc 1440
accgaattcg attttaattt cgatcaacag acctctcaga acatcaaaaa ccagctggca 1500
gagctgaacg cgaccaacat ttacaccgtg ctggacaaga tcaagctgaa cgcgaagatg 1560
aatattctga ttcgcgacaa gcgttttcat tacgatcgta acaacatcgc ggtgggtgca 1620
gatgaaagcg tggtgaagga agcgcatcgc gaggtgatca actctagcac ggagggcctg 1680
ctgctgaaca tcgacaaaga cattcgcaaa attctgagcg gctacattgt tgaaattgaa 1740
gacaccgaag gtctgaagga agtgatcaac gatcgctatg acatgctgaa cattagcagc 1800
ctgcgccagg acggcaagac cttcattgac ttcaagaagt acaacgacaa gctgccactg 1860
tatatttcta atccaaacta caaggtgaac gtgtatgcgg tgacc 1905

<210> SEQ ID NO 96
<211> LENGTH: 2055
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Truncated version of SEQ ID No. 1 (bp. 103-2157)

<400> SEQUENCE: 96
gtgacctcta gcacgaccgg cgatctgagc attccgagca gcgaactgga gaacattccg 60
agcgagaacc agtactttca gtctgcgatt tggagcggct tcatcaaagt gaagaaaagc 120
gatgagtata cctttgcgac gtctgcggat aaccatgtga ccatgtgggt ggacgatcag 180
gaagtgatca acaaagcgag caacagcaac aagattcgcc tggagaaggg tcgcctgtat 240
cagatcaaga ttcagtatca gcgcgagaat ccgaccgaga aaggcctgga tttcaaactg 300
tactggaccg atagccagaa caagaaagaa gtgattagct ctgataacct gcaactgccg 360
gaactgaaac agaagagcag caacagccgc aagaaacgca gcacctctgc aggcccgacc 420
gttccagatc gcgacaacga tggcattccg gacagcctgg aagtggaagg ttataccgtt 480
gatgtgaaga acaaacgcac ctttctgagc ccgtggatta gcaacattca tgagaagaaa 540
ggcctgacca agtacaaaag cagcccggag aagtggagca ccgcgagcga tccgtatagc 600
gactttgaga aagtgaccgg ccgcattgat aagaacgtga gcccggaagc gcgtcaccca 660
ctggttgcag cgtatccgat tgtgcatgtt gacatggaga acatcattct gagcaagaac 720
gaagatcaga gcacccagaa cacggatagc cagacccgca cgatcagcaa gaacaccagc 780
acgagccgta cccataccag cgaagtgcat ggcaatgcgg aagtgcatgc gagcttcttt 840
gacattggtg gcagcgtgag cgcgggcttc agcaacagca acagcagcac cgtggcgatt 900
gatcatagcc tgagcctggc gggcgaacgt acctgggcgg aaaccatggg cctgaacacg 960
gcggatacgg cacgtctgaa tgcgaacatt cgctatgtga acaccggtac cgcgccaatc 1020
tataacgttc tgccgaccac gagcctggtg ctgggcaaga atcagaccct ggcgaccatc 1080
aaagcgaaag agaaccagct gtctcagatt ctggcaccga acaactacta tccgagcaag 1140
aacctggcac cgattgcact gaatgcgcag gatgacttca gcagcacccc gatcaccatg 1200
aactacaatc agtttctgga gctggagaag accaaacaac tgcgcctgga taccgatcag 1260
gtgtatggca acattgcgac ctacaacttt gagaacggcc gcgttcgcgt ggataccggt 1320
agcaactggt ctgaagtgct gccgcagatt caggaaacga ccgcgcgcat catcttcaac 1380
ggcaaagatc tgaacctggt ggaacgtcgc atcgcggcag tgaacccatc tgatccactg 1440
gaaacgacca aaccggacat gaccctgaaa gaagcgctga agattgcatt tggcttcaac 1500
gaaccgaatg gcaacctgca gtatcagggc aaagacatca ccgagtttga cttcaacttt 1560
gatcaacaga cctctcagaa catcaagaac cagctggcag aactgaatgc gaccaacatc 1620
tacaccgtgc tggacaagat caaactgaac gcaaagatga acattctgat tcgtgacaaa 1680
cgcttccact atgatcgtaa caacattgcg gtgggtgcag atgaaagcgt tgtgaaagaa 1740
gcgcatcgtg aagtgatcaa ctctagcacc gaaggcctgc tgctgaacat tgacaaagac 1800
atccgtaaga ttctgagcgg ctacattgtg gagattgaag ataccgaagg tctgaaagaa 1860
gtgatcaacg atcgctatga catgctgaac atctctagcc tgcgccagga tggcaagacc 1920
ttcattgact tcaagaagta caacgacaaa ctgccgctgt acatcagcaa tccgaactac 1980
aaagtgaacg tgtatgcggt gaccaaagag aacaccatca ttaacccaag cgagaatggc 2040
gataccagca ccaac 2055

<210> SEQ ID NO 97
<211> LENGTH: 2055
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Sequence variant (99%) of SEQ ID No. 96

<400> SEQUENCE: 97
gtgacctcta gcacgaccgg cgatctgagc attccgtcta gcgaactgga gaacattccg 60
agcgagaacc agtactttca gtctgcgatt tggagcggct tcatcaaagt gaagaaaagc 120
gatgagtata cctttgcgac gtctgcggat aaccatgtga ccatgtgggt ggacgatcag 180
gaagtgatca acaaagcgag caacagcaac aagattcgcc tggagaaggg tcgcctgtat 240
cagatcaaga ttcagtatca gcgcgagaat ccgaccgaga aaggcctgga tttcaaactg 300
tactggaccg atagccagaa caagaaggaa gtgattagct ctgataacct gcaactgccg 360
gaactgaaac agaagagcag caacagccgc aagaaacgca gcacctctgc aggcccgacc 420
gttccagatc gcgataacga tggcattccg gacagcctgg aagtggaagg ttataccgtt 480
gatgtgaaaa acaaacgcac ctttctgagc ccgtggatta gcaacattca tgagaagaaa 540
ggcctgacga agtacaaaag cagcccggag aagtggagca ccgcgagcga tccgtatagc 600
gactttgaga aagtgaccgg ccgcattgat aagaacgtga gcccggaagc gcgtcaccca 660
ctggttgcag cgtatccgat tgtgcatgtt gacatggaga acatcattct gagcaagaac 720
gaagatcaga gcacccagaa cacggatagc cagacccgca cgatcagcaa gaacaccagc 780
acgagccgta cccataccag cgaagtgcat ggcaacgcgg aagtgcatgc gagcttcttt 840
gacattggtg gcagcgtgag cgcgggcttc agcaatagca acagcagcac cgtggcgatt 900
gaccatagcc tgagcctggc gggcgaacgt acctgggcag aaaccatggg cctgaacacg 960
gcggatacgg cacgtctgaa tgcgaacatt cgctatgtga ataccggtac cgcgccaatc 1020
tataacgttc tgccgaccac gagcctggtg ctgggcaaga accagaccct ggcgaccatc 1080
aaagcgaaag agaaccagct gtctcagatt ctggcaccga acaactacta tccgagcaag 1140
aacctggcgc cgattgcact gaatgcgcag gatgacttca gcagcacccc gatcaccatg 1200
aactacaatc agtttctgga gctggagaag accaaacaac tgcgcctgga taccgatcag 1260
gtgtatggca acattgcgac ctacaacttt gagaacggcc gcgttcgcgt ggataccggt 1320
agcaactggt ctgaagtgct gccgcagatt caggaaacca ccgcgcgcat catcttcaac 1380
ggcaaagacc tgaacctggt ggaacgtcgc atcgcggcag tgaacccatc tgatccactg 1440
gaaacgacca aaccggacat gaccctgaaa gaagcgctga agattgcatt tggcttcaac 1500
gaaccgaatg gcaacctgca gtatcagggc aaagacatca ccgagtttga cttcaacttt 1560
gatcaacaga ccagccagaa catcaagaac cagctggcag aactgaatgc gaccaacatc 1620
tacaccgtgc tggacaagat caaactgaac gcaaagatga acattctgat tcgtgataaa 1680
cgcttccact atgatcgtaa caacattgcg gtgggtgcag atgaaagcgt tgtgaaagaa 1740
gcgcatcgtg aagtgatcaa ctctagcacc gaaggcctgc tgctgaacat tgacaaagac 1800
atccgtaaga ttctgagcgg ctacattgtg gagattgaag ataccgaagg tctgaaagaa 1860
gtgatcaacg atcgctatga catgctgaac atctctagcc tgcgccagga tggcaagacc 1920
ttcattgact tcaagaagta caacgacaaa ctgccgctgt acatcagcaa tccgaactac 1980
aaagtgaacg tgtatgcggt gaccaaagag aacaccatca ttaacccaag cgagaatggc 2040
gataccagca ccaac 2055

<210> SEQ ID NO 98
<211> LENGTH: 2055
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Sequence variant (98%) of SEQ ID No. 96

<400> SEQUENCE: 98
gtgacctcta gcacgaccgg cgatctgagc attccgtcta gcgaactgga gaacattccg 60
agcgagaacc agtactttca gtctgcaatt tggagcggct tcatcaaagt gaagaaaagc 120
gatgagtata cctttgcgac gtctgcggat aaccatgtga ccatgtgggt ggacgatcag 180
gaagtgatca acaaagcgag caacagcaac aagattcgcc tggagaaggg tcgcctgtat 240
cagattaaga ttcagtatca gcgcgagaat ccgaccgaga aaggcctgga ttttaaactg 300
tattggaccg atagccagaa caagaaggaa gtgattagca gcgataacct gcaactgccg 360
gaactgaaac aaaagagcag caacagccgc aagaaacgca gcacctctgc aggcccgacc 420
gttccagatc gcgataacga tggcattccg gacagcctgg aagtggaagg ttataccgtt 480
gatgtgaaaa acaaacgcac ctttctgagc ccgtggatta gcaacattca tgaaaagaaa 540
ggcctgacga agtacaaaag cagcccggag aagtggagca ccgcgagcga tccgtacagc 600
gactttgaga aagtgaccgg ccgcattgat aagaacgtga gcccggaagc gcgtcaccca 660
ctggttgcag cgtatccgat tgtgcatgtt gacatggaga acatcattct gagcaagaac 720
gaagatcagt ctacccagaa cacggatagc cagacccgca cgatcagcaa gaacaccagc 780
acgagccgta cccataccag cgaagtgcat ggcaacgcgg aagtgcatgc gagcttcttc 840
gacattggtg gcagcgtgag cgcgggcttc agcaatagca acagcagcac cgtggcgatt 900
gaccatagcc tgagcctggc gggcgaacgt acctgggcag aaaccatggg cctgaacacg 960
gcggatacgg cacgtctgaa tgcgaacatt cgctatgtga ataccggtac cgcgccaatc 1020
tataacgttc tgccgaccac gagcctggtg ctgggcaaga accagaccct ggcgaccatc 1080
aaagcgaaag agaaccagct gtctcagatt ctggcaccga acaactacta tccgagcaag 1140
aacctggcgc cgattgcgct gaatgcgcag gatgacttca gcagcacccc gatcaccatg 1200
aactacaatc agtttctgga gctggagaag accaaacagc tgcgcctgga caccgatcag 1260
gtgtatggca acattgcgac ctacaacttt gagaacggcc gcgttcgcgt ggataccggt 1320
agcaactggt ctgaagtgct gccgcagatt caggaaacca ccgcgcgcat catcttcaac 1380
ggcaaagacc tgaacctggt ggaacgtcgc atcgcggcag tgaacccatc tgatccactg 1440
gagacgacca aaccggatat gaccctgaaa gaagcgctga agattgcatt tggcttcaac 1500
gaaccgaatg gcaacctgca gtatcagggc aaagacatca ccgagtttga cttcaacttt 1560
gatcaacaga ccagccagaa catcaagaac cagctggcag aactgaatgc gaccaacatc 1620
tacaccgtgc tggacaagat caaactgaac gcaaagatga acatcctgat tcgtgataaa 1680
cgcttccact atgatcgtaa caacattgcg gtgggtgcag atgaaagcgt tgtgaaagaa 1740

-continued gcgcatcgtg aagtgatcaa ctctagcacc gaaggcctgc tgctgaacat tgacaaagac 1800
atccgtaaga ttctgagcgg ctacattgtg gagattgaag ataccgaagg tctgaaagaa 1860
gtgatcaacg atcgctatga tatgctgaac atctctagcc tgcgccagga cggcaagacc 1920
ttcattgact tcaagaagta caacgacaaa ctgccgctgt acatcagcaa tccgaactac 1980
aaagtgaacg tgtatgcggt gaccaaagag aacaccatca ttaacccaag cgagaatggc 2040
gataccagca ccaac 2055

<210> SEQ ID NO 99
<211> LENGTH: 2055
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Sequence variant (97%) of SEQ ID No. 96

<400> SEQUENCE: 99
gtgacctcta gcacgaccgg cgatctgagc attccgagca gcgaactgga gaacattccg 60
tctgagaacc agtactttca gtctgcaatt tggagcggct tcatcaaagt gaagaagagc 120
gatgagtata cctttgcgac ctctgcggat aaccatgtga ccatgtgggt ggacgatcag 180
gaagtgatca acaaagcgag caacagcaac aagattcgcc tggagaaggg tcgcctgtat 240
cagattaaga ttcagtacca gcgcgagaat ccgaccgaga agggcctgga ttttaaactg 300
tattggaccg atagccagaa caagaaggag gtgattagca gcgataacct gcaactgccg 360
gaactgaaac aaaagagcag caacagccgc aagaaacgca gcacctctgc aggcccgacc 420
gttccagatc gcgataacga tggcattccg gacagcctgg aagtggaggg ttataccgtt 480
gatgtgaaaa acaaacgcac ctttctgagc ccgtggatta gcaacattca tgaaaaaaaa 540
ggcctgacga agtacaaaag cagcccggag aagtggagca ccgcaagcga tccgtacagc 600
gactttgaaa aagtgaccgg ccgcattgat aagaacgtga gcccggaagc gcgtcaccca 660
ctggttgcag cgtatccgat tgtgcatgtt gacatggaga acattattct gagcaagaac 720
gaagatcagt ctacccagaa cacggatagc cagacccgca cgatcagcaa gaacaccagc 780
acgagccgta cccataccag cgaagtgcat ggcaacgcgg aagtgcatgc gagcttcttc 840
gacattggtg gcagcgtgag cgcgggcttc agcaatagca acagcagcac cgtggcgatt 900
gaccatagcc tgagcctggc gggcgaacgt acctgggcag aaaccatggg cctgaacacg 960
gcggataccg cacgtctgaa tgcgaacatt cgctatgtga atacgggtac cgcgccaatc 1020
tataacgttc tgccgaccac gagcctggtg ctgggcaaga accagacgct ggcgaccatc 1080
aaagcgaaag agaaccagct gtctcagatt ctggcaccga acaactacta tccgagcaag 1140
aacctggcgc cgattgcgct gaatgcgcag gatgacttca gcagcacccc gatcaccatg 1200
aactacaatc agtttctgga gctggagaag accaaacagc tgcgcctgga caccgatcag 1260
gtgtatggca acatcgcgac ctataacttt gaaaacggcc gcgttcgcgt ggataccggt 1320
agcaactggt ctgaagtgct gccgcagatt caggaaacca ccgcgcgcat catcttcaac 1380
ggcaaagacc tgaacctggt ggaacgtcgc atcgcggcag tgaacccatc tgatccactg 1440
gagacgacca aaccggatat gaccctgaaa gaagcgctga agattgcatt tggcttcaac 1500
gaaccgaatg gcaacctgca gtatcagggc aaagacatca ccgagtttga cttcaacttt 1560
gatcaacaga ccagccagaa catcaaaaac cagctggcgg aactgaatgc gaccaacatc 1620
tacaccgtgc tggacaagat caaactgaac gcaaagatga acatcctgat tcgtgataaa 1680
cgcttccact atgatcgtaa caacattgcg gtgggtgcag atgagagcgt tgtgaaagaa 1740
gcgcatcgtg aagtgatcaa ctctagcacc gaaggcctgc tgctgaacat tgacaaagac 1800
atccgtaaga ttctgagcgg ctacattgtg gagattgaag ataccgaagg tctgaaagaa 1860
gtgatcaacg atcgctatga tatgctgaac atctctagcc tgcgccagga cggcaagacc 1920
ttcattgact tcaagaagta caacgacaaa ctgccgctgt acatcagcaa tccgaactac 1980
aaagtgaacg tgtatgcggt gaccaaagaa aacaccatca ttaacccaag cgagaatggc 2040
gataccagca ccaac 2055

<210> SEQ ID NO 100
<211> LENGTH: 2055
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Sequence variant (96%) of SEQ ID No. 96

<400> SEQUENCE: 100
gtgacgtcta gcacgaccgg cgatctgagc attccgagct ctgaactgga gaacattccg 60
tctgagaacc agtactttca gtctgcaatt tggagcggct tcatcaaagt gaagaaaagc 120
gatgaatata cctttgcgac ctctgcggat aaccatgtga ccatgtgggt ggacgatcag 180
gaagtgatca acaaagcgag caacagcaac aagattcgcc tggagaaggg tcgcctgtat 240
caaattaaga ttcagtacca gcgcgagaac ccgaccgaga agggcctgga ttttaaactg 300
tattggaccg atagccagaa caagaaggag gtgattagca gcgataacct gcaactgccg 360
gagctgaaac agaaaagcag caacagccgc aagaaacgca gcacctctgc aggcccgacc 420
gttccagatc gcgataacga tggcattccg gacagcctgg aagtggaggg ttataccgtt 480
gacgtgaaga acaaacgcac ctttctgagc ccgtggatca gcaacattca tgaaaaaaaa 540
ggcctgacca agtacaaaag cagcccggag aagtggagca ccgcaagcga tccgtacagc 600
gattttgaaa aagtgaccgg ccgcattgat aagaacgtga gcccggaagc gcgtcaccca 660
ctggttgcag cgtatccgat tgtgcatgtt gacatggaga acattattct gagcaagaac 720
gaagatcagt ctacccagaa cacggatagc cagacccgca cgattagcaa gaacaccagc 780
acgagccgta cccataccag cgaagtgcat ggcaacgcgg aagtgcatgc gagcttcttc 840
gacattggtg gcagcgtgag cgcgggcttc agcaatagca acagcagcac cgtggcgatt 900
gatcatagcc tgagcctggc gggcgaacgt acctgggcag aaaccatggg cctgaacacg 960
gcggataccg cacgtctgaa tgcgaacatt cgctatgtga acacgggtac cgcgccaatc 1020
tataacgttc tgccgaccac gagcctggtg ctgggcaaga accagacgct ggcgaccatc 1080
aaagcgaaag agaaccagct gtctcagatt ctggcaccga acaactacta tccgagcaag 1140
aacctggcgc cgattgcgct gaatgcgcag gacgacttca gcagcacccc gatcaccatg 1200
aactacaacc agtttctgga gctggagaag accaaacagc tgcgcctgga caccgatcag 1260
gtgtatggca acatcgcgac ctataacttt gaaaacggcc gcgttcgcgt ggataccggt 1320
agcaactgga gcgaagtgct gccgcagatt caggaaacca ccgcgcgcat catcttcaac 1380
ggcaaagacc tgaatctggt ggaacgtcgc atcgcggcag tgaatccatc tgatccactg 1440
gagacgacca aaccggatat gaccctgaaa gaggcgctga agattgcatt tggcttcaac 1500
gaaccgaacg gcaacctgca gtatcagggc aaagacatca ccgagtttga cttcaatttt 1560

```
gatcaacaga ccagccagaa catcaaaaac cagctggcgg aactgaatgc gaccaacatc   1620

tacaccgtgc tggacaagat caaactgaac gcaaagatga acatcctgat tcgtgataaa   1680

cgcttccact atgatcgtaa caatattgcg gtgggtgcag atgaaagcgt tgtgaaagaa   1740

gcgcatcgtg aagtgatcaa ctctagcacc gaaggcctgc tgctgaacat tgacaaggac   1800

atccgtaaga ttctgagcgg ctacattgtg gagattgaag ataccgaagg tctgaaagaa   1860

gtgatcaacg atcgctatga tatgctgaac atctctagcc tgcgccagga cggcaagacc   1920

ttcattgact tcaagaagta caacgacaaa ctgccgctgt acatcagcaa cccgaattac   1980

aaagtgaacg tgtatgcggt gaccaaagaa aacaccatca ttaacccaag cgagaatggc   2040

gataccagca ccaac                                                    2055
```

```
<210> SEQ ID NO 101
<211> LENGTH: 2055
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Sequence variant (95%) of SEQ ID No. 96

<400> SEQUENCE: 101
```

```
gtgacgtcta gcacgaccgg cgatctgagc attccgagct ctgaactgga gaacattccg     60

tctgagaacc agtactttca gtctgcaatt tggagcggct tcatcaaagt gaagaaaagc    120

gatgaatata cctttgcgac ctctgcggat aaccatgtga ccatgtgggt ggacgatcag    180

gaagttatca acaaagcgag caacagcaac aagattcgcc tggagaaggg tcgcctgtat    240

caaattaaga ttcagtacca gcgcgagaac ccgaccgaga agggcctgga ttttaaactg    300

tattggaccg atagccagaa caagaaggag gtgattagca gcgataacct gcaactgccg    360

gagctgaaac agaaaagcag caacagccgt aagaaacgca gcacctctgc aggcccgacc    420

gttccagatc gcgataacga tggcattccg gacagcctgg aagtggaggg ttataccgtt    480

gacgtgaaga acaaacgcac ctttctgagc ccgtggatca gcaacattca tgagaaaaaa    540

ggcctgacca agtacaaaag cagcccggaa aagtggagca ccgcaagcga tccgtacagc    600

gactttgaaa aagtgaccgg ccgcattgac aagaacgtga gcccggaagc gcgtcaccca    660

ctggttgcgg cgtatccgat tgtgcatgtg gatatggaaa acattattct gagcaagaac    720

gaagatcagt ctacccaaaa cacggatagc cagacccgca cgattagcaa gaacaccagc    780

acgagccgta cccataccag cgaagtgcat ggcaacgcgg aagtgcatgc gagcttcttc    840

gacattggtg gcagcgtgag cgcgggcttc agcaatagca acagcagcac cgtggcgatt    900

gatcatagcc tgagcctggc gggcgaacgt acctgggcag aaaccatggg cctgaacacg    960

gcggataccg cacgcctgaa tgcgaacatt cgctatgtga acacgggtac cgcgccaatc   1020

tataacgttc tgccgaccac gagcctggtg ctgggcaaga accagacgct ggcgaccatc   1080

aaagcaaaag agaaccagct gtctcagatt ctggcaccga acaactacta tccgagcaag   1140

aacctggcgc cgattgcgct gaatgcgcag gatgacttta gcagcacccc gatcaccatg   1200

aactacaacc agtttctgga gctggagaag accaaacagc tgcgcctgga caccgatcag   1260

gtgtatggca acatcgcgac ctataacttt gaaaacggcc gcgttcgcgt ggataccggt   1320

agcaactgga gcgaagtgct gccacagatt caggaaacca ccgcgcgcat catcttcaac   1380

ggcaaagacc tgaatctggt ggaacgtcgc atcgcggcag tgaatccatc tgatccgctg   1440

gagacgacca aaccggatat gaccctgaag gaggcgctga agattgcatt tggcttcaac   1500
```

```
gaaccgaacg gcaacctgca gtatcagggc aaagacatca ccgagttcga tttcaatttt   1560

gatcagcaga ccagccagaa catcaaaaac cagctggcgg agctgaatgc gaccaacatc   1620

tacaccgtgc tggacaagat caaactgaac gcaaagatga acatcctgat tcgtgataaa   1680

cgcttccact atgatcgcaa caatattgcg gtgggtgcag atgaaagcgt tgtgaaagaa   1740

gcgcatcgtg aagtgatcaa ctctagcacc gaaggcctgc tgctgaacat tgacaaggac   1800

atccgtaaga ttctgagcgg ctacattgtg gagattgaag ataccgaagg tctgaaagaa   1860

gtgatcaacg accgttatga tatgctgaac atctctagcc tgcgccagga cggcaagacc   1920

ttcattgact tcaaaaagta caacgacaaa ctgccgctgt acatcagcaa cccgaattac   1980

aaagtgaacg tgtatgcggt gaccaaagaa aacaccatca ttaacccaag cgagaatggc   2040

gataccagca ccaac                                                    2055
```

<210> SEQ ID NO 102
<211> LENGTH: 2055
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Sequence variant (94%) of SEQ ID No. 96

<400> SEQUENCE: 102

```
gtgacgtcta gcacgaccgg cgatctgagc attccgagct ctgaactgga aaatattccg     60

agcgagaacc agtactttca gtctgcaatt tggagcggct ttatcaaagt gaagaaaagc    120

gatgaatata cctttgcgac cagcgcggat aaccatgtga ccatgtgggt ggacgatcag    180

gaagttatca acaaagcgag caacagcaac aagattcgcc tggagaaggg tcgcctgtat    240

caaattaaga ttcagtacca gcgtgagaac ccgaccgaga agggcctgga ttttaaactg    300

tattggaccg atagccagaa caagaaggag gtgattagca gcgataacct gcaactgccg    360

gagctgaaac agaaaagcag caacagccgt aagaaacgca gcaccagcgc aggcccgacc    420

gttccagatc gcgataacga tggcattccg gatagcctgg aagtggaggg ttataccgtg    480

gacgtgaaga acaaacgcac ctttctgtct ccgtggatca gcaacattca tgagaaaaaa    540

ggcctgacca agtacaaaag cagcccggaa aagtggtcta ccgcaagcga tccgtactct    600

gactttgaaa aagtgaccgg ccgcattgac aagaacgtga gcccggaagc gcgtcaccca    660

ctggttgcgg cgtatccgat tgtgcatgtt gatatggaga acatcattct gagcaagaac    720

gaagatcaga gcacccaaaa cacggatagc cagacccgca cgatttctaa gaacaccagc    780

acgagccgta cccataccag cgaagtgcat ggcaacgcgg aagtgcatgc gagcttcttc    840

gacattggtg gcagcgtgag cgcgggcttc agcaatagca acagcagcac cgtggcgatt    900

gatcatagcc tgagcctggc gggcgaacgc acctgggcag aaaccatggg cctgaacacg    960

gcggataccg cacgcctgaa tgcgaacatt cgctatgtga acacgggtac cgcgccaatc   1020

tataacgttc tgccgaccac cagcctggtg ctgggcaaga accagacgct ggcgaccatc   1080

aaagcaaaag agaaccagct gtctcagatt ctggcaccga acaactacta tccgagcaag   1140

aacctggcgc cgattgcgct gaatgcgcag gatgacttta gcagcacccc gatcaccatg   1200

aactacaacc agttcctgga gctggagaag accaaacagc tgcgcctgga caccgatcag   1260

gtgtatggca acatcgcgac ctataacttt gaaaacggcc gcgttcgcgt ggataccggt   1320

agcaactgga gcgaagtgct gccacagatt caggaaacca ccgcgcgcat catcttcaac   1380
```

-continued

```
ggcaaagacc tgaatctggt ggaacgtcgc atcgcggcag tgaacccatc tgacccgctg   1440

gagacgacca aaccggatat gaccctgaag gaggcgctga agattgcgtt tggcttcaac   1500

gaaccgaacg gcaacctgca gtatcagggc aaagacatca ccgagttcga tttcaatttt   1560

gatcagcaga cgagccagaa tatcaaaaac cagctggcgg agctgaatgc gaccaacatc   1620

tacaccgtgc tggacaagat caaactgaac gcaaagatga acatcctgat tcgtgataaa   1680

cgcttccact atgatcgcaa caatattgca gtgggtgcag atgaaagcgt tgtgaaagaa   1740

gcgcatcgtg aagtgatcaa ctctagcacc gaaggcctgc tgctgaacat tgacaaggac   1800

atccgtaaga ttctgagcgg ctacattgtg gagattgaag ataccgaagg tctgaaagaa   1860

gtgattaacg accgttatga tatgctgaac atctctagcc tgcgccagga cggcaagacc   1920

ttcattgact tcaaaaagta caacgacaaa ctgccgctgt acatcagcaa cccgaactac   1980

aaagtgaacg tgtatgcggt gaccaaagaa aacaccatca ttaacccaag cgagaatggc   2040

gataccagca ccaac                                                    2055
```

<210> SEQ ID NO 103
<211> LENGTH: 2055
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Sequence variant (93%) of SEQ ID No. 96

<400> SEQUENCE: 103

```
gtgacgagca gcacgaccgg cgatctgagc attccgagct ctgaactgga aaacattccg     60

agcgagaacc agtactttca gtctgcaatc tggagcggct tcatcaaagt gaagaaaagc    120

gatgaatata ccttcgcgac cagcgcggat aaccatgtga ccatgtgggt ggacgatcag    180

gaagttatca acaaagcgag caacagcaac aagattcgcc tggagaaagg tcgtctgtat    240

cagattaaga ttcagtacca gcgtgagaac ccgaccgaga agggcctgga ttttaaactg    300

tattggaccg atagccagaa caagaaggag gtgattagca gcgataacct gcaactgccg    360

gagctgaaac agaaaagcag caacagccgc aagaaacgta gcaccagcgc aggcccgacc    420

gttccagatc gcgataacga tggcattccg gatagcctgg aagtggaggg ttataccgtg    480

gacgtgaaga ataaacgcac ctttctgtct ccgtggatca gcaacatcca tgagaaaaaa    540

ggcctgacca agtacaagag cagcccggaa aagtggtcta ccgcaagcga cccgtattct    600

gactttgaaa aagtgaccgg ccgcatcgat aagaacgtga gcccggaagc gcgtcaccca    660

ctggttgcgg cgtatccgat tgtgcatgtt gatatggaga acattattct gagcaagaac    720

gaagatcaga gcacccaaaa cacggatagc cagacccgca cgatttctaa gaataccagc    780

acgagccgta cccataccag cgaagtgcat ggcaacgcgg aagtgcatgc gagcttcttc    840

gacattggtg gcagcgtgtc tgcgggcttc agcaatagca acagcagcac cgtggcgatt    900

gatcatagcc tgagcctggc gggcgaacgc acctgggcag aaaccatggg cctgaacacg    960

gcggataccg cacgcctgaa tgcgaacatt cgctatgtga acacgggtac cgcgccaatc   1020

tataacgttc tgccgaccac cagcctggtg ctgggcaaga accagacgct ggcgaccatc   1080

aaagcaaaag aaaatcagct gtctcagatt ctggcaccga acaactacta tccgagcaag   1140

aacctggcgc cgattgcgct gaacgcgcag gatgacttta gcagcacccc gatcaccatg   1200

aactacaacc agttcctgga gctggagaag accaaacagc tgcgcctgga caccgatcag   1260

gtgtatggca acatcgcgac ctataacttt gagaacggcc gcgttcgcgt ggataccggt   1320
```

```
agcaactgga gcgaagtgct gccacagatt caggaaacca ccgcgcgcat tatctttaac   1380

ggcaaagacc tgaatctggt ggaacgtcgc atcgcggcag tgaacccatc tgacccgctg   1440

gagacgacca aaccggatat gaccctgaag gaggcgctga agattgcgtt cggcttcaac   1500

gaaccgaacg gcaacctgca atatcagggc aaagacatca ccgagtttga tttcaatttt   1560

gatcagcaga cgagccagaa tatcaaaaac cagctggcgg agctgaacgc gaccaacatc   1620

tacaccgtgc tggacaagat caaactgaac gcaaagatga acattctgat tcgtgataaa   1680

cgctttcact atgatcgcaa caatattgca gtgggtgcag atgaaagcgt tgtgaaagaa   1740

gcgcatcgcg aagtgatcaa ctctagcacc gaaggcctgc tgctgaacat tgacaaggac   1800

atccgtaaga ttctgagcgg ctacattgtg gagattgaag ataccgaagg tctgaaagaa   1860

gtgattaacg accgttacga tatgctgaac atctctagcc tgcgccagga cggcaagacc   1920

ttcattgact tcaaaaagta caacgacaaa ctgccgctgt acatcagcaa cccgaactac   1980

aaagtgaacg tgtatgcggt gaccaaagaa aacaccatca ttaacccaag cgagaatggc   2040

gataccagca ccaac                                                    2055
```

```
<210> SEQ ID NO 104
<211> LENGTH: 2055
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Sequence variant (92%) of SEQ ID No. 96

<400> SEQUENCE: 104
```

```
gtgacgagca gcacgaccgg cgatctgagc attccgagct ctgaactgga gaatattccg     60

agcgagaacc agtactttca gtctgcaatc tggagcggct tcattaaagt gaagaagagc    120

gatgaatata ccttcgcgac cagcgcggat aaccatgtga ccatgtgggt ggatgaccag    180

gaagttatca acaaagcgag caacagcaac aagattcgcc tggaaaaagg tcgtctgtat    240

cagattaaga ttcagtacca gcgtgagaac ccgaccgaga agggcctgga ttttaaactg    300

tattggacgg atagccagaa caagaaggaa gtgattagca gcgataacct gcagctgccg    360

gagctgaaac agaaaagctc taacagccgc aagaaacgta gcaccagcgc aggcccgacc    420

gttccagatc gcgataacga tggcattccg gatagcctgg aagtggaggg ttataccgtg    480

gacgtgaaga ataaacgcac ctttctgtct ccgtggatca gcaacatcca tgagaaaaaa    540

ggcctgacca agtacaaaag cagcccggaa aagtggtcta cggcaagcga cccgtattct    600

gactttgaaa aagtgaccgg ccgcatcgat aagaacgtga gcccggaagc gcgtcatcca    660

ctggttgcgg cgtatccgat tgtgcatgtt gatatggaga acattattct gagcaagaac    720

gaagatcaga gcacccaaaa cacggatagc cagacccgca cgatttctaa aaataccagc    780

acgagccgta cccataccag cgaagtgcac ggcaacgcgg aagtgcatgc gagcttcttc    840

gatattggtg gcagcgtgtc tgcgggcttc agcaatagca acagcagcac cgtggcgatt    900

gatcatagcc tgagcctggc gggcgaacgc acctgggcag aaaccatggg cctgaacacc    960

gcggataccg cacgcctgaa tgcgaacatt cgctatgtga acacgggcac cgcgccaatc   1020

tataacgttc tgccgaccac cagcctggtg ctgggtaaga accagacgct ggcgaccatc   1080

aaggcaaaag aaaatcagct gtctcagatt ctggcaccga acaactacta tccgagcaag   1140

aacctggcgc cgattgcgct gaacgcgcag gatgacttta gcagcacccc gatcaccatg   1200
```

aactacaacc agttcctgga actggagaag accaaacaac tgcgcctgga caccgatcag 1260
gtgtatggca acatcgcgac ctataacttt gagaacggcc gcgttcgcgt ggataccggt 1320
agcaactgga gcgaagtgct gccacagatt caggaaacca ccgcgcgcat tatctttaac 1380
ggcaaagacc tgaatctggt ggaacgtcgc atcgcggcag tgaacccaag cgacccgctg 1440
gagacgacca aaccggatat gaccctgaag gaggcgctga aaattgcgtt cggcttcaac 1500
gagccgaacg gcaacctgca atatcagggc aaagacatca ccgagtttga tttcaatttt 1560
gatcagcaga ccagccagaa tatcaaaaac cagctggcgg agctgaacgc gaccaacatc 1620
tacaccgtgc tggacaagat caaactgaac gcaaagatga acattctgat tcgtgataaa 1680
cgctttcact atgatcgcaa caacattgca gtgggtgcag atgaaagcgt tgtgaaagaa 1740
gcgcatcgcg aagtgatcaa ctctagcacc gaaggcctgc tgctgaacat cgacaaggac 1800
atccgtaaga ttctgagcgg ctacattgtg gagattgagg ataccgaagg tctgaaagaa 1860
gtgattaacg accgttacga catgctgaac atctctagcc tgcgccagga cggcaagacc 1920
ttcattgact tcaagaagta caacgacaaa ctgccgctgt acatcagcaa cccgaactac 1980
aaagtgaacg tgtatgcggt gaccaaagaa aacaccatca ttaacccaag cgagaatggc 2040
gataccagca ccaac 2055

<210> SEQ ID NO 105
<211> LENGTH: 2055
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Sequence variant (91%) of SEQ ID No. 96

<400> SEQUENCE: 105
gtgacgagca gcacgaccgg cgacctgagc attccgagct ctgaactgga gaatattccg 60
agcgagaacc agtactttca gtctgcgatc tggagcggct tcattaaagt gaagaaaagc 120
gatgaatata ccttcgcgac cagcgcggat aaccatgtga ccatgtgggt ggatgaccag 180
gaagttatca acaaagcgag caacagcaac aagattcgtc tggaaaaagg tcgtctgtat 240
cagattaaga ttcagtacca gcgtgaaaac ccgaccgaga agggcctgga tttcaaactg 300
tattggacgg atagccagaa caagaaggag gtgattagca gcgataacct gcagctgccg 360
gagctgaaac agaaaagctc taacagccgc aagaaacgta gcacctctgc aggcccgacc 420
gttccagacc gcgataacga tggcattccg gatagcctgg aagtggaggg ctataccgtg 480
gacgtgaaga ataaacgcac ctttctgtct ccgtggatca gcaacatcca tgagaaaaaa 540
ggcctgacca agtacaaaag cagcccggaa aagtggagca ccgcaagcga cccgtattct 600
gattttgaaa aggtgaccgg ccgcatcgat aagaacgtga gcccggaagc gcgtcatcca 660
ctggttgcgg cgtatccgat tgtgcatgtt gatatggaga acattattct gagcaagaac 720
gaagatcaga gcacccaaaa cacggatagc cagacgcgca cgatttctaa aaataccagc 780
accagccgta cccataccag cgaagtgcac ggcaacgcgg aggtgcatgc gagcttcttt 840
gatattggtg gcagcgtgtc tgcgggtttc agcaacagca acagcagcac cgtggcgatt 900
gatcatagcc tgtctctggc gggcgaacgt acctgggcag aaaccatggg cctgaacacc 960
gcggataccg cacgcctgaa tgcgaacatt cgctatgtga acacgggcac cgcgccaatc 1020
tataacgttc tgccgaccac cagcctggtg ctgggtaaga accagacgct ggcgaccatc 1080
aaggcaaaag aaaatcagct gtctcagatt ctggcaccga acaactatta tccgagcaag 1140
aacctggcgc cgattgcgct gaacgcgcag gatgacttta gcagcacccc gatcaccatg 1200
aactacaacc agttcctgga actggagaag accaaacaac tgcgcctgga caccgatcag 1260
gtgtatggca acatcgcgac ctacaacttt gagaacggcc gcgttcgcgt ggataccggt 1320
agcaactgga gcgaagtgct gccacagatt caggaaacca ccgcgcgcat catctttaac 1380
ggcaaagatc tgaatctggt ggaacgccgc attgcagcag tgaacccaag cgacccgctg 1440
gagacgacca aaccggatat gaccctgaag gaggcgctga aaattgcgtt cggcttcaac 1500
gaaccgaacg gcaacctgca atatcagggc aaagacatca cggagtttga tttcaatttt 1560
gatcagcaga ccagccagaa tattaaaaac cagctggcgg agctgaacgc aaccaacatc 1620
tacaccgtgc tggataagat caaactgaac gcgaagatga acatcctgat tcgcgataaa 1680
cgctttcact atgatcgcaa caatattgca gtgggtgcag acgaaagcgt tgtgaaagaa 1740
gcgcatcgcg aagtgatcaa cagcagcacc gaaggcctgc tgctgaacat cgacaaggac 1800
atccgtaaga ttctgagcgg ctacattgtg gagattgagg acaccgaagg tctgaaagaa 1860
gtgattaacg accgttacga catgctgaac atctctagcc tgcgccagga cggcaagacc 1920
ttcattgact tcaagaagta caacgataaa ctgccgctgt acatcagcaa cccgaactac 1980
aaagtgaacg tgtatgcggt gaccaaagaa aacaccatca ttaatccaag cgagaacggc 2040
gataccagca ccaac 2055

<210> SEQ ID NO 106
<211> LENGTH: 2211
<212> TYPE: DNA
<213> ORGANISM: Artificial Sequence
<220> FEATURE:
<223> OTHER INFORMATION: Description of Artificial Sequence: Synthetic
consensus polynucleotide

<400> SEQUENCE: 106
atggaagtta aacaggagaa ccgtttgttg aatgaatgcg aatctagttc tcaggggttg 60
ctgggctact attttagtga tttgaatttt caggcaccga tggttgttac ctcttgtact 120
accggggatt tgtgtattcc tagttgtgag ttggagaata ttccgtggga gaaccagtat 180
tttcagtctg ctatttggtg cggctttatc aaagttaaga agagtgatga gtataccttt 240
gctacttctg ctgataatca tgtgaccatg tgggtggatg atcaggaagt gattaataaa 300
gcttgtaatt gtaacaagat tcgcttggag aagggtcgct tgtatcagat caagattcag 360
tatcagcgcg agaatcctac tgagaaaggc ttggatttca agttgtactg gaccgattgt 420
cagaataaga aagaagtgat ttgttgtgat aacttgcaat tgccggaatt gaaacagaag 480
tgttggaact gccgcaagaa gcgcagtacc tgtgctggcc ctacggttcc agatcgtgac 540
aatgatggca ttcctgattg cttggaggtg gaaggttata cggttgatgt gaagaataaa 600
cgcacttttc tttgcccgtg gatttgtaat attcatgaga agaaaggctt gaccaagtat 660
aaatgctgtc ctgagaagtg gagcacggct tgtgatccgt atagtgattt tgagaaggtt 720
accggccgga ttgataagaa tgtgtgcccg gaggcgcgtc accccttgt tgcagcttat 780 ccgattgtgc atgttgatat ggagaatatt attctgtgca agaatgagga tcagtgcacc 840
cagaatactg atagtcagac gcgcacgatc agtaagaata cttgtacgag tcgtacccat 900
actagtgaag tgcatggcaa tgcggaagtg catgcgtggt tctttgatat tggtgggagt 960
gtgtgtgcgg gctttagtaa ttggaattgc agtacggtgg cgattgatca ttgcctgtgt 1020
ctggcggggg aacgtacttg ggctgaaacc atgggtttga atacggctga tacggcacgt 1080

-continued

```
ttgaatgcga atattcgcta tgtgaatact ggtacggctc caatctataa cgttttgccg   1140

acgacttggt tggtgttggg caagaatcag accctggcga ccattaaagc taaggagaac   1200

cagttgtgtc agattcttgc acctaataat tattatcctt gtaagaactt ggcgccgatt   1260

gcattgaatg cgcaggatga tttcagttgt actccgatta ccatgaatta caatcagttt   1320

cttgagttgg agaagacgaa acaattgcgc ttggatacgg atcaggtgta tgggaatatt   1380

gcgacctaca attttgagaa tggccgcgtt cgggtggata ccggttggaa ctggtgtgaa   1440

gtgttgccgc agattcagga aacgactgcg cgtatcattt ttaatggcaa agatttgaat   1500

ctggtggaac gtcggatcgc ggcggttaat ccttgtgatc cattggaaac gactaaaccg   1560

gatatgacct tgaaagaagc gcttaagatt gcatttggct ttaacgaacc gaatggcaac   1620

ttgcagtatc aggggaaaga catcaccgag tttgatttta attttgatca acagacctct   1680

cagaatatca agaatcagtt ggcggaattg aatgcgacta acatctatac tgtgttggat   1740

aagatcaaat tgaatgcaaa gatgaatatt ttgattcgtg ataaacgttt tcattatgat   1800

cgtaataaca ttgcggttgg tgcggatgag tgcgttgtta aggaggctca tcgtgaagtg   1860

attaattctt gcaccgaggg cttgttgttg aatattgata aggatatccg taagattttg   1920

tgcggttata ttgtggagat tgaagatact gaaggtctta aagaagttat caatgatcgc   1980

tatgatatgt tgaatatttc tagtttgcgg caggatggca agacctttat tgattttaag   2040

aagtataatg ataaattgcc gttgtatatc agtaatccga attataaggt gaatgtgtat   2100

gctgttacta aagagaacac tattattaat cctagtgaga atggggatac tagtaccaac   2160

gggatcaaga agattttgat cttttgtaag aaaggctatg agattggcta a           2211
```

```
<210> SEQ ID NO 107
<211> LENGTH: 21
<212> TYPE: PRT
<213> ORGANISM: Homo sapiens

<400> SEQUENCE: 107

Ile Lys Leu Asn Ala Lys Met Asn Ile Leu Ile Arg Asp Lys Arg Phe
1               5                   10                  15

His Tyr Asp Arg Asn
            20


<210> SEQ ID NO 108
<211> LENGTH: 9
<212> TYPE: PRT
<213> ORGANISM: Macaca fascicularis

<400> SEQUENCE: 108

Pro Leu Tyr Ile Ser Asn Pro Asn Tyr
1               5


<210> SEQ ID NO 109
<211> LENGTH: 21
<212> TYPE: PRT
<213> ORGANISM: Homo sapiens

<400> SEQUENCE: 109

Pro Ile Tyr Asn Val Leu Pro Thr Thr Ser Leu Val Leu Gly Lys Asn
1               5                   10                  15

Gln Thr Leu Ala Thr
            20


<210> SEQ ID NO 110
<211> LENGTH: 12
```

-continued

```
<212> TYPE: PRT
<213> ORGANISM: Homo sapiens

<400> SEQUENCE: 110

Ser Leu Val Leu Gly Lys Asn Gln Thr Leu Ala Thr
1               5                   10


<210> SEQ ID NO 111
<211> LENGTH: 16
<212> TYPE: PRT
<213> ORGANISM: Homo sapiens

<400> SEQUENCE: 111

Arg Leu Tyr Gln Ile Lys Ile Gln Tyr Gln Arg Glu Asn Pro Thr Glu
1               5                   10                  15
```